US010596228B2

(12) United States Patent
Kotenko et al.

(10) Patent No.: US 10,596,228 B2
(45) Date of Patent: Mar. 24, 2020

(54) METHODS FOR INCREASING LEVELS OF INTERFERON ACTIVITY WITH AN INTERFERON LAMBDA 3 POLYPEPTIDE

(71) Applicant: Rutgers, The State University of New Jersey, New Brunswick, NJ (US)

(72) Inventors: Sergei V. Kotenko, East Brunswick, NJ (US); Grant F. Gallagher, Milltown, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 0 days.

(21) Appl. No.: 15/869,503

(22) Filed: Jan. 12, 2018

(65) Prior Publication Data
US 2018/0243377 A1 Aug. 30, 2018

Related U.S. Application Data

(60) Continuation of application No. 14/694,297, filed on Apr. 23, 2015, now Pat. No. 9,907,832, which is a continuation of application No. 12/898,320, filed on Oct. 5, 2010, now abandoned, which is a division of application No. 10/503,866, filed as application No. PCT/US03/03942 on Feb. 10, 2003, now Pat. No. 7,820,793.

(60) Provisional application No. 60/418,474, filed on Oct. 15, 2002, provisional application No. 60/355,196, filed on Feb. 8, 2002.

(51) Int. Cl.
*A61K 38/21* (2006.01)
*C07K 14/715* (2006.01)
*C07K 14/555* (2006.01)
*A61K 38/17* (2006.01)
*A61K 39/395* (2006.01)
*C07K 16/24* (2006.01)
*C07K 16/28* (2006.01)
*G01N 33/68* (2006.01)
*A61K 38/00* (2006.01)
*A61K 39/00* (2006.01)

(52) U.S. Cl.
CPC .......... *A61K 38/21* (2013.01); *A61K 38/1793* (2013.01); *A61K 39/3955* (2013.01); *C07K 14/555* (2013.01); *C07K 14/7156* (2013.01); *C07K 16/249* (2013.01); *C07K 16/2866* (2013.01); *G01N 33/6866* (2013.01); *A61K 38/00* (2013.01); *A61K 2039/507* (2013.01); *C07K 2319/00* (2013.01); *G01N 2333/555* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 7,820,793 B2 | 10/2010 | Kotenko et al. | 530/351 |
| 8,715,637 B2 | 5/2014 | Kotenko et al. | 424/85.4 |
| 9,907,832 B2 | 3/2018 | Kotenko et al. | |
| 2003/0104579 A1 | 6/2003 | Baum et al. | 435/69.5 |
| 2004/0029228 A1 | 2/2004 | Presnell et al. | 435/69.1 |
| 2004/0138122 A1 | 7/2004 | Klucher et al. | 514/3.7 |
| 2004/0146988 A1 | 7/2004 | Sheppard et al. | 435/69.51 |

FOREIGN PATENT DOCUMENTS

WO   WO 02/02627 A2   1/2002

OTHER PUBLICATIONS

Steen et al Journal of Interferon & Cytokine Research, 2010; vol. 30, No. 8, pp. 597-602.*
Cheng et al, J Antimicrobial Chemotherapy; 2012; vol. 67, pp. 1080-1087.*
Witte et al, Cytokine & Growth Factor Reviews; 2010; vol. 21, pp. 237-251.*
Li et al, Acta Pharmacologica Sinica, 2006, vol. 74, No. 4, pp. 453-459.*
NCBI Genbank Accession No. AW340139 [gi:6836765] with Revision History—Jan. 31, 2000-Jan. 5, 2011.
NCBI Genbank Accession No. XM_089078 [gi:18547427] submitted Jul. 31, 2002.
Bork, P. "Powers and Pitfalls in Sequence Analysis: The 70% Hurdle" Genome Res. 2000 10:398-400.
Doerks, T. "Protein Annotation: Detective Work for Function Prediction" TIG 1998 14(6):248-250.
Kotenko et al. "IFN-λs Mediate Antiviral Protection through a Distinct Class II Cytokine Receptor Complex" Nature Immunology 2003 4(1): 69-77.
Sheppard et al. "IL-28, IL-29 and their Class II Cytokine Receptor IL-28R" Nature Immunology 2003 4(1):63-68.
Skolnick, J. and Fetrow, J. "From Genes to Protein Structure and Function: Novel Applications of Computational Approaches in the Genomic Era" Tibtech 2000 18:34-39.

(Continued)

*Primary Examiner* — Bridget E Bunner
*Assistant Examiner* — Fozia Hamud
(74) *Attorney, Agent, or Firm* — Licata & Tyrrell P.C.

(57) ABSTRACT

A novel IFN-α/β independent ligand receptor system which upon engagement leads, among other things, to the establishment of an anti-viral state is disclosed. Further disclosed are three closely positioned genes on human chromosome 19 that encode distinct but highly homologous proteins, designated IFN-λ1, IFN-λ2, IFN-λ3, based inter alia, in their ability to induce antiviral protection. Expression of these proteins is induced upon viral infection. A receptor complex utilized by all three IFN-λ proteins for signaling is also disclosed. The receptor complex is generally composed of two subunits, a novel receptor designated IFN-λR1 or CRF2-12, and a second subunit, IL-10R2 or CRF2-4, which is also a shared receptor component for the IL-10 and IL-22 receptor complexes. The gene encoding IFN-λR1 is generally widely expressed, including many different cell types and tissues. Expression of these proteins is induced by immune events, including, for example, upon viral infection. Apoptotosis may also be induced under effective conditions.

5 Claims, 43 Drawing Sheets

Specification includes a Sequence Listing.

(56) References Cited

OTHER PUBLICATIONS

Tokuriki, N. and Tawfik, D. "Stability Effects of Mutations and Protein Evolvability" Current Opinion in Structural Biology 2009 19:596-604.
Well, J.A. "Additivity of Mutational Effects in Proteins" Biochemistry 1990 29(37):8509-8517.
Zhu et al. "Novel Type 1 Interferon IL-28A Suppresses Hepatitis C Viral RNA Replication" Virology Journal 2005 2(80) 1-12.
Office Communication dated Dec. 4, 2009 in U.S. Appl. No. 10/503,866, filed Aug. 6, 2004.
Office Communication dated Mar. 29, 2013 in U.S. Appl. No. 12/898,141, filed Oct. 5, 2010.
Office Communication dated Apr. 30, 2014 in U.S. Appl. No. 12/898,320, filed Oct. 5, 2010.
Office Communication dated Oct. 23, 2014 in U.S. Appl. No. 12/898,320, filed Oct. 5, 2010.
Office Communication dated Mar. 26, 2015 in U.S. Appl. No. 12/898,320, filed Oct. 5, 2010.
International Search Report in WO 03/066002, dated Aug. 14, 2003, PCT.
International Preliminary Examination Report in WO 03/066002, dated Feb. 10, 2005, PCT.
Abushahba et al. "Antitumor activity of Type I and Type III interferons in BNL hepatoma model" Cancer Immunology Immunotherapy 2010 59:1059-1071.
http://stedmansonline.com/index.aspx; 2016; enteries for Parasitic Infection; diabetes mellitus; systemic lupus; Allergy; cancer.
Planet et al. "Lambda Interferon Restructures the Nasal Microbiome and Increases Susceptibility to *Staphylococcus aureus* Superinfection" mBio 2016 7:1-12.
Syedbasha M. & Egli a. "Interferon Lambda: Modulating Immunity in Infectious Diseases" Frontiers in Immunology 2017 8:1-13.
Office Communication dated Jun. 28, 2016 in U.S. Appl. No. 14/694,297, filed Apr. 23, 2015.
Office Communication dated Feb. 14, 2017 in U.S. Appl. No. 14/694,297, filed Apr. 23, 2015.
Office Communication dated Aug. 8, 2017 in U.S. Appl. No. 14/694,297, filed Apr. 23, 2015.
Office Communication dated Nov. 2, 2017 in U.S. Appl. No. 14/694,297, filed Apr. 23, 2015.

* cited by examiner 1 gccATGGCGG GGCCCGAGCG CTGGGGCCCC CTGCTCCTGT GCCTGCTGCA
  51 GGCCGCTCCA GGGAGGCCCC GTCTGGCCCC TCCCCAGAAT GTGACGCTGC
 101 TCTCCCAGAA CTTCAGCGTG TACCTGACAT GGCTCCCAGG GCTTGGCAAC
 151 CCCCAGGATG TGACCTATTT TGTGGCCTAT CAGAGCTCTC CCACCCGTAG
 201 ACGGTGGCGC GAAGTGGAAG AGTGTGCGGG AACCAAGGAG CTGCTATGTT
 251 CTATGATGTG CCTGAAGAAA CAGGACCTGT ACAACAAGTT CAAGGGACGC
 301 GTGCGGACGG TTTCTCCCAG CTCCAAGTCC CCTGGGTGG AGTCCGAATA
 351 CCTGGATTAC CTTTTTGAAG TGGAGCCGGC CCCACCTGTC CTGGTGCTCA
 401 CCCAGACGGA GGAGATCCTG AGTGCCAATG CCACGTACCA GCTGCCCCCC
 451 TGCATGCCCC CACTGGATCT GAAGTATGAG GTGGCATTCT GGAAGGAGGG
 501 GGCCGGAAAC AAGACCCTAT TTCCAGTCAC TCCCCATGGC CAGCCAGTCC
 551 AGATCACTCT CCAGCCAGCT GCCAGCGAAC ACCACTGCCT CAGTGCCAGA
 601 ACCATCTACA CGTTCAGTGT CCCGAAATAC AGCAAGTTCT CTAAGCCCAC
 651 CTGCTTCTTG CTGGAGGTCC CAGAAGCCAA CTGGGCTTTC CTGGTGCTGC
 701 CATCGCTTCT GATACTGCTG TTAGTAATTG CCGCAGGGGG TGTGATCTGG
 751 AAGACCCTCA TGGGGAACCC CTGGTTTCAG CGGGCAAAGA TGCCACGGGC
 801 CCTGGACTTT TCTGGACACA CACACCCTGT GGCAACCTTT CAGCCCAGCA
 851 GACCAGAGTC CGTGAATGAC TTGTTCCTCT GTCCCCAAAA GGAACTGACC
 901 AGAGGGGTCA GGCCGACGCC TCGAGTCAGG GCCCCAGCCA CCCAACAGAC
 951 AAGATGGAAG AAGGACCTTG CAGAGGACGA AGAGGAGGAG GATGAGGAGG
1001 ACACAGAAGA TGGCGTCAGC TTCCAGCCCT ACATTGAACC ACCTTCTTTC
1051 CTGGGGCAAG AGCACCAGGC TCCAGGGCAC TCGGAGGCTG GTGGGGTGGA
1101 CTCAGGGAGG CCCAGGGCTC CTCTGGTCCC AAGCGAAGGC TCCTCTGCTT
1151 GGGATTCTTC AGACAGAAGC TGGGCCAGCA CTGTGGACTC CTCCTGGGAC
1201 AGGGCTGGGT CCTCTGGCTA TTTGGCTGAG AAGGGGCCAG GCCAAGGGCC
1251 GGGTGGGGAT GGGCACCAAG AATCTCTCCC ACCACCTGAA TTCTCCAAGG

FIG. 1A

```
1301 ACTCGGGTTT CCTGGAAGAG CTCCCAGAAG ATAACCTCTC CTCCTGGGCC
1351 ACCTGGGGCA CCTTACCACC GGAGCCGAAT CTGGTCCCTG GGGGACCCCC
1401 AGTTTCTCTT CAGACACTGA CCTTCTGCTG GGAAAGCAGC CCTGAGGAGG
1451 AAGAGGAGGC GAGGGAATCA GAAATTGAGG ACAGCGATGC GGGCAGCTGG
1501 GGGGCTGAGA GCACCCAGAG GACCGAGGAC AGGGGCCGGA CATTGGGGCA
1551 TTACATGGCC AGGTGAgctg tccccgaca tcccaccgaa tctgatgctg
1601 ctgctgcctt tgcaaggact actgggcttc caagaaact caagagcctc
1651 cgtacctccc ctgggcggcg gagggcatt gcacttccgg gaagtccacc
1701 tagcggctgt ttgcctgtcg ggctgagcaa caagatgccc ctccctcctg
1751 tgacccgccc tctttaggct gagctataag agggtggac acagggtggg
1801 ctgaggtcag aggttggtgg ggtgtcatca cccccattgt cctagggtg
1851 acaggccagg gggaaaaatt atccccggac aacatgaaac aggtgaggtc
1901 aggtcactgc ggacatcaag ggcggacacc accaagggc cctctggaac
1951 ttgagaccac tggaggcaca cctgctatac ctcatgcctt tcccagcagc
2001 cactgaactc ccccatccca gggctcagcc tcctgattca tgggtcccct
2051 agttaggccc agataaaaat ccagttggct gagggttttg gatgggaagg
2101 gaagggtggc tgtcctcaaa tcctggtctt tggagtcatg gcactgtacg
2151 gttttagtgt cagacagacc ggggttcaaa tcccagctct gctgttcact
2201 ggttgtatga tcttggggaa gacatcttcc ttctctgcct cggcttcctc
2251 atctgcagct acgcctgggt gtggtgaggg ttctagggga tctcagatgt
2301 gtgtagcacg gagcctgctg tgtcctgggt gctctctacg tggtggccgg
2351 tagaattctc catctatcca ggctccagga gaccctggg catctcccac
2401 ctgtggcccc taaacccaga gtgactgaga gcacttaaca ttcagcttgt
2451 ctcatcccca gtctacctcc ttccttctac cctcactgcc tcccagtcag
2501 gagagtgagc tctcagaagc cagagcccca cccaagggga ccctggtctc
2551 tccgccttca cctagcaatg ggaaccctgc ttcccagggg aggaaccaac
2601 tgctccacct tctagggacc cagtttgttg gagtaggaca gtaacatggc
```

FIG. 1B 2651 aggaatcgga cttctgggcc tgtaatccca gtttggatgg cacgttagac
2701 tcttggttga ccgttgtggt ccttagaagt cccattctcc cttccagtta
2751 tgagaaacca atgccttcta gattcaggtg actatcctta cctggggtg
2801 ctgatgcatc ctcagttaac ctacacccac ctgaatatag atgagcgtag
2851 ctgagttttc acccgtagga ccgaagtgtt ttgtggtgga gtatctgaac
2901 aaccttggct ctgtggccat tcaacctgcc aggactaaca tttctggatt
2951 tgtgaagaag ggatcttcaa agccattgaa cccacagagc tgtgttgctt
3001 taaagccacc acaagggtac agcattaaat ggcagaactg gaaaagcttc
3051 ttaggcatc tcatccaggg attctcaaac catgtccccc agaggccttg
3101 ggctgcagtt gcaggggcg ccatggggct ataggagcct cccactttca
3151 ccagagcagc ctcactgtgc cctgattcac acactgtggc tttccacgtg
3201 aggttttgtt tagagggatc cactactcaa gaaaagtta gcaaaccact
3251 cctttgttg caaaggagct gaggtcaagg gtggcaaagg cacttgtcca
3301 aggtcgccca gcagtgctgc tctgatgact tgtgcacatc cccaagggta
3351 agagcttcga tctctgcaca gccgggccaa cctctgaccc cttgtccatg
3401 tcagtaaaat atgaaggtca cagccaggat ttctaagggt caggaggcct
3451 tcaccgctgc tggggcacac acacacacat gcatacacac atacgacaca
3501 cacctgtgtc tccccagggg ttttccctgc agtgaggctt gtccagatga
3551 ttgagcccag gagaggaaga acaaacaaac tacggagctg gggagggctg
3601 tggcttgggg ccagctccca gggaaattcc cagacctgta ccgatgttct
3651 ctctggcacc agccgagctg cttcgtggag gtaacttcaa aaaagtaaaa
3701 gctatcatca gcatcatctt agacttgtat gaaataacca ctccgtttct
3751 attcttaaac cttaccattt tgttttgtt ttgttttttt gagtcggagt
3801 tttgttcttt ttgcctaggc tggagtgcag tggtacaatc tcggctcact
3851 gcaacctcca cctcccgggt tcaagtgatt ctcctgcctc agcctcccaa
3901 gtagctggga ttacaggcac ccgccaccac acctggctaa tttttttgta
3951 tttttagtag agacggggtt tcaccatgtt ggccaggctg gtctcgaact

FIG. 1C

```
4001 cctgacctca ggtgatccgc ccgcctcggc ctcccaaagt gctgggatta
4051 caggcgtgag ccaccgcgcc cagccaaacc ttactatttt tttaaagaat
4101 tttttccaga gtttaatttc tgacatagct taagttttcc agtaactcta
4151 aactccatct cctttatcgt cattaagtca ttcacaaaaa gccaggagaa
4201 gcatttggaa agggcatgat aatcagtata ataatttgcc ttgtgtggtc
4251 agcacttaac tgtttacaaa gcccttcac gtgcacagca ggtgggaact
4301 gcgcggtgtg ggctgggcct gcgctggaag catatcccgt gaaaagtgtt
4351 agtgccttag gtgaaagcaa catgtatccc tttagactac taacggtata
4401 tgttgttctt atgtatttgt atttatttct attttttcta tgtttatgtc
4451 atatttaaac gatatcctac tgcttgttgg tattacccta aactgtttaa
4501 ataaagagct ctatttttaa agaaaaaagg tacaattga
```

FIG. 1D

```
  1 MAGPERWGPL LLCLLQAAPG RPRLAPPQNV TLLSQNFSVY LTWLPGLGNP
 51 QDVTYFVAYQ SSPTRRRWRE VEECAGTKEL LCSMMCLKKQ DLYNKFKGRV
101 RTVSPSSKSP WVESEYLDYL FEVEPAPPVL VLTQTEEILS ANATYQLPPC
151 MPPLDLKYEV AFWKEGAGNK TLFPVTPHGQ PVQITLQPAA SEHHCLSART
201 IYTFSVPKYS KFSKPTCFLL EVPEANWAFL VLPSLLILLL VIAAGGVIWK
251 TLMGNPWFQR AKMPRALDFS GHTHPVATFQ PSRPESVNDL FLCPQKELTR
301 GVRPTPRVRA PATQQTRWKK DLAEDEEEED EEDTEDGVSF QPYIEPPSFL
351 GQEHQAPGHS EAGGVDSGRP RAPLVPSEGS SAWDSSDRSW ASTVDSSWDR
401 AGSSGYLAEK GPGQGPGGDG HQESLPPPEF SKDSGFLEEL PEDNLSSWAT
451 WGTLPPEPNL VPGGPPVSLQ TLTFCWESSP EEEEEARESE IEDSDAGSWG
501 AESTQRTEDR GRTLGHYMAR
```

FIG. 2

 BLAST 2 SEQUENCES RESULTS

BLAST 2 SEQUENCES RESULTS VERSION BLASTP 2.1.2 [OCT-19-2000]

MATRIX BLOSUM62  GAP OPEN: 11  GAP EXTENSION: 1
X_DROPOFF: 50  EXPECT: 10.0  WORDSIZE: 3  FILTER  ALIGN

SEQUENCE 1 LCL|HS1_4516_26_7_6    LENGTH 423 (1..423)
SEQUENCE 2 GI 7657691              LENGTH 553 (1..553)

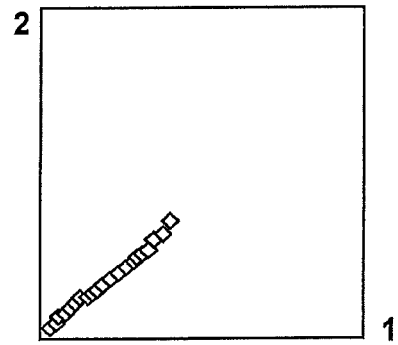

NOTE: THE STATISTICS (BITSCORE AND EXPECT VALUE) IS CALCULATED BASED ON TEH SIZE OF NR DATABASE
SCORE=55.4 BITS (131), EXPECT=2E-06
IDENTITIES=54/190 (28%), POSITIVES=75/190 (39%), GAPS=28/190 (14%)

```
QUERY:   9 PLLLCLLQAAPGRP------RLAPPQNVTLLSQNFSVYLTWLPGLG-NPQDVTYFVAYQS 61
           PLLL LL A  GR        L  P N+T LS N   LWP G     VTY V Y
SBJCT:  16 PLLLLLLAAPWGRAVPCVSGGLPKPANITFLSINMKNVLQWTPPEGLQGVKVTYTVQYFI 75
TISSUE  33                ****************************************
FACTOR

QUERY:  62 SPTRRRWREVEECAGTKELLCSMMCLKKQDLYNKFKGRVRTVSPSSKSPWVESEYLDYLF 121
              +++W   EC       C +   + D +++ +V+ +  +  S W ES
SBJCT:  76 YG-QKKWLNKSECRNINRTYCDLSA-ETSDYEHQYYAKVKAIWGTKCSKWAESGRFYPFL 133
TISSUE  76 ** ********************* ***********************************
FACTOR

QUERY: 122 EVEPAPPVLVLTQTEEILSANAT---------YQLPPCMPPL--DLKYEVAF-------- 162
           E +  PP + LT E+ +S  T          LP M +   +LKY V+
SBJCT: 134 ETQIGPPEVALTTDEKSISVVLTAPEKWKRNPEDLPVSMQQIYSNLKYNVSVLNTKSNRT 193
TISSUE 134 ************************************************************
FACTOR

QUERY: 163 WKEGAGNKTL 172
           W +   N TL
SBJCT: 194 WSQCVTNHTL 203
TISSUE 194
FACTOR
```

HTTP://WWW.NCBI.NLM.NIH.GOV/GORF/WBLAST2.CGI

*FIG. 4*

ALIGNMENT RESULTS FILE: SEQUENCES.ALN

```
CRF2-12   ----------MAGPERWGPLLLCLLQAAPGRPRLAPPQNVTLLSQNFSVYITWLPGLGNPQDVTYFVAYQSSPTRRRWRE
IL10RA    ----------MLPCLVVLAALLSLRLGSDAHGTELPSPPSVWFEAEFFHHILHWTEIPNQSEST-QEVALLRYGIESENS
IL10RB    -------MAWSLGSWLGGCLLVSALGMVPPPENVRMSVNFKNIIQWESPAFAKGNL---T-FTAQYLSYRIF
IL20RA    MRAPGRPALRPLPLPPLLILLAAPWGRAVPCVSGGLPKPANITELSINMKNVLQWTPEGLQVKVTYTVQYFIYQKKMLN
IL20RB    ----------MKHLLLMWSPVIAPGETVYYSVEYQGEY------ESL--WIPSSW--
IL22RA    ----------MRTLTILTVGSLAAHAPEDPSDLLQHVKFQSSNFENIITWDSGPEGTPDT--VYSIEYKTYGERLWVA
IL22BP    ----------MMPKHCFLGFLLSFFLTGVAGTQSTHESLKEQRVQEQSRNFHNIIQWQPGRALTGNSSVYFVQYKIYGQRCWKN

CRF2-12   VEEC AGTKELII CSMMCLKKQDLYNKFKGRVRTVSPSSKSPWVESEYLDYLFEVEPAPHVLV ITQTEEII SANATYQLPPCMPP
IL10RA    ISNCSQTLSYDLTAVTLDLYHSNGYR-ARVRAVDGSRHSNWTVTNTRFSVDEVTLTVGSVNLEIHNGFILGKIQIPRPKMAPA
IL10RB    QDKCMNTLTECDFSSLSKYGDHTL---RVRAEFADEHSDW-VNITFCPVDTIIGPFGMQVEVLADSIHMRFLAPKIE---N
IL20RA    KSECRNINRTYCDLSAETSDYEHQLY-AKVKGTKCSKWAESGREYPFLETQIGPPEVAL

```
         12            21           30           39           48           57
ATG GCG GGG CCC GAG CGC TGG GGC CCC CTG CTC CTG TGC CTG CTG CAG GCC GCT
 M   A   G   P   E   R   W   G   P   L   L   L   C   L   L   Q   A   A 66            75           84           93          102          111
CCA GGG AGG CCC CGT CTG GCC CCT CCC CAG AAT GTG ACG CTG CTC TCC CAG AAC
 P   G   R   P   R   L   A   P   P   Q   N   V   T   L   L   S   Q   N 120           129          138          147          156          165
TTC AGC GTG TAC CTG ACA TGG CTC CCA GGG CTT GGC AAC CCC CAG GAT GTG ACC
 F   S   V   Y   L   T   W   L   P   G   L   G   N   P   Q   D   V   T 174           183          192          201          210          219
TAT TTT GTG GCC TAT CAG AGC TCT CCC ACC CGT AGA CGG TGG CGC GAA GTG GAA
 Y   F   V   A   Y   Q   S   S   P   T   R   R   R   W   R   E   V   E 228           237          246          255          264          273
GAG TGT GCG GGA ACC AAG GAG CTG CTA TGT TCT ATG ATG TGC CTG AAG AAA CAG
 E   C   A   G   T   K   E   L   L   C   S   M   M   C   L   K   K   Q 282           291          300          309          318          327
GAC CTG TAC AAC AAG TTC AAG GGA CGC GTG CGG ACG GTT TCT CCC AGC TCC AAG
 D   L   Y   N   K   F   K   G   R   V   R   T   V   S   P   S   S   K 336           345          354          363          372          381
TCC CCC TGG GTG GAG TCC GAA TAC CTG GAT TAC CTT TTT GAA GTG GAG CCG GCC
 S   P   W   V   E   S   E   Y   L   D   Y   L   F   E   V   E   P   A 390           399          408          417          426          435
CCA CCT GTC CTG GTG CTC ACC CAG ACG GAG GAG ATC CTG AGT GCC AAT GCC ACG
 P   P   V   L   V   L   T   Q   T   E   E   I   L   S   Y   EA  N 444           453          462          471          480          489
TAC CAG CTG CCC CCC TGC ATG CCC CCA CTG GAT CTG AAG TAT GAG GTG GCA TTC
 A   T   Y   Q   L   P   P   C   M   P   P   L   D   L   KV  A   F 498           507          516          525          534          543
TGG AAG GAG GGG GCC GGA AAC AAG ACC CTA TTT CCA GTC ACT CCC CAT GGC CAG
 W   K   E   G   A   G   N   K   T   L   F   P   V   T   P   H   G   Q 552           561          570          579          588          597
CCA GTC CAG ATC ACT CTC CAG CCA GCT GCC AGC GAA CAC CAC TGC CTC AGT GCC
 P   V   Q   I   T   L   Q   P   A   A   S   E   H   H   C   L   S   A 606           615          624          633          642          651
AGA ACC ATC TAC ACG TTC AGT GTC CCG AAA TAC AGC AAG TTC TCT AAG CCC ACC
 R   T   I   Y   T   F   S   V   P   K   Y   S   K   F   S   K   P   T
```

FIG. 7A

```
      660         669         678         687         696         705
TGC TTC TTG CTG GAG GTC CCA GAA GCC AAC TGG GCT TTC CTG GTG CTG CCA TCG
 C   F   L   L   E   V   P   E   A   N   W   A   F   L   V   L   P   S
          714         723         732         741         750         759
CTT CTG ATA CTG CTG TTA GTA ATT GCC GCA GGG GGT GTG ATC TGG AAG ACC CTC
 L   L   I   L   L   L   V   I   A   A   G   G   V   I   W   K   T   L
          768         777         786         795         804         813
ATG GGG AAC CCC TGG TTT CAG CGG GCA AAG ATG CCA CGG GCC CTG GAC TTT TCT
 M   G   N   P   W   F   Q   R   A   K   M   P   R   A   L   D   F   S
          822         831         840         849         858         867
GGA CAC ACA CAC CCT GTG GCA ACC TTT CAG CCC AGC AGA CCA GAG TCC GTG AAT
 G   H   T   H   P   V   A   T   F   Q   P   S   R   P   E   S   V   N
          876         885         894         903         912         921
GAC TTG TTC CTC TGT CCC CAA AAG GAA CTG ACC AGA GGG GTC AGG CCG ACG CCT
 D   L   F   L   C   P   Q   K   E   L   T   R   G   V   R   P   T   P
          930         939         948         957         966         975
CGA GTC AGG GCC CCA GCC ACC CAA CAG ACA AGA TGG AAG AAG GAC CTT GCA GAG
 R   V   R   A   P   A   T   Q   Q   T   R   W   K   K   D   L   A   E
          984         993        1002        1011        1020        1029
GAC GAA GAG GAG GAG GAT GAG GAG GAC ACA GAA GAT GGC GTC AGC TTC CAG CCC
 D   E   E   E   E   D   E   E   D   T   E   D   G   V   S   F   Q   P
         1038        1047        1056        1065        1074        1083
TAC ATT GAA CCA CCT TCT TTC CTG GGG CAA GAG CAC CAG GCT CCA GGG CAC TCG
 Y   I   E   P   P   S   F   L   G   Q   E   H   Q   A   P   G   H   S
         1092        1101        1110        1119        1128        1137
GAG GCT GGT GGG GTG GAC TCA GGG AGG CCC AGG GCT CCT CTG GTC CCA AGC GAA
 E   A   G   G   V   D   S   G   R   P   R   A   P   L   V   P   S   E
         1146        1155        1164        1173        1182        1191
GGC TCC TCT GCT TGG GAT TCT TCA GAC AGA AGC TGG GCC AGC ACT GTG GAC TCC
 G   S   S   A   W   D   S   S   D   R   S   W   A   S   T   V   D   S
         1200        1209        1218        1227        1236        1245
TCC TGG GAC AGG GCT GGG TCC TCT GGC TAT TTG GCT GAG AAG GGG CCA GGC CAA
 S   W   D   R   A   G   S   S   G   Y   L   A   E   K   G   P   G   Q
         1254        1263        1272        1281        1290        1299
GGG CCG GGT GGG GAT GGG CAC CAA GAA TCT CTC CCA CCA CCT GAA TTC TCC AAG
 G   P   G   G   D   G   H   Q   E   S   L   P   P   P   E   F   S   K
         1308        1317        1326        1335        1344        1353
GAC TCG GGT TTC CTG GAA GAG CTC CCA GAA GAT AAC CTC TCC TCC TGG GCC ACC
 D   S   G   F   L   E   E   L   P   E   D   N   L   S   S   W   A   T
```

FIG. 7B

```
      1362           1371           1380           1389           1398           1407
TGG GGC ACC TTA CCA CCG GAG CCG AAT CTG GTC CCT GGG GGA CCC CCA GTT TCT
 W   G   T   L   P   P   E   P   N   L   V   P   G   G   P   P   V   S
      1416           1425           1343           1443           1452           1461
CTT CAG ACA CTG ACC TTC TGC TGG GAA AGC AGC CCT GAG GAG GAA GAG GAG GCG
 L   Q   T   L   T   F   C   W   E   S   S   P   E   E   E   E   E   A
      1470           1479           1488           1497           1506           1515
AGG GAA TCA GAA ATT GAG GAC AGC GAT GCG GGC AGC TGG GGG GCT GAG AGC ACC
 R   E   S   E   I   E   D   S   D   A   G   S   W   G   A   E   S   T
      1524           1533           1542           1551           1560
CAG AGG ACC GAG GAC AGG GGC CGG ACA TTG GGG CAT TAC ATG GCC AGG TGA  3'
 Q   R   T   E   D   R   G   R   T   L   G   H   Y   M   A   R   *
```

FIG. 7C

```
              12             21             30             39             48             57
ATG GCG GGG CCC GAG CGC TGG GGC CCC CTG CTC CTG TGC CTG CTG CAG GCC GCT
Met Ala Gly Pro Glu Arg Trp Gly Pro Leu Leu Leu Cys Leu Leu Gln Ala Ala
              66             75             84             93            102            111
CCA GGG AGG CCC CGT CTG GCC CCT CCC CAG AAT GTG ACG CTG CTC TCC CAG AAC
Pro Gly Arg Pro Arg Leu Ala Pro Pro Gln Asn Val Thr Leu Leu Ser Gln Asn
             120            129            138            147            156            165
TTC AGC GTG TAC CTG ACA TGG CTC CCA GGG CTT GGC AAC CCC CAG GAT GTG ACC
Phe Ser Val Tyr Leu Thr Trp Leu Pro Gly Leu Gly Asn Pro Gln Asp Val Thr
             174            183            192            201            210            219
TAT TTT GTG GCC TAT CAG AGC TCT CCC ACC CGT AGA CGG TGG CGC GAA GTG GAA
Tyr Phe Val Ala Tyr Gln Ser Ser Pro Thr Arg Arg Arg Trp Arg Glu Val Glu
             228            237            246            255            264            273
GAG TGT GCG GGA ACC AAG GAG CTG CTA TGT TCT ATG ATG TGC CTG AAG AAA CAG
Glu Cys Ala Gly Thr Lys Glu Leu Leu Cys Ser Met Met Cys Leu Lys Lys Gln
             282            291            300            309            318            327
GAC CTG TAC AAC AAG TTC AAG GGA CGC GTG CGG ACG GTT TCT CCC AGC TCC AAG
Asp Leu Tyr Asn Lys Phe Lys Gly Arg Val Arg Thr Val Ser Pro Ser Ser Lys
             336            345            354            363            372            381
TCC CCC TGG GTG GAG TCC GAA TAC CTG GAT TAC CTT TTT GAA GTG GAG CCG GCC
Ser Pro Trp Val Glu Ser Glu Tyr Leu Asp Tyr Leu Phe Glu Val Glu Pro Ala
             390            399            408            417            426            435
CCA CCT GTC CTG GTG CTC ACC CAG ACG GAG GAG ATC CTG AGT GCC AAT GCC ACG
Pro Pro Val Leu Val Leu Thr Gln Thr Glu Glu Ile Leu Ser Ala Asn Ala Thr
             444            453            462            471            480            489
TAC CAG CTG CCC CCC TGC ATG CCC CCA CTG GAT CTG AAG TAT GAG GTG GCA TTC
Tyr Gln Leu Pro Pro Cys Met Pro Pro Leu Asp Leu Lys Tyr Glu Val Ala Phe
             498            507            516            525            534            543
TGG AAG GAG GGG GCC GGA AAC AAG ACC CTA TTT CCA GTC ACT CCC CAT GGC CAG
Trp Lys Glu Gly Ala Gly Asn Lys Thr Leu Phe Pro Val Thr Pro His Gly Gln
             552            561            570            579            588            597
CCA GTC CAG ATC ACT CTC CAG CCA GCT GCC AGC GAA CAC CAC TGC CTC AGT GCC
Pro Val Gln Ile Thr Leu Gln Pro Ala Ala Ser Glu His His Cys Leu Ser Ala
             606            615            624            633            642            651
AGA ACC ATC TAC ACG TTC AGT GTC CCG AAA TAC AGC AAG TTC TCT AAG CCC ACC
Arg Thr Ile Tyr Thr Phe Ser Val Pro Lys Tyr Ser Lys Phe Ser Lys Pro Thr
```

FIG. 8A

|     | 660 |     |     | 669 |     |     | 678 |     |     | 687 |     |     | 696 |     |     | 705 |     |
| --- | --- | --- | --- | --- | --- | --- | --- | --- | --- | --- | --- | --- | --- | --- | --- | --- | --- |
| TGC | TTC | TTG | CTG | GAG | GTC | CCA | GAA | GCC | AAC | TGG | GCT | TTC | CTG | GTG | CTG | CCA | TCG |
| Cys | Phe | Leu | Leu | Glu | Val | Pro | Glu | Ala | Asn | Trp | Ala | Phe | Leu | Val | Leu | Pro | Ser |
|     | 714 |     |     | 723 |     |     | 732 |     |     | 741 |     |     | 750 |     |     | 759 |     |
| CTT | CTG | ATA | CTG | CTG | TTA | GTA | ATT | GCC | GCA | GGG | GGT | GTG | ATC | TGG | AAG | ACC | CTC |
| Leu | Leu | Ile | Leu | Leu | Leu | Val | Ile | Ala | Ala | Gly | Gly | Val | Ile | Trp | Lys | Thr | Leu |
|     | 768 |     |     | 777 |     |     | 786 |     |     | 795 |     |     | 804 |     |     | 813 |     |
| ATG | GGG | AAC | CCC | TGG | TTT | CAG | CGG | GCA | AAG | ATG | CCA | CGG | GCC | CTG | GAC | TTT | TCT |
| Met | Gly | Asn | Pro | Trp | Phe | Gln | Arg | Ala | Lys | Met | Pro | Arg | Ala | Leu | Asp | Phe | Ser |
|     | 822 |     |     | 831 |     |     | 840 |     |     | 849 |     |     | 858 |     |     | 867 |     |
| GGA | CAC | ACA | CAC | CCT | GTG | GCA | ACC | TTT | CAG | CCC | AGC | AGA | CCA | GAG | TCC | GTG | AAT |
| Gly | His | Thr | His | Pro | Val | Ala | Thr | Phe | Gln | Pro | Ser | Arg | Pro | Glu | Ser | Val | Asn |
|     | 876 |     |     | 885 |     |     | 894 |     |     | 903 |     |     | 912 |     |     | 921 |     |
| GAC | TTG | TTC | CTC | TGT | CCC | CAA | AAG | GAA | CTG | ACC | AGA | GGG | GTC | AGG | CCG | ACG | CCT |
| Asp | Leu | Phe | Leu | Cys | Pro | Gln | Lys | Glu | Leu | Thr | Arg | Gly | Val | Arg | Pro | Thr | Pro |
|     | 930 |     |     | 939 |     |     | 948 |     |     | 957 |     |     | 966 |     |     | 975 |     |
| CGA | GTC | AGG | GCC | CCA | GCC | ACC | CAA | CAG | ACA | AGA | TGG | AAG | AAG | GAC | CTT | GCA | GAG |
| Arg | Val | Arg | Ala | Pro | Ala | Thr | Gln | Gln | Thr | Arg | Trp | Lys | Lys | Asp | Leu | Ala | Glu |
|     | 984 |     |     | 993 |     |     | 1002 |    |     | 1011 |    |     | 1020 |    |     | 1029 |    |
| GAC | GAA | GAG | GAG | GAG | GAT | GAG | GAG | GAC | ACA | GAA | GAT | GGC | GTC | AGC | TTC | CAG | CCC |
| Asp | Glu | Glu | Glu | Glu | Asp | Glu | Glu | Asp | Thr | Glu | Asp | Gly | Val | Ser | Phe | Gln | Pro |
|     | 1038 |    |     | 1047 |    |     | 1056 |    |     | 1065 |    |     | 1074 |    |     | 1083 |    |
| TAC | ATT | GAA | CCA | CCT | TCT | TTC | CTG | GGG | CAA | GAG | CAC | CAG | GCT | CCA | GGG | CAC | TCG |
| Tyr | Ile | Glu | Pro | Pro | Ser | Phe | Leu | Gly | Gln | Glu | His | Gln | Ala | Pro | Gly | His | Ser |
|     | 1092 |    |     | 1101 |    |     | 1110 |    |     | 1119 |    |     | 1128 |    |     | 1137 |    |
| GAG | GCT | GGT | GGG | GTG | GAC | TCA | GGG | AGG | CCC | AGG | GCT | CCT | CTG | GTC | CCA | AGC | GAA |
| Glu | Ala | Gly | Gly | Val | Asp | Ser | Gly | Arg | Pro | Arg | Ala | Pro | Leu | Val | Pro | Ser | Glu |
|     | 1146 |    |     | 1155 |    |     | 1164 |    |     | 1173 |    |     | 1182 |    |     | 1191 |    |
| GGC | TCC | TCT | GCT | TGG | GAT | TCT | TCA | GAC | AGA | AGC | TGG | GCC | AGC | ACT | GTG | GAC | TCC |
| Gly | Ser | Ser | Ala | Trp | Asp | Ser | Ser | Asp | Arg | Ser | Trp | Ala | Ser | Thr | Val | Asp | Ser |
|     | 1200 |    |     | 1209 |    |     | 1218 |    |     | 1227 |    |     | 1236 |    |     | 1245 |    |
| TCC | TGG | GAC | AGG | GCT | GGG | TCC | TCT | GGC | TAT | TTG | GCT | GAG | AAG | GGG | CCA | GGC | CAA |
| Ser | Trp | Asp | Arg | Ala | Gly | Ser | Ser | Gly | Tyr | Leu | Ala | Glu | Lys | Gly | Pro | Gly | Gln |
|     | 1254 |    |     | 1263 |    |     | 1272 |    |     | 1281 |    |     | 1290 |    |     | 1299 |    |
| GGG | CCG | GGT | GGG | GAT | GGG | CAC | CAA | GAA | TCT | CTC | CCA | CCA | CCT | GAA | TTC | TCC | AAG |
| Gly | Pro | Gly | Gly | Asp | Gly | His | Gln | Glu | Ser | Leu | Pro | Pro | Pro | Glu | Phe | Ser | Lys |
|     | 1308 |    |     | 1317 |    |     | 1326 |    |     | 1335 |    |     | 1344 |    |     | 1353 |    |
| GAC | TCG | GGT | TTC | CTG | GAA | GAG | CTC | CCA | GAA | GAT | AAC | CTC | TCC | TCC | TGG | GCC | ACC |
| Asp | Ser | Gly | Phe | Leu | Glu | Glu | Leu | Pro | Glu | Asp | Asn | Leu | Ser | Ser | Trp | Ala | Thr |

FIG. 8B

```
      1362          1371          1380          1389          1398          1407
TGG GGC ACC TTA CCA CCG GAG CCG AAT CTG GTC CCT GGG GGA CCC CCA GTT TCT
--- --- --- --- --- --- --- --- --- --- --- --- --- --- --- --- --- ---
Trp Gly Thr Leu Pro Pro Glu Pro Asn Leu Val Pro Gly Gly Pro Pro Val Ser
      1416          1425          1343          1443          1452          1461
CTT CAG ACA CTG ACC TTC TGC TGG GAA AGC AGC CCT GAG GAG GAA GAG GAG GCG
--- --- --- --- --- --- --- --- --- --- --- --- --- --- --- --- --- ---
Leu Gln Thr Leu Thr Phe Cys Trp Glu Ser Ser Pro Glu Glu Glu Glu Glu Ala
      1470          1479          1488          1497          1506          1515
AGG GAA TCA GAA ATT GAG GAC AGC GAT GCG GGC AGC TGG GGG GCT GAG AGC ACC
--- --- --- --- --- --- --- --- --- --- --- --- --- --- --- --- --- ---
Arg Glu Ser Glu Ile Glu Asp Ser Asp Ala Gly Ser Trp Gly Ala Glu Ser Thr
      1524          1533          1542          1551          1560
CAG AGG ACC GAG GAC AGG GGC CGG ACA TTG GGG CAT TAC ATG GCC AGG TGA   3'
--- --- --- --- --- --- --- --- --- --- --- --- --- --- --- --- ---
Gln Arg Thr Glu Asp Arg Gly Arg Thr Leu Gly His Tyr Met Ala Arg ***
```

FIG. 8C

```
         10         20         30         40         50         60
  ATGGCNGGNC CNGARMGNTG GGGNCCNYTN YTNYTNTGYY TNYTNCARGC NGCNCCNGGN
         70         80         90        100        110        120
  MGNCCNMGNY TNGCNCCNCC NCARAAYGTN ACNYTNYTNW SNCARAAYTT YWSNGTNTAY
        130        140        150        160        170        180
  YTNACNTGGY TNCCNGGNYT NGGNAAYCCN CARGAYGTNA CNTAYTTYGT NGCNTAYCAR
        190        200        210        220        230        240
  WSNWSNCCNA CNMGNMGNMG NTGGMGNGAR GTNGARGART GYGCNGGNAC NAARGARYTN
        250        260        270        280        290        300
  YTNTGYWSNA TGATGTGYYT NAARAARCAR GAYYTNTAYA AYAARTTYAA RGGNMGNGTN
        310        320        330        340        350        360
  MGNACNGTNW SNCCNWSNWS NAARWSNCCN TGGGTNGARW SNGARTAYYT NGAYTAYYTN
        370        380        390        400        410        420
  TTYGARGTNG ARCCNGCNCC NCCNGTNYTN GTNYTNACNC ARACNGARGA RATHYTNWSN
        430        440        450        460        470        480
  GCNAAYGCNA CNTAYCARYT NCCNCCNTGY ATGCCNCCNY TNGAYYTNAA RTAYGARGTN
        490        500        510        520        530        540
  GCNTTYTGGA ARGARGGNGC NGGNAAYAAR ACNYTNTTYC CNGTNACNCC NCAYGGNCAR
        550        560        570        580        590        600
  CCNGTNCARA THACNYTNCA RCCNGCNGCN WSNGARCAYC AYTGYYTNWS NGCNMGNACN
        610        620        630        640        650        660
  ATHTAYACNT TYWSNGTNCC NAARTAYWSN AARTTYWSNA ARCCNACNTG YTTYYTNYTN
        670        680        690        700        710        720
  GARGTNCCNG ARGCNAAYTG GGCNTTYYTN GTNYTNCCNW SNYTNYTNAT HYTNYTNYTN
        730        740        750        760        770        780
  GTNATHGCNG CNGGNGGNGT NATHTGGAAR ACNYTNATGG GNAAYCCNTG GTTYCARMGN
        790        800        810        820        830        840
  GCNAARATGC CNMGNGCNYT NGAYTTYWSN GGNCAYACNC AYCCNGTNGC NACNTTYCAR
        850        860        870        880        890        900
  CCNWSNMGNC CNGARWSNGT NAAYGAYYTN TTYYTNTGYC CNCARAARGA RYTNACNMGN
        910        920        930        940        950        960
  GGNGTNMGNC CNACNCCNMG NGTNMGNGCN CCNGCNACNC ARCARACNMG NTGGAARAAR
        970        980        990       1000       1010       1020
  GAYYTNGCNG ARGAYGARGA RGARGARGAY GARGARGAYA CNGARGAYGG NGTNWSNTTY
       1030       1040       1050       1060       1070       1080
  CARCCNTAYA THGARCCNCC NWSNTTYYTN GGNCARGARC AYCARGCNCC NGGNCAYWSN
       1090       1100       1110       1120       1130       1140
  GARGCNGGNG GNGTNGAYWS NGGNMGNCCN MGNGCNCCNY TNGTNCCNWS NGARGGNWSN
       1150       1160       1170       1180       1190       1200
  WSNGCNTGGG AYWSNWSNGA YMGNWSNTGG GCNWSNACNG TNGAYWSNWS NTGGGAYMGN
       1210       1220       1230       1240       1250       1260
  GCNGGNWSNW SNGGNTAYYT NGCNGARAAR GGNCCNGGNC ARGGNCCNGG NGGNGAYGGN
```

FIG. 9A

```
          1270       1280       1290       1300       1310       1320
     CAYCARGARW SNYTNCCNCC NCCNGARTTY WSNAARGAYW SNGGNTTYYT NGARGARYTN
          1330       1340       1350       1360       1370       1380
     CCNGARGAYA AYYTNWSNWS NTGGGCNACN TGGGGNACNY TNCCNCCNGA RCCNAAYYTN
          1390       1400       1410       1420       1430       1440
     GTNCCNGGNG GNCCNCCNGT NWSNYTNCAR ACNYTNACNT TYTGYTGGGA RWSNWSNCCN
          1450       1460       1470       1480       1490       1500
     GARGARGARG ARGARGCNMG NGARWSNGAR ATHGARGAYW SNGAYGCNGG NWSNTGGGGN
          1510       1520       1530       1540       1550       1560
     GCNGARWSNA CNCARMGNAC NGARGAYMGN GGNMGNACNY TNGGNCAYTA YATGGCNMGN
          1570       1580       1590       1600       1610       1620
     .......... .......... .......... .......... .......... ..........
```

```
                                              130                                                 140
       Phe Glu Val Glu Pro Ala Pro Pro Val Leu Val Leu Thr Gln Thr Glu Glu Ile Leu Ser
       TTY GAR GTN GAR CCN GCN CCN CCN GTN YTN GTN YTN ACH CAR ACN GAR GAR ATH YTN WSN
       TTT GAA GTT GAA CCT GCT CCT CCT GTT TTA GTT TTA ACT CAA ACT GAA GAA ATT TTA TCT
       TTC GAG GTC GAG CCC GCC CCC CCC GTC TTG GTC TTG ACC CAG ACC GAG GAG ATC TTG TCC
               GTA         CCA GCA CCA CCA GTA CTT GTA CTT ACA     ACA         ATA CTT TCA
               GTG         CCG GCG CCG CCG GTG CTC GTG CTC ACG     ACG             CTC TCG
                                                    CTA     CTA                         CTA AGT
                                                    CTG     CTG                         CTG AGC
                                              150                                                 160
       Ala Asn Ala Thr Tyr Gln Leu Pro Pro Cys Met Pro Pro Leu Asp Leu Lys Tyr Glu Val
       GCN AAY GCN ACN TAY CAR YTN CCN CCN TGY ATG CCN CCN YTN GAY YTN AAR TAY GAR GTN
       GCT AAT GCT ACT TAT CAA TTA CCT CCT TGT ATG CCT CCT TTA GAT TTA AAA TAT GAA GTT
       GCC AAC GCC ACC TAC CAG TTG CCC CCC TGC     CCC CCC TTG GAC TTG AAG TAC GAG GTC
       GCA     GCA ACA         CTT CCA CCA         CCA CCA CTT     CTT                 GTA
       GCG     GCG ACG         CTC CCG CCG         CCG CCG CTC     CTC                 GTG
                                   CTA                         CTA CTA
                                   CTG                         CTG CTG
                                              170                                                 180
       Ala Phe Trp Lys Glu Gly Ala Gly Asn Lys Thr Leu Phe Pro Val Thr Pro His Gly Gln
       GCN TTY TGG AAR GAR GGN GCN GGN AAY AAR ACN YTN TTY CCN GTN ACN CCN CAY GGN CAR
       GCT TTT TGG AAA GAA GGT GCT GGT AAT AAA ACT TTA TTT CCT GTT ACT CCT CAT GGT CAA
       GCC TTC     AAG GAG GGC GCC GGC AAC AAG ACC TTG TTC CCC GTC ACC CCC CAC GGC CAG
       GCA             GGA GCA GGA         ACA CTT     CCA GTA ACA CCA         GGA
       GCG             GGG GCG GGG         ACG CTC     CCG GTG ACG CCG         GGG
                                                   CTA
                                                   CTG
                                              190                                                 200
       Pro Val Gln Ile Thr Leu Gln Pro Ala Ala Ser Glu His His Cys Leu Ser Ala Arg Thr
       CCN GTN CAR ATH ACN YTN CAR CCN GCN GCN WSN GAR CAY CAY TGY YTN WSN GCN MGN ACN
       CCT GTT CAA ATT ACT TTA CAA CCT GCT GCT TCT GAA CAT CAT TGT TTA TCT GCT CGT ACT
       CCC GTC CAG ATC ACC TTG CAG CCC GCC GCC TCC GAG CAC CAC TGC TTG TCC GCC CGC ACC
       CCA GTA     ATA ACA CTT     CCA GCA GCA TCA                 CTT TCA GCA CGA ACA
       CCG GTG         ACG CTC     CCG GCG GCG TCG                 CTC TCG GCG CGG ACG
                               CTA                     AGT                 CTA AGT     AGA
                               CTG                     AGC                 CTG AGC     AGG
                                              210                                                 220
       Ile Tyr Thr Phe Ser Val Pro Lys Tyr Ser Lys Phe Ser Lys Pro Thr Cys Phe Leu Leu
       ATH TAY ACN TTY WSN GTN CCN AAR TAY WSN AAR TTY WSN AAR CCN ACN TGY TTY YTN YTN
       ATT TAT ACT TTT TCT GTT CCT AAA TAT TCT AAA TTT TCT AAA CCT ACT TGT TTT TTA TTA
       ATC ACC ACC TTC TCC GTC CCC AAG TAC TCC AAG TTC TCC AAG CCC ACC TGC TTC TTG TTG
       ATA ACA ACA     TCA GTA CCA     TAC TCA     TTC TCA     CCA ACA         CTT CTT
           ACG ACG     TCG GTG CCG         TCG         TCG     CCG ACG         CTC CTC
                       AGT                     AGT         AGT                 CTA CTA
                       AGC                     AGC         AGC                 CTG CTG
                                              230                                                 240
       Glu Val Pro Glu Ala Asn Trp Ala Phe Leu Val Leu Pro Ser Leu Leu Ile Leu Leu Leu
       GAR GTN CCN GAR GCN AAY TGG GCN TTY YTN GTN YTN CCN WSN YTN YTN ATH YTN YTN YTN
       GAA GTT CCT GAA GCT AAT TGG GCT TTT TTA GTT TTA CCT TCT TTA TTA ATT TTA TTA TTA
       GAG GTC CCC GAG GCC AAC     GCC TTC TTG GTC TTG CCC TCC TTG TTG ATC TTG TTG TTG
           GTA CCA     GCA             GCA     CTT GTA CTT CCA TCA CTT CTT ATA CTT CTT CTT
           GTG CCG     GCG             GCG     CTC GTG CTC CCG TCG CTC CTC     CTC CTC CTC
                                                                   CTA CTA     AGT CTA CTA CTA
                                                                   CTG CTG     AGC CTG CTG CTG
```

FIG. 10B

| | | | | | | | | 250 | | | | | | | | | 260 |
|---|---|---|---|---|---|---|---|---|---|---|---|---|---|---|---|---|---|
| Val | Ile | Ala | Ala | Gly | Gly | Val | Ile | Trp | Lys | Thr | Leu | Met | Gly | Asn | Pro | Trp | Phe | Gln | Arg |
| GTN | ATH | GCN | GCN | GGN | GGN | GTN | ATH | TGG | AAR | ACN | YTN | ATG | GGN | AAY | CCN | TGG | TTY | CAR | MGN |
| GTT | ATT | GCT | GCT | GGT | GGT | GTT | ATT | TGG | AAA | ACT | TTA | ATG | GGT | AAT | CCT | TGG | TTT | CAA | CGT |
| GTC | ATC | GCC | GCC | GGC | GGC | GTC | ATC |   | AAG | ACC | TTG |   | GGC | AAC | CCC |   | TTC | CAG | CGC |
| GTA | ATA | GCA | GCA | GGA | GGA | GTA | ATA |   |   | ACA | CTT |   | GGA |   | CCA |   |   |   | CGA |
| GTG |   | GCG | GCG | GGG | GGG | GTG |   |   |   | ACG | CTC |   | GGG |   | CCG |   |   |   | CGG |
|   |   |   |   |   |   |   |   |   |   |   | CTA |   |   |   |   |   |   |   | AGA |
|   |   |   |   |   |   |   |   |   |   |   | CTG |   |   |   |   |   |   |   | AGG |

| | | | | | | | | 270 | | | | | | | | | 280 |
|---|---|---|---|---|---|---|---|---|---|---|---|---|---|---|---|---|---|
| Ala | Lys | Met | Pro | Arg | Ala | Leu | Asp | Phe | Ser | Gly | His | Thr | His | Pro | Val | Ala | Thr | Phe | Gln |
| GCN | AAR | ATG | CCN | MGN | GCN | YTN | GAY | TTY | WSN | GGN | CAY | ACN | CAY | CCN | GTN | GCN | ACN | TTY | CAR |
| GCT | AAA | ATG | CCT | CGT | GCT | TTA | GAT | TTT | TCT | GGT | CAT | ACT | CAT | CCT | GTT | GCT | ACT | TTT | CAA |
| GCC | AAG |   | CCC | CGC | GCC | TTG | GAC | TTC | TCC | GGC | CAC | ACC | CAC | CCC | GTC | GCC | ACC | TTC | CAG |
| GCA |   |   | CCA | CGA | GCA | CTT |   |   | TCA | GGA |   | ACA |   | CCA | GTA | GCA | ACA |   |   |
| GCG |   |   | CCG | CGG | GCG | CTC |   |   | TCG | GGG |   | ACG |   | CCG | GTG | GCG | ACG |   |   |
|   |   |   |   | AGA |   | CTA |   |   | AGT |   |   |   |   |   |   |   |   |   |   |
|   |   |   |   | AGG |   | CTG |   |   | AGC |   |   |   |   |   |   |   |   |   |   |

| | | | | | | | | 290 | | | | | | | | | 300 |
|---|---|---|---|---|---|---|---|---|---|---|---|---|---|---|---|---|---|
| Pro | Ser | Arg | Pro | Glu | Ser | Val | Asn | Asp | Leu | Phe | Leu | Cys | Pro | Gln | Lys | Glu | Leu | Thr | Arg |
| CCN | WSN | MGN | CCN | GAR | WSN | GTN | AAY | GAY | YTN | TTY | YTN | TGY | CCN | CAR | AAR | GAR | YTN | ACN | MGN |
| CCT | TCT | CGT | CCT | GAA | TCT | GTT | AAT | GAT | TTA | TTT | TTA | TGT | CCT | CAA | AAA | GAA | TTA | ACT | CGT |
| CCC | TCC | CGC | CCC | GAG | TCC | GTC | AAC | GAC | TTG | TTC | TTG | TGC | CCC | CAG | AAG | GAG | TTG | ACC | CGC |
| CCA | TCA | CGA | CCA |   | TCA | GTA |   |   | CTT |   | CTT |   | CCA |   |   |   | CTT | ACA | CGA |
| CCG | TCG | CGG | CCG |   | TCG | GTG |   |   | CTC |   | CTC |   | CCG |   |   |   | CTC | ACG | CGG |
|   | AGT | AGA |   |   | AGT |   |   |   | CTA |   | CTA |   |   |   |   |   | CTA |   | AGA |
|   | AGC | AGG |   |   | AGC |   |   |   | CTG |   | CTG |   |   |   |   |   | CTG |   | AGG |

| | | | | | | | | 310 | | | | | | | | | 320 |
|---|---|---|---|---|---|---|---|---|---|---|---|---|---|---|---|---|---|
| Gly | Val | Arg | Pro | Thr | Pro | Arg | Val | Arg | Ala | Pro | Ala | Thr | Gln | Gln | Thr | Arg | Trp | Lys | Lys |
| GGN | GTN | MGN | CCN | ACN | CCN | MGN | GTN | MGN | GCN | CCN | GCN | ACN | CAR | CAR | ACN | MGN | TGG | AAR | AAR |
| GGT | GTT | CGT | CCT | ACT | CCT | CGT | GTT | CGT | GCT | CCT | GCT | ACT | CAA | CAA | ACT | CGT | TGG | AAA | AAA |
| GGC | GTC | CGC | CCC | ACC | CCC | CGC | GTC | CGC | GCC | CCC | GCC | ACC | CAG | CAG | ACC | CGC |   | AAG | AAG |
| GGA | GTA | CGA | CCA | ACA | CCA | CGA | GTA | CGA | GCA | CCA | GCA | ACA |   |   | ACA | CGA |   |   |   |
| GGG | GTG | CGG | CCG | ACG | CCG | CGG | GTG | CGG | GCG | CCG | GCG | ACG |   |   | ACG | CGG |   |   |   |
|   |   | AGA |   |   |   | AGA |   | AGA |   |   |   |   |   |   |   | AGA |   |   |   |
|   |   | AGG |   |   |   | AGG |   | AGG |   |   |   |   |   |   |   | AGG |   |   |   |

| | | | | | | | | 330 | | | | | | | | | 340 |
|---|---|---|---|---|---|---|---|---|---|---|---|---|---|---|---|---|---|
| Asp | Leu | Ala | Glu | Asp | Glu | Glu | Glu | Glu | Asp | Glu | Glu | Asp | Thr | Glu | Asp | Gly | Val | Ser | Phe |
| GAY | YTN | GCN | GAR | GAY | GAR | GAR | GAR | GAR | GAY | GAR | GAR | GAY | ACN | GAR | GAY | GGN | GTN | WSN | TTY |
| GAT | TTA | GCT | GAA | GAT | GAA | GAA | GAA | GAA | GAT | GAA | GAA | GAT | ACT | GAA | GAT | GGT | GTT | TCT | TTT |
| GAC | TTG | GCC | GAG | GAC | GAG | GAG | GAG | GAG | GAC | GAG | GAG | GAC | ACC | GAG | GAC | GGC | GTC | TCC | TTC |
|   | CTT | GCA |   |   |   |   |   |   |   |   |   |   | ACA |   |   | GGA | GTA | TCA |   |
|   | CTC | GCG |   |   |   |   |   |   |   |   |   |   | ACG |   |   | GGG | GTG | TCG |   |
|   | CTA |   |   |   |   |   |   |   |   |   |   |   |   |   |   |   |   | AGT |   |
|   | CTG |   |   |   |   |   |   |   |   |   |   |   |   |   |   |   |   | AGC |   |

| | | | | | | | | 350 | | | | | | | | | 360 |
|---|---|---|---|---|---|---|---|---|---|---|---|---|---|---|---|---|---|
| Gln | Pro | Tyr | Ile | Glu | Pro | Pro | Ser | Phe | Leu | Gly | Gln | Glu | His | Gln | Ala | Pro | Gly | His | Ser |
| CAR | CCN | TAY | ATH | GAR | CCN | CCN | WSN | TTY | YTN | GGN | CAR | GAR | CAY | CAR | GCN | CCN | GGN | CAY | WSN |
| CAA | CCT | TAT | ATT | GAA | CCT | CCT | TCT | TTT | TTA | GGT | CAA | GAA | CAT | CAA | GCT | CCT | GGT | CAT | TCT |
| CAG | CCC | TAC | ATC | GAG | CCC | CCC | TCC | TTC | TTG | GGC | CAG | GAG | CAC | CAG | GCC | CCC | GGC | CAC | TCC |
|   | CCA |   | ATA |   | CCA | CCA | TCA |   | CTT | GGA |   |   |   |   | GCA | CCA | GGA |   | TCA |
|   | CCG |   |   |   | CCG | CCG | TCG |   | CTC | GGG |   |   |   |   | GCG | CCG | GGG |   | TCG |
|   |   |   |   |   |   |   | AGT |   | CTA |   |   |   |   |   |   |   |   |   | AGT |
|   |   |   |   |   |   |   | AGC |   | CTG |   |   |   |   |   |   |   |   |   | AGC |

```
                                        490                                                    500
Glu Glu Glu Glu Glu Ala Arg Glu Ser Glu Ile Glu Asp Ser Asp Ala Gly Ser Trp Gly
GAR GAR GAR GAR GAR GCN MGN GAR WSN GAR ATH GAR GAY WSN GAY GCN GGN WSN TGG GGN
─── ─── ─── ─── ─── ─── ─── ─── ─── ─── ─── ─── ─── ─── ─── ─── ─── ─── ─── ───
GAA GAA GAA GAA GAA GCT CGT GAA TCT GAA ATT GAA GAT TCT GAT GCT GGT TCT TGG GGT
GAG GAG GAG GAG GAG GCC CGC GAG TCC GAG ATC GAG GAC TCC GAC GCC GGC TCC     GGC
                    GCA CGA     TCA     ATA         TCA     GCA GGA TCA     GGA
                    GCG CGG     TCG                 TCG     GCG GGG TCG     GGG
                        AGA     AGT                 AGT             AGT
                        AGG     AGC                 AGC             AGC
                                        510                                                    520
Ala Glu Ser Thr Gln Arg Thr Glu Asp Arg Gly Arg Thr Leu Gly His Tyr Met Ala Arg
GCN GAR WSN ACN CAR MGN ACN GAR GAY MGN GGN MGN ACN YTN GGN CAY TAY ATG GCN MGN
─── ─── ─── ─── ─── ─── ─── ─── ─── ─── ─── ─── ─── ─── ─── ─── ─── ─── ─── ───
GCT GAA TCT ACT CAA CGT ACT GAA GAT CGT GGT CGT ACT TTA GGT CAT TAT ATG GCT CGT
GCC GAG TCC ACC CAG CGC ACC GAG GAC CGC GGC CGC ACC TTG GGC CAC TAC         GCC CGC
GCA     TCA ACA     CGA ACA         CGA GGA CGA ACA CTT GGA                 GCA CGA
GCG     TCG ACG     CGG ACG         CGG GGG CGG ACG CTC GGG                 GCG CGG
            AGT         AGA                             CTA                     AGA
            AGC         AGG                             CTG                     AGG
```

FIG. 10E

```
        10         20         30         40         50         60
   GCTGTCCCCC GACATCCCAC CGAATCTGAT GCTGCTGCTG CCTTTGCAAG GACTACTGGG
        70         80         90        100        110        120
   CTTCCCAAGA AACTCAAGAG CCTCCGTACC TCCCCTGGGC GGCGGAGGGG CATTGCACTT
       130        140        150        160        170        180
   CCGGGAAGTC CACCTAGCGG CTGTTTGCCT GTCGGCTGA GCAACAAGAT GCCCCTCCCT
       190        200        210        220        230        240
   CCTGTGACCC GCCCTCTTTA GGCTGAGCTA TAAGAGGGGT GGACACAGGG TGGGCTGAGG
       250        260        270        280        290        300
   TCAGAGGTTG GTGGGGTGTC ATCACCCCCA TTGTCCCTAG GGTGACAGGC CAGGGGGAAA
       310        320        330        340        350        360
   AATTATCCCC GGACAACATG AAACAGGTGA GGTCAGGTCA CTGCGGACAT CAAGGGCGGA
       370        380        390        400        410        420
   CACCACCAAG GGGCCCTCTG GAACTTGAGA CCACTGGAGG CACACCTGCT ATACCTCATG
       430        440        450        460        470        480
   CCTTTCCCAG CAGCCACTGA ACTCCCCCAT CCCAGGGCTC AGCCTCCTGA TTCATGGGTC
       490        500        510        520        530        540
   CCCTAGTTAG GCCCAGATAA AAATCCAGTT GGCTGAGGGT TTTGGATGGG AAGGGAAGGG
       550        560        570        580        590        600
   TGGCTGTCCT CAAATCCTGG TCTTTGGAGT CATGGCACTG TACGGTTTTA GTGTCAGACA
       610        620        630        640        650        660
   GACCGGGGTT CAAATCCAG CTCTGCTGTT CACTGGTTGT ATGATCTTGG GGAAGACATC
       670        680        690        700        710        720
   TTCCTTCTCT GCCTCGGCTT CCTCATCTGC AGCTACGCCT GGGTGTGGTG AGGGTTCTAG
       730        740        750        760        770        780
   GGGATCTCAG ATGTGTGTAG CACGGAGCCT GCTGTGTCCT GGGTGCTCTC TACGTGGTGG
       790        800        810        820        830        840
   CCGGTAGAAT TCTCCATCTA TCCAGGCTCC AGGAGACCCC TGGGCATCTC CCACCTGTGG
       850        860        870        880        890        900
   CCCCTAAACC CAGAGTGACT GAGAGCACTT AACATTCAGC TTGTCTCATC CCCAGTCTAC
       910        920        930        940        950        960
   CTCCTTCCTT CTACCCTCAC TGCCTCCCAG TCAGGAGAGT GAGCTCTCAG AAGCCAGAGC
       970        980        990       1000       1010       1020
   CCCACCCAAG GGGACCCTGG TCTCTCCGCC TTCACCTAGC AATGGGAACC CTGCTTCCCA
      1030       1040       1050       1060       1070       1080
   GGGGAGGAAC CAACTGCTCC ACCTTCTAGG GACCCAGTTT GTTGGAGTAG GACAGTAACA
      1090       1100       1110       1120       1130       1140
   TGGCAGGAAT CGGACTTCTG GGCCTGTAAT CCCAGTTTGG ATGGCACGTT AGACTCTTGG
      1150       1160       1170       1180       1190       1200
   TTGACCGTTC TGGTCCTTAG AAGTCCCATT CTCCCTTCCA GTTATGAGAA ACCAATGCCT
      1210       1220       1230       1240       1250       1260
   TCTAGATTCA GGTGACTATC CTTACCTGGG GGTGCTGATG CATCCTCAGT TAACCTACAC
```

FIG. 11A

```
         1270       1280       1290       1300       1310       1320
   CCACCTGAAT ATAGATGAGC GTAGCTGAGT TTTCACCCGT AGGACCGAAG TGTTTTGTGG
         1330       1340       1350       1360       1370       1380
   TGGAGTATCT GAACAACCTT GGCTCTGTGG CCATTCAACC TGCCAGGACT AACATTTCTG
         1390       1400       1410       1420       1430       1440
   GATTTGTGAA GAAGGGATCT TCAAAGCCAT TGAACCCACA GAGCTGTGTT GCTTTAAAGC
         1450       1460       1470       1480       1490       1500
   CACCACAAGG GTACAGCATT AAATGGCAGA ACTGGAAAAG CTTCTTAGGG CATCTCATCC
         1510       1520       1530       1540       1550       1560
   AGGGATTCTC AAACCATGTC CCCCAGAGGC CTTGGGCTGC AGTTGCAGGG GGCGCCATGG
         1570       1580       1590       1600       1610       1620
   GGCTATAGGA GCCTCCCACT TTCACCAGAG CAGCCTCACT GTGCCCTGAT TCACACACTG
         1630       1640       1650       1660       1670       1680
   TGGCTTTCCA CGTGAGGTTT TGTTTAGAGG GATCCACTAC TCAAGAAAAA GTTAGCAAAC
         1690       1700       1710       1720       1730       1740
   CACTCCTTTT GTTGCAAAGG AGCTGAGGTC AAGGGTGGCA AAGGCACTTG TCCAAGGTCG
         1750       1760       1770       1780       1790       1800
   CCCAGCAGTG CTGCTCTGAT GACTTGTGCA CATCCCCAAG GGTAAGAGCT TCGATCTCTG
         1810       1820       1830       1840       1850       1860
   CACAGCCGGG CCAACCTCTG ACCCCTTGTC CATGTCAGTA AAATATGAAG GTCACAGCCA
         1870       1880       1890       1900       1910       1920
   GGATTTCTAA GGGTCAGGAG GCCTTCACCG CTGCTGGGGC ACACACACAC ACATGCATAC
         1930       1940       1950       1960       1970       1980
   ACACATACGA CACACACCTG TGTCTCCCCA GGGGTTTTCC CTGCAGTGAG GCTTGTCCAG
         1990       2000       2010       2020       2030       2040
   ATGATTGAGC CCAGGAGAGG AAGAACAAAC AAACTACGGA GCTGGGGAGG GCTGTGGCTT
         2050       2060       2070       2080       2090       2100
   GGGGCCAGCT CCCAGGGAAA TTCCCAGACC TGTACCGATG TTCTCTCTGG CACCAGCCGA
         2110       2120       2130       2140       2150       2160
   GCTGCTTCGT GGAGGTAACT TCAAAAAAGT AAAAGCTATC ATCAGCATCA TCTTAGACTT
         2170       2180       2190       2200       2210       2220
   GTATGAAATA ACCACTCCGT TTCTATTCTT AAACCTTACC ATTTTTGTTT TGTTTTGTTT
         2230       2240       2250       2260       2270       2280
   TTTTGAGTCG GAGTTTTGTT CTTTTTGCCT AGGCTGGAGT GCAGTGGTAC AATCTCGGCT
         2290       2300       2310       2320       2330       2340
   CACTGCAACC TCCACCTCCC GGGTTCAAGT GATTCTCCTG CCTCAGCCTC CCAAGTAGCT
         2350       2360       2370       2380       2390       2400
   GGGATTACAG GCACCCGCCA CCACACCTGG CTAATTTTTT TGTATTTTTA GTAGAGACGG
         2410       2420       2430       2440       2450       2460
   GGTTTCACCA TGTTGGCCAG GCTGGTCTCG AACTCCTGAC CTCAGGTGAT CCGCCCGCCT
         2470       2480       2490       2500       2510       2520
   CGGCCTCCCA AAGTGCTGGG ATTACAGGCG TGAGCCACCG CGCCCAGCCA AACCTTACTA
         2530       2540       2550       2560       2570       2580
   TTTTTTTAAA GAATTTTTTC CAGAGTTTAA TTTCTGACAT AGCTTAAGTT TTCCAGTAAC
```

FIG. 11B

```
           2590       2600       2610       2620       2630       2640
      TCTAAACTCC ATCTCCTTTA TCGTCATTAA GTCATTCACA AAAAGCCAGG AGAAGCATTT
           2650       2660       2670       2680       2690       2700
      GGAAAGGGCA TGATAATCAG TATAATAATT TGCCTTGTGT GGTCAGCACT TAACTGTTTA
           2710       2720       2730       2740       2750       2760
      CAAAGCCCTT TCACGTGCAC AGCAGGTGGG AACTGCGCGG TGTGGGCTGG GCCTGCGCTG
           2770       2780       2790       2800       2810       2820
      GAAGCATATC CCGTGAAAG TGTTAGTGCC TTAGGTGAAA GCAACATGTA TCCCTTTAGA
           2830       2840       2850       2860       2870       2880
      CTACTAACGG TATATGTTGT TCTTATGTAT TTGTATTTAT TTCTATTTTT TCTATGTTTA
           2890       2900       2910       2920       2930       2940
      TGTCATATTT AAACGATATC CTACTGCTTG TTGGTATTAC CCTAAACTGT TTAAATAAAG
           2950       2960       2970       2980       2990       3000
      AGCTCTATTT TTAAAGAAAA AAGGTACAAT TGA.......  ..........  ..........
```

FIG. 11C

MOUSE CRF2-12 cDNA

```
  51  TTGCAGAGCG CCCTAGGAAG GCCCCGTCTA GCCCCACCCA GAAACGTGAC
 101  ACTCTTCTCC CAGAACTTCA CTGTTTACCT GACATGGCTT CCGGGGCTTG
 151  GGAGCCCCCC AAATGTGACC TATTTCGTGA CCTACCAAAG CTATATCAAA
 201  ACCGGTTGGC GACCAGTGGA GCATTGTGCA GGTATCAAGG CTCTGGTGTG
 251  TCCCCTGATG TGCCTGAAGA AACTGAACCT GTACTCCAAG TTCAAAGGAC
 301  GAGTACAGGC AGCTTCCGCA CACGGCAGGT CCCCACGGGT GGAGTCCCGG
 351  TACCTGGAAT ACCTTTTTGA CGTGGAGCTA GCCCCGCCCA CCCTGGTGCT
 401  CACCCAGATG GAGAAGATCC TAAGGGTCAA CGCTACCTAC CAGCTGCCAC
 451  CTTGCATGCC GTCGCTGGAA CTGAAGTACC AGGTGGAATT CTGGAAGGAG
 501  GGTCTGGGAA GCAAGACCCT GTTTCCTGAC ACTCCCTATG CCAGCCAGT
 551  GCAGATTCCT CTCCAGCAAG GTGCTAGCCG ACGCCACTGC CTCAGCGCCA
 601  GAACCGTCTA TACCTTAATT GACATTAAGT ACAGCCAGTT CTCTGAGCCC
 651  AGCTGCATCT TCCTAGAGGC TCCAGGGGAC AAAAGAGCTG TCCTGGCAAT
 701  GCCCTCACTC TTGCTTCTAC TGATAGCAGC CGTTGCAGCA GGTGTGGCAT
 751  GGAAGATAAT GAAAGGAAAC CCCTGGTTTC AGGGGGTGAA GACGCCCCGG
 801  GCACTGGACT TTTCTGAATA CAGATACCCA GTGGCAACCT TTCAGCCCAG
 851  TGGACCTGAG TTCTCTGATG ACTTGATCCT TTGTCCCCAG AAGGAACTGA
 901  CCATAAGGAA CAGGCCAGCC CCTCAGGTCA GAAACCCAGC CACGCTACAG
 951  GCAGGACCAG AAAGAGACAG TACTGAGGAT GAAGACGAGG ACACAGACTA
1001  CGATGACGAC GGTGACAGCG TCCAGCCCTA CCTGGAACGG CCCCTCTTCA
1051  TCAGCGAGAA GCCCCGGGTT ATGGAACACT CGGAGACAGA CGAGTCTGGG
1101  GTGGATTCAG GGGGCCTTG GACATCCCCA GTTGGGAGTG ACGGCTCCTC
1151  TGCATGGGAC TCTTCAGACA GGAGCTGGTC CAGCACAGGG GACTCCTCAT
1201  ATAAGGATGA AGTTGGGTCT TCCAGCTGTT TGGACCGAAA GGAGCCGGAC
```

FIG. 12A

```
1251 CAGGCGCCCT GTGGGGATTG GCTCCAGGAG GCTCTCCCAT GCCTGGAATT
1301 TTCTGAGGAC TTGGGCACCG TGGAAGAGCC TCTGAAGGAT GGCCTCTCCG
1351 GGTGGAGGAT TTCTGGTTCC TTATCCTCAA AGAGAGATCT GGCTCCTGTG
1401 GAGCCCCAG TTTCTCTTCA GACACTGACT TTCTGCTGGG TCAACAATCC
1451 TGAGGGGGAG GAGGAACAGG AGGACGAGGA GGAAGAGGAG GAGGAGGAGG
1501 AGGAGGAAGA CTGGGAATCA GAACCTAAGG GCAGCAATGC CGGCTGTTGG
1551 GGCACTTCAA GCGTGCAGAG GACGGAGGTC AGGGGCCGGA TGCTGGGAGA
1601 TTACTTGGTC AGGTGAgctg gccctggtgg tccatctaca cattctctac
1651 tgcacttccc ctggaccaca gacacctccg agagtcatgt ccctttgagt
1701 ggtagccaag gtcctggcca ttcgtaatgg atctttatgg cactttgtcg
1751 ttgggattga gttgtaagat gtcaccattt ccaatgaccc accagctata
1801 ggtgacctgt gagcgggaca gagctgtgat cagagactag ttgagttcca
1851 atctgcccat tgtccctggg atgacgggcc tgatggaaaa atcatcctgt
1901 gataaaatga aacaggtgaa gccaggtgac tgtggacacc aagggtagat
1951 acgccctagt ccataagtca cacacagcat tgcgcaaaac agacctcggt
2001 ccaaatcact actctgctgt ttctgatagt cactgagcaa gcgactctta
2051 acctctcaac ctcagcttcc ccttctgcag cagtcctgtg ggtatgggga
2101 ggtaacaggt gacacagggc caccaatgtc acatgtactg actaggcact
2151 agaaccctcc atc
```

FIG. 12B

MOUSE CRF2-12

```
  1 MWRADRWAPL LLFLLQSALG RPRLAPPRNV TLFSQNFTVY LTWLPGLGSP
 51 PNVTYFVTYQ SYIKTGWRPV EHCAGIKALV CPLMCLKKLN LYSKFKGRVQ
101 AASAHGRSPR VESRYLEYLF DVELAPPTLV LTQMEKILRV NATYQLPPCM
151 PSLELKYQVE FWKEGLGSKT LFPDTPYGQP VQIPLQQGAS RRHCLSARTV
201 YTLIDIKYSQ FSEPSCIFLE APGDKRAVLA MPSLLLLLIA AVAAGVAWKI
251 MKGNPWFQGV KTPRALDFSE YRYPVATFQP SGPEFSDDLI LCPQKELTIR
301 NRPAPQVRNP ATLQAGPERD STEDEDEDTD YDDDGDSVQP YLERPLFISE
351 KPRVMEHSET DESGVDSGGP WTSPVGSDGS SAWDSSDRSW SSTGDSSYKD
401 EVGSSSCLDR KEPDQAPCGD WLQEALPCLE FSEDLGTVEE PLKDGLSGWR
451 ISGSLSSKRD LAPVEPPVSL QTLTFCWVNN PEGEEEQEDE EEEEEEEEEE
501 DWESEPKGSN AGCWGTSSVQ RTEVRGRMLG DYLVR
```

```
  1 MAGPERWGPLLLCLLQAAPGRPRLAPPQNVTLLSQNFSVYLTWLPGLGNPQDVTYFVAYQSSPTRRRWREVEECAGTKELLCSMMCLKKQDLYNKFKGRV 100
101 RTVSPSSKSPWVESEYLDYLFEVEPAPPVLVLIQTEEILSANATYQLPPCMPPLDLKYEVAFWKEGAGNKTLFPVTPHGQPVQITLQPAASEHHCLSART 200
201 IYTFSVPKYSKFSKPTICFLLEVPEANWAFLVLPSLLLLLLVIAAGGVIWKTLMGNPWFQRAKMPRALDFSGHTHPVATFQPSRPESVNDLFLCPQKELLTR 300
301 GVRPTPRVRAPATQQTFRWKKDLAEDEEEEDEEFDTEDGVSFQPYIEPPSFLGQEHQAPGHSEAGGVDSGRPRAPLVPSEGSSAWDSSDRSWASTVDSSWDR 400
401 AGSSGYLAEKGPGQGPGGDGHQESLPPPEFSKDSGFLEELPEDNLSSWATWGTLPPEPNLVPGGPPVSLQTLTFCWESSPEEEEARESELEDSDAGSWG 401
501 AESTQRTEDRGRTLGHYMAR
```

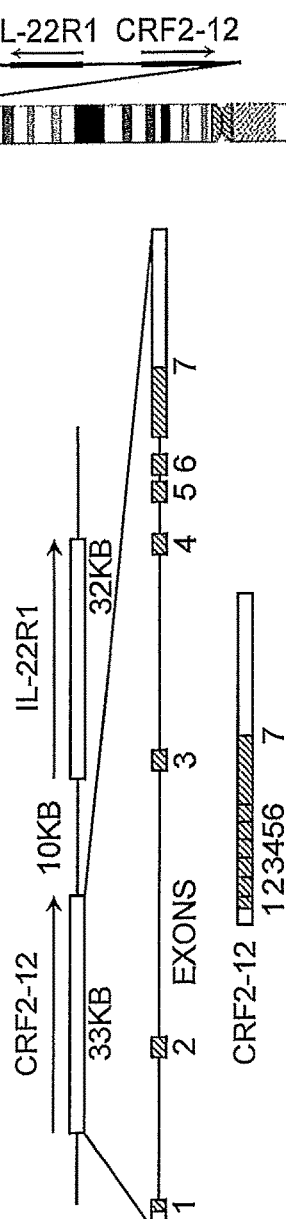

FIG. 14B

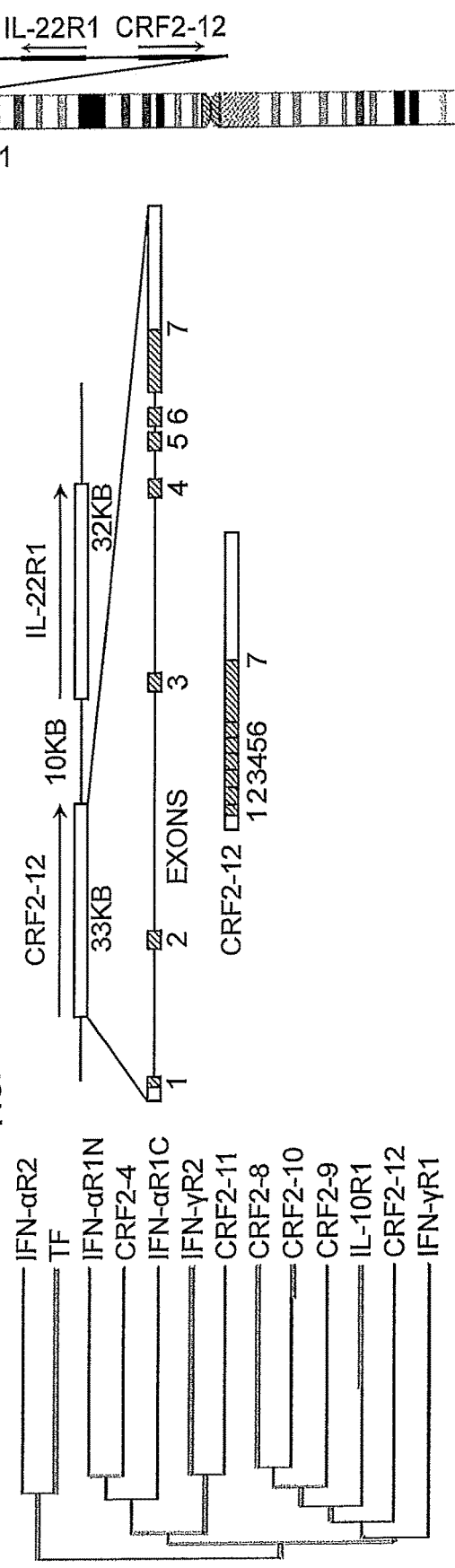

IFN-λ1

FIG. 16A

```
  1 atggctgcag cttggaccgt ggtgctggtg actttggtgc taggcttggc cgtggcaggc
 61 cctgtcccca cttccaagcc caccacaact gggaagggct gccacattgg caggttcaaa
121 tctctgtcac cacaggagct agcgagcttc aagaaggcca gggacgcctt ggaagagtca
181 ctcaagctga aaaactggag ttgcagctct cctgtcttcc ccgggaattg ggacctgagg
241 cttctccagg tgagggagcg ccctgtggcc cccagccctg gaggacgtcc tagaccagcc cctt cacacc
301 gtcctggagg ccgctgctgg gccagccctg gaggacgtcc tagaccagcc cctccacacc
361 ctgcaccaca tcctctccca gctccaggcc tgtatccagc ctcagcccac agcagggccc
421 aggccccggg gccgctcca ccactggctg caccggctc aggaggcccc caaaaaggag
481 tccgctggct gcctggaggc atctgtcacc ttcaacctct tccgcctcct cacgcgagac
541 ctcaaatatg tggccgatgg gaacctgtgt ctgagaacgt caacccaccc tgagtccacc
601 tga
```

FIG. 16B

MAAAWTVVLVTLVLGLAVAGPVPTSKPTPTGKGCHIGRFKSLSPQELASFKKARDALEESLKLKNWSCSSPVFPGNWDLRLLQVRE
RPVALEAELALTLKVLEAAAGPALEDVLDQPLHTLHHILSQLQACIQPQPTAGPRPRGRLHHWLHRLQEAPKKESAGCLEASVFEN
LFRLLTRDLKYVADGNLCLRTSTHPEST

IFN-λ2

FIG. 17A

```
  1 atgactgggg actgcacgcc agtgctggtg ctgatggccg cagtgctgac cgtgactgga
 61 gcagttcctg tcgccaggct ccacggggct ctcccggatg caagggcctg ccacatagcc
121 cagttcaagt ccctgtctcc acaggagctg caggcccttta agagggccaa agatgcctta
181 gaagagtcgc ttctgctgaa ggactgcagg tgccactccc gcctcttccc caggacctgg
241 gacctgaggc agctgcaggt gagggagcgc cccatggctt tggaggctga gctggccctg
301 acgctgaagg ttctggaggc caccgctgac actgaccag cccctggtga cgtcttggac
361 cagcccttc acaccctgca ccatatcctc tcccagttcc gggcctgtat ccagcctcag
421 cccacggctg ggcccaggc ccggggccgc ctccaccatt ggctgtaccg gctccaggag
481 gccccaaaaa aggagtcccc tggctgcctc gaggcctctg tcaccttcaa cctcttccgc
541 ctcctcacgc gagacctgaa ttgtgttgcc agtggggacc tgtgtgtctg a
```

FIG. 17B

MTGDCTPVLVLMAAVLTVTGAVPVARLHGALPDARGCHIAQFKSLSPQELQAFKRAKDALEESLLLKDCRCHSRLFPRTWDLRQLQ
VRERPMALEAELALTLKVLEATADTDPALVDVLDQPLHTLHHILSQFRACIQPQPTAGPRARGRLHHWLYRLQEAPKKESPGCLEA
SVTFNLFRLLTRDLNCVASGDLCV

IFN-λ3

FIG. 18A

```
  1 atgaccgggg actgcatgcc agtgctggtg ctgatggccg cagtgctgac cgtgactgga
 61 gcagttcctg tcgccaggct ccgcggggct ctcccggatg caaggggctg ccacatagcc
121 cagttcaagt ccctgtctcc acaggagctg caggccttta gagggccaa agatgcctta
181 gaagagtcgc ttctgctgaa ggactgcaag tgccgctccc gcctcttccc caggacctgg
241 gacctgaggc agctgcaggt gagggagcgc ccgtgctt tggaggctga gctgccctg
301 acgctgaagg ttctggaggc ctccgctgac actgacccag ccctggggga tgtcttggac
361 cagcccttc acaccctgca ccatatcctc tcccagctcc gggcctgtat ccagcctcag
421 cccacggcag ggcccaggac ccggggccgc ctccaccatt ggctgtaccg gctccaggag
481 gccccaaaa aggagtcccc tggctgcctc gaggcctctg tcacctttca cctcttccgc
541 ctcctcacgc gagacctgaa ttgtgttgcc agcggggacc tgtgtgtctg a
```

FIG. 18B

MTGDCMPVLVLMAAVLTVTGAVPVARLRGALPDARGCHIAQFKSLSPQELQAFKRAKDALEESLLLKDCKCRSRLFPRTWDLRQLQ
VRERPVALEAELALTLKVLEASADTDPALGDVLDQPLHTLHHILSQLRACIQPQPTAGPRTRGRLHHWLYRLQEAPKKESPGCLEA
SVTFNLFRLLTRDLNCVASGDLCV

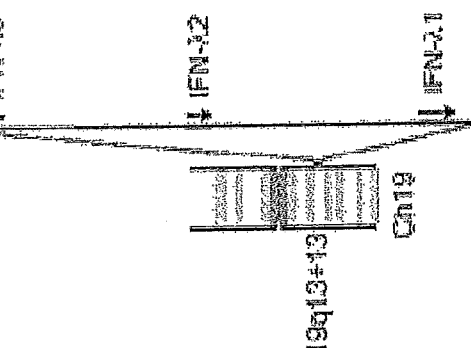
FIG. 19D
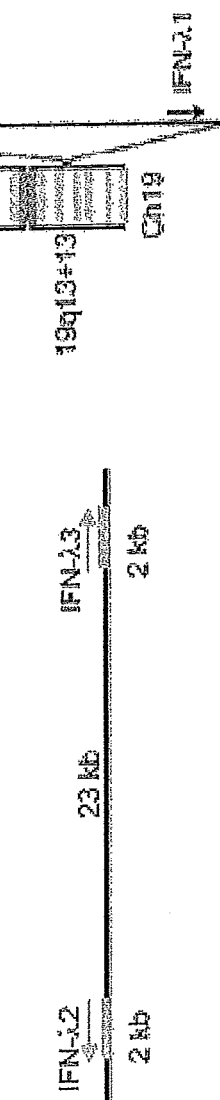
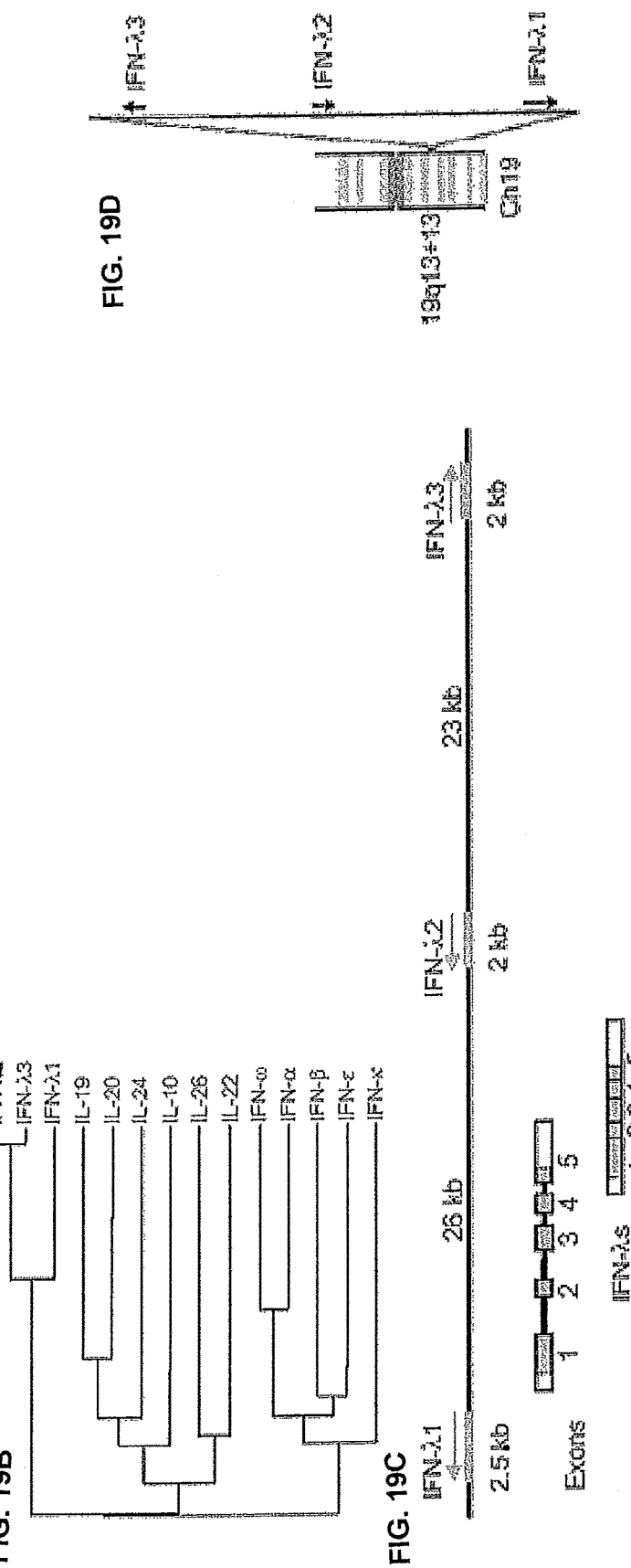
FIG. 19A
FIG. 19B
FIG. 19C

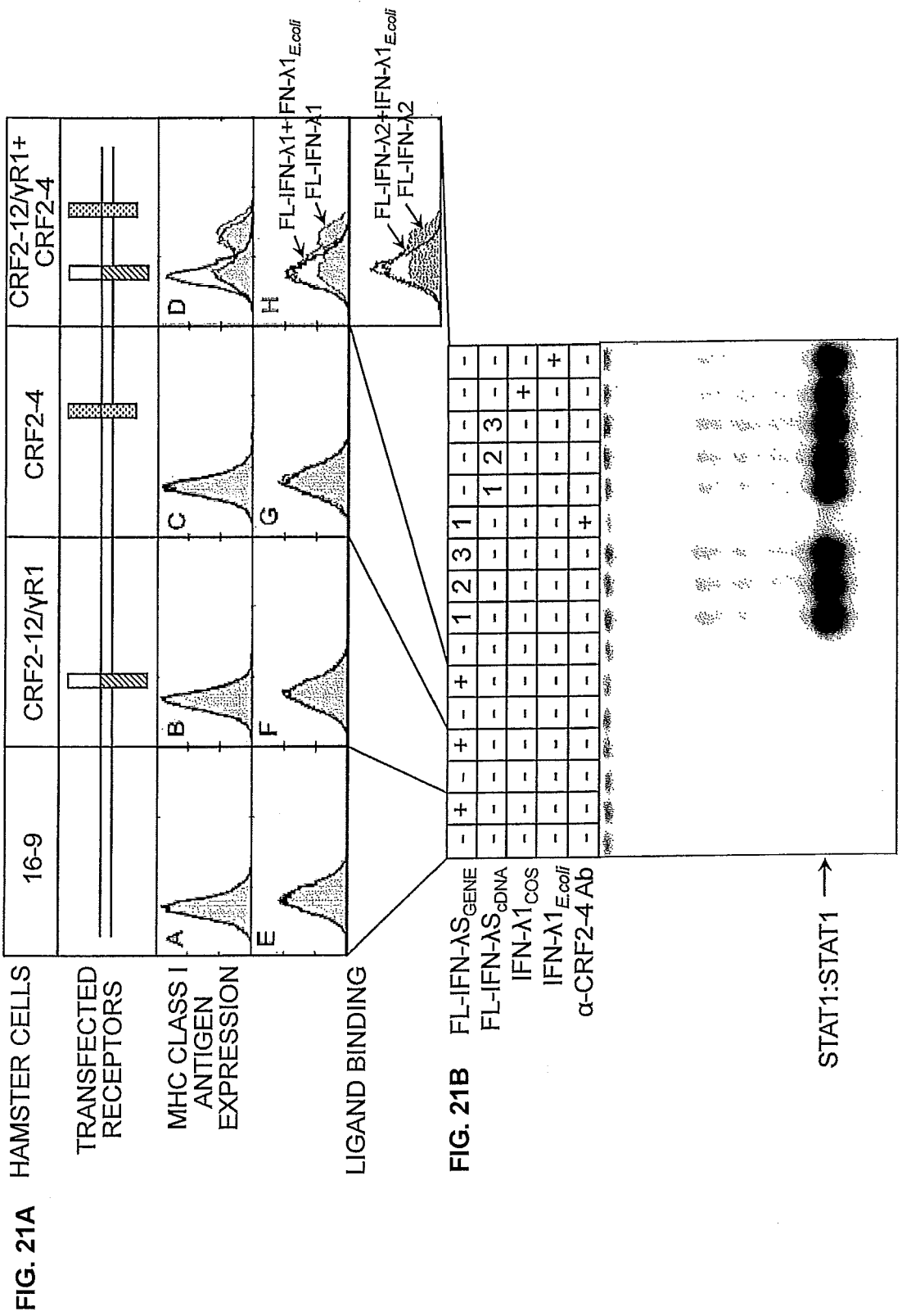

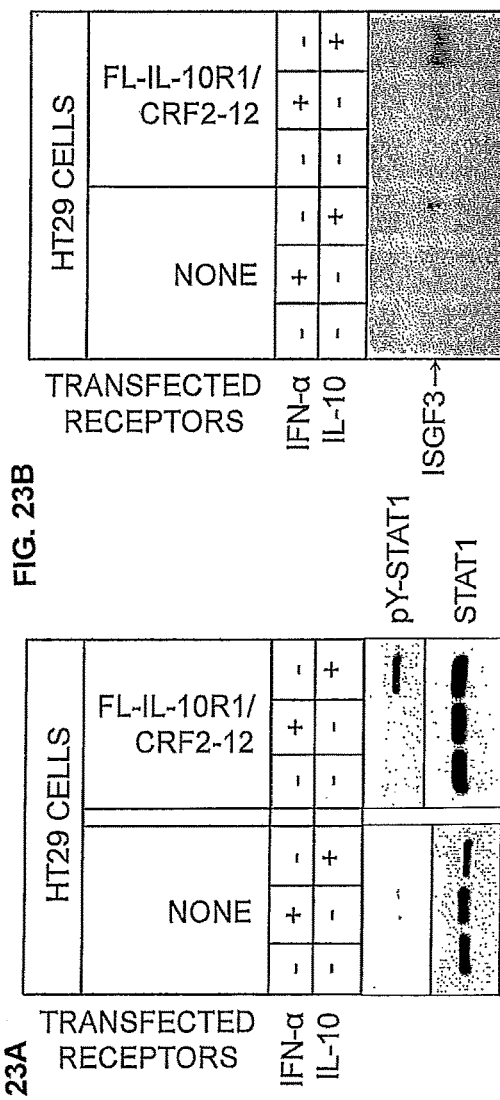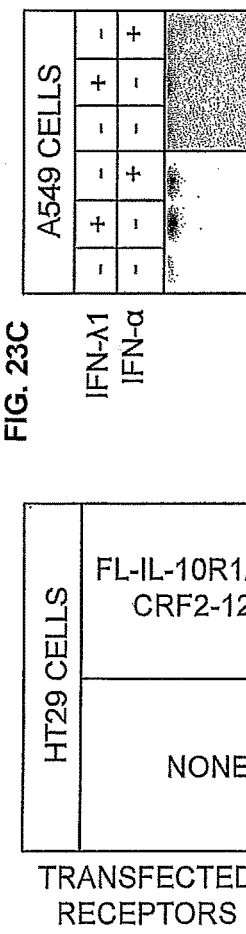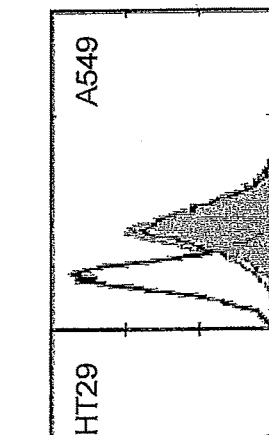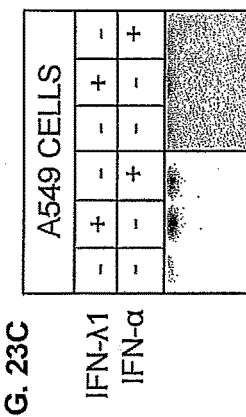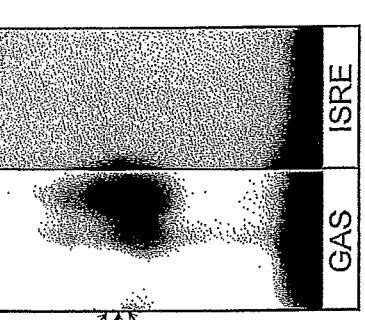
FIG. 23A
FIG. 23B
FIG. 23C
FIG. 23D

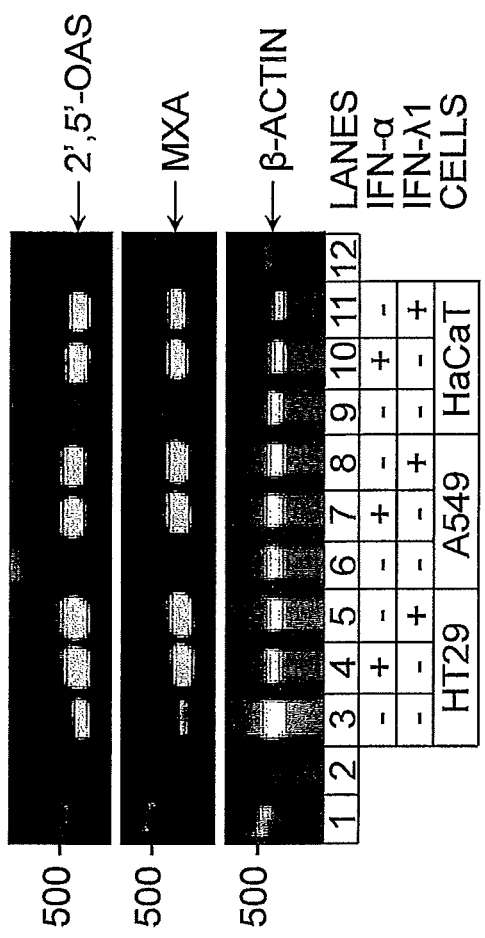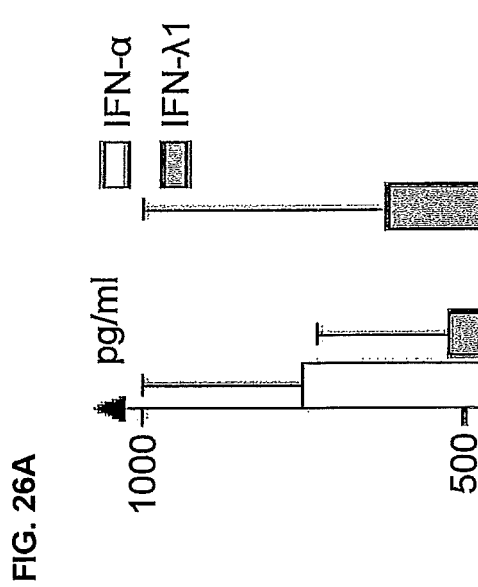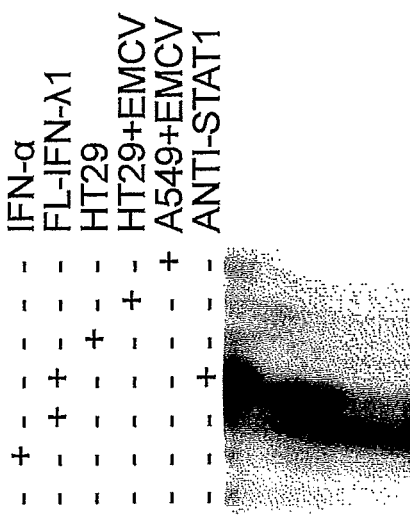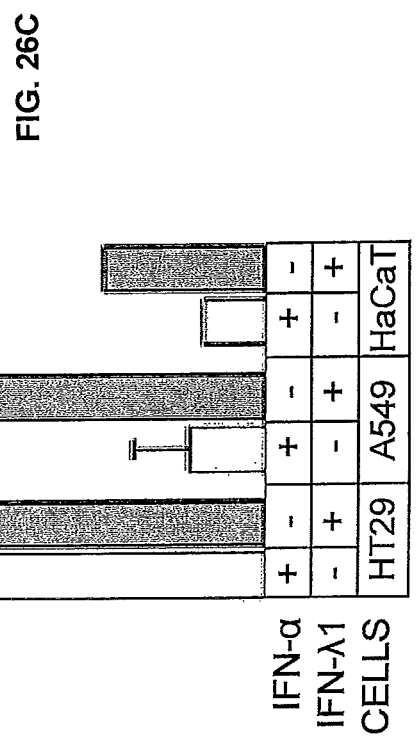
FIG. 26B
FIG. 26C
FIG. 26A

IFN-λ1
MAAAWTVVLVTLVLGLAVAGPVPTSKPTPTGKGCHIGRFKSLSPQELASFKKARDALEESLKLKNWSCSS 70
PVFPGNWDLRLLQVRERPVALEAELALTLKVLEAAAGPALEDVLDQPLHTLHHILSQLQACIQPQPTAGP 140
RPRGRLHHWLHRLQEAPKKESAGCLEASVTFNLFRLLTRDLKYVADGNLCLRTSTHPEST* 200

IFN-λ2
MTGDCTPVLVLMAAVLTVTGAVPVARLHGALPDARGCHIAQFKSLSPQELQAFKRAKDALEESLLLKDCR 70
CHSRLFPRTWDLRQLQVRERPMALEAELALTLKVLEATADTDPALVDVLDQPLHTLHHILSQFRACIQPQ 140
PTAGPRARGRLHHWLYRLQEAPKKESPGCLEASVTFNLFRLLTRDLNCVASGDLCV* 196

IFN-λ3
MTGDCMPVLVLMAAVLTVTGAVPVARLRGALPDARGCHIAQFKSLSPQELQAFKRAKDALEESLLLKDCK 70
CRSRLFPRTWDLRQLQVRERPVALEAELALTLKVLEASADTDPALGDVLDQPLHTLHHILSQLRACTQPQ 140
PTAGPRTRGRLHHWLYRLQEAPKKESPGCLEASVTFNLFRLLTRDLNCVASGDLCV* 196

FIG. 27

METHODS FOR INCREASING LEVELS OF INTERFERON ACTIVITY WITH AN INTERFERON LAMBDA 3 POLYPEPTIDE

INTRODUCTION

This patent application is a continuation of U.S. patent application Ser. No. 14/694,297 filed Apr. 23, 2015, now issued as U.S. Pat. No. 9,907,832, which is a continuation of U.S. patent application Ser. No. 12/898,320 filed Oct. 5, 2010, now abandoned, which is a divisional of U.S. patent application Ser. No. 10/503,866 filed Aug. 6, 2004, now issued as U.S. Pat. No. 7,820,793, which is the National Stage of International Application No. PCT/US2003/003942 filed Feb. 10, 2003, which claims benefit of priority to U.S. Provisional Application Ser. No. 60/418,474 filed Oct. 15, 2002 and 60/355,196 filed Feb. 8, 2002; the teachings of each of which are incorporated herein by reference in their entireties.

STATEMENT OF GOVERNMENT GRANT

This invention was made with government support under Grant No. AI51139 awarded by the National Institute of Allergy and Infectious Diseases. The government has certain rights in the invention.

FIELD OF THE INVENTION

The present invention relates to three novel human genes encoding related polypeptides that are members of the interferon family and a novel receptor and receptor complex responsive to these novel interferons. More specifically, isolated nucleic acid molecules are provided encoding human polypeptides named IFN-$\lambda$1, IFN-$\lambda$2 and IFN-$\lambda$3 and IFN-$\lambda$R1. Polypeptides are also provided, as are vectors, host cells and recombinant methods for producing the same. Also provided are diagnostic methods for detecting disorders and therapeutic methods for treating disorders. The invention further relates to screening methods for identifying agonists and antagonists of IFN-$\lambda$1, IFN-$\lambda$2 and IFN-$\lambda$3 and IFN-$\lambda$R1.

BACKGROUND OF THE INVENTION

Cytokines are small soluble regulatory molecules of the mammalian immune system. They control the growth, function and differentiation of a wide variety of cells and are therefore at the heart of all processes in which the body defends itself from infection of any nature. Banyer et al., 2000, Rev Immunogenet 2, 359-373. Recently six new ligands with limited homology to IL-10 have been identified. (Reviewed in Kontenko, et al., (2002)). Only a very limited amount is known about the function of these IL-10 homologous ligands. Jiang et al., 1995, reported cloning melanoma differentiation associated gene 7 (mda-7), an IL-10 homolog as a protein whose expression is elevated in terminally-differentiated human melanoma cells. Soo et al., 1999, reported expression of the rat mda-7 paralog was linked to wound healing; Zhang et al., 2000, designated the protein c49a and linked it to ras transformation. The protein has also been designated mob-5. The expression of rat mda-7 (c49a) was localized primarily to fibroblast-like cells at the wound edge and base. Soo, et al, 1999, further reported that during wound healing the level of c49a mRNA was transiently elevated 9 to 12-fold above unwounded controls. In addition, expression of rat mda-7 (mob-5) was demonstrated to be induced by expression of oncogenic ras. Moreover, mob-5 and its putative receptor are oncogenic ras specific targets; mob-5 binds to the cell surface of ras-transformed cells but not of parental untransformed cells. Zhang et al., 2000.

Saeki, et al., Oncogene 21(29):4558-66 (2002), reported that in addition to the overexpression of the melanoma differentiation associated gene-7 (mda-7) in vitro resulting in suppression of lung cancer cell proliferation, overexpression of the mda-7 gene in human non-small cell lung carcinoma cells in vivo has an effect on tumor growth. In particular, Saeki, et al., reported that adenovirus-mediated overexpression of MDA-7 in p53-wild-type A549 and p53-null H1299 subcutaneous tumors resulted in significant tumor growth inhibition through induction of apoptosis, and that decreased CD31/PECAM expression and upregulation of APO2/TRAIL were observed in tumors expressing MDA-7. According to the authors, the data demonstrates that Ad-mda7 functions as a multi-modality anti-cancer agent, possessing both pro-apoptotic and anti-angiogenic properties and thus may potentially serve as a therapeutic agent against human lung cancer.

Knappe et al., J Virol 74(8):3881-7 (2000) reported cloning another IL-10 homolog, designated ak155, as a protein expressed by herpes virus saimiri-transformed T lymphocytes.

Gallagher et al., Genes Immunl (7):442-50 (2000) reported the identification and cloning of a gene and corresponding cDNAs encoding a homologue of IL-10, which they designated IL-19. According to Gallagher et al., IL-19 expression was induced in monocytes by *Salmonella* lipopolysaccharide (LPS) treatment, but IL-19 did not bind or signal through the canonical IL-10 receptor complex, suggesting existence of an IL-19 specific receptor complex, the identity of which remained to be discovered.

Blumberg et al., Cell 104(1):9-19 (2001), also reported cloning a protein with homology to IL-10, which they designated Zcyto10 (GenBank accession number AF224266) or IL-20. Several lines of evidence demonstrate that IL-20 may play a functional role in epidermal development and psoriasis.

Dumoutier, et al., J Immunol 164(4): 1814-9 (2000) reported cloning IL-TIF (IL-10 related T cell-derived inducible factor), an IL-10 homolog, expressed by IL-9 treated murine T cells. Dumoutier, et al., Proc Natl Acad Sci USA 97(18): 10144-9 (2000) and Xie, et al., J Biol Chem 275 (40):31335-9 (2000) reported cloning IL-TIF's human orthologue (human IL-22). According to these reports, murine IL-22 expression can be induced by IL-9 in thymic lymphomas, T cells and mast cells in vitro and by LPS in various organs in vivo, and IL-TIF injection induced production of acute phase reactants in mouse liver, suggesting involvement of IL-TIF in the inflammatory response.

With the sequence of the human genome being completed, cytokines and receptors have been discovered "in silico." Currently there are 11 members of the class II cytokine receptor family with assigned functions. Kotenko, S. V. (2002) Cytokine Growth Factor Rev. 13, 223-240; Kotenko, et al., (2000) Oncogene 19, 2557-2565; Dumoutier, et al., (2002) Eur Cytokine Netw. 13, 5-15; Fickenscher, et al., (2002) Trends Immunol 23, 89-96. These receptors are primarily utilized for signaling by members of two cytokine families, IFN and IL-10. The IFN family is further divided to type I and type II IFNs. The type II group is represented by a single member, IFN-$\gamma$, whereas the type I group is comprised of 13 IFN-$\alpha$ species (data were obtained from the website of the National Center for Biotechnology Information with the use of various software tools for analyzing genome and EST databases available at the site.), a single species of IFN-β, IFN-ω and IFN-κ (Lafleur, et al., (2001) J Biol Chem 276, 39765-39771), and a mouse cytokine designated limitin (Oritani, et al., (2000) Nat. Med 6, 659-666) for which a human homolog has not yet been identified (and may not exist).

All known type I IFN genes are clustered on human chromosome 9. There is at least one additional member of this family positioned in the same cluster.

The family of IL-10-related cytokines consists of six members of cellular origin, IL-10, IL-19, IL-20, IL-22, IL-24 and IL-26, as well as several viral cytokines (for review see Kotenko, S. V. (2002) Cytokine Growth Factor Rev. 13, 223-240; Dumoutier, et al., (2002) Eur Cytokine Netw. 13, 5-15; Fickenscher, et al., (2002) Trends Immunol 23, 89-96).

All of these cytokines possess important biological activities. Several members of the IL-10 family are involved in a complex regulation of inflammatory responses. Whereas anti-inflammatory activity of IL-10 (on macrophages) is well characterized (Moore, et al., (2001) Annu. Rev Immunol 19, 683-765), the functions of the other IL-10-related cytokines are not well defined. IL-22 upregulates expression of several acutephase proteins in liver and hepatoma cells, and induces expression of pancreatitis-associated protein (PAPI) in pancreatic acinar cells (Dumoutier, et al., (2000) Proc Natl Acad Sci USA 97, 10144-10149; Aggarwal, et al., (2001) J Interferon Cytokine Res 21, 1047-1053).

IL-20 seems to be involved in regulation of normal skin development because IL-20-transgenic mice display skin abnormalities characterized by altered epidermal differentiation with hypoproliferation of keratinocytes (Blumberg, et al., (2001) Cell 104, 9-19).

The activities of IL-19 and IL-24 are not well characterized. However the fact that they share receptors with IL-20 and IL-22 indicates that they may share at least a subset of biological activities as well. No information about the factional activities or the receptor for IL-26 is currently available.

Type I and type II IFNs are important immunomodulators. Type II or immune IFN (IFN-γ) is a Th1-type cytokine which regulates both innate and adaptive immunity. IFN-γ stimulates cell-mediated immune responses which are critical for mediating protection against infection by intracellular parasites infections (many viruses) and is a part of antiviral defense.

Type I IFNs are well known for their ability to induce antiviral protection in wide variety of cells. They also activate host adaptive and innate immune forces to eliminate viral infections.

Antiviral protection is a highly complex process which involves several levels of defense starting with efforts of an infected cell to prevent the replication of a virus and warn other cells about viral presence, and finishing with the engagement of an entire army of immune protective forces to combat virus propagation in a body. It seems that the main task of a first set of cells undergoing primary infection is to release signals to neighboring cells and immune system in general to alert them about viral presence and to force them to build antiviral protection before a virus infects them. Thus, the next wave of infected cells are better prepared to fight and upon sensing the presence of a virus through various means activate intracellular mechanisms of antiviral protection or even commit suicide (apoptosis) to prevent viral replication (reviewed in Levy, et al., (2001) Cytokine Growth Factor Rev 12, 143-156 and Samuel, C. E. (2001) Clin Microbiol Rev 14, 778-809). These alert signals are also produced by a subset of dendritic cells, which are able to sense the presence of a virus through mechanisms not necessarily involving viral entry into the cells. It is always a race between viral replication and development of cellular and immune defense forces that determines severity, duration and outcome of a viral infection.

Type I IFNs have been known for their ability to induce antiviral protection on both cellular and immune levels. Virus-induced robust production and secretion of IFNs leads to the induction of expression of many proteins with antiviral actions. The most well studied proteins in this respect are double-stranded RNA-activated protein kinase (PKR), 2',5'-oligoadenylate synthetase (OAS) and Mx proteins. These IFN-inducible proteins prevent viral replication through various mechanisms. dsRNA-activated PKR phosphorylates translation-initiation factor eIF-2α blocking protein synthesis. OAS activates Rnase L which cleaves mRNA and rRNA, thus inhibiting viral replication on both transcriptional and translational levels. Clearly, such drastic measures affect cellular viability; indeed, both enzymes have been implicated in apoptosis.

Mx proteins are GTPases and some of them possess antiviral activity. The mechanism of their action is not completely understood. Mx proteins are found associated with viral ribonucleoprotein complexes and can interfere with their transcriptional functioning and/or trafficking.

Several other IFN-inducible proteins are likely to participate in cellular antiviral protection through mechanisms which remain to be determined. IFNs also modulate function of several type of immune cells (NK, CD-8+ and DC cells) in the direction favorable for clearing viral infection (reviewed in Biron, C. A. (2001) Immunity 14, 661-664 and Le Bon, A. & Tough, D. F. (2002) Curr. Opin. Immunol 14, 432-436).

There is a certain pattern of a ligand-receptor complex composition within the IFN and IL-10 families (Kotenko, 2002). A specific receptor complex for a particular ligand from these families is composed of two different receptor chains with distinct functions. The receptor chains within a given receptor complex can be divided into two types denoted R1 and R2 based on their functions in signaling. Although both R1 and R2 receptors are associated with Jak tyrosine kinases, only R1 type subunits have along intracellular domain, are phosphorylated on Tyr residues after receptor engagement, therefore drive recruitment of various signaling molecules and, thus, determine the specificity of cytokine signaling. R2 type subunits possess a short intracellular domain and support signaling by brining tyrosine kinase to a receptor complex but do not determine the specificity of signaling. The length of the CRF2-12 intracellular domain indicated that this receptor represents the R1 type subunit.

There are five known receptor chains which can combine to form two-chain receptors for one or more of the six known ligands of the IL-10 family, but these five known receptors do not by themselves allow the full potential repertoire of IL-10 homologue signaling to be realized. That is, there are too many ligands and not enough receptors. Furthermore and most importantly, the wide and well-characterized in vivo and in vitro activities of cytokines and their receptors acting in concert demonstrated a clear need for and clinical potential of novel cytokines, cytokine receptors, cytokine mimics, blockers, agonists and antagonists. The present invention addresses these needs directly.

Type I IFNs are thought to exert their biological activities through binding to the specific cell surface receptor complex composed of two chains IFN-αR1 and IFN-αR2c (reviewed in Domanski, et al., (1996) Cytokine Growth Factor Rev 7, 143-151). IFNαR2c is a signal-competent splice variant encoded by the IFNAR2 gene. Studies with IFN-α/β receptor knockout mice in which either subunit of the IFN-α receptor complex have been disrupted demonstrate an essential role for IFN-α signaling in the induction of antiviral resistance (Steinhoff, et al., (1995) J Virol 69, 2153-2158; Muller, et al., (1994) Science 264, 1918-1921; Hwang, et al., (1995) Proc Natl Acad Sci USA 92, 11284-11288} However, the loss of antiviral protection to different viruses is variable in IFN-α receptor knockout mice. For instance, infection with rotavirus proceeds similarly in mice with disrupted or intact IFN-α receptor system (Angel, et al., (1999) J Interferon Cytokine Res 19, 655-659).

IFNs appear to share a common receptor mechanism, the type I IFN-R composed of IFNAR1 and IFNAR2 subunits. IFNAR2 has membrane bound forms that can be short or long and soluble forms. IFN induced receptor dimerization of the IFNAR1 and IFNAR2c chains initiates a signaling cascade that involves tyrosine phosphorylation of the Tyk2 and Jak1 tyrosine kinases and subsequent phosphorylation of the STAT1 and STAT2 proteins (Stark et al., Ann. Rev. Biochem. 67:227-64 (1998); Science 296:1632-1657 (2002)). Association of the phosphorylated STATs with the p48 DNA binding subunit, forms the ISGF3 multisubunit complex that translocates to the nucleus and binds to interferon-stimulated response elements (ISRE) found upstream of the interferon inducible genes. While the type I IFNs bind the same receptor there appears to be subsequent signaling differences. In contrast to the type I IFNs there is only one member of the type II IFN, namely IFN gamma, which is encoded by a single gene (containing three introns) located on chromosome 12. The protein is produced predominantly by T lymphocytes and NK cells, is 166 amino acids in length and shows no homology to type I interferons.

A range of biological activities are associated with IFNs including antiviral, antimicrobial, tumor anti-proliferative, anti-proliferative, enhancement of NK cell activity, induction of MHC class I expression, and immunoregulatory activities. IFN alpha is marketed by Schering Plough (Intron; IFN alpha 2B) and Hoffman La Roche (Roferon; IFN alpha 2A). Therapeutic uses include the treatment of Hairy Cell leukemia, Chronic myelogenous leukemia, low grade non-Hodgkin lymphoma, cutaneous T cell lymphoma carcinoid tumors, renal cell carcinoma, squamous epithelial tumors of the head and neck, multiple myeloma, and malignant melanoma. With regards to viral disease, Interferon alpha has been found to aid the treatment of chronic active hepatitis, caused by either Hepatitis B or C viruses. IFN beta has been demonstrated to have clinical benefit in the treatment of multiple sclerosis. Clinical trials with Interferon gamma have shown potential in the treatment of cutaneous and also visceral leishmanias.

Both recombinant interferons and interferons isolated from natural sources have been approved in the United States for treatment of auto-immune diseases, condyloma acuminatum, chronic hepatitis C, bladder carcinoma, cervical carcinoma, laryngeal papillomatosis, fungoides mycosis, chronic hepatitis B, Kaposi's sarcoma in patients infected with human immunodeficiency virus, malignant melanoma, hairy cell leukemia and multiple sclerosis.

Members of the type I interferon family have also been shown to influence neural cell activity and growth (see, for example, Dafny et al., Brain Res. 734:269 (1996); Pliopsys and Massimini, Neuroimmunomodulation 2:31 (1995)). In addition, intraventricular injection of neural growth factors has been shown to influence learning in animal models (see, for example, Fischer et al., Nature 329:65 (1987)).

IFNs have been used clinically for anti-viral therapy, for example, in the treatment of AIDS (HIV infection) (Lane, Semin. Oncol. 18:46-52 (1991)), viral hepatitis including chronic hepatitis B, hepatitis C (Woo, M. H. and Brunakis, T. G., Ann. Parmacother, 31:330-337 (1997); Gibas, A. L., Gastroenterologist, 1:129-142 (1993)), hepatitis D, papilloma viruses (Levine, L. A. et al., Urology 47:553-557 (1996)), herpes (Ho, M., Ann. Rev. Med. 38:51-59 (1987)), viral encephalitis (Wintergerst et al., Infection, 20:207-212 (1992)), respiratory syncytial virus, panencephalitis, and other therapies, for example, mycosis fungoides and in the prophylaxis of rhinitis and respiratory infections (Ho, M., Annu. Rev. Med. 38:51-59 (1987)).

IFNs have been suggested for anti-parasite therapy, for example, IFN-gamma for treating *Cryptosporidium paryum* infection (Rehg, J. E., J. Infect. Des. 174:229-232 (1996)).

Anti-bacterial: IFNs have been used clinically for anti-bacterial therapy. For example, IFN-gamma has been used in the treatment of multidrug-resistant pulmonary tuberculosis (Condos, R. et al., Lancet 349:1513-1515 (1997)).

Interferon therapy has been used in the treatment of numerous cancers (e.g., hairy cell leukemia (Hoffmann et al., Cancer Treat. Rev. 12 (Suppl. B): 33-37 (1985)), acute myeloid leukemia (Stone, R. M. et al. Am. J. Clin. Oncol. 16:159-163 (1993)), osteosarcoma (Strander, H. et al., Acta Oncol. 34:877-880 (1995)), basal cell carcinoma (Dogan, B. et al., Cancer Lett. 91:215-219 (1995)), glioma (Fetell, M. R. et al., Cancer 65: 78-83 (1990)), renal cell carcinoma (Aso, Y. et al. Prog. Clin. Biol. Res. 303:653-659 (1989)), multiple myeloma (Peest, D. et al., Br. J. Haematol. 94:425-432 (1996)), melanoma (Ikic, D. et al., Int. J. Dermatol. 34:872-874 (1995)), myelogenous leukemia, colorectal cancer, cutaneous T cell lymphoma, myelodysplastic syndrome, glioma, head and neck cancer, breast cancer, gastric cancer, anti-cancer vaccine therapy, and Hodgkin's disease (Rybak, M. E. et al., J. Biol. Response Mod. 9:1-4 (1990)). Synergistic treatment of advanced cancer with a combination of alpha interferon and temozolomide has also been reported (Patent publication WO 9712630 to Dugan, M. H.).

IFNs have been used clinically for immunotherapy or more particularly, for example, to prevent graft vs. host rejection, or to curtail the progression of autoimmune diseases, such as arthritis, multiple sclerosis, or diabetes. IFN-beta is approved of sale in the United States for the treatment (i.e., as an immunosuppressant) of multiple sclerosis. Recently it has been reported that patients with multiple sclerosis have diminished production of type I interferons and interleukin-2 (Wandinger, K. P. et al., J. Neurol. Sci. 149: 87-93 (1997)). In addition, immunotherapy with recombinant IFN-alpha (in combination with recombinant human IL-2) has been used successfully in lymphoma patients following autologous bone marrow or blood stem cell transplantation that may intensify remission following translation (Nagler, A. et al., Blood 89: 3951-3959 (June 1997)).

The administration of IFN-gamma has been used in the treatment of allergies in mammals (See, International Patent Publication WO 8701288 to Parkin, J. M. and Pinching, A. J.). It has also recently been demonstrated that there is a reduced production of IL-12 and IL-12-dependent IFN-gamma release inpatients with allergic asthma (van der Pouw Kraan, T. C. et al., J Immunol. 158:5560-5565 (1997)). Thus, IFN may be useful in the treatment of allergy by inhibiting the humoral response. Interferons may be used as an adjuvant or coadjuvant to enhance or simulate the immune response in cases of prophylactic or therapeutic vaccination (Heath, A. W. and Playfair, J. H. L., Vaccine 10:427-434 (1992)), such as in anti-cancer vaccine therapy.

Interferons have been used to treat corneal haze.

SUMMARY OF THE INVENTION

The present invention provides an isolated nucleic acid molecule comprising a polynucleotide having a nucleotide sequence, for example, including: a nucleotide sequence encoding the CRF2-12 polypeptide having the complete amino acid sequence of SEQ ID NO: 2; a nucleotide sequence encoding the CRF2-12 polypeptide having the complete amino acid sequence of SEQ ID NO: 2 excepting the N-terminal methionine (i.e., residues 2-520 of SEQ ID NO: 2); a nucleotide sequence encoding the mature CRF2-12 polypeptide shown as residues P19-520 of SEQ ID NO: 2; a nucleotide sequence encoding the CRF2-12 polypeptide extracellular domain; a nucleotide sequence encoding the extracellular domain of the CRF2-12 protein in plasmid pEF-CRF2-12/γR1; a nucleotide sequence encoding the extracellular domain of the CRF2-12 protein in plasmid pEF3-FLγR2/αR2c; a nucleotide sequence encoding the intracellular domain of the CRF2-12 protein in plasmid pEF-FLCRF2-12; and a nucleotide sequence complementary to any of these nucleotide sequences.

The present invention also provides an isolated nucleic acid molecule comprising a polynucleotide having a nucleotide sequence, for example, including: a nucleotide sequence encoding a chimeric receptor comprising the extracellular domain of CRF2-12 and the intracellular domain of another membrane bound receptor; a nucleotide sequence encoding a chimeric receptor comprising the extracellular domain of CRF2-12 and the intracellular domain of another membrane bound tyrosine kinase receptor; a nucleotide sequence encoding a chimeric receptor comprising the extracellular domain of CRF2-12 and the intracellular domain of a cytokine receptor; a nucleotide sequence encoding a chimeric receptor comprising the extracellular domain of CRF2-12 and the intracellular domain of an IFN R1 type receptor; a nucleotide sequence encoding a chimeric receptor comprising the extracellular domain of CRF2-12 and the intracellular domain of IFNγR1; a nucleotide sequence encoding the chimeric protein in plasmid pEF-CRF2-12/γR1; and a nucleotide sequence complementary to any of these nucleotide sequences.

The present invention also provides an isolated nucleic acid molecule comprising a polynucleotide having a nucleotide sequence, for example, including: a nucleotide sequence encoding a chimeric receptor comprising the intracellular domain of CRF2-12 and the extracellular domain of another membrane bound receptor; a nucleotide sequence encoding a chimeric receptor comprising the intracellular domain of CRF2-12 and the extracellular domain of another membrane bound tyrosine kinase receptor; a nucleotide sequence encoding a chimeric receptor comprising the intracellular domain of CRF2-12 and the extracellular domain of a cytokine receptor; a nucleotide sequence encoding a chimeric receptor comprising the intracellular domain of CRF2-12 and the extracellular domain of an IFN R1 type receptor; a nucleotide sequence encoding a chimeric receptor comprising the intracellular domain of CRF2-12 and the extracellular domain of IL-10R I; a nucleotide sequence encoding the chimeric protein in plasmid pEF-IL-10R1/IFN-λR1; and a nucleotide sequence complementary to any of these nucleotide sequences.

The present invention also provides an isolated nucleic acid molecule comprising a polynucleotide having a nucleotide sequence, for example, including: a tandem vector having a nucleotide sequence encoding two receptors, wherein the first receptor is an R1 type receptor and the second receptor is an R2 type receptor, and wherein the expression of each receptor is controlled by separate promoters and polyadenylation signals; a tandem vector having a nucleotide sequence encoding two receptors, wherein the first receptor comprises the extracellular domain of CRF2-12 and the second receptor is an R2 type receptor, and wherein the expression of each receptor is controlled by separate promoters and polyadenylation signals; a tandem vector having a nucleotide sequence encoding two receptors, wherein the first receptor comprises the intracellular domain of CRF2-12 and the second receptor is an R2 type receptor, and wherein the expression of each receptor is controlled by separate promoters and polyadenylation signals; a tandem vector having a nucleotide sequence encoding two receptors, wherein the first receptor comprises CRF2-12 and the second receptor is an R2 type receptor, and wherein the expression of each receptor is controlled by separate promoters and polyadenylation signals; any of the above tandem vectors, wherein the R2 type receptor comprises CRF2-4; the tandem vector pEF-CRF2-12/γR1+CRF2-4; and a nucleotide sequence complementary to any of these nucleotide sequences.

The present invention also provides isolated nucleic acid molecules comprising a polynucleotide encoding at least a portion of one of the IFNλ polypeptides having the complete amino acid sequence shown of SEQ ID NOS: 8, 10 and 12.

The nucleotide sequence determined by sequencing the IFN-λ1 clone, which is shown in FIG. 16 (SEQ ID NO: 7), contains an open reading frame encoding a full length polypeptide of 200 amino acid residues, including an initiation codon encoding an N-terminal methionine.

The nucleotide sequence determined by sequencing the IFN-λ2 clone, which is shown in FIG. 17 (SEQ ID NO: 9), contains an open reading frame encoding a full length polypeptide of 196 amino acid residues, including an initiation codon encoding an N-terminal methionine.

The nucleotide sequence determined by sequencing the IFN-λ3 clone, which is shown in FIG. 18 (SEQ ID NO: 11), contains an open reading frame encoding a full length polypeptide of 196 amino acid residues, including an initiation codon encoding an N-terminal methionine.

Nucleic acid molecules of the invention include those encoding the complete amino acid sequence excepting the N-terminal methionine shown in SEQ ID NOS: 8, 10 and 12, which molecules also can encode additional amino acids fused to the N-terminus of the amino acid sequences of IFN-λ1, IFN-λ2 and IFN-λ3.

Nucleic acid molecules of the invention include those encoding the complete amino acid sequence excepting the N-terminal methionine shown in SEQ ID NOS: 8, 10 and 12, which molecules also can encode additional amino acids fused to the N-terminus of the amino acid sequences of IFN-λ1, IFN-λ2, and IFN-λ3.

The encoded polypeptides have a predicted leader sequence of 22 amino acids, shown as the boxed consensus in FIG. 19A.

Thus, one aspect of the invention provides an isolated nucleic acid molecule comprising a polynucleotide comprising a nucleotide sequence, for example, including: a nucleotide sequence encoding the IFN-λ1 polypeptide having the complete amino acid sequence of SEQ ID NO: 8; a nucleotide sequence encoding the IFN-λ1 polypeptide having the complete amino acid sequence of SEQ ID NO: 8 excepting the N-terminal methionine (i.e., residues 2-200 of SEQ ID NO: 8); a nucleotide sequence encoding the mature IFN-λ1 polypeptide shown as residues 23-200 of SEQ ID NO: 8; a nucleotide sequence of the genomic fragment encoding the complete IFN-λ1 gene contained in plasmid pEF-FL-IFN-λ1 gene; a nucleotide sequence encoding the complete polypeptide encoded by the cDNA contained in plasmid pEF-FL-IFN-λ1; a nucleotide sequence encoding the mature polypeptide encoded by the human cDNA contained in plasmid pEF-FL-IFN-λ1; a nucleotide sequence encoding the mature polypeptide encoded by the human cDNA contained in plasmid pEF2-FL-IFN-λ1; and a nucleotide sequence complementary to any of these nucleotide sequences.

Another aspect of the invention provides an isolated nucleic acid molecule comprising a polynucleotide comprising a nucleotide sequence, for example, including: a nucleotide sequence encoding the IFN-λ2.1 polypeptide having the complete amino acid sequence of SEQ ID NO: 10; a nucleotide sequence encoding the IFN-λ2.1 polypeptide having the complete amino acid sequence of SEQ ID NO: 10 excepting the N-terminal methionine (i.e., residues 2-196 of SEQ ID NO: 10); a nucleotide sequence encoding the mature IFN-λ2.1 polypeptide shown as residues 23-196 of SEQ ID NO:10; a nucleotide sequence encoding IFN-λ2.2 polypeptide (residues M12-196 of SEQ ID NO: 10); a nucleotide sequence encoding IFN-λ2.2 polypeptide residues A13-196 of SEQ ID NO: 10; a nucleotide sequence encoding the mature IFN-λ2.2 polypeptide shown as residues P31-196 of SEQ ID NO: 10; a nucleotide sequence encoding IFN-λ2.3 polypeptide (residues M92-196 of SEQ ID NO: 10); a nucleotide sequence encoding IFN-λ2.3 polypeptide residues A93-196 of SEQ ID NO: 10; a nucleotide sequence encoding the mature IFN-λ2.3 polypeptide shown as residues P113-196 of SEQ ID NO: 10; the nucleotide sequence of the genomic fragment encoding the complete IFN-λ2 gene contained in plasmid pEF-FL-IFN-λ2 gene; a nucleotide sequence encoding a polypeptide encoded by the cDNA contained in plasmid pEF-FL-IFN-λ2; a nucleotide sequence encoding the mature polypeptide encoded by the cDNA contained in clone pEF-FL-IFN-λ2; and a nucleotide sequence complementary to any of these nucleotide sequences.

Another aspect of the invention provides an isolated nucleic acid molecule comprising a polynucleotide comprising a nucleotide sequence, for example, including: a nucleotide sequence encoding the IFN-λ3.1 polypeptide having the complete amino acid sequence of SEQ ID NO: 12; a nucleotide sequence encoding the IFN-λ3.1 polypeptide having the complete amino acid sequence of SEQ ID NO: 12 excepting the N-terminal methionine (i.e., residues 2-196 of SEQ ID NO: 12); a nucleotide sequence encoding the mature IFN-λ3.1 polypeptide shown as residues P23-196 of SEQ ID NO:12; a nucleotide sequence encoding IFN-λ3.2 polypeptide (residues M6-196 of SEQ ID NO: 12); a nucleotide sequence encoding IFN-λ3.3 polypeptide (residues M12-196 of SEQ ID NO: 12); a nucleotide sequence encoding IFN-λ3.2 polypeptide residues P7-196 of SEQ ID NO: 12; a nucleotide sequence encoding IFN-λ3.3 polypeptide residues A13-196 of SEQ ID NO: 12; a nucleotide sequence encoding the mature IFN-λ3.2 polypeptide shown as residues P31-196 of SEQ ID NO: 12; the nucleotide sequence of the genomic fragment encoding the complete IFN-λ3 gene contained in plasmid pEF-FL-IFN-λ3 gene; a nucleotide sequence encoding a polypeptide encoded by the cDNA contained in plasmid pEF-FL-IFN-λ3; a nucleotide sequence encoding a mature polypeptide encoded by the cDNA contained in plasmid pEF-FL-IFN-λ3; and a nucleotide sequence complementary to any of these nucleotide sequences.

Further embodiments of the invention include isolated nucleic acid molecules that comprise a polynucleotide having a nucleotide sequence at least 80%, 85%, or 90% identical, more preferably at least 91%, 92%, 93%, and 94% and most preferably at least 95%, 96%, 97%, 98% or to any of the nucleotide sequences, above, or a polynucleotide which hybridizes under stringent hybridization conditions to a polynucleotide of the present invention. This polynucleotide of the present invention, which hybridizes understringent conditions defined herein does not hybridize to a polynucleotide having a nucleotide sequence consisting of only A residues or of only T residues. An additional nucleic acid embodiment of the invention relates to an isolated nucleic acid molecule comprising a polynucleotide that encodes the amino acid sequence of an epitope-bearing portion of a polypeptide having an amino acid sequence described above.

A further aspect of the invention is a DNA sequence that represents the complete regulatory region of a gene of the present invention. DNA constructs containing the regulatory region are also provided. Further, host cells comprising such constructs, which cells are in vitro or in vivo, are also encompassed by the present invention.

The present invention also relates to recombinant vectors, which include the isolated nucleic acid molecules of the present invention, to host cells containing the recombinant vectors, as well as to methods of making such vectors and host cells and for using them for production of polypeptides or peptides of the present invention by recombinant techniques.

The invention further provides isolated polypeptides comprising an amino acid sequence, for example, including: the amino acid sequence of the full-length IFN-λ1 polypeptide having the complete amino acid sequence of SEQ ID NO: 8; the amino acid sequence of the full-length IFN-λ1 polypeptide having the complete amino acid sequence of SEQ ID NO: 8 excepting the N-terminal methionine (i.e., residues 2-200 of SEQ ID NO: 8); the amino acid sequence the mature IFN-λ1 polypeptide shown as residues 23-200 of SEQ ID NO: 8; an IFN-λ1 polypeptide encoded by the genomic fragment encoding the IFN-λ1 gene contained in plasmid pEF-FL-IFN-λ1 gene; an polypeptide encoded by the cDNA contained in plasmid pEF-FL-IFN-λ1; a mature IFN-λ1 polypeptide encoded by the cDNA contained in plasmid pEF-FL-IFN-λ1. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

The invention further provides isolated polypeptides comprising an amino acid sequence, for example, including: the IFN-λ2.1 polypeptide having the complete amino acid sequence of SEQ ID NO: 10; the IFN-λ2.1 polypeptide having the complete amino acid sequence of SEQ ID NO: 10 excepting the N-terminal methionine (i.e., residues 2-196 of SEQ ID NO: 10); the mature IFN-λ2.1 polypeptide shown as residues 23-196 of SEQ ID NO: 10; the IFN-λ2.2 polypeptide shown as residues M12-196 of SEQ ID NO: 10; the IFN-λ2.2 polypeptide shown as residues A13-196 of SEQ ID NO: 10; the mature IFN-λ2.2 polypeptide shown as residues P31-196 of SEQ ID NO: 10; the IFN-λ2.3 polypeptide shown as residues M92-196 of SEQ ID NO: 10; the IFN-λ2.3 polypeptide shown as residues A93-196 of SEQ ID NO: 10; the mature IFN-λ2.3 polypeptide shown as residues P113-196 of SEQ ID NO: 10; a IFN-λ.2 polypeptide coded by plasmid pEF-FL-IFN-λ2 gene; a polypeptide encoded by the cDNA contained in plasmid pEF-FL-IFN-λ2; a mature polypeptide encoded by the cDNA contained in clone pEF-FL-IFN-λ2. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

The invention further provides isolated polypeptides comprising an amino acid sequence, for example, including: a IFN-λ3.1 polypeptide having the complete amino acid sequence of SEQ ID NO: 12; a IFN-λ3.1 polypeptide having the complete amino acid sequence of SEQ ID NO: 12 excepting the N-terminal methionine (i.e., residues 2-196 of SEQ ID NO: 12); a mature IFN-λ3.1 polypeptide shown as residues P23-196 of SEQ ID NO: 12; a IFN-λ3.2 polypeptide shown as residues M6-196 of SEQ ID NO: 12; a IFN-A3.3 polypeptide shown as residues M12-196 of SEQ ID NO: 12; a IFN-λ3.2 polypeptide shown as residues P7-196 of SEQ ID NO: 12; a IFN-λ3.3 polypeptide shown as residues A13-196 of SEQ ID NO: 12; a mature IFN-λ3.2 polypeptide shown as residues P31-196 of SEQ ID NO: 12; a IFN-λ3 polypeptide coded by plasmid pEF-FL-IFN-λ3 gene; a polypeptide encoded by the cDNA contained in plasmid pEF-FL-IFN-λ3; a mature polypeptide encoded by the cDNA contained in clone pEF-FL-IFN-λ3. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a polypeptide of the present invention having an amino acid sequence described above. Peptides or polypeptides having the amino acid sequence of an epitope-bearing portion of a polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a polypeptide having an amino acid sequence described above. The invention further provides methods for isolating antibodies that bind specifically to a polypeptide having an amino acid sequence as described herein. Such antibodies are useful therapeutically as described below.

The invention also provides for pharmaceutical compositions comprising a polypeptide of the present invention. The invention also provides for pharmaceutical compositions comprising combinations of polypeptides of the present invention.

In one embodiment, the invention provides for a composition comprising IFN-λ1.

In another embodiment, the invention provides for a composition comprising IFN-λ2.

In another embodiment, the invention provides for a composition comprising IFN-λ3.

In one embodiment, the invention provides for a composition comprising a combination of polypeptides of the present invention, wherein the ratio of IFN-λ1:IFN-λ2:IFN-λ3 is described by the formula m:n:o, wherein m may be any number between 0 and 1000, n may be any number between 0 and 1000 and o may be any number between 0 and 1000, and wherein at least one of m, n or o is different from 0. The invention also provides for a composition comprising a combination of polypeptides of the present invention, wherein the ratio of IFN-λ1:IFN-λ2:IFN-λ3 is described by the formula m:n:o, wherein m may be any number between 0 and 1000, n may be any number between 0 and 1000 and o may be any number between 0 and 1000, and wherein at least two of m, n or o are different from 0. The invention further provides for a composition comprising a combination of polypeptides of the present invention, wherein the ratio of IFN-λ1:IFN-λ2:IFN-λ3 is described by the formula m:n:o, wherein m may be any number between 0 and 1000, n may be any number between 0 and 1000 and o may be any number between 0 and 1000, and wherein all three of m, n and o are different from 0. The compositions may be employed, for instance, as a positive control an assays for IFN-λ activity, as a positive control for CRF2-12 receptor and receptor complex activity, or as a pharmaceutical composition to treat immune system-related disorders, and other disorders such as viral infection, parasitic infection, bacterial infection, cancer, autoimmune disease, multiple sclerosis, lymphoma and allergy. Methods of treating individuals in need of polypeptides of the present invention are also provided.

The invention also provides for pharmaceutical compositions comprising an antibody of the present invention. The invention also provides for pharmaceutical compositions comprising combinations of antibodies of the present invention. In one embodiment, the invention provides a composition comprising a combination of anti-IFN-λ1 specific antibody, anti-IFN-λ2 specific antibody and anti-IFN-λ3 specific antibody, wherein the ratio of anti-IFN-λ1 specific antibody:anti-IFN-λ2 specific antibody:anti-IFN-λ3 specific antibody is described by the formula x:y:z, wherein x may be any number between 0 and 1000, y may be any number between 0 and 1000 and z may be any number between 0 and 1000, and wherein at least one of x, y or z is different from 0. The invention also provides for pharmaceutical compositions comprising a combination of anti-IFN-λ1 specific antibody, anti-IFN-λ2 specific antibody and anti-IFN-λ3 specific antibody, wherein the ratio of anti-IFN-λ1 specific antibody:anti-IFN-λ2 specific antibody:anti-IFN-λ3 specific antibody is described by the formula x:y:z, wherein x may be any number between 0 and 1000, y may be any number between 0 and 1000 and z may be any number between 0 and 1000, and wherein at least two of x, y or z are different from 0. The invention also provides for pharmaceutical composition comprising a combination of anti-IFN-λ1 specific antibody, anti-IFN-λ2 specific antibody and anti-IFN-λ3 specific antibody, wherein the ratio of anti-IFN-λ1 specific antibody:anti-IFN-λ2 specific antibody:anti-IFN-λ3 specific antibody is described by the formula x:y:z, wherein x may be any number between 0 and 1000, y may be any number between 0 and 1000 and z may be any number between 0 and 1000, and wherein all three of x, y or z are different from 0.

The compositions maybe employed, for instance, to treat immune system-related disorders, and other disorders such as viral infection, parasitic infection, bacterial infection, cancer, autoimmune disease, multiple sclerosis, lymphoma and allergy. Methods of treating individuals in need of polypeptides of the present invention are also provided.

The invention further provides compositions comprising a polynucleotide or a polypeptide for administration to cells in vitro, to cells ex vivo and to cells in vivo, or to a multicellular organism. In certain particularly preferred embodiments of this aspect of the invention, the compositions comprise a polynucleotide for the expression of a polypeptide of the present invention in a host organism for use to treat a disease. Particularly preferred in this regard is expression in a human patient for treatment of a dysfunction associated with aberrant endogenous activity of an interferon or a receptor thereof.

The present invention also provides a screening method for identifying compounds capable of enhancing or inhibiting a biological activity of the polypeptides of the present invention, which involves contacting a receptor which is activated by the polypeptides of the present invention with the candidate compound in the presence of a polypeptide of the present invention, assaying, for example, anti-viral activity or MHC expression in the presence of the candidate compound and the polypeptide of the present invention, and comparing the activity to a standard level of activity, the standard being assayed when contact is made between the receptor and a polypeptide of the present invention in the absence of the candidate compound. In this assay, an increase in activity over the standard indicates that the candidate compound is an agonist and a decrease in activity compared to the standard indicates that the compound is an antagonist of the activity of the polypeptide of the present invention.

The present invention also provides a screening method for identifying compounds capable of enhancing or inhibiting a biological activity of the polypeptides of the present invention, which involves contacting a receptor which is activated by an IFN-λ with the candidate compound in the presence and in the absence of the IFN-λ, assaying for receptor activity in the presence of the candidate compound and the IFN-λ, assaying for receptor activity in the presence of the candidate compound and the absence of the IFN-λ, and comparing the activity to a standard level of activity, the standard being assayed when contact is made between the receptor and the IFN-λ in the absence of the candidate compound.

Expression of the polypeptides of the present invention can be regulated by double stranded RNA as well as other cytokines.

Polypeptides and antibodies directed to those polypeptides are useful to provide immunological probes for differential identification of a number of disorders, particularly of the immune system, significantly higher or lower levels of expression of genes of the present invention may be detected in certain tissues (e.g., cancerous and wounded tissues), cells or bodily fluids (e.g., serum, plasma, urine, synovial fluid or spinal fluid) taken from an individual having such a disorder, relative to a standard gene expression level, i.e., the expression level of the gene in healthy tissue from an individual not having the disorder. Thus, the invention provides a diagnostic method useful during diagnosis of such a disorder, which involves: (a) assaying the expression level of an mRNA or polypeptide of the present invention in cells or body fluid of an individual; (b) comparing the expression level with a standard expression level, whereby an increase or decrease in the assayed expression level compared to the standard expression level is indicative of disorder.

An additional aspect of the invention is related to a method for treating an individual in need of an increased level of interferon activity in the body comprising administering to such an individual a composition comprising a therapeutically effective amount of an isolated polypeptide of the invention, combinations thereof, or an agonist thereof, or administration of DNA encoding one or more effective polypeptides of the present invention.

A still further aspect of the invention is related to a method for treating an individual in need of a decreased level of interferon activity in the body comprising, administering to such an individual a composition comprising a therapeutically effective amount of an antagonist. Preferred antagonists for use in the present invention are IFN-λ-specific antibodies. Also preferred are antibodies specific for CRF2-12. Also preferred are antibodies specific for the extracellular domain of CRF2-12. Particularly preferred are monoclonal antibodies.

A still further aspect of the invention is related to a method for treating viral, parasitic, cancerous, allergic and other medical conditions wherein the compositions of the present invention are effective.

A still further aspect of the invention is related to a method for modulating the function of immune cells, including, for example isotype switching.

Another aspect of the present invention is the characterization of genetic disorders defined by polymorphisms in the genes or chromosomal loci of the present invention.

In another embodiment, the compositions of the present invention serve as an adjuvant for vaccination.

BRIEF DESCRIPTION OF THE FIGURES

FIGS. 1A through 1D show the nucleotide sequence (SEQ ID NO: 1) of human CRF2-12 cDNA, with capital letters representing a predicted coding sequence.

FIG. 2 shows a deduced amino acid sequence (SEQ ID NO: 2) for human CRF2-12.

FIG. 4 shows an alignment between the amino acid sequence of the extracellular portion of CRF2-12 (SEQ ID NO:42) and that of IL22R1 (SEQ ID NO:43).

FIG. 5 shows an alignment of the CRF2-12 polypeptide (SEQ ID NO: 2) of the present invention with several other members of the IL-10 receptor polypeptide family. Shown are (labeled IL10Ra; SEQ ID NO:44), (labeled IL10Rb; SEQ ID NO:45), (labeled IL20Ra; SEQ ID NO:46), (labeled IL20Rb; SEQ ID NO:47), (labeled IL22Ra; SEQ ID NO:48), (labeled IL22BP; SEQ ID NO:49). Amino acids identical to the CRF2-12 polypeptide are boxed. By examining the regions of the boxed amino acids, the skilled artisan can readily identify conserved domains between the polypeptides. These conserved domains are preferred embodiments of the present invention.

FIGS. 6A and 6B show an alignment of the CRF2-12 polypeptide (SEQ ID NO:2) of the present invention with several other members of the class-II cytokine receptor polypeptide family. Shown is (labeled ar2; SEQ ID NO:50), (labeled tfec; SEQ ID NO:51), (labeled crf28; SEQ ID NO:52), (labeled crf210; SEQ ID NO:53), labeled crf29; SEQ ID NO:54), (labeled il10r1; SEQ ID NO:55), (labeled ar1n; SEQ ID NO:56), (labeled il10r2; SEQ ID NO:57), (labeled ar1c; SEQ ID NO:58), (labeled gr2; SEQ ID NO:59), (labeled hudirs1ec; SEQ ID NO:60), (labeled gr1; SEQ ID NO:61). Amino acids identical to the CRF2-12 polypeptide are boxed. By examining the regions of the boxed amino acids, the skilled artisan can readily identify conserved domains between the polypeptides. These conserved domains are preferred embodiments of the present invention.

FIGS. 7A through 7C show the nucleotide sequence (SEQ ID NO: 62) and the deduced amino acid sequence (SEQ ID NO: 2) of human CRF2-12

FIGS. 8A through 8C show the nucleotide sequence (SEQ ID NO: 1) and the deduced amino acid sequence (SEQ ID NO: 2) of human CRF2-12 using an alternative, three-letter, notation sometimes used to describe amino acid sequences.

FIGS. 9A and 9B represent the single letter nucleotide sequence (SEQ ID NO: 3) which fully describes and defines the codon usages possible for encoding the deduced amino acid sequence (SEQ ID NO: 2) of human CRF2-12.

FIGS. 10A through 10E show how the redundant code (SEQ ID NO:3) defines possible individual codons encoding the deduced amino acid sequence (SEQ ID NO: 2) of human CRF2-12.

FIGS. 11A through 11C show the 3'UTR portion of CRF2-12 (SEQ ID NO: 4).

FIGS. 12A and 12B show the nucleotide sequence (SEQ ID NO: 5) of mouse CRF2-12 cDNA, with capital letters representing a predicted coding sequence.

FIG. 13 shows a deduced amino acid sequence (SEQ ID NO: 6) for mouse CRF2-12.

FIGS. 14A through 14D show the deduced amino acid sequence (SEQ ID NO:2) of human CRF2-12 (see FIG. 14A), a phylogenetic tree derived from an alignment of the extracellular domains of the class II cytokine receptor (see FIG. 14B), the organization of the CRF2-12 gene (see FIG. 14C), and a schematic diagram of human chromosome 1 (see FIG. 14D).

More specifically, FIG. 14A shows the deduced amino acid sequence (SEQ ID NO:2) of human CRF2-12, where the first boxed region, region a, constitutes the signal sequence, the first non-boxed region, region b, constitutes the predicted intracellular domain, the second boxed region, region c, constitutes the predicted transmembrane domain, and the second non-boxed region, region d, constitutes the predicted extracellular domain of human CRF2-12. Potential glycosylation sites are underlined as well as the C-terminal intracellular Tyr-based motif which is also homologous to those within the IFN-αR2c intracellular domain and is likely to participate in Stat activation. Three tyrosine residues within the intracellular domain, which are potential targets for phosphorylation, are marked with dots.

FIG. 14B shows a phylogenetic tree derived from an alignment of the extracellular domains of the class II cytokine receptors, which assigns CRF2-12 to a subgroup with several other receptors including CRF2-8, CRF2-9, CRF2-10, IL-10R1 and IFN-γR1. Alignment was generated by the program PILEUP of the Wisconsin Package Version 9.1, Genetics Computer Group (GCG), Madison, Wis. was used with the following parameters: the gap creation penalty 1, the gap extension penalty 1. The CLUSTAL X program was used to create the phylogenetic tree.

FIG. 14C shows the organization of the CRF2-12 gene. The gene is composed of 7 exons (shaded boxes) and its structure correlates well with the common conserved architecture of other genes encoding CRF members. The first exon contains the 5'-UTR (open box) and the signal peptide. Exons 2, 3, 4 and 5 and a part of exon 6 encode the extracellular domain. Exon 6 also encodes the transmembrane domain and the beginning of the intracellular domain. Exon 7 covers the rest of the intracellular domain and the 3'-UTR (open box).

FIG. 14D a schematic diagram of human chromosome 1, shows that the CRF2-12 gene and the IL-22R1 gene are transcribed in the same direction toward the telomere and are positioned approximately 10 kb apart. Chromosomal localization of the CRF2-12 gene and its close neighbor, the IL-22R1 gene as well as the ideogram of human chromosome 1 was generated from the NCBI database. The genes are transcribed in the same direction as indicated by the arrow. Schematic exon/intron structure of the CRF2-12 gene is shown. Coding regions of exons are shaded and the segments corresponding to 5' and 3' untranslated regions are left open.

FIG. 15A is a northern blot, and shows that CRF2-12 mRNA is expressed at variable levels in all the tumor cell lines examined, including hematopoietic (HL-60, K-562, MOLT-4 and Raji) and non-hematopoietic (HeLa, SW480, A549, and G-361) cell lines. Northern blotting was performed on two blots containing mRNA isolated from: (A) human cancer cell lines (promyelocytic leukemia HL-60, epitheloid carcinoma HeLa S3, lymphoblastic leukemia MOLT-4, Burkitt's lymphoma Raji, colorectal adenocarcinoma, SW480, lung carcinoma A549 and melanoma 0361) and (B) normal human fetal tissues (heart, kidney, skin, small intestine) and adult lung. Arrows pointing to the CRF2-12 and the b-actin transcripts. Equal RNA loading was assessed by evaluating the expression of the b-actin gene.

FIGS. 16A and 16B show the nucleotide sequence (SEQ ID NO: 7; FIG. 16A) and the deduced amino acid sequence (SEQ ID NO: 8; FIG. 16B) of IFN-λ1.

FIGS. 17A and 17B show the nucleotide sequence (SEQ ID NO: 9; FIG. 17A) and the deduced amino acid sequence (SEQ ID NO: 10; FIG. 17B) of IFN-λ2.

FIGS. 18A and 18B show the nucleotide sequence (SEQ ID NO: 11; FIG. 18A) and the deduced amino acid sequence (SEQ ID NO: 12; FIG. 18A) of IFN-λ3.

FIGS. 19A through 19D show a sequence alignment of polypeptides IFN-λ1 (SEQ ID NO: 8), IFN-λ2 (SEQ ID NO: 10) and IFN-λ3 (SEQ ID NO: 12) (see FIG. 19A), a phylogenetic tree for IFN-λ. proteins (see FIG. 19B), a schematic showing the gene structure and chromosomal localization for IFN-λ genes (see FIG. 19C) and the chromosomal localization for IFN genes (see FIG. 19D).

More specifically, FIG. 19A shows a sequence alignment of polypeptides IFN-λ1 (SEQ ID NO: 8), IFN-λ2 (SEQ ID NO: 10) and IFN-λ3 (SEQ ID NO: 12). Identical residues are boxed. The consensus sequence (SEQ ID NO:63) is shown on the bottom with the predicted signal peptide boxed. Positions of corresponding introns are indicated by arrows. By examining the regions of the boxed amino acids, the skilled artisan can readily identify conserved domains between the polypeptides. These conserved domains are preferred embodiments of the present invention. Amino acid (a.a.) residues are numbered starting from the Met residue (signal peptide a.a. are included).

FIG. 19B shows a phylogenetic tree for IFN-λ proteins generated as described in the FIG. 14 legend.

FIG. 19C is a schematic showing the gene structure and chromosomal localization for IFN-λ genes as well as the direction of transcription (arrows). Coding regions of exons are shaded and the segments corresponding to 5' and 3' untranslated regions are left open.

FIG. 19D shows the chromosomal localization for IFN genes as well as the direction of transcription (arrows).

Figure 20A:
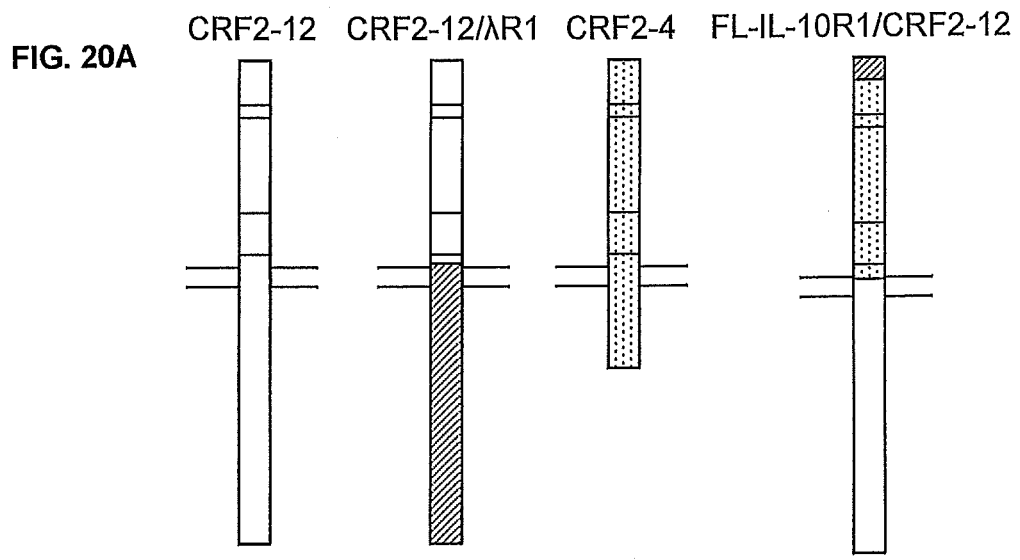
FIGS. 20A through 20C show a diagrammatic illustration of transmembrane receptors encoded by various cDNA expression vectors (see FIG. 20A), a diagrammatic illustration of IFN-λs and their derivatives (see FIG. 20B), and a western blot showing the expression of FL-I IFN-λs and FL-IFN-λ1-P in COS cells (see FIG. 20C).

More specifically, FIG. 20A, from left to right, is a diagrammatic illustration of transmembrane receptors encoded by cDNA expression vectors encoding i) intact CRF2-12 ii) a chimeric CRF2-12/γR1 receptor that has the CRF2-12 extracellular domain fused to the transmembrane and intracellular domains of the human IFN-γR1 chain, iii) CRF2-4, the second chain of the human IL-10 and IL-22 receptor complexes and iv) a FLAG tagged chimeric IL-10R1/CRF2-12 receptor that has the IL-10RI extracellular domain fused to the transmembrane and intracellular domains of CRF2-12.

Figure 20B:
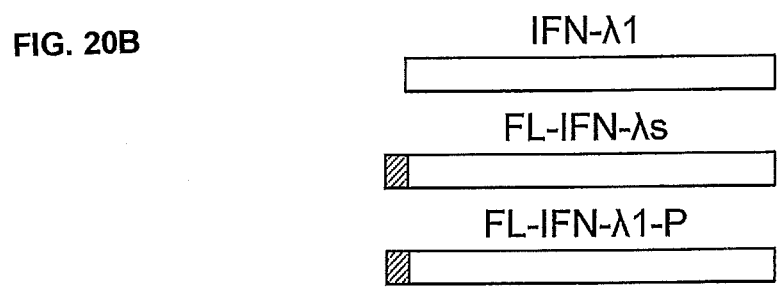

FIG. 20B is a diagrammatic illustration of IFN-λs and their derivatives. From top to bottom, i) represents IFN-λs; ii) represents IFN-λs tagged at the N-terminus with the FLAG epitope (FL-IFN-λs); iii) represents IFN-λs tagged at the C-terminus with the Arg-Arg-Ala-Ser-Val-Ala sequence (SEQ ID NO:64) that contains the consensus amino acid motif recognizable by the catalytic subunit of the cAMP-dependent protein kinase (FL-IFN-λs-P).

Figure 20C:
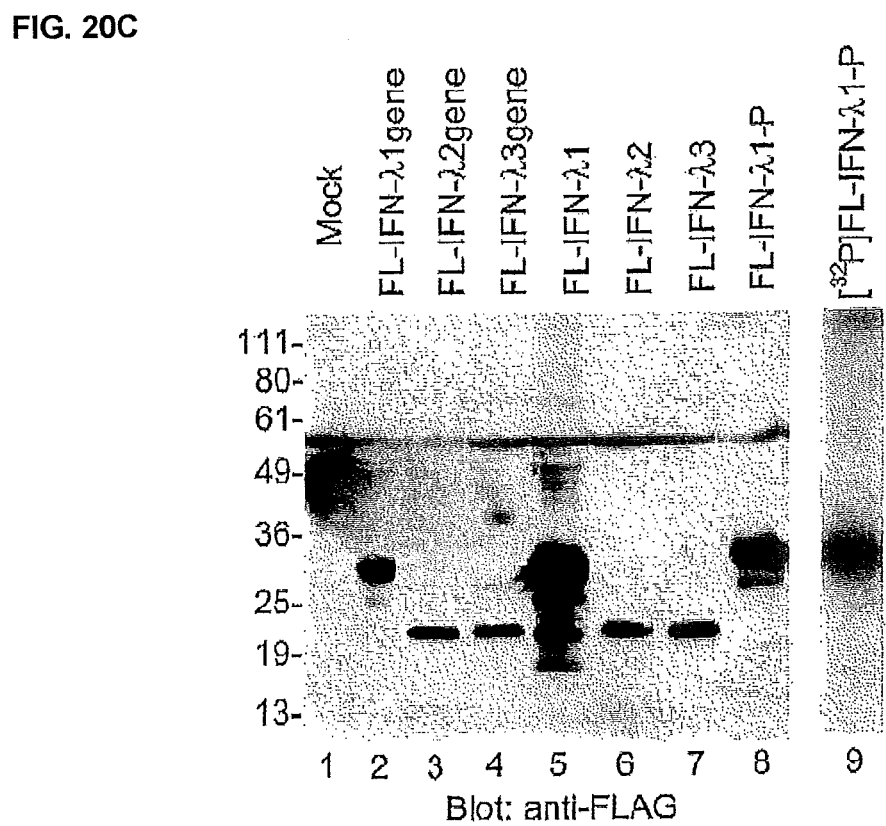

FIG. 20C is a western blot showing the expression of FL-I IFN-λs and FL-IFN-λ1-P in COS cells. Western blotting analysis with anti-FLAG antibody of conditioned media from COS-1 cells transfected with plasmids pEF-SPFL (lane 1, mock), pEF-FL-IFN-λ1 gene (lane 2, FL-IFN-λ1 gene), pEF-FL-IFN-λ2 gene (lane 3, FL-IFN-λ2 gene), pEF-FL-IFN-λ3 gene (lane 4, FL-IFN-λ3 gene), pEF-FL-IFN-λ1 (lane 5, FL-IFN-λ1), pEF-FL-IFN-λ2 (lane 6, FL-IFN-λ2), pEF-FL-IFN-λ3 (lane 7, FL-IFN-λ3). FL-IFN-λ1-P was purified from conditioned media by affinity chromatography and evaluated by Western blotting with anti-FLAG antibody (lane 8). Lane 9 represents an autoradiograph of the SDS-PAGE gel containing radiolabeled FL-IFN-λ1-P. The molecular weight markers are shown on the left.

FIGS. 21A and 21B show MHC class I antigen expression, ligand binding and EMSA performed on hamster cells.

More specifically, FIG. 21A. Four cell lines used in these experiments are schematically shown (top panels): the parental Chinese hamster 16-9 cells and cells expressing the human CRF2-12/gR1 chimeric receptor or human IL-10R2 alone or both receptors together. The cells were left untreated (open areas, thick lines) or treated with conditioned media (100 ml) from COS cells transfected with plasmid pEF-FL-IFN-λ1 (FL-IFN-λ1; shaded areas, thin lines) or with E. coli produced IFN-λ1 (IFN-λ1 E. coli, 100 ng; open areas, thin lines) and the ability of IFN-λ1 to upregulate MHC class I antigen expression was demonstrated by flow cytometry (panels A, B, C and D). The cells were also tested for their ability to bind FL-IFN-λs (panels E, F, G, H and I). The cells were incubated for three hours at 20° C. with conditioned medium from COS-I cells transfected with one of the following plasmids: the control vector pEF-SPFL (open areas, thick lines); the pEF-FL-IFN-λ1 (FL-IFN-λ1; open areas, thin lines; panels E, F, G and H) or the pEF-FL-IFN-λ2 (FL-IFN-λ2; shaded areas, thin lines; panel I). Specificity binding was demonstrated by ligand binding competition. Cells expressing both chains were co-incubated with either FL-IFN-λ1 or FL-IFN-λ2 (100 ml of conditioned media from COS cells expressing FL-IFN-λ1/2) and with E. coli produced IFN-λ1 lacking the FLAG epitope (IFN-λ1E. coli, 1 mg/ml) (open areas, thin lines; panels H and I). Ligand binding to the cell surface was determined by flow cytometry with anti-FLAG antibody (Sigma) as the primary antibody and fluorescein isothiocyanate-conjugated goat anti-mouse IgG (Santa Cruz) as the secondary antibody. The ordinate represents relative cell numbers, and the abscissa relative fluorescence (logarithmic scale).

FIG. 21B. The hamster cells described in FIG. 21A row 1 were left untreated or treated with various stimuli: conditioned media (100 ml) form COS cells transfected with plasmids pEF-FL-IFN-λ 1/2/3 gene (FL-IFN-λs gene), pEF-FL-IFN-λ 1/2/3 (FL-IFN-λs), PEF-IFN-λ1 (IFN-λ1 COS). Numbers 1, 2 and 3 in treatment lanes reflect which IFN-λ protein (IFN-λ1, IFN-λ2 and IFN-λ3, respectively) was used for the treatment. E. coli produced IFN-λ1 was also evaluated (IFN-λ1 E. coli). Anti-CRF2-4 antibody (1 mg) was added to the cells 30 minutes before IFN-λ treatment.

Figure 22:
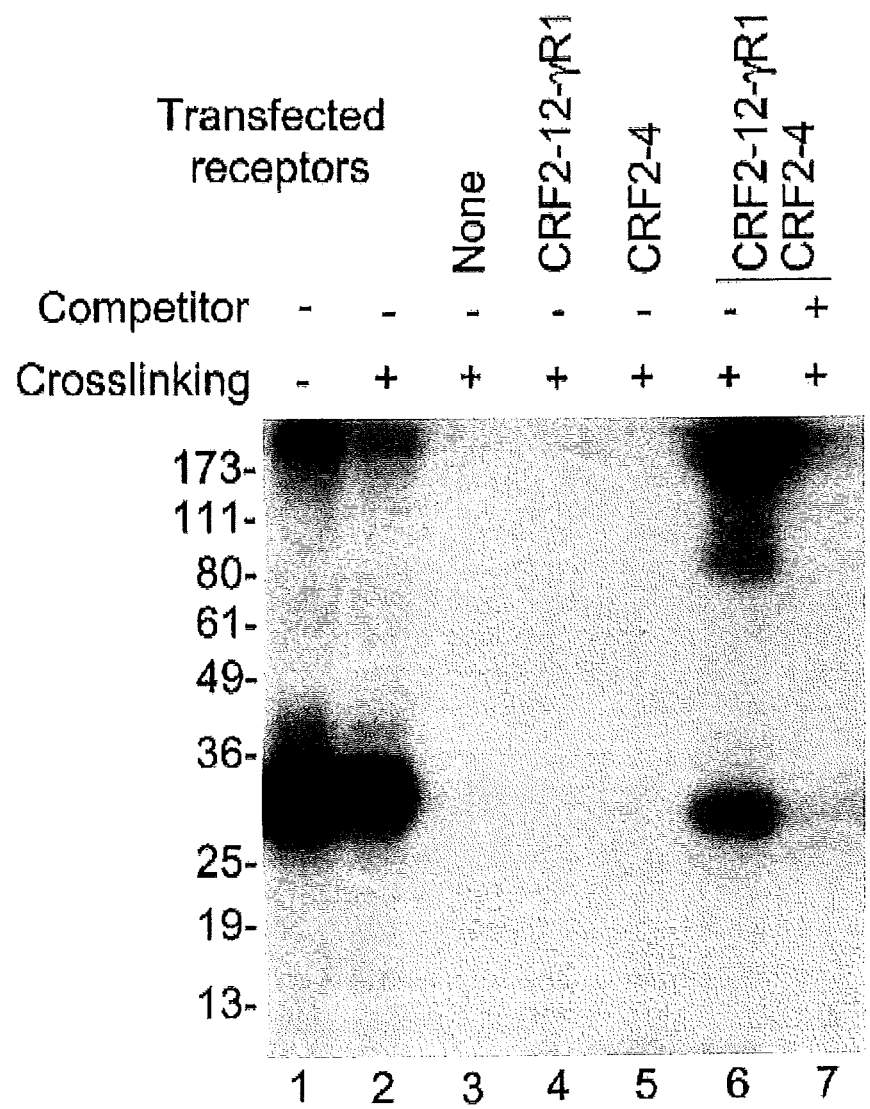

FIG. 22 shows the results of experiments wherein ligand was crosslinked to hamster cells transfected with receptor subunit combinations. Untreated 32P-labeled FL-IFN-λ1-P ([32P]FL-IFN-λ1-P) was loaded as a control (lane 1). ([32P] FL-IFN-λ1-P) was also incubated in DMEM medium with 10% FBS and crosslinking in solution was performed as described (32) (lane 2). The untransfected and transfected hamster cells described in FIG. 22 row 1 were incubated with 32P-labeled FL-IFN-λ1-P with or without addition of a 100-fold excess of unlabeled IFN-λ1 (competitor), washed, harvested and crosslinked. The extracted crosslinked complexes were analyzed on 7.5% SDS-PAGE. The molecular weight markers are shown on the left.

FIGS. 23A through 23D show western blots (see FIG. 23A), and EMSA gels (see FIGS. 23B and 23C) and flow cytometry graphs (see FIG. 23D).

More specifically, FIG. 23A shows western blots, wherein the ability of chimeric FL-IL-10R1/CRF2-12 receptor to activate Stat in response to IL-10 and IFN-α in HT-29 cells was analyzed.

FIG. 23B shows an EMSA gel, wherein modified ISGF3 binding to ISRE in response to IL-10 and IFN-α in HT-29 cells expressing the chimeric FL-IL-10R1/CRF2-12 receptor was analyzed.

FIG. 23C shows EMSA gels, wherein A549 cells response to IFN-λ1 and IFN-α was measured by their ability to modify binding to GAS and ISRE DNA probes as indicated. Positions of Stat DNA-binding complexes in EMSAs are indicated by arrows.

FIG. 23D are flow cytometry graphs showing the level of MHC class I antigen expression in HeLa, HT29 and A549 in response to treatment with conditioned medium from COS cells transfected with plasmid pEF-FL-IFN-λ1 (FL-IFN-λ1; shaded areas, thin lines) or treatment with Hu-IFN-a (100 un/ml; open areas, thin lines) as compared to control cells left untreated (open areas, thick lines). The ordinate represents relative cell numbers, and the abscissa relative fluorescence (logarithmic scale).

Figure 24A:
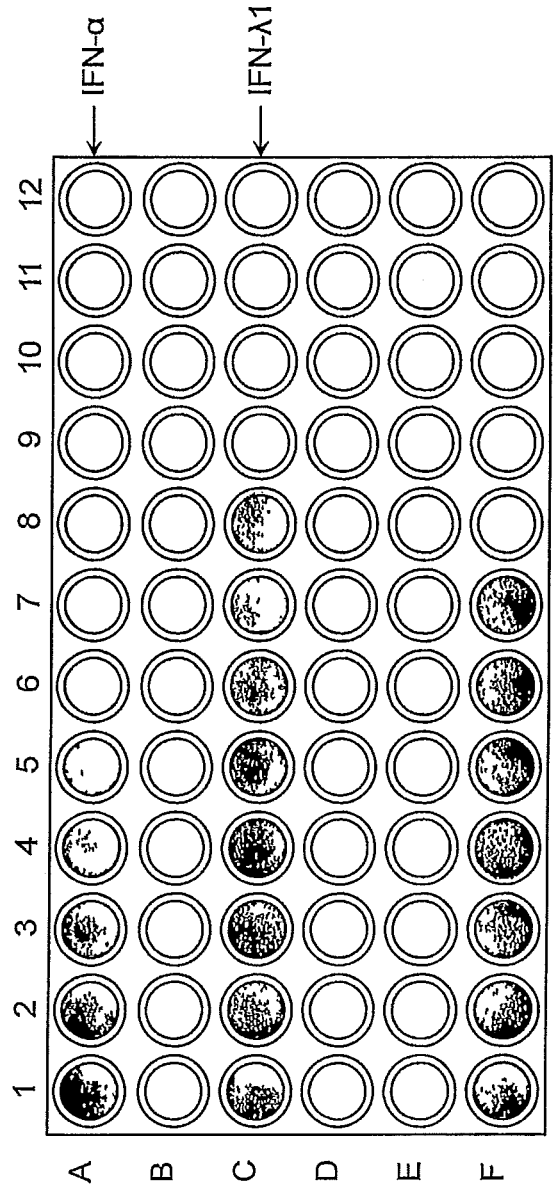
Figure 24B:
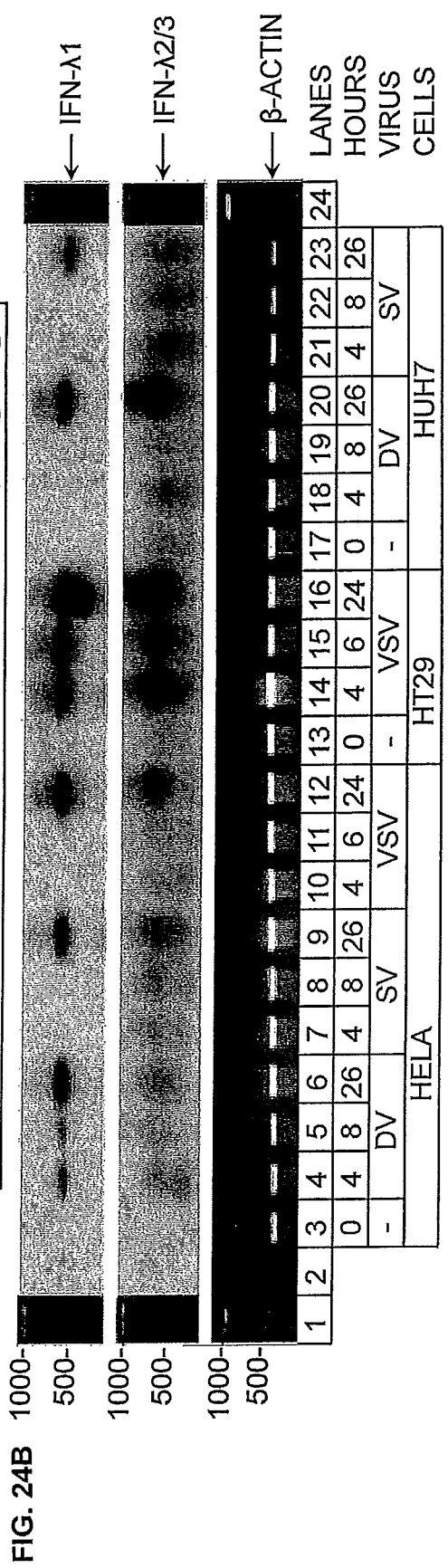

FIGS. 24A and 24B show one of several biological activities of IFN-λs. FIG. 24A shows cell survival and antiviral protection in response to IFN-λ1. An equal amount of cells were plated in all wells and treated with two-fold serial dilutions of ligands, as indicated (rows A and C). Twenty-four hours later the virus was added in all wells except for the first seven wells in row F. Row C shows that HT29 cells exhibit a dose dependent survival response to vesicular stomatitis virus (VSV) in response to administration of increasing IFN-λ1 concentrations. Row A shows the dose dependent response to IFN-α, a positive control.

FIG. 24B shows the change in IFN-λs mRNA expression in virus-infected cells. HeLa cells were left untreated (lane 3) or infected with either Dengue virus (DV, lanes 4-6) Sindbis virus (SV, lanes 7-9) or vesicular stomatitis virus (VSV, lanes 10-12). HT29 cells were left untreated (lane 13) or infected with VSV (lanes 14-16). HuH7 cells were left untreated (lane 17) or infected with DV (lanes 18-20) or SV (lanes 21-23). Cells were collected at post-infection times shown in the Figure, RNA was isolated and RT-PCR was performed as described in Materials and Methods. Water was used as a negative control for RT-PCR (lane 2). 1 kb ladder was run in lanes 1 and 24.

Figure 25:
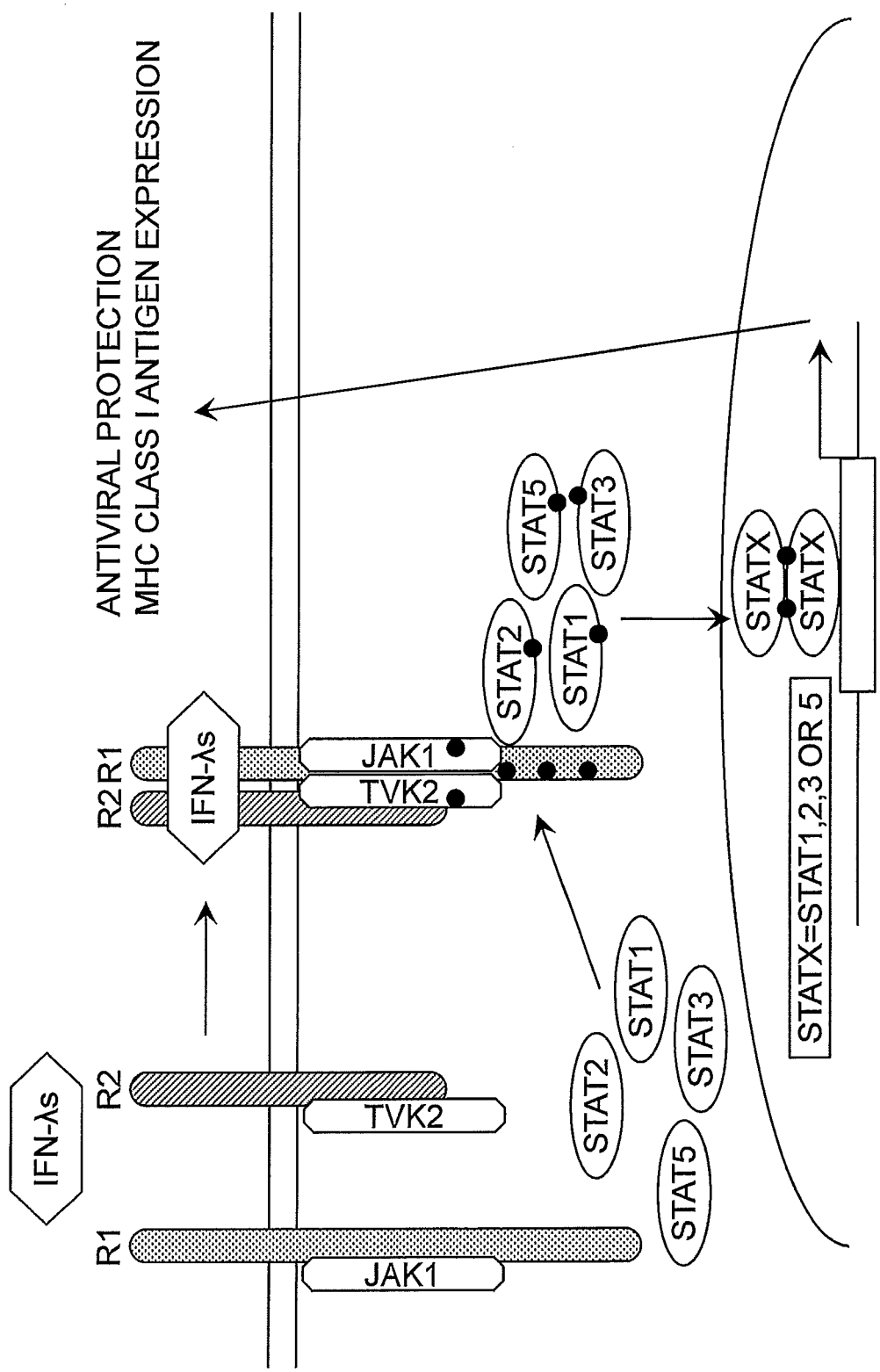

FIG. 25 is a schematic model of IFN-λs interaction with the CRF2-12 receptor system. In one aspect of the invention IFN-λs are monomers. In another embodiment of the present invention, IFN-λs are multimers of and between the three members of the IFN-λ family. In another embodiment of the present invention a multimer may contain other members of the cytokine family, including the IFN and IL-10 families of cytokines. A functional IFN-λ receptor complex may include two receptor chains, for example, the unique CRF2-12 (IFN-λR1) chain and the CRF2-4 (or IL-10R2) chain. The IL-10R2 chain is a shared common chain for at least three receptor complexes, the IL-10, IL-22 and IFN-λ receptor complexes. When expressed alone, neither chain of the IFN-λ receptor complex is capable of IFN-λ binding. Expression of both chains is required for ligand binding and for assembling of the functional receptor complex. Ligand binding leads to the formation of the heterodimeric receptor complex and to the initiation of a signal transduction cascade. The CRF2-4 chain is associated with Tyk2 (Kotenko, S. V., Izotova, L. S., Mirochnitchenko, O. V., Esterova, E., Dickensheets, H., Donnelly, R. P. & Pestka, S. (2001) J Biol Chem 276, 2725-2732 and Levy, D. E. & Garcia-Sastre, A. (2001) Cytokine Growth Factor Rev 12, 143-156) and the IFN-λ R1 chain is likely to interact with Jak 1. Upon the ligand-induced heterodimerization of IFN-λ, receptor chains receptor-associated Jaks cross activate each other, phosphorylate the IFN-λR1 intracellular domain and, thus, initiate the cascade of signal transduction events. Stat1, Stat2, Stat3 and Stat5 are activated by IFN-λ leading to activation of biological activities, such as upregulation of MHC class I antigen expression and induction of antiviral protection.

FIGS. 26A through 26C. Antiviral response. (FIG. 26A) Antiviral protection in response to IFN-λ1 was evaluated on either HT29, A549 or HaCaT cells infected with vesicular stomatitis virus (VSV) using cytopathic effect (CPE) reduction assay performed in 96-well microtiter plate. IFN-α was used as a positive control. Antiviral activity is shown as the amount of IFN-α or IFN-λ1 for 50% protection of the cells from CPE. (FIG. 26B) Expression of ISRE-controlled genes encoding 2',5'-oligoadenylate synthetase (2=, 5=–OAS) and MxA protein in response to IFN-α and IFN-λ1 was evaluated by RT-PCR. Cells were treated for 16 h with indicated ligands, RNA was isolated and subjected to RT-PCR. (FIG. 26C) The hamster cells expressing IFN-λRI/λRI+IL-10R2 were left untreated or treated with various stimuli: conditioned media from COS cells containing FL-IFN-; IFN-λ2 (1000 u/ml); and conditioned media from untreated HT29 cells (HT29) or EMCV-infected HT-29 or A549 cells (HT29+EMCV and A549+EMCN). Where indicated STAT1 Ab was added to shift the mobility of the STAT-DNA-binding complexes.

FIG. 27 shows further amino acid sequences for IFN-λ1 (SEQ ID NO:65), IFN-λ2 (SEQ ID NO:10) and IFN-λ3 (SEQ ID NO:12).

DETAILED DESCRIPTION OF THE INVENTION

The present invention provides isolated nucleic acid molecules comprising a novel family of cytokines designated IFN-λ, their specific functional receptor complex, and characterization of their signaling and biological activity.

The present invention further provides two receptor proteins, CRF2-12 and IL-10R2 (CRF2-4), that comprise a functional receptor complex for these novel ligands.

The present invention further provides a novel IFN-α/β-independent ligand-receptor system which upon engagement leads to the establishment of an antiviral state.

All references cited herein are incorporated herein by reference in their entirety, including the figures and sequences.

Three closely positioned genes on human chromosome 19 encode distinct but highly homologous proteins which we designated IFN-λ1, IFN-λ2 and IFN-λ3 based to their ability to induce antiviral protection. Expression of these proteins is induced upon viral infection. A receptor complex which is utilized by all three IFN-λ proteins for signaling is a further embodiment of the present invention. This complex is composed of two subunits, a novel receptor designated IFN-λR1 or CRF2-12, and a second subunit, IL-10R2 or CRF2-4, which is also a shared receptor component for the IL-10 and IL-22 receptor complexes. Binding of IFN-λs to the receptor complex induces signaling through the Jak-Stat signal transduction pathway, including activation of the ISGF3 transcription complex, the same complex that is activated by signaling through the IFN-α/β receptor complex. Stat recruitment is largely mediated by the IFN-αR2c intracellular domain (Kotenko, S. V., Izotova, L. S., Mirochnitchenko, O. V., Lee, C. & Pestka, S. (1999) Proc Natl Acad Sci USA 96, 5007-5012 and Prejean, C. & Colamonici, 0. R. (2000) Semin. Cancer Biol 10, 83-92).

It is interesting to note that there is a Tyr-based motif (Tyr517MetAlaArgStop; SEQ ID NO:66) at the C-terminus of the IFN-λR1 intracellular domain which is also present at the end of the IFN-αR2c intracellular domain (Tyr512IleMetArgStop; SEQ ID NO:67) which is competent in Stat activation during IFN-α signaling ((39); Y. Ge, S. V. K. and S. Pestka unpublished). This motif is also conserved in mouse IFN-λR1 (TyrLeuValArgStop: SEQ ID NO:68)3. Thus, the IFN-λ and IFN-α/β signaling pathways at least partially overlap. As a consequence, at least some of their biological activities are similar, including induction of antiviral protection and up-regulation of MHC class I antigen expression. According with their antiviral activity, the expression of IFN-λs mRNAs is induced by viral infections in several cell lines and in dendritic cells in response to polyI:C treatment.

The signal transduction pathways and biological activities of IFN-λs and IFN-α overlap. In another embodiment of the present invention, an IFN-λ may be used as a substitute, or in combination with, IFN-α. In another aspect of the present invention, IFN-λs can synergize with IFN-α in mediating resistance to viral infections (or plays an independent primary role in establishment of resistance to certain viruses), and other conditions for which IFN-α is effective.

In another embodiment of the present invention, an IFN-λ or a combination of IFN-λs may be used to treat, ameliorate or prevent conditions for which IFN-α is not effective, for example, viral infections of the gastrointestinal tract.

Figure 3:
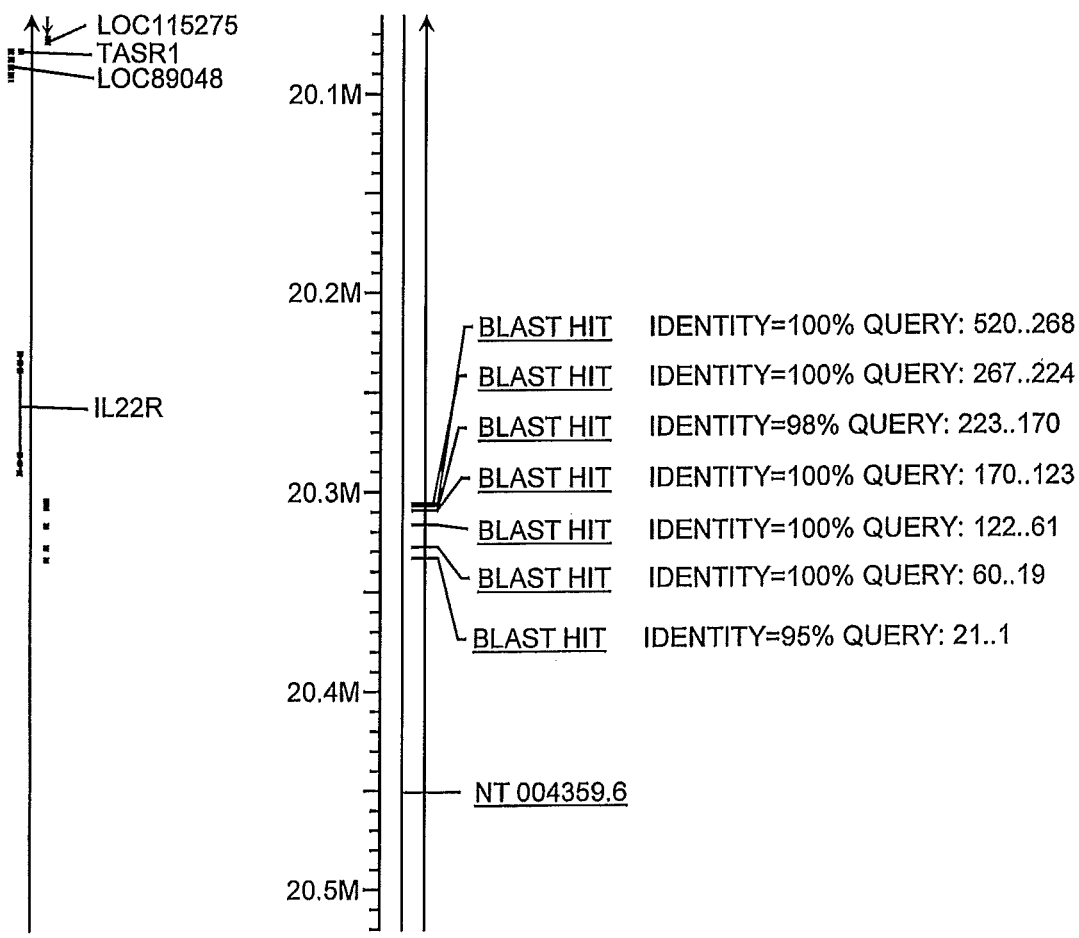
FIG. 3 shows the CRF2-12 gene is located on human chromosome 1, between 20.2 million bases and 20.4 million bases, adjacent to and telomeric of the gene for IL22R1 receptor chain, in the cytogenic region 1p36.11-1p36.12.

A new receptor protein designated as "CRF2-12", one possible nucleotide sequence which can encode the complete CRF2-12 protein is FIG. 1 and the complete polypeptide CRF2-12 has the amino acid sequence in FIG. 2. Automated analysis of the protein sequence using the "Pa" package revealed the presence of the following features in the CRF2-12 polypeptide: region a) a leader sequence/signal peptide comprising residues 1-20 or thereabouts; region b) an extracellular region between residues 20-228 or thereabouts; region c) a transmembrane region between residues 228-244 or thereabouts; and region d) an intracellular region/cytoplasmic tail region between residues 244-520 or thereabouts. The CRF2-12 gene is expressed in spleen, placenta and other tissues and is located on human chromosome 1, between 20.2 million bases and 20.4 million bases, adjacent to and telomeric of the gene for IL22R1 receptor chain, in the cytogenic region lp36.11-lp36.12, as shown in FIG. 3. The present invention provides methods for detecting genetic abnormalities in patients, developing knock-out mice or transgenically altered mice, see FIGS. 12 and 13, treatment of a variety of disorders including but not limited to inflammatory disorders, malignant disorders and disorders associated with autoimmunity. In addition, the invention includes diagnostic kits comprising several antibodies such as ELISA kits, or 'in situ hybridization'. Finally, the invention includes therapeutic agents that comprise complementary cDNA, RNA sequences or variants thereof.

The 208 amino acid polypeptide fragment of CRF2-12 region b shares significant identity and similarity with the corresponding extracellular portion of members of the class-II cytokine receptor family. As illustrated in FIG. 4, marked similarity exists between the extracellular portion of CRF2-12 and that of IL22R1. The 208 amino polypeptide fragment of CRF2-12 region b therefore represents the extracellular domain of a new member of the class-II cytokine receptor family. The similarity between CRF2-12 and other members of the IL-10 receptor family is shown in FIG. 5, while its broader relationship with other members of the class-II cytokine receptor family is shown in FIG. 6.

As used herein, unless otherwise specified, the term cytokine includes proteins which are variously termed "interferons", "interleukins", "colony-stimulating factors", "tumor necrosis factors" and so on. Indeed, these terms are frequently used interchangeably with the term cytokine. Cytokines are known to elicit biological activities via binding to specific membrane-bound receptors.

As used herein, unless otherwise specified, the term Extracellular Domains includes those of the receptors composed of one or more proteins, which have proteins outside the cell.

As used herein, unless otherwise specified, the term Transmembrane Domains includes those of the receptors composed of one or more proteins, which extend through the cell membrane.

As used herein, unless otherwise specified, the term Intracellular Domains includes those of the receptors composed of one or more proteins, which extend into the cytoplasm of the cell.

The present invention describes and defines isolated polypeptides of greater than or equal to 70% identity to the amino acid reference sequence revealed in FIG. 2, covering both the whole polypeptide and specific regions "a", "b", "c" and "d" as defined below.

Region "a", to be residues 1-19, 1-20, 1-21 and/or 1-22, and may be termed herein the signal sequence.

Region "b" to be residues 19-226, 19-227, 19-228, 19-230, 20-226, 20-227, 20-228, 20-229, 20-230, 21-226, 21-227, 21-228, 21-229, 21-230, 22-226, 22-227, 22-228, 22-229, 22-230, and may be termed herein the extracellular domain.

Region "c" to be residues 226-242, 226-243, 226-244, 226-245, 226-246, 227-242, 227-243, 227-244, 227-245, 227-246, 228-242, 228-243, 228-244, 228-245, 228-246, 229-242, 229-243, 229-244, 229-245, 229-246, 230-242, 230-243, 230-244, 230-245, 230-246, and may be termed herein the transmembrane domain.

Region "d" to be residues 242-520, 243-520, 244-520, 245-520, 246-520, and may be termed herein the intracellular domain.

The present invention also describes and defines isolated polypeptides comprising at least 12 contiguous amino acids of the polypeptide sequence shown in FIG. 2, selected from groups "a", "b", "c" and/or "d".

In the present invention, "isolated" refers to material removed from its original environment (e.g., the natural environment if it is naturally occurring). For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein of the present invention refers to a protein capable of being directed to the ER, secretory vesicles, or the extracellular space as a result of a signal sequence, as well as proteins of the present invention released into the extracellular space without necessarily containing a signal sequence. If the secreted proteins of the present invention is released into the extracellular space, the secreted proteins of the present invention can undergo extracellular processing to produce a "mature" proteins of the present invention. Release into the extracellular space can occur by many mechanisms, including exocytosis and proteolytic cleavage.

A "membrane" associated polypeptide of the present invention may be utilized as a polypeptide integrated in a lipid membrane, such as a membrane-bound polypeptide, an intracellular polypeptide expressed in the cell's secretory pathway, a polypeptide expressed in the plasma membrane at the cell surface or as a polypeptide integrated synthetically into membrane-like structures such as in liposomes or micelles.

The polynucleotides of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. The polynucleotides of the present invention may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

Polypeptides of the present invention can be composed of amino acids joined to each other by peptide bonds or modified peptide bonds, i.e., peptide isoesteres, and may contain amino acids other than the 20 gene-encoded amino acids. The polypeptides of the present invention may be modified by either natural processes, such as post-translational processing, or by chemical modification techniques which are well known in the art. Such modifications are well described in basic texts and in more detailed monographs, as well as in a voluminous research literature. Modifications can occur anywhere in the polypeptides of the present invention, including the peptide backbone, the amino acid side-chains and the amino or carboxyl termini. It will be appreciated that the same type of modification may be present in the same or varying degrees at several sites in the polypeptides of the present invention. Also, the polypeptides of the present invention may contain many types of modifications. Polypeptides of the present invention may be branched, for example, as a result of ubiquitination, and they may be cyclic, with or without branching. Cyclic, branched, and branched cyclic polypeptides of the present invention may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182: 626-646 (1990); Rattan et al., Ann NY Acad Sci 663:48-62 (1992).)

Polypeptides of the present invention "having biological activity" refers to polypeptides exhibiting activity similar, but not necessarily identical to, an activity of a polypeptides of the present invention (e.g., anti-viral activity, ability to bind an antibody which binds a polypeptide of the present invention, ability to bind to CRF2-12, or as described in the example section herein), including mature forms, as measured in a particular biological assay, with or without dose dependency. In the case where dose dependency does exist, it need not be identical to that of the polypeptides of the present invention, but rather substantially similar to the dose-dependence in the activity as compared to the polypeptides of the present invention (i.e., the candidate polypeptide will exhibit greater activity or not more than about 25-fold less and, preferably, not more than about tenfold less activity, and most preferably, not more than about three-fold less activity relative to the polypeptides of the present invention.)

"Regulatory regions" is intended to include promoters, enhancers and/or other expression control elements (e.g., polyadenylation signals), which may be in any effective relationship with the coding sequence. Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc.

IFN-λs are expressed mainly in all cells, and particularly in dendritic cells natural cytokine producing cells. Expression of the proteins and polypeptides of the present invention may be regulated in any effective manner. For example, by double stranded RNA, anti-sense technology, as well as cytokines and effective small molecules.

By upregulating the level of CRF2-12 expression in virus-infected cells or in tumor cells we can force these cells undergo apoptosis or antiproliferative effect in response to IFN-λs. Enhanced expression of CRF2-12 can be, perhaps, induced by some agents, or simply achieved by targeted delivery of CRF2-12 expression construct into virus- or other pathogen-infected cells, or malignant cells. CRF2-12 expression can be replaced by expression of a chimeric receptor, such as IL-10R1/CRF2-12 described above. The extracellular domain of such chimeric receptor can be substituted by the extracellular domain of various receptors. If such chimeric receptors are expressed in target cells (malignant cells or pathogen-infected cells), these cells can be killed by the treatment with the appropriate ligand which binds to the extracellular domain of the chimeric receptor and induce signaling through the CRF2-12 intracellular domain. Some cancers express autocrine growth factors to maintain cancer growth, or express certain cytokines such as IL-10 to suppress the immune system. Thus, by using the extracellular domain of an appropriate receptor in combination with the intracellular domain of CRF2-12, cancer cells expressing such chimeric receptor can be killed by their own growth factors or cytokines. The extracellular domain of IL-10RI seems to be most useful since many cancers, particularly advanced cancers, produce high level of IL-10.

Therapeutic Indications

The first embodiment is the use of IFN-λs to induce antiviral protection to treat viral infections in both humans and other mammals. Such protection may be induced for the treatment of an ongoing infection or for prophylaxis of anticipated infections, including but not limited to common recurring infections such as influenza, and circumstances requiring emergency prophylaxis, such as a bioweapon attack.

Another embodiment is the use of IFN-λs to induce apoptosis to treat hyperproliferative disorders in both humans and other mammals. And in addition, to withdraw interferon lambda in order to prevent apoptosis, for the treatment of hypoproliferative disorders in humans and other mammals. It is understood that the stated administration or withdrawal of IFN lambda also included other methods of manipulation of the IFN lambda/receptor signaling mechanism which have similar effects to direct ligand manipulation. Such means might include, but are not limited to antibody moieties or other binding structures which bind the receptor, mimicking or blocking ligand effects and or interference with downstream signaling events resulting from receptor engagement. It will be realized that hypo and hyper proliferative disorders will include all human malignancies and other overgrowths such as benign tumors and cysts in addition to disease causing or promoting systems which include the over-growth or under-growth of one or more individual cell types. Such systems may include any and all disorders of the immune system, including autoimmune diseases, the digestive system, the haematopoietic system, the nervous and neuronal system, the cardiovascular system, the respiratory system, tooth eruption and other such bodily mechanisms, such as growth and development of fetuses and juveniles where the natural, regular and programmed selective growth and death of cells may become disrupted.

A further embodiment is the control of the glycosylation of IFN-λ1 as a target for drug development to induce either an antiviral effect or induce cell death to treat either humans or other mammals. Other mechanisms for manipulating the affinity or selective action of interferon lambda, such as changing of one or more amino acids of the IFN-lambda peptide sequence, or insertion or removal of short peptide elements to/from the natural IFN-lambda sequence are also envisaged.

Another embodiment is the use of IFN-λs to upregulate MHC class I antigen expression and, thus, stimulate immune response against viruses, other pathogens and tumors in both humans and other mammals.

A final embodiment is the use of novel sequences in gene therapy to treat either humans or other mammals, including but not limited to the substitution of interferon lambda sequences from other mammals to the human sequence in order to manipulate the ligand affinity for its natural receptor, or to induce therapeutic signaling or blocking of an unrelated receptor. Furthermore, the construction of chimeric molecules, comprised of IFN lambda sequences and peptide sequenced from human or other mammalian cytokines, growth factors etc for the purpose of therapy, research and or teaching is also envisaged.

The present invention also includes variations of CRF2-12. It will be recognized by someone trained in the art that mutations can exist in a peptide sequence, which do not affect the function of the protein. Often, these occur naturally but can be produced artificially by substituting one or more amino acid residues for the natural ones. Such so-called "conservative" substitutions include but are not limited to; the substitution of one acidic amino acid for another (e.g. Aspartic acid for glutamic acid), one non-polar amino acid for another (e.g. Glycine for alanine), one hydrophobic amino acid for another (e.g. Leucine for isoleucine), one basic amino acid for another (e.g. Lysine for arginine), and so on. Examples of amino acids in similar groups are widely known and accepted in the field. Such conservative changes in the peptide sequence therefore fall within the scope of this invention. It will be further recognized by someone trained in the art that mutations, resulting or created as above, can exist in a peptide sequence which alter the function of a protein and/or its ability to interact with other proteins. In particular, the mutation may alter the ability of the receptor to bind a natural ligand and/or alter the consequences of ligand binding by preventing the receptor from transmitting a signal or by enhancing the signal. Such non-conservative changes fall within the scope of this invention and are included in it.

The present invention also describes and defines isolated nucleic acid molecules, which encode the CRF2-12 polypeptides, its fragments and mutants. An illustrative nucleic acid sequence which can encode CRF2-12 is given in FIG. 1. This nucleic acid sequence will encode all the CRF2-12 fragments and peptides described in regions "a", "b", "c" and "d". Translated products of nucleic acid sequences are usually quoted in a single-letter code, as shown in FIG. 2, and FIG. 7 illustrates the translation of the nucleic acid sequence revealed in FIG. 1. An alternative, three-letter, notation is sometimes used to describe the translation of nucleic acid sequence and this is shown in FIG. 8, for CRF2-12.

As is widely recognized in the art, there is redundancy in the translation of nucleic acid sequences. Often, several triplet codons may be translated to the identical amino acid. The present invention presupposes that natural variation at any of the triplet codons may result in a nucleic acid sequence which varies at one or more positions from the illustrative sequence revealed in FIG. 1 will still result in an identical translation product to that revealed in FIG. 2, indeed that such variations are not only possible but likely, especially between individuals from different ethnic backgrounds. Such redundancy will also apply to the natural or man-made conservative and/or non-conservative amino-acid changes referred to above. The IUPAC convention for writing nucleic acid sequences allows for the use of single letters which may define two or more nucleotides, in addition to the four unique nucleotides (A, C, G, T). These are widely known in the art. FIG. 9, reveals the single-letter nucleic acid sequence, which fully describes and defines the possible extent of variation in a gene encoding CRF2-12, while FIG. 10 expands this to show how the redundant code defines possible individual codons.

As is widely recognized in the art, portions of genes which encode peptides (exons) are usually separated from one another by intervening, non-coding nucleic acid sequences (introns). Such introns are integral parts of the gene. The coding sequence for CRF2-12 revealed in FIG. 1 is distributed within at least seven exons and six intervening introns. The present invention incorporates these exons and introns to form part of the gene describing CRF2-12. Also widely recognized is the fact that following the coding portion of a gene comes a non-coding portion, which is a part of the last exon, the so-called "3'UTR". The present invention describes and defines the 3'UTR for the CRF2-12 gene and this is revealed in FIG. 11.

As is widely recognized in the art, multi-exon genes, such as the gene for CRF2-12, may exist as splice variants, where one or more coding exons are missing, resulting in a shorter translation product, or added, resulting in a translation product which can be either longer or shorter. The present invention provides for the naturally-occurring presence of such splice variants and incorporates them. In its primary form, the gene product CRF2-12 is expected to be found embedded within the membranes of cells. However, it will be recognized by those knowledgeable in the art that splice variants can occur which exclude the transmembrane and intracellular portions of the protein, resulting in a protein which is freed into the extracellular milieu. Such variants would result in a soluble CRF2-12 and so soluble CRF2-CRF2-12 is included in the scope of this invention.

As is widely recognized in the art, individuals may vary in one or more nucleotide residues within a given gene, such as the CRF2-12 gene. Such natural variations are often referred to as "allelic variants." These variants are useful for the prediction and monitoring of diseases, particularly diseases involving CRF2-12 or adjacent genes.

As is common practice in the art, cell-bound receptor structures similar in nature to CRF2-12, are often produced from an artificially constructed polynucleotide, such that the product of said nucleotide comprises the specific invention (in this case the extracellular portion of CRF2-12 or parts thereof) operationally and functionally joined to a protein or protein fragment with the property of improving the pharmacokinetics of the specific invention. A molecule frequently used in this way is the so-called Fc region of human immunoglobulin, resulting in a chimeric molecule (in this case CRF2-12 and Fe) encoded from a single polynucleotide. An example of this in clinical use today is the hybrid TNF(p75) receptor/Fc molecule. The present invention anticipates the use of the CRF2-I 2 gene for the construction of such chimeric polynucleotides, which are thereby incorporated in the scope of the invention.

As is common knowledge in the art, cell-surface receptors of the CRF family, such as the interleukin-10 receptor, the interleukin-20 receptor and the interleukin-22 receptor exist functionally as two or more individual polypeptide chains. Furthermore, it will be appreciated that synthetic chimeric polynucleotides can be produced which encode the extracellular portions of one or more of the known members of the CRF family (including, but not limited to: interleukin-10 receptor alpha, interleukin-10 receptor beta, interleukin-20 receptor alpha, interleukin-20 receptor beta, interleukin-22 receptor alpha, interferon gamma receptor components, interleukin alpha/beta receptor components) in association with CRF2-12. Such chimeric polypeptides might represent the natural specificity of CRF2-12 or a novel specificity which depend upon the presence of the CRF2-12 polypeptide. The present invention therefore incorporates such chimeric molecules and their resultant specificities where, in addition to CRF2-12 said chimeric polypeptide contains sequences from one or more other members of the CRF family and constitute novel, soluble receptor entities. It is anticipated that such novel soluble receptor entities would find use in the treatment of diseases described previously.

The present invention, CRF2-12 and its various embodiments, constitute a receptor for IFN-λ. The receptor nature of CRF2-12 will allow other ligands to be identified by processes commonly used in the art. For example, one aspect of the present invention includes a method of screening for CRF2-12 ligands which includes the steps of binding a polypeptide including CRF2-12 to a solid, inert matrix and passing over the resultant complexes a biological mixture which contains a potential CRF2-12 ligand, whereby the ligand is retained and then harvesting the ligand in a purified form using methods well-established in the art (such as ion-exchange) and identified. Since the identification of CRF2-12 ligand is wholly dependent upon the present invention, CRF2-12 ligands are therefore included in the scope of the present invention.

Polypeptides and Fragments

The invention further provides an isolated IFN-λ1 polypeptide having the amino acid sequence encoded by pEF-FL-IFN-λ1 gene, an isolated IFN-λ1 polypeptide having the amino acid sequence encoded by pEF-FL-IFN-λ1, an isolated IFN-λ1 polypeptide having the amino acid sequence in SEQ ID NO: 8, or a peptide or polypeptide comprising a portion of the above polypeptides.

The invention further provides an isolated IFN-λ2 polypeptide having the amino acid sequence encoded by pEF-FL-IFN-λ2 gene, an isolated IFN-λ2 polypeptide having the amino acid sequence encoded by pEF-FL-IFN-λ2, an isolated IFN-λ2 polypeptide having the amino acid sequence in SEQ ID NO: 10, or a peptide or polypeptide comprising a portion of the above polypeptides.

The invention further provides an isolated IFN-λ3 polypeptide having the amino acid sequence encoded by pEF-FL-IFN-λ3 gene, an isolated IFN-λ3 polypeptide having the amino acid sequence encoded by pEF-FL-IFN-λ3, an isolated IFN-λ3 polypeptide having the amino acid sequence in SEQ ID NO: 12, or a peptide or polypeptide comprising a portion of the above polypeptides.

The invention further provides an isolated polypeptide comprising an amino acid sequence of the full-length IFN-λ1 polypeptide having the complete amino acid sequence of SEQ ID NO: 8. The invention further provides an isolated polypeptide comprising the amino acid sequence of the full-length IFN-λ1 polypeptide having the complete amino acid sequence of SEQ ID NO: 8 excepting the N-terminal methionine (i.e., residues 2-200 of SEQ ID NO: 8). The invention further provides an isolated polypeptide comprising the amino acid sequence of the mature IFN-λ1 polypeptide shown as residues 23-200 of SEQ ID NO: 8. The invention further provides an isolated polypeptide comprising an IFN-λ1 polypeptide encoded by the genomic fragment encoding the IFN-2l gene contained in plasmid pEF-FL-IFN-λ1 gene. The invention further provides an isolated polypeptide comprising an IFN-λ1 polypeptide encoded by the cDNA contained in plasmid pEF-FL-IFN-λ1. The invention further provides an isolated polypeptide comprising a mature IFN-λ1 polypeptide encoded by the cDNA contained in plasmid pEF-FL-IFN-λ1. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

The invention further provides an isolated polypeptide comprising the IFN-λ2 polypeptide having the complete amino acid sequence of SEQ ID NO: 10. The invention further provides an isolated polypeptide comprising the IFN-λ2 polypeptide having the complete amino acid sequence of SEQ ID NO: 10 excepting the N-terminal methionine (i.e., residues 2-196 of SEQ ID NO: 10). The invention further provides an isolated polypeptide comprising the mature IFN-λ2 polypeptide shown as residues 23-196 of SEQ ID NO: 10. The invention further provides an isolated polypeptide comprising the IFN-λ2 polypeptide shown as residues M 12-196 of SEQ ID NO: 10.

The invention further provides an isolated polypeptide comprising the IFN-λ2 polypeptide shown as residues A13-196 of SEQ ID NO: 10. The invention further provides an isolated polypeptide comprising the mature IFN-λ2 polypeptide shown as residues P31-196 of SEQ ID NO: 10. The invention further provides an isolated polypeptide comprising the IFN-λ2 polypeptide shown as residues M92-196 of SEQ ID NO: 10. The invention further provides an isolated polypeptide comprising the IFN-λ2 polypeptide shown as residues A93-196 of SEQ ID NO: 10. The invention further provides an isolated polypeptide comprising the mature IFN-λ2 polypeptide shown as residues P 113-196 of SEQ ID NO: 10. The invention further provides an isolated polypeptide comprising a IFN-λ2 polypeptide coded by plasmid pEF-FL-IFN-λ2 gene.

The invention further provides an isolated polypeptide comprising a polypeptide encoded by the cDNA contained in plasmid pEF-FL-IFN-λ2. The invention further provides an isolated polypeptide comprising a mature polypeptide encoded by the cDNA contained in clone pEF-FL-IFN-λ2. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

The invention further provides an isolated polypeptide comprising a IFN-λ3.1 polypeptide having the complete amino acid sequence of SEQ ID NO: 12. The invention further provides an isolated polypeptide comprising a IFN-λ3 polypeptide having the complete amino acid sequence of SEQ ID NO: 12 excepting the N-terminal methionine (i.e., residues 2-196 of SEQ ID NO: 12). The invention further provides an isolated polypeptide comprising a mature polypeptide shown as residues P23-196 of SEQ ID NO: 12. The invention further provides an isolated polypeptide comprising a IFN-λ3 polypeptide shown as residues M6-196 of SEQ ID NO: 12. The invention further provides an isolated polypeptide comprising a IFN-3 polypeptide shown as residues M 12-196 of SEQ ID NO: 12. The invention further provides an isolated polypeptide comprising a IFN-λ3 polypeptide shown as residues P7-196 of SEQ ID NO: 12. The invention further provides an isolated polypeptide comprising a IFN-λ3 polypeptide shown as residues A13-196 of SEQ ID NO: 12.

The invention further provides an isolated polypeptide comprising a mature IFN-λ3 polypeptide shown as residues P31-196 of SEQ ID NO: 12. The invention further provides an isolated polypeptide comprising a IFN-λ3 polypeptide coded by plasmid pEF-FL-IFN-λ3 gene.

The invention further provides an isolated polypeptide comprising a polypeptide encoded by the cDNA contained in plasmid pEF-FL-IFN-λ3. The invention further provides an isolated polypeptide comprising a mature polypeptide encoded by the cDNA contained in clone pEF-FL-IFN-λ3. The polypeptides of the present invention also include polypeptides having an amino acid sequence at least 80% identical, more preferably at least 90% identical, and still more preferably 95%, 96%, 97%, 98% or 99% identical to those described above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a polypeptide of the present invention having an amino acid sequence described above.

Peptides or polypeptides having the amino acid sequence of an epitope-bearing portion of a polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a polypeptide having an amino acid sequence described above. The invention further provides methods for isolating antibodies that bind specifically to a polypeptide having an amino acid sequence as described herein. Such antibodies are useful therapeutically as described below.

To improve or alter the characteristics of the polypeptides of the present invention, protein engineering may be employed. In addition, recombinant DNA technology known to those skilled in the art, including, for example, site directed mutagenesis, can be used to create novel mutant proteins or "muteins" including single or multiple amino acid substitutions, deletions, additions or fusion proteins.

Modified polypeptides of the present invention can show, e.g., enhanced or decreased (i.e., blocking) activity or increased stability. In addition, they may be purified in higher yields, show better solubility than the corresponding natural polypeptide, and be more effective therapeutically, at least under certain purification, storage and administration conditions.

Unless otherwise specified, a "polypeptide fragment" refers to an amino acid having a sequence which is a portion of that contained in SEQ ID NO: 2, SEQ ID NO:8, SEQ ID NO:10 or SEQ ID NO:12, or is encoded by the nucleic acid sequence in plasmids pEF-CRF2-12/γR1+CRF2-4, pEF-IL-1 OR1/IFN-λR1, pEF-CRF2-12/γR1, pEF-FLCRF2-12, pEF-CRF2-12, pEF-CRF2-12/γR1, pEF-FL-IFN-λ1, pEF-FL-IFN-λ2, pEF-FL-IFN-λ3, pEF-FL-IFN-λ1 gene, pEF-FL-IFN-λ2 gene or pEF-FL-IFN-λ3 gene.

The protein or polypeptide fragments of the present invention may be complete within itself, or it may be comprised within a larger polypeptide of which the fragment forms a part or region, most preferably as a single continuous region.

Representative examples of polypeptide fragments of the receptor of the present invention include, for example, fragments comprising, or alternatively consisting of, from about amino acid number 1-20, 20-228, 228-244 or 244-520 or the end of the coding region of SEQ ID NO: 2.

In another aspect of the present invention, differences as well as similarities between sequences may comprise a preferred embodiment of a protein or polypeptide of the present invention. Conserved domains or sequences may indicate that the conserved domain or sequence is indispensable for function. Differences in the amino acid composition of proteins or polypeptides are also an important aspect of the present invention. For example, a difference in an amino acid at a single position may trigger an unwanted immunological response against a protein or polypeptide. This may occur, for example, when the protein or polypeptide is being used therapeutically. In addition, an amino acid difference may affect the potency or the functionality of the proteins or polypeptides of the present invention.

Representative examples of polypeptide or polypeptide fragments of the IFN-λs of the present invention include, for example, polypeptides comprising, or alternatively consisting of:

R38-L47 of SEQ ID NO: 8, wherein Q49 may be any polar or charged amino acid, for example K;

F39-L47 of SEQ ID NO: 8, wherein Q49 may be any polar or charged amino acid, for example K;

S49-E58 of SEQ ID NO: 8, wherein S49 may be any amino acid having a small side chain, i.e., G, A, S, C, or the like, preferably S or A and most preferably S, R54 may be any charged amino acid, i.e., D, E, K or R, preferably R or K, and most preferably R, L57 may be any hydrophobic amino acid, i.e., A, V, F, P, M, I or L, preferably L or I, most preferably L;

F50-E59 of SEQ ID NO: 8, wherein R54 may be any charged amino acid, i.e., D, E, K or R, preferably R or K, and most preferably R, L57 may be any hydrophobic amino acid, i.e., A, V, F, P, M, I or L, preferably L or I, most preferably L, E59 may be any charged amino acid, i.e., D, E, K or R, preferably E or K, most preferably E;

A90-K100 of SEQ ID NO: 8, wherein E92 may be any charged amino acid, i.e., D, E, K or R, preferably E or Q, and most preferably E, L95 may be any hydrophobic amino acid, i.e., A, V, F, P, M, I or L, preferably L or V, most preferably L;

W149-A156 of SEQ ID NO: 8;
G163-T170 of SEQ ID NO: 8;
N I 72-K182 of SEQ ID NO: 8;
An exact match for W77-L191 of SEQ ID NO: 8;
An exact match for W149-L191 of SEQ ID NO: 8;
An exact match for C34-T170 of SEQ ID NO: 8;
An exact match for C34-T178 of SEQ ID NO: 8;
An exact match for C34-T200 of SEQ ID NO: 8;
An exact match for W77-T170 of SEQ ID NO: 8;
An exact match for W77-T178 of SEQ ID NO: 8;
An exact match for W77-T200 of SEQ ID NO: 8;
An exact match for W149-T170 of SEQ ID NO: 8;
An exact match for W149-T178 of SEQ ID NO: 8;
An exact match for W149-T200 of SEQ ID NO: 8;

C37-E61 of SEQ ID NO: 10, wherein Q48 may be any polar or charged amino acid, for example D, E, K, R, S, T, Y, H, C, N, Q, W, preferably Q or K, most preferably, Q, R55 may be any charged amino acid, i.e., D, E, K or R, preferably R or K, most preferably R, L60 may be any hydrophobic amino acid, i.e., A, V, F, P, M, I or L, preferably L or I, most preferably L;

C37-E62 of SEQ ID NO: 10, wherein Q48 may be any polar or charged amino acid, for example D, E, K, R, S, T, Y, H, C, N, Q, W, preferably Q or K, most preferably, Q, R55 may be any charged amino acid, i.e., D, E, K or R, preferably R or K, most preferably R, L60 may be any hydrophobic amino acid, i.e., A, V, F, P, M, I or L, preferably L or I, most preferably L, E62 may be any charged amino acid, i.e., D, E, K or R, preferably E or K, most preferably E;

W80-P91 of SEQ ID NO: 10, wherein R83 may be any charged amino acid, i.e., D, E, K or R, preferably R or K, most preferably R, R88 may be any charged amino acid, i.e., D, E, K or R, preferably R or Q, most preferably R;

W154-A161 of SEQ ID NO: 10, wherein Y156 may be any polar amino acid, i.e., S, T, Y, H, C, N, Q, W, preferably Y or H, most preferably Y;

K164-T175 of SEQ ID NO: 10, wherein S166 may be any polar amino acid, i.e., S, T, Y, H, C, N, Q, W, preferably S or T, most preferably S;

N I 77-T183 of SEQ ID NO: 10;
An exact match for C37-T175 of SEQ ID NO: 10;
An exact match for C37-T183 of SEQ ID NO: 10;
An exact match for C37-V196 of SEQ ID NO: 10;
An exact match for W80-T175 of SEQ ID NO: 10;
An exact match for W80-T183 of SEQ ID NO: 10;
An exact match for W80-V196 of SEQ ID NO: 10;
An exact match for W154-T175 of SEQ ID NO: 10;
An exact match for W154-T183 of SEQ ID NO: 10;
An exact match for W154-V196 of SEQ ID NO: 10;

C37-E61 of SEQ ID NO: 12, wherein Q48 may be any polar or charged amino acid, for example D, E, K, R, S, T, Y, H, C, N, Q, W, preferably Q or K, most preferably, Q, R55 may be any charged amino acid, i.e., D, E, K or R, preferably R or K, most preferably R, L60 may be any hydrophobic amino acid, i.e., A, V, F, P, M, I or L, preferably L or I, most preferably L;

C37-E62 of SEQ ID NO: 12, wherein Q48 may be any polar or charged amino acid, for example D, E, K, R, S, T, Y, H, C, N, Q, W, preferably Q or K, most preferably, Q, R55 may be any charged amino acid, i.e., D, E, K or R, preferably R or K, most preferably R, L60 may be any hydrophobic amino acid, i.e., A, V, F, P, M, I or L, preferably L or I, most preferably L, E62 may be any charged amino acid, i.e., D, E, K or R, preferably E or K, most preferably E;

W80-P91 of SEQ ID NO: 12, wherein R83 may be any charged amino acid, i.e., D, E, K or R, preferably R or K, most preferably R, R88 may be any charged amino acid, i.e., D, E, K or R, preferably R or K, most preferably R;

W154-A161 of SEQ ID NO: 12, wherein Y156 may be any polar amino acid, i.e., S, T, Y, H, C, N, Q, W, preferably Y or H, most preferably Y;

K164-T175 of SEQ ID NO: 12, wherein S166 may be any polar amino acid, i.e., S, T, Y, H, C, N, Q, W, preferably S or T, most preferably S; N177-T183 of SEQ ID NO: 12;
An exact match for C37-T175 of SEQ ID NO: 12;
An exact match for C37-T183 of SEQ ID NO: 12;
An exact match for C37-V196 of SEQ ID NO: 12;
An exact match for W80-T175 of SEQ ID NO: 12;
An exact match for W80-T183 of SEQ ID NO: 12;
An exact match for W80-V196 of SEQ ID NO: 12;
An exact match for W154-T175 of SEQ ID NO: 12;
An exact match for W154-T183 of SEQ ID NO: 12;
An exact match for W154-V196 of SEQ ID NO: 12.

In another embodiment the present invention, in any given polypeptide of the present invention, a specific amino acid is an exact match at a particular position. These amino acids distinguish between the forms of IFN-λ, and between allelic variations of a single form.

In another set of embodiments, the following positions, each independently or in combination, is preferred: position 2 of SEQ ID NO: 8 is not T, most preferably it is A, position 4 of SEQ ID NO: 8 is not D, most preferably it is A, position 5 of SEQ ID NO: 8 is not C, most preferably it is W, position 6 of SEQ ID NO: 8 is not M, most preferably it is T, position 7 of SEQ ID NO: 8 is not P, most preferably it is V, position 11 of SEQ ID NO: 8 is not L, most preferably it is T, position 13 of SEQ ID NO: 8 is not A, most preferably it is V, position 14 of SEQ ID NO: 8 is not A, most preferably it is L, position 15 of SEQ ID NO: 8 is not V, most preferably it is G, position 17 of SEQ ID NO: 8 is not T, most preferably it is A, position 19 of SEQ ID NO: 8 is not T, most preferably it is A, position 21 of SEQ ID NO: 8 is not A, most preferably it is P, position 24 of SEQ ID NO: 8 is not V, most preferably it is T, position 25 of SEQ ID NO: 8 is not A, most preferably it is S, position 26 of SEQ ID NO: 8 is not R, most preferably it is K, position 27 of SEQ ID NO: 8 is not A, most preferably it is P, position 28 of SEQ ID NO: 8 is not L, most preferably it is T, position 29 of SEQ ID NO: 8 is not T, most preferably it is P, position 30 of SEQ ID NO: 8 is not D, most preferably it is T, position 31 of SEQ ID NO: 8 is not A, most preferably it is G, position 32 of SEQ ID NO: 8 is not R, most preferably it is K, position of SEQ ID NO: 837 is not A, most preferably it is G, position 38 of SEQ ID NO: 8 is not Q, most preferably it is R, position 48 of SEQ ID NO: 8 is not Q, most preferably it is A, position 52 of SEQ ID NO: 8 is not R, most preferably it is K, position 54 of SEQ ID NO: 8 is not K, most preferably it is R, position 62 of SEQ ID NO: 8 is not L, most preferably it is K, position 65 of SEQ ID NO: 8 is not D, most preferably it is N, position 66 of SEQ ID NO: 8 is not T or C, most preferably it is W, position 67 of SEQ ID NO: 8 is not R or K, most preferably it is S, position 69 of SEQ ID NO: 8 is not R or H, most preferably it is S, position 71 of SEQ ID NO: 8 is not R, most preferably it is P, position 72 of SEQ ID NO: 8 is not L, most preferably it is V, position 75 of SEQ ID NO: 8 is not R, most preferably it is G, position 76 of SEQ ID NO: 8 is not T, most preferably it is N, position 81 of SEQ ID NO: 8 is not Q, most preferably it is L, position 89 of SEQ ID NO: 8 is not M, most preferably it is V, position 105 of SEQ ID NO: 8 is not T or S, most preferably it is A, position 106 of SEQ ID NO: 8 most preferably is A, position 107 of SEQ ID NO: 8 most preferably is G, position 111 of SEQ ID NO: 8 is not V or G, most preferably it is E, position 128 of SEQ ID NO: 8 is not F, most preferably it is L, position 129 of SEQ ID NO: 8 is not R, most preferably it is Q, position 142 of SEQ ID NO: 8 is not A or T, most preferably it is P, position 151 of SEQ ID NO: 8 is not Y, most preferably it is H, position 162 of SEQ ID NO: 8 is not P, most preferably it is A, position 182 of SEQ ID NO: 8 is not N, most preferably it is K, position 183 of SEQ ID NO: 8 is not C, most preferably it is Y, position 186 of SEQ ID NO: 8 is not S, most preferably it is D, position 188 of SEQ ID NO: 8 is not D, most preferably it is N, position 191 of SEQ ID NO: 8 is not V, most preferably it is L, position 192 of SEQ ID NO: 8 most preferably is R, position 193 of SEQ ID NO: 8 most preferably is T, position 194 of SEQ ID NO: 8 most preferably is S, position 195 of SEQ ID NO: 8 most preferably is T, position 196 of SEQ ID NO: 8 most preferably is H, position 197 of SEQ ID NO: 8 most preferably is P, position 198 of SEQ ID NO: 8 most preferably is E, position 199 of SEQ ID NO: 8 most preferably is S, position 200 of SEQ ID NO: 8 most preferably is T.

In another set of embodiments, the following positions, each independently or in combination, is preferred: position 2 of SEQ ID NO: 10 is not A, most preferably it is T; position 3 of SEQ ID NO: 10 is not A, most preferably it is G; position 4 of SEQ ID NO: 10 is not A, most preferably it is D; position 5 of SEQ ID NO: 10 is not W, most preferably it is C; position 6 of SEQ ID NO: 10 is not M, most preferably it is T; position 7 of SEQ ID NO: 10 is not V, most preferably it is P; position 11 of SEQ ID NO: 10 is not T, most preferably it is L; position 12 of SEQ ID NO: 10 is not L, most preferably it is M; position 13 of SEQ ID NO: 10 is not V, most preferably it is A; position 14 of SEQ ID NO: 10 is not L, most preferably it is A; position 15 of SEQ ID NO: 10 is not G, most preferably it is V; position 17 of SEQ ID NO: 10 is not A, most preferably it is T; position 19 of SEQ ID NO: 10 is not A, most preferably it is T; position 21 of SEQ ID NO: 10 is not P, most preferably it is A; position 24 of SEQ ID NO: 10 is not T, most preferably it is V; position 25 of SEQ ID NO: 10 is not S, most preferably it is A; position 26 of SEQ ID NO: 10 is not K, most preferably it is R; position 27 of SEQ ID NO: 10 most preferably is L; position 28 of SEQ ID NO: 10 is not R, most preferably it is H; position 29 of SEQ ID NO: 10 most preferably is G; position 30 of SEQ ID NO: 10 is not P, most preferably it is A; position 31 of SEQ ID NO: 10 is not T, most preferably it is L; position 33 of SEQ ID NO: 10 is not T, most preferably it is D; position 34 of SEQ ID NO: 10 is not G, most preferably it is A; position 35 of SEQ ID NO: 10 is not K, most preferably it is R; position 40 of SEQ ID NO: 10 is not G, most preferably it is A; position 41 of SEQ ID NO: 10 is not R, most preferably it is Q; position 51 of SEQ ID NO: 10 is not A, most preferably it is Q; position 52 of SEQ ID NO: 10 is not S, most preferably it is A; position 55 of SEQ ID NO: 10 is not K, most preferably it is R; position 57 of SEQ ID NO: 10 is not R, most preferably it is K; position 65 of SEQ ID NO: 10 is not K, most preferably it is L; position 68 of SEQ ID NO: 10 is not N, most preferably it is D; position 69 of SEQ ID NO: 10 is not W, most preferably it is C; position 70 of SEQ ID NO: 10 is not S or K, most preferably it is R; position 72 of SEQ ID NO: 10 is not R or S, most preferably it is H; position 74 of SEQ ID NO: 10 is not P, most preferably it is R; position 75 of SEQ ID NO: 10 is not V, most preferably it is L; position 78 of SEQ ID NO: 10 is not G, most preferably it is R; position 79 of SEQ ID NO: 10 is not N, most preferably it is T; position 84 of SEQ ID NO: 10 is not L, most preferably it is Q; position 92 of SEQ ID NO: 10 is not V, most preferably it is M; position 108 of SEQ ID NO: 10 is not S or A, most preferably it is T; position 110 of SEQ ID NO: 10 most preferably is D; position 111 of SEQ ID NO: 10 most preferably is T; position 112 of SEQ ID NO: 10 is not G, most preferably it is D; position 116 of SEQ ID NO: 10 is not G or E, most preferably it is V; position 133 of SEQ ID NO: 10 is not L, most preferably it is F; position 134 of SEQ ID NO: 10 is not Q, most preferably it is R; position 147 of SEQ ID NO: 10 is not T or P, most preferably it is A; position 156 of SEQ ID NO: 10 is not H, most preferably it is Y; position 167 of SEQ ID NO: 10 is not A, most preferably it is P; position 187 of SEQ ID NO: 10 is not K, most preferably it is N; position 188 of SEQ ID NO: 10 is not Y, most preferably it is C; position 191 of SEQ ID NO: 10 is not D, most preferably it is S; position 193 of SEQ ID NO: 10 is not N, most preferably it is D; position 196 of SEQ ID NO: 10 is not L, most preferably it is V.

In another set of embodiments, the following positions, each independently or in combination, is preferred: position 2 of SEQ ID NO: 12 is not A, most preferably it is T; position 3 of SEQ ID NO: 12 is not A, most preferably it is G; position 4 of SEQ ID NO: 12 is not A, most preferably it is D; position 5 of SEQ ID NO: 12 is not W, most preferably it is C; position 6 of SEQ ID NO: 12 is not T, most preferably it is M; position 7 of SEQ ID NO: 12 is not V, most preferably it is P; position 11 of SEQ ID NO: 12 is not T, most preferably it is L; position 12 of SEQ ID NO: 12 is not L, most preferably it is M; position 13 of SEQ ID NO: 12 is not V, most preferably it is A; position 14 of SEQ ID NO: 12 is not L, most preferably it is A; position 15 of SEQ ID NO: 12 is not G, most preferably it is V; position 17 of SEQ ID NO: 12 is not A, most preferably it is T; position 19 of SEQ ID NO: 12 is not A, most preferably it is T; position 21 of SEQ ID NO: 12 is not P, most preferably it is A; position 24 of SEQ ID NO: 12 is not T, most preferably it is V; position 25 of SEQ ID NO: 12 is not S, most preferably it is A; position 26 of SEQ ID NO: 12 is not K, most preferably it is R; position 27 of SEQ ID NO: 12 most preferably is L; position 28 of SEQ ID NO: 12 is not H, most preferably is R; position 29 of SEQ ID NO: 12 most preferably is G; position 30 of SEQ ID NO: 12 is not P, most preferably it is A; position 31 of SEQ ID NO: 12 is not T, most preferably it is L; position 33 of SEQ ID NO: 12 is not T, most preferably it is D; position 34 of SEQ ID NO: 12 is not G, most preferably it is A; position 35 of SEQ ID NO: 12 is not K, most preferably it is R; position 40 of SEQ ID NO: 12 is not G, most preferably it is A; position 41 of SEQ ID NO: 12 is not R, most preferably it is Q; position 51 of SEQ ID NO: 12 is not A, most preferably it is Q; position 52 of SEQ ID NO: 12 is not S, most preferably it is A; position 55 of SEQ ID NO: 12 is not K, most preferably it is R; position 57 of SEQ ID NO: 12 is not R, most preferably it is K; position 65 of SEQ ID NO: 12 is not K, most preferably it is L; position 68 of SEQ ID NO: 12 is not N, most preferably it is D; position 69 of SEQ ID NO: 12 is not W, most preferably it is C; position 70 of SEQ ID NO: 12 is not S or R, most preferably it is K; position 72 of SEQ ID NO: 12 is not H or S, most preferably it is R; position 74 of SEQ ID NO: 12 is not P, most preferably it is R; position 75 of SEQ ID NO: 12 is not V, most preferably it is L; position 78 of SEQ ID NO: 12 is not G, most preferably it is R; position 79 of SEQ ID NO: 12 is not N, most preferably it is T; position 84 of SEQ ID NO: 12 is not L, most preferably it is Q; position 92 of SEQ ID NO: 12 is not M, most preferably it is V; position 108 of SEQ ID NO: 12 is not T or A, most preferably it is S; position 110 of SEQ ID NO: 12 most preferably is D; position 111 of SEQ ID NO: 12 most preferably is T; position 112 of SEQ ID NO: 12 is not G, most preferably it is D; position 116 of SEQ ID NO: 12 is not V or E, most preferably it is G; position 133 of SEQ ID NO: 12 is not F, most preferably it is L; position 134 of SEQ ID NO: 12 is not Q, most preferably it is R; position 147 of SEQ ID NO: 12 is not A or P, most preferably it is T; position 156 of SEQ ID NO: 12 is not H, most preferably it is Y; position 167 of SEQ ID NO: 12 is not A, most preferably it is P; position 187 of SEQ ID NO: 12 is not K, most preferably it is N; position 188 of SEQ ID NO: 12 is not Y, most preferably it is C; position 191 of SEQ ID NO: 12 is not D, most preferably it is S; position 193 of SEQ ID NO: 10 is not N, most preferably it is D; position 196 of SEQ ID NO: 12 i-s not L, most preferably it is V.

In another set of embodiments, the positions described supra, may be reversely altered such that one IFN-2 type may more closely resemble another type, or alternatively, an allele.

Polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

For many proteins, including the extracellular domain of membrane associated protein or the mature form(s) of a secreted protein, it is known in the art that one or more amino acids may be deleted from the N-terminus or C-terminus without substantial loss of biological function. However, even if deletion of one or more amino acids from the N-terminus or C-terminus of a protein results in modification of loss of one or more biological functions of the protein, other biological activities may still be retained.

Thus, the ability of the shortened protein to induce and/or bind to antibodies which recognize the complete protein generally will be retained when less than the majority of the residues of the complete protein are removed from the N-terminus. Whether a particular polypeptide lacking N-terminal residues of a complete protein retains such immunologic activities can readily be determined by routine methods described herein and otherwise known in the art.

Interferon gamma has been reported to show up to ten times higher activities by deleting 8-10 amino acid residues from the carboxy terminus of the protein (Dobeli et al., J. Biotechnology 7:199-216 (1988). In, the present case deletions of C-terminal amino acids of the IFN-λ polypeptides of the present invention may retain some biological activity, such as antiviral activity, modulation of MHC, apoptosis eliciting activity expression or binding to the receptor complex comprising IFN-λR1.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete protein generally will be retained when less than the majority of the residues of the complete protein are removed from the C-terminus. Whether a particular polypeptide lacking C-terminal residues of a complete protein retains such immunologic activities can readily be determined by routine methods described herein and otherwise known in the art.

The present application is also directed to nucleic acid molecules comprising, or alternatively, consisting of, a polynucleotide sequence encoding the polypeptide described above. The present invention also encompasses the above polynucleotide sequences fused to a heterologous polynucleotide sequence.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the IFN-λ polypeptides described above. The present invention also encompasses the above polynucleotide sequences fused to a heterologous polynucleotide sequence.

Preferably, the polynucleotide fragments of the invention encode a polypeptide which demonstrates an IFN-λ. functional activity. By a polypeptide demonstrating an IFN-λ "functional activity" is meant, a polypeptide capable of displaying one or more known functional activities associated with a full-length (complete) an IFN-λ protein. Such functional activities include, but are not limited to, biological activity (e.g., anti-viral activity, modulation of MHC expression, immunomodulatory activity, regulator of tumor cell growth, ability to induce apoptosis), antigenicity (ability to bind, or compete with an IFN-λ polypeptide for binding, to an anti-IFN-λ antibody), immunogenicity (ability to generate antibody which binds to an IFN-λ polypeptide), ability to bind to and/or activate the receptor complex comprising IFN-λR1, and the like.

The functional activity of the polypeptides of the present invention, and fragments, variants derivatives, and analogs thereof, can be assayed by various methods.

For example, in one embodiment where one is assaying for the ability to bind or compete with a full-length IFN-λ polypeptide for binding to anti-IFN-λ antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, physiological correlates of IFN-λ binding to its substrates (signal transduction) can be assayed. In addition, assays described herein and otherwise known in the art may routinely be applied to measure the ability of IFN-λ polypeptides and fragments, variants derivatives and analogs thereof to elicit IFN-λ related biological activity (either in vitro or in vivo). Other methods will be known to the skilled artisan and are within the scope of the invention.

It also will be recognized by one of ordinary skill in the art that some amino acid sequences of the IFN-λ polypeptides can be varied without significant effect on the structure or function of the protein.

Thus, the invention further includes variations of the IFN-λ polypeptide which show substantial IFN-λ polypeptide activity or which include regions of IFN-λ protein such as the protein portions discussed below. Such mutants include deletions, insertions, inversions, repeats, splice variants and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," Science 247: 1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

Thus, the fragment, derivative or analog of the polypeptides of SEQ ID NO: 2, SEQ ID NO: 6, SEQ ID NO: 8, SEQ ID NO: 10, SEQ ID NO: 12 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol, or albumin), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the polypeptides of the present invention may include one or more amino acid substitutions, deletions or additions, either from natural mutations or human manipulation. As indicated, changes are preferably of a minor nature, such as conservative amino acid substitutions that do not significantly affect the folding or activity of the protein. Additional variant polypeptides of the present invention include expression variants that enhance secretion or increase the biological activity of the polypeptide of the present invention.

Amino acids in the polypeptides of the present invention that are essential for function can be identified by methods known in the art, such as site-directed mutagenesis or alanine-scanning mutagenesis (Cunningham and Wells, Science 244:1081-1085 (1989).) The latter procedure introduces single alanine mutations at every residue in the molecule. The resulting mutant molecules are then tested for biological activity such as receptor binding, in vitro proliferative activity or interferon receptor activation.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Replacement of amino acids can also change the selectivity of the binding of a ligand to cell surface receptors. For example, Ostade et al., Nature 361:266-268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., J. Mol. Biol. 224:899-904 (1992) and de Vos et al. Science 255:306-312 (1992)).

The polypeptides of the present invention are preferably provided in an isolated form, and preferably are substantially purified. The polypeptides may be produced, isolated and purified by any effective manner known in the art.

For example, recombinantly produced versions of IFN-λS and soluble CRF2-12 polypeptides can be substantially purified by the one-step method described in Smith and Johnson, Gene 67:31-40 (1988). Polypeptides of the invention also can be purified from natural or recombinant sources using specific antibodies of the invention, described infra, in methods which are well known in the art of protein purification. By "% similarity" for two polypeptides is intended, for example, a similarity score produced by comparing the amino acid sequences of the two polypeptides. This may be done, for example, using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a query amino acid sequence of a polypeptide of the invention it is intended that the amino acid sequence of the subject polypeptide is identical to the query sequence except that the subject polypeptide sequence may include up to five amino acid alterations per each 100 amino acids of the query amino acid sequence of the present invention. In other words, to obtain a polypeptide having an amino acid sequence at least 95% identical to a query amino acid sequence, up to 5% of the amino acid residues in the subject sequence may be inserted, deleted, or substituted with another amino acid, or a number of amino acids up to 5% of the total amino acid residues in the query sequence may be inserted into the subject sequence. These alterations of the subject sequence may occur at the amino or carboxy terminal positions of the reference amino acid sequence or anywhere between those terminal positions, interspersed either individually among residues in the reference sequence or in one or more contiguous groups within the reference sequence.

As described in detail below, the polypeptides of the present invention can also be used to raise polyclonal and monoclonal antibodies, which are useful in assays for detecting IFN-λ protein expression and CRF2-12 protein expression, as described below, or as agonists and antagonists capable of enhancing or inhibiting IFN-λ protein function and CRF2-12 receptor or receptor complex function. Further, such polypeptides can be used in the yeast two-hybrid system to "capture" IFN-λ binding proteins, and proteins that bind to the intracellular, extracellular or the transmembrane domain of the CRF2-12 receptor or the receptor complex. Captured proteins are candidate agonists and antagonists according to the present invention. The yeast two hybrid system is described in Fields and Song, Nature 340:245-246 (1989).

Among the especially preferred polypeptide fragments of the invention are fragments characterized by structural or functional attributes of the proteins and polypeptides of the present invention. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program).

Other preferred regions include: Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; Karplus-Schulz predicted flexible regions; and Jameson-Wolf high antigenic index regions, as predicted using the default parameters of these computer programs. Polynucleotides encoding these polypeptides are also encompassed by the invention.

It has been reported that Interferon alpha possesses a wide variety of antiviral, anti-proliferative and immunomodulative biological activities. These multiple activities of interferon are thought to be mediated through interaction with specific cell-surface receptors. The interferon receptor generally is believed to consists of more than one individual polypeptide component and different parts of the interferon molecule are thought to contribute to certain interferon activities via interaction with distinct chains of the interferon receptor complex. Wang et al., J. Immunol 152:705-715; Uze et al. J. Mol. Biol 243:245-257 (1994). The structure-functional organization of the type 1 interferon molecule, the interferon receptor complex, and the role of distinct receptor chains in signal transduction has been analyzed. Danilkovitch et al. Hybridoma 16:69-75 (1997); Pontzer et al. J. Interferon Res 14: 133-141 (1994); Danilkovich et al., Immunology Letters 31:15-20 (1991). Polypeptide fragments of the present invention, therefore, may be used to mediate antiviral, antiproliferative, apoptotic and immunomodulative biological activities.

Polypeptide fragments from the C-terminus of Interferon-alpha2 exhibit antiproliferative activity on normal human peripheral blood lymphocytes. Epitopes involving amino acids 124-144 of the Interferon-alpha2 molecule are thought to be responsible for receptor binding and for the manifestation of interferon antiproliferative properties. Danilkovich et al. Immunology Letters, supra. Polypeptide fragments from the carboxy-terminal region of Interferon-tau are thought to be involved in the antiviral activity by a mechanism and specificity shared by alpha Interferons. Pontzer et al. Proc. Natl. Acad. Sci. USA 87:5945-5949 (1990). Accordingly, polypeptide fragments of the present invention may be used as physiological regulators of tumor cell growth, anti-proliferative activity, anti-viral activity apoptotic activity and immunomodulatory activity.

Many polynucleotide sequences, such as EST sequences, are publicly available and accessible through sequence databases. Some of these sequences are related to SEQ ID NOS: 1-12 and may have been publicly available prior to conception of the present invention. Preferably, such related polynucleotides are specifically excluded from the scope of the present invention.

The present invention encompasses polypeptides comprising, or alternatively consisting of, an epitope of the polypeptide having an amino acid sequence of SEQ ID NO: 2, SEQ ID NO: 6, SEQ ID NO: 8, SEQ ID NO: 10, SEQ ID NO: 12. The present invention further encompasses polynucleotide sequences encoding an epitope of a polypeptide sequence of the invention, polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human, mouse, rabbit or rat. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein.

Immunospecific binding excludes non-specific binding but does not necessarily exclude cross-reactivity with other antigens. Antigenic epitopes need not necessarily be Immunogenic.

Fragments which function as epitopes may be produced by any conventional means. (See, e.g., Boughten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 12, at least 13, at least 14, at least 15, at least 20, at least 25, at least 30, at least 11, least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to any effective method, including in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide. Anti-peptide antibody titer may also be boosted by coupling the peptide to a macromolecular carrier, such as keyhole limpet hemacyanin (KLH) or tetanus toxoid.

Peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of antic-peptide antibody which can be detected, for example, by ELISA assay using free peptide adsorbed to a solid surface. The titer of anti-peptide antibodies in serum from an immunized animal may be increased by any effective method. For example, by selection of anti-peptide antibodies by adsorption to the peptide on a solid support and elution of the selected antibodies according to methods well known in the art.

The polypeptides of the present invention (e.g., those comprising an immunogenic or antigenic epitope) can be fused to heterologous polypeptide sequences. For example, the polypeptides of the present invention (including fragments or variants thereof) may be fused with the constant domain of immunoglobulins (IgA, IgE, IgG, IgM), or portions thereof (CH1, CH2, CH3, or any combination thereof and portions thereof) resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent O 413 622, and U.S. Pat. No. 5,766,883, issued Jun. 16, 1998, herein incorporated by reference in their entirety)).

Such fusion proteins as those described above may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605, 793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety).

Recombinant and Synthetic Production of Polypeptides of the Invention

The present invention also relates to vectors which include the isolated DNA molecules of the present invention, host cells which are genetically engineered with the recombinant vectors, and the production of polypeptides or fragments of polypeptides of the present invention by recombinant and synthetic techniques. The vector may be any effective vector. These include, for example, a phage, plasmid, viral or retroviral vector. Retroviral vectors may be replication competent or replication defective. In the latter case, viral propagation generally will occur only in complementing host cells.

The polynucleotides of the present invention, or encoding the polypeptides or polypeptide fragments of the present invention may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter. Any effective promoter may be used. These include the phage lambda PL promoter, the E. coli lac, trp, phoA and tac promoters, the SV40 early and late promoters and promoters of retroviral LTRs, to name a few. Other suitable promoters will be known to the skilled artisan. The expression constructs preferably also contain sites for transcription initiation, termination and, in the transcribed region, a ribosome binding site for translation in an effective position with respect to the DNA insert of the invention. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Any effective marker may be used. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimuriuin cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, PBLUESCRIPT vectors, pNH8A, pNH16a, pNH18A, pNH46A, available from STRATAGENE Cloning Systems, Inc.; and ptrc99a, pKK223-3, pKK233-3, pDR540, pRIT5 available from PHARMACIA Biotech, Inc. Among preferred eukaryotic vectors are pWLNEO, pSV2CAT, pOG44, pXT1 and pSG available from STRATAGENE; and pSVK3, pBPV, pMSG and pSVL available from PHARMACIA. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from INVITROGEN, Carlsbad, Calif.). Other suitable vectors will be readily apparent to the skilled artisan.

Introduction of the construct into the host cell can be effected by any effective means, including naked nucleic acid, use of a gene gun, calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986). It is specifically contemplated that polypeptides or polypeptide fragments of the present invention may be expressed by a host cell lacking a recombinant vector.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-0464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., J. Molecular Recognition 8:52-58 (1995) and K. Johanson et al., J. Biol. Chem. 270:9459-9471 (1995).

The polypeptide and polypeptide fragments of the present invention may be recovered and purified from recombinant cell cultures in any effective manner. For example, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. For example, see Lin et al., "Purification of Recombinant Human Interferon Beta expressed in E. coli" Methods in Enzymology 119: 183-192 (1986), which is hereby incorporated by reference in its entirety. Most preferably, high performance liquid chromatography ("HPLC") is employed for purification.

Further methods that may be used for production and isolation of the polypeptides of the present invention are disclosed in U.S. Pat. No. 6,433,145.

Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins—also is efficiently removed in most prokaryotes, for some proteins this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material, and/or to include genetic material (e.g., heterologous polynucleotide sequences) that is operably associated with polynucleotides of the invention, and which activates, alters, and/or amplifies endogenous polynucleotides of the present invention. For example, techniques known in the art maybe used to operably associate heterologous control regions (e.g., promoter and/or enhancer) and endogenous polynucleotide sequences of the present invention via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijistra et al., Nature 342:435-438 (1989), the disclosures of each of which are incorporated by reference in their entireties).

In addition, polypeptides of the invention can be chemically synthesized using any effective technique (e.g., see Creighton, 1983, Proteins: Structures and Molecular Principles, W.H. Freeman & Co., NY., and Hunkapiller et al., Nature, 310: 105-111 (1984)). For example, a polypeptide or a fragment of a polypeptide of the present invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, alpha-amino isobutyric acid, 4-aminobutyric acid, Abu, 2-aminobutyric acid, alpha-Abu, alpha-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alpha-alanine, fluoroamino acids, designer amino acids such as alpha-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London SerA 317:415 (1986)).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include, one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20: 1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($CISO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

The polypeptides of the invention may be in monomers or multimers (i.e., dimers, trimers, tetramers and higher multimers). Accordingly, the present invention relates to monomers and multimers of the polypeptides of the invention, their preparation, and compositions containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides having an identical sequence.

As used herein, the term heteromer refers to a multimer containing one or more heterologous polypeptides (i.e., polypeptides having different sequences). In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Any effective multimer may be formed. For example, in one embodiment of the present invention, IFN-λs form multimers of and between two of the three members, including, for example, IFN-λ1/IFN-λ2, IFN-λ1/IFN-λ3 and IFN-λ2/IFN-λ3, or multimers with all three members of the IFN-λ family. In another embodiment of the present invention an effective multimer contains other members of the cytokine family, including the IFN and IL-10 families of cytokines.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence. In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the present invention. In one example, covalent associations are between the heterologous sequence contained in a fusion protein of the invention (see, e.g., U.S. Pat. No. 5,478,925). In a specific example, the covalent associations are between the heterologous sequence contained in an –Fc fusion protein of the invention (as described herein). In another specific example, covalent associations of fusion proteins of the invention are between heterologous polypeptide sequences from another protein that is capable of forming covalently associated multimers, such as for example, osteoprotegerin (see, e.g., International Publication No: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

In another example, proteins of the invention are associated by interactions between FLAG polypeptide sequence contained in fusion proteins of the invention containing FLAG polypeptide sequence. In a further embodiment, associations proteins of the invention are associated by interactions between heterologous polypeptide sequence contained in FLAG fusion proteins of the invention and anti-FLAG antibody.

Further methods that may be used for production multimers of the present invention are disclosed in U.S. Pat. No. 6,433,145, and are hereby incorporated by reference in their entirety.

Antibodies

The polypeptides of the invention also relate to antibodies and T-cell antigen receptors (TCR) which immunospecifically bind a polypeptide, polypeptide fragment and/or an epitope of a polypeptide of the present invention (as determined by immunoassays well known in the art for assaying specific antibody-antigen binding).

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, the immunoglobulin molecules of the invention are IgG1. In another specific embodiment, the immunoglobulin molecules of the invention are IgG4.

Antibodies of the invention include, but are not limited to, polyclonal, monoclonal, multispecific, human, humanized or chimeric antibodies, single chain antibodies, Fab fragments, F(ab) fragments, fragments produced by a Fab expression library, anti-idiotypic (anti-Id) antibodies (including, e.g., anti-Id antibodies to antibodies of the invention), and epitope-binding fragments of any of the above.

Most preferably the antibodies are human antigen-binding antibody fragments of the present invention and include, but are not limited to, Fab, Fab' and F(ab)2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues. Preferred epitopes of the invention include those that include a sequence homology between IFN-λ forms and alleles. Also preferred are epitopes that include sequence differences between IFN-λ forms and alleles. These can be ascertained by those of ordinary skill in the art, and are further described in the polypeptide section of the present specification.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein).

Antibodies of the present invention may also be described or specified in terms of their binding affinity to a polypeptide of the invention. Preferred binding affinities include those with a dissociation constant or Kd less than $5\times10^{-2}$ M, $10^{-2}$M, $5\times10^{-3}$ M, $10^{-3}$ M, $5\times10^{-4}$ M, $10^{-4}$M, $5\times10^{-5}$ M, $10^{-5}$M, $5\times10^{-6}$ M, $10^{-6}$ M, $5\times10^{-7}$ M, $10^{-7}$ M, $5\times10^{-8}$M, $10^{-8}$M, $5\times10^{-9}$M, $10^{-9}$M, $5\times10^{-10}$M, $10^{-10}$ M, $5\times10^{-11}$ M, $10^{-11}$ M, $5\times10^{-12}$ M, $10^{-12}$M, $5\times10^{-13}$ M, $10^{-13}$M, $5\times10^{-14}$M, $10^{-14}$ M, $5\times10^{-15}$ M, or $10^{-15}$M.

The invention also provides antibodies that competitively inhibit binding of an antibody to an epitope of the invention as determined by any method known in the art for determining competitive binding, for example, the immunoassays described herein, or the ability of the antibody to block the biological activity of the CRF2-12 receptor or receptor complex, the ability to block binding of the polypeptides of the present invention to the CRF2-12 receptor or receptor complex, or the ability of the antibody to block signal transduction from the receptor or receptor complex. The antibodies may be directed either towards the receptor or the IFN-λ polypeptides of the present invention. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies that disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies that do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra, or in the EXAMPLES section infra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies that activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Hanop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17): 11295-11301 (1997); Taryman et al., Neuron 14(4):755-762 (1995); Muller et al., Structure 6(9): 1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO. 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Antibody fragments which recognize specific epitopes may be generated by known techniques. For example, Fab and F(ab)2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles that carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864, 869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229: 1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al. U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; International Publication No. WO91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix. Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology. John Wiley & Soils, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine, the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not, intended by way of limitation).

Immunoprecipitation protocols generally comprise lysing a population of cells in a lysis buffer such as RIPA buffer (1% NP-40 or TRITON X-100, 1% sodium deoxycholate, 0.1% SDS, 0.15 M NaCl, 0.01 M sodium phosphate at pH 7.2, 1% TRASYLOL) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G SEPHAROSE beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with SEPHAROSE beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating a surface, for example the well of a 96 well microtiter plate, with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another embodiment, a kit comprises a set of antibodies that can specifically bind, and thus distinguish between, the IFN-λ1, IFN-λ2 and/or the IFN-λ3 polypeptides of the present invention. In a specific embodiment, the kits of the present invention contain a substantially isolated polypeptide comprising an epitope which is specifically immunoreactive with each antibody included in the kit. Preferably, the kits of the present invention further comprise a control antibody which does not react with the polypeptides of interest. In another specific embodiment, the kits of the present invention contain a means for detecting the binding of an antibody to a polypeptide of interest (e.g., the antibody may be conjugated to a detectable substrate such as a fluorescent, compound, an enzymatic substrate, a radioactive compound or a luminescent compound, or a second antibody which recognizes the first antibody may be conjugated to a detectable substrate).

In another embodiment, a kit comprises a set of antibodies that can specifically bind, and thus distinguish between, alleles of IFN-λ1, IFN-λ2 and/or the IFN-λ3 polypeptides of the present invention. In a specific embodiment, the kits of the present invention contain a substantially isolated polypeptide comprising an epitope which is specifically immunoreactive with each antibody included in the kit. Preferably, the kits of the present invention further comprise a control antibody which does not react with the polypeptides of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptides of the present invention, when fused to a second protein, can be used as an antigenic tag. Antibodies raised against the polypeptides of the present invention can be used to indirectly detect the second protein by binding to the polypeptide. Moreover, because secreted proteins target cellular locations based on trafficking signals, the polypeptides can be used as targeting molecules once fused to other proteins.

Examples of domains that can be fused to the polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptides of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

The polypeptides of the present invention may be fused with heterologous polypeptide sequences. For example, the polypeptides of the present invention may be fused parts of the constant domain of immunoglobulins (IgA, IgE, IgG, IgM) or portions thereof (CH1, CH2, CH3, and any combination thereof, including both entire domains and portions thereof), or albumin (including but not limited to recombinant albumin), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331: 84-86 (1988)). Fusion proteins that have a disulfide-linked dimeric structure due to the IgG part can also be more efficient in binding and neutralizing other molecules than the monomeric polypeptide or polypeptide fragment of the present invention alone (Fountoulakis et al., J. Biochem. 270:3958-3964 (1995)). Polynucleotides comprising or alternatively consisting of nucleic acids which encode these fusion proteins are also encompassed by the invention Similarly, EP-A-0 464 533 (Canadian cunterp art 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fe part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences, such as, a peptide which facilitates purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for, instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art.

Therapeutic Uses

The present invention is further directed to antibody-based therapies which involve administering an effective amount of antibodies of the present invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g., as mediated by complement (CDC) or by effector cells (ADCC). Some of these approaches are described in more detail below.

The antibodies of this invention may be advantageously utilized in combination with other monoclonal or chimeric antibodies, or with lymphokines or hematopoietic growth factors (such as, e.g., KDI, IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $5\times10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic, recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into, the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in anon-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MOCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into, cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5): 155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids, of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J Immunol. 154:5590-5600 (1995); and Vil et al., Proc. Natl. Acad. Sci. USA 89: 11337-11341 (1992) (said references incorporated by reference in their entireties).

As discussed, supra, the polypeptides corresponding to a polypeptide, polypeptide fragment, or a variant of the polypeptides of the present invention may be fused or conjugated to the above antibody portions to increase the in vivo half life of the polypeptides or for use in immunoassays using methods known in the art. Further, the polypeptides corresponding to the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the FLAG tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and putomycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, .beta.-interferon, nerve growth factor, platelet derived growth factor, tissue plasminogen activator, an apoptotic agent, e.g., TNF-alpha, TNF-beta, lymphotoxin alpha, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-I ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-5.6 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by. Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Nucleic Acid Molecules

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells, purified (partially or substantially) DNA molecules in solution and synthetic polynucleotides. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogenous solution containing the clone and other members of the library) or a chromosome isolated or removed from a cell or cell lysate (e.g., a "chromosome spread", as in a karyotype), is not "isolated" for the purposes of this invention. As discussed further herein, isolated nucleic acid molecules according to the present invention may be produced naturally, recombinantly or synthetically.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and wash in IX SSC and 0.5% SDS at 6-5° C. for 15 minutes. Very high stringency hybridization is defined as hybridization in 6×SSC, SX Denhardt's solution, 0.5% SDS and 100 µg/ml denatured salmon sperm DNA at 42° C., and wash in 0.1×SSC and 0.5% SDS at 65° C. for 15 minutes.

As one of ordinary skill would appreciate, due to the possibilities of sequencing errors discussed above, the actual complete polypeptides of the present invention may be somewhat longer or shorter. More generally, the actual open reading frame may be anywhere in the range of ±20 amino acids, more likely in the range of ±10 amino acids, of that predicted from the methionine codon at the N-terminus shown in (SEQ ID NOS: 1, 3, 5, 7, 9, 11).

The present invention also relates to the genes of the present invention corresponding to SEQ ID NOS: 1, 2, 3, 4, 5, 6, 7, 8, 9, 10, 11 and/or 12. The genes of the present invention can be isolated in accordance with known methods using the sequence information disclosed herein. Such methods include preparing probes or primers from the disclosed sequence and identifying or amplifying the genes of the present invention from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NOS: 1, 2, 3, 4, 5, 6, 7, 8, 9, 10, 11 and/or 12, using information from the sequences disclosed herein. For example, allelic variants and/or species homologs may be isolated and identified by making suitable probes or primers from the sequences provided herein and screening a suitable nucleic acid source for allelic variants and/or the desired homologue. See also, for example, U.S. Patent Application Pub. No. 2002 039763, which is incorporated herein by reference in its entirety, including the sequences.

Unless otherwise specified, the term expression vector generally means any effective nucleic acid having a promoter operably linked to the nucleic acid molecule to be expressed and which in its part may be operably linked to an effective transcription terminator, preferably such that the expression vector effectively expresses the nucleic acid molecule to be expressed given suitable conditions.

The nucleic acid compositions of the present invention can be prepared in any suitable manner.

The polypeptides encoded by the nucleic acid compositions of the present invention may be in the form of the secreted protein, including the mature form, or may be a part of a larger protein, such as a fusion protein. It is often advantageous to include a nucleic acid encoding an additional amino acid sequence which contains secretory or leader sequences, pro-sequences, sequences which aid in purification, such as multiple histidine residues, FLAG sequences, or an additional sequence for stability during recombinant production.

Nucleic acids encoding polypeptides of the present invention, particularly IFN-λs, soluble receptor polypeptides and antibodies of the present invention, are preferably provided in an isolated form, and preferably are substantially purified.

The present invention also provides an isolated nucleic acid molecule comprising a nucleotide sequence encoding a chimeric receptor comprising the extracellular domain of CRF2-12 and the intracellular domain of another membrane bound receptor. The present invention also provides an isolated nucleic acid molecule comprising a nucleotide sequence encoding a chimeric receptor comprising the extracellular domain of CRF2-12 and the intracellular domain of another membrane bound tyrosine kinase receptor. The present invention also provides an isolated nucleic acid molecule comprising a nucleotide sequence encoding a chimeric receptor comprising the extracellular domain of CRF2-12 and the intracellular domain of a cytokine receptor. The present invention also provides an isolated nucleic acid molecule comprising a nucleotide sequence encoding a chimeric receptor comprising the extracellular domain of CRF2-12 and the intracellular domain of an IFNλRI type receptor. The present invention also provides an isolated nucleic acid molecule comprising a nucleotide sequence encoding a chimeric receptor comprising the extracellular domain of CRF2-12 and the intracellular domain of IFN R1. The present invention also provides an isolated nucleic acid molecule comprising a nucleotide sequence encoding the chimeric protein in plasmid pEF-CRF2-12/γR1. The present invention also provides an isolated nucleic acid molecule comprising a nucleotide sequence complementary to any of these nucleotide sequences.

The present invention also provides an isolated nucleic acid molecule comprising a nucleotide sequence encoding a chimeric receptor comprising the intracellular domain of CRF2-12 and the extracellular domain of another membrane bound receptor. The present invention also provides an isolated nucleic acid molecule comprising a nucleotide sequence encoding a chimeric receptor comprising the intracellular domain of CRF2-12 and the extracellular domain of another membrane bound tyrosine kinase receptor. The present invention also provides an isolated nucleic acid molecule comprising a nucleotide sequence encoding a chimeric receptor comprising the intracellular domain of CRF2-12 and the extracellular domain of a cytokine receptor; a nucleotide sequence encoding a chimeric receptor comprising the intracellular domain of CRF2-12 and the extracellular domain of an IFNλR1 type receptor. The present invention also provides an isolated nucleic acid molecule comprising a nucleotide sequence encoding a chimeric receptor comprising the intracellular domain of CRF2-12 and the extracellular domain of IL-10RI. The present invention also provides an isolated nucleic acid molecule comprising a nucleotide sequence encoding the chimeric protein in plasmid pEF-IL-10R1/IFN-λR1. The present invention also provides an isolated nucleic acid molecule comprising a nucleotide sequence complementary to any of these nucleotide sequences.

The present invention also provides an isolated nucleic acid molecule comprising a tandem vector having a nucleotide sequence encoding two receptors, wherein the first receptor is an R1 type receptor and the second receptor is an R2 type receptor, and wherein the expression of each receptor is controlled by separate promoters and polyadenylation signals. The present invention also provides an isolated nucleic acid molecule comprising a tandem vector having a nucleotide sequence encoding two receptors, wherein the first receptor comprises the extracellular domain of CRF2-12 and the second receptor is an R2 type receptor, and wherein the expression of each receptor is controlled by separate promoters and polyadenylation signals. The present invention also provides an isolated nucleic acid molecule comprising a tandem vector having a nucleotide sequence encoding two receptors, wherein the first receptor comprises the intracellular domain of CRF2-12 and the second receptor is an R2 type receptor, and wherein the expression of each receptor is controlled by separate promoters and polyadenylation signal. The present invention also provides an isolated nucleic acid molecule comprising a tandem vector having a nucleotide sequence encoding two receptors, wherein the first receptor comprises CRF2-12 and the second receptor is an R2 type receptor, and wherein the expression of each receptor is controlled by separate promoters and polyadenylation signals. The present invention also provides an isolated nucleic acid molecule comprising any of the above tandem vectors, wherein the R2 type receptor comprises CRF2-4. The present invention also provides an isolated nucleic acid molecule comprising the tandem vector pEF-CRF2-12/γR1+CRF2-4. The present invention also provides an isolated nucleic acid molecule comprising a nucleotide sequence complementary to any of these nucleotide sequences.

The present invention also provides isolated nucleic acid molecules comprising a polynucleotide encoding at least a portion of one of the IFN-λ polypeptides having the complete amino acid sequence shown of SEQ ID NOS: 8, 10 and 12.

The nucleotide sequence determined by sequencing the IFN-λ1 clone, which is shown in FIG. 16 (SEQ ID NO: 7), contains an open reading frame encoding a full length polypeptide of 200 amino acid residues, including an initiation codon encoding an N-terminal methionine.

The nucleotide sequence determined by sequencing the IFN-λ2 clone, which is shown in FIG. 17 (SEQ ID NO: 9), contains an open reading frame encoding a full length polypeptide of 196 amino acid residues, including an initiation codon encoding an N-terminal methionine.

The nucleotide sequence determined by sequencing the IFN-λ3 clone, which is shown in FIG. 18 (SEQ ID NO: 11), contains an open reading frame encoding a full length polypeptide of 196 amino acid residues, including an initiation codon encoding an N-terminal methionine.

The present invention also provides isolated nucleic acid molecules encoding the complete amino acid sequence excepting the N-terminal methionine shown in SEQ ID NOS: 8, 10 and 12, which molecules also can encode additional amino acids fused to the N-terminus of the amino acid sequences of IFN-λ1, IFN-λ2 and/or IFN-λ3.

Another aspect of the invention provides an isolated nucleic acid molecule comprising a nucleotide sequence encoding the IFN-λ1 polypeptide having the complete amino acid sequence of SEQ ID NO: 8. Another aspect of the invention provides an isolated nucleic acid molecule comprising a nucleotide sequence encoding the IFN-λ1 polypeptide having the complete amino acid sequence of SEQ ID NO: 8 excepting the N-terminal methionine (i.e., residues 2-200 of SEQ ID NO: 8). Another aspect of the invention provides an isolated nucleic acid molecule comprising a nucleotide sequence encoding the mature IFN-λ1 polypeptide shown as residues 23-200 of SEQ ID NO: 8. Another aspect of the invention provides an isolated nucleic acid molecule comprising a nucleotide sequence of the genomic fragment encoding the complete IFN-λ1 gene contained in plasmid pEF-FL-IFN-2d gene. Another aspect of the invention provides an isolated nucleic acid molecule comprising a nucleotide sequence encoding the complete polypeptide encoded by the cDNA contained in plasmid pEF-FL-IFN-λ1; a nucleotide sequence encoding the mature polypeptide encoded by the human cDNA contained in plasmid pEF-FL-IFN-λ1. Another aspect of the invention provides an isolated nucleic acid molecule comprising a nucleotide sequence complementary to any of these nucleotide sequences.

Another aspect of the invention provides an isolated nucleic acid molecule comprising a nucleotide sequence encoding the IFN-λ2 polypeptide having the complete amino acid sequence of SEQ ID NO: 10. Another aspect of the invention provides an isolated nucleic acid molecule comprising a nucleotide sequence encoding the IFN-λ2 polypeptide having the complete amino acid sequence of SEQ ID NO: 10 excepting the N-terminal methionine (i.e., residues 2-196 of SEQ ID NO: 10). Another aspect of the invention provides an isolated nucleic acid molecule comprising a nucleotide sequence encoding the mature IFN-λ2 polypeptide shown as residues 23-196 of SEQ ID NO: 10. Another aspect of the invention provides an isolated nucleic acid molecule comprising a nucleotide sequence encoding IFN-λ2 polypeptide (residues M12-196 of SEQ ID NO: 10). Another aspect of the invention provides an isolated nucleic acid molecule comprising a nucleotide sequence encoding IFN-λ2 polypeptide residues AB-196 of SEQ ID NO: 10. Another aspect of the invention provides an isolated nucleic acid molecule comprising a nucleotide sequence encoding the mature IFN-λ2 polypeptide shown as residues P31-196 of SEQ ID NO: 10. Another aspect of the invention provides an isolated nucleic acid molecule comprising a nucleotide sequence encoding IFN-λ2 polypeptide (residues M92-196 of SEQ ID NO: 10). Another aspect of the invention provides an isolated nucleic acid molecule comprising a nucleotide sequence encoding IFN-λ2 polypeptide residues A93-196 of SEQ ID NO: 10. Another aspect of the invention provides an isolated nucleic acid molecule comprising a nucleotide sequence encoding the mature IFN-λ2 polypeptide shown as residues P31-196 of SEQ ID NO:10. Another aspect of the invention provides an isolated nucleic acid molecule comprising a nucleotide sequence of the genomic fragment encoding the complete IFN-λ2 gene contained in plasmid pEF-FL-IFN-λ2 gene. Another aspect of the invention provides an isolated nucleic acid molecule comprising a nucleotide sequence encoding a polypeptide encoded by the cDNA contained in plasmid pEF-FL-IFN-λ2 gene. Another aspect of the invention provides an isolated nucleic acid molecule comprising a nucleotide sequence encoding the mature polypeptide encoded by the cDNA contained in clone pEF-FL-IFN-λ2. Another aspect of the invention provides an isolated nucleic acid molecule comprising a nucleotide sequence complementary to any of these nucleotide sequences.

Another aspect of the invention provides an isolated nucleic acid molecule comprising a nucleotide sequence encoding the IFN-λ3 polypeptide having the complete amino acid sequence of SEQ ID NO: 12. Another aspect of the invention provides an isolated nucleic acid molecule comprising a nucleotide sequence encoding the IFN-λ3 polypeptide having the complete amino acid sequence of SEQ ID NO: 12 excepting the N-terminal methionine (i.e., residues 2-196 of SEQ ID NO: 12). Another aspect of the invention provides an isolated nucleic acid molecule comprising a nucleotide sequence encoding the mature IFN-λ3 polypeptide shown as residues P23-196 of SEQ ID NO: 12. Another aspect of the invention provides an isolated nucleic acid molecule comprising a nucleotide sequence encoding IFN-λ3 polypeptide (residues M6-196 of SEQ ID NO: 12). Another aspect of the invention provides an isolated nucleic acid molecule comprising a nucleotide sequence encoding IFN-λ3 polypeptide (residues MI 2-196 of SEQ ID NO: 12). Another aspect of the invention provides an isolated nucleic acid molecule comprising a nucleotide sequence encoding IFN-λ3 polypeptide residues P7-196 of SEQ ID NO: 12. Another aspect of the invention provides an isolated nucleic acid molecule comprising a nucleotide sequence encoding IFN-λ3 polypeptide residues A13-196 of SEQ ID NO: 12. Another aspect of the invention provides an isolated nucleic acid molecule comprising a nucleotide sequence encoding the mature IFN-λ3 polypeptide shown as residues P31-196 of SEQ ID NO: 12. Another aspect of the invention provides an isolated nucleic acid molecule comprising a nucleotide sequence of the genomic fragment encoding the complete IFN-λ3 gene contained in plasmid pEF-FL-IFN-λ3 gene. Another aspect of the invention provides an isolated nucleic acid molecule comprising a nucleotide sequence encoding a polypeptide encoded by the cDNA contained in plasmid pEF-FL-IFN-λ3. Another aspect of the invention provides an isolated nucleic acid molecule comprising a nucleotide sequence encoding a mature polypeptide encoded by the cDNA contained in plasmid pEF-FL-IFN-λ3. Another aspect of the invention provides an isolated nucleic acid molecule comprising a nucleotide sequence complementary to any of these nucleotide sequences.

The invention also provides isolated nucleic acid molecules comprising a polynucleotide encoding at least a portion of one of the IFN-λ polypeptides described in the "Polypeptides" section of the present disclosure.

Further embodiments of the invention include isolated nucleic acid molecules that comprise a polynucleotide having a nucleotide sequence at least 80%, 85%, or 90% identical, more preferably at least 91%, 92%, 93%, and 94% and most preferably at least 95%, 96%, 97%, 98% or to any of the nucleotide sequences, above, or a polynucleotide which hybridizes under stringent hybridization conditions to a polynucleotide of the present invention. This polynucleotide of the present invention, which hybridizes under stringent conditions does not hybridize to a polynucleotide having a nucleotide sequence consisting of only A residues or of only T residues. An additional nucleic acid embodiment of the invention relates to an isolated nucleic acid molecule comprising a polynucleotide that encodes the amino acid sequence of an epitope-bearing portion of a polypeptide having an amino acid sequence described above.

A further aspect of the invention is a DNA sequence that represents the complete upstream and downstream regulatory regions of the genes of the present invention. DNA constructs containing the regulatory region are also provided. Further, host cells comprising such constructs, which cells are in vitro or in vivo, are also encompassed by the present invention.

The present invention also relates to recombinant vectors, which include the isolated nucleic acid molecules of the present invention, to host cells containing the recombinant vectors, as well as to methods of making such vectors and host cells and for using them for production of polypeptides or peptides of the present invention by recombinant techniques.

Leader and Mature Sequences

The amino acid sequence of the complete proteins of the present invention includes a leader sequence and a mature protein, as shown in FIGS. 14A and 19A. Accordingly, the present invention provides nucleic acid molecules encoding a mature form of the proteins of the present invention having the polypeptide sequence of SEQ ID NOS: 2, 6, 8, 10 and/or 12. Polynucleotides encoding the mature forms are also encompassed by the invention.

According to the current understanding in the art, once export of a growing protein chain across the rough endoplasmic reticulum has been initiated, proteins secreted by mammalian cells have the signal or secretory leader sequence cleaved from the complete polypeptide to produce a secreted "mature" form of the protein. In some instances, proteins having a signal or leader sequence may be retained intracellularly or at the cell surface. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequences encoding mature polypeptides of the present invention having the amino acid sequence encoded by the human cDNA in clones pEF-FL-IFN-λ1, pEF-FL-IFN-λ2 and/or pEF-FL-IFN-λ3 and genomic fragments encoded by pEF-FL-IFN-λ1 gene, pEF-FL-IFN-λ2 gene and/or pEF-FL-IFN-λ3 gene. By the "mature polypeptides" of the present invention having the amino acid sequence encoded by the human cDNA in clones pEF-FL-IFN-λ1, pEF-FL-IFN-λ2 and/or pEF-FL-IFN-λ3 and genomic fragments encoded by pEF-FL-IFN-λ1 gene, pEF-FL-IFN-λ2 gene and/or pEF-FL-IFN-λ3 gene is meant the mature form(s) of the proteins of the present invention produced by expression in a mammalian cell (e.g., COS cells, as described below) from the open reading frame encoded by the human DNA sequence of the clone contained in the vector or a portion of the DNA sequence of the clone contained in the vector fused to a heterologous signal sequence.

Methods for predicting whether a protein has a secretory leader as well as the cleavage point for that leader sequence are available. For instance, the method of McGeoch (Virus Res. 3:271-286 (1985)) uses the information from a short N-terminal charged region and a subsequent uncharged region of the complete (uncleaved) protein. The method of von Heinje (Nucleic Acids Res. 14:4683-4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75-80% (von Heinje, supra). However, the two methods do not always produce the same predicted cleavage point(s) for a given protein.

As indicated, nucleic acid molecules of the present invention may be in the form of RNA, or in the form of DNA. The DNA may be double-stranded or single-stranded. Single-stranded DNA or RNA may be the coding strand, also known as the sense strand, or it may be the non-coding strand, also referred to as the anti-sense strand.

In a further embodiment, polynucleotides of the invention comprise a portion of the coding sequences. In another embodiment, the polynucleotides comprising coding sequences do not contain coding sequences of a genomic flanking gene (i.e., 5' or 3' to the genes of the present invention of interest in the genome).

In addition, isolated nucleic acid molecules of the invention include DNA molecules which comprise a sequence substantially different from those described above but which, due to the degeneracy of the genetic code, still encodes a polypeptides of the present invention of the present invention. Of course, the genetic code and species—specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*, yeast, bacillus, plants, or any other effective host).

Treatment

The IFN-λ compositions of the present invention have been shown to activate the CRF2-12 receptor and receptor complex of the present invention, activating many of the same signal-transduction pathway elements as treatment with IFN-α. However the CRF2-12 receptor and receptor complex of the present invention is not responsive to IFN-α or β. Accordingly, IFN-λ compositions of the present invention should have a clinical advantage to treatment with other interferons. One of these advantages derives from the widespread presence of receptors responsive to IFN-λs, particularly since there is an area of non-overlap between the IFN-α/β receptor complex distribution and the IFN-λ receptor complex distribution. Accordingly, the compositions of the present invention may encounter greater clinically efficacy for certain therapies, known in the art, for which this family of cytokines has been found to be useful. Some of these uses are listed in U.S. Pat. No. 6,472,512, which is incorporated herein by reference in its entirety.

Thus, the invention provides a method of treatment of an individual in need of an increased level of interferon activity comprising administering to such an individual a pharmaceutical composition of the present invention in an amount effective to increase the interferon activity level in such an individual.

Compositions of the invention may also be useful in treating diseases, disorders, and/or conditions of the immune system. Therefore, it will be appreciated that conditions caused by a decrease in the standard or normal level of interferon activity in an individual, particularly disorders of the immune system, can be treated by administration of polynucleotides, polypeptides, or agonists or antagonists of the compositions of the present invention. Thus, the invention also provides a method of treatment of an individual in need of an increased level of interferon activity comprising administering to such an individual a pharmaceutical composition comprising a therapeutic amount of polynucleotides, polypeptides, or agonists or antagonists of compositions of the present invention, effective to increase the interferon activity level in such an individual.

Particularly preferred is treatment of individuals that, for any reason, but preferably one unrelated to the effectiveness of IFNλ, are unresponsive to IFN-α, IFN-β, IFN-omega, KDI, and other cytokines or interferons.

Particularly preferred are conditions that may be treated, prevented, ameliorated or diagnosed through the biological effects of a composition of the present invention. These include, for example, conditions responsive to modulation of the JAK-Stat pathway; conditions responsive to modulation of the ISFG-3 complex; and other such activities modulated by receptors responsive to polypeptides and fragments of the present invention, preferably CRF2-12 and the CRF2-12 receptor complex.

In another embodiment, the allelic type of an individual may be determined for a gene or combination of genes of the present invention. The allelic type may be used in the treatment, prevention, amelioration or diagnosis of disorders related to the compositions of the present invention. For example, it may be determined that an individual has an allelic type that is non-functional. In such case, administration of a functional composition in accordance with the present invention would be effective in the treatment of the diagnosed condition. In another embodiment, the allelic type is determined prior to administration of a composition of the present invention, and the allelic type administered is matched to the allelic type of the individual to which the composition is to be administered. In such manner, immune reactions may be avoided against the composition, or the incidence of such occurrences decreased.

The allelic type of an individual may be determined in any effective manner. For example, the following techniques may be useful in such determination: immunotyping of material from the individual, measurement of biological effects of material obtained from the individual, PCR of genomic or other effective nucleic acid from the individual, RT-PCR of mRNA or other effective nucleic acid from the individual (e.g., from a biopsy, or the like), RFLP, repeat polymorphism linkage (ca repeats, or the like), sequencing, hybridization, or any other effective technique.

Compositions of the present invention may be used clinically for any anti-viral therapy for which they are effective. For example, in the treatment of AIDS, viral hepatitis including chronic hepatitis B, hepatitis C, papilloma viruses (e.g., condylomaacuminatum, laryngeal papillomatosis), viral encephalitis, and in the prophylaxis of rhinitis and respiratory infections.

In a specific embodiment, compositions of the present invention are useful in the treatment, prevention, detection and/or diagnosis of an unregulated growth, e.g., a cancer, some examples would include hairy cell leukemia, bladder carcinoma, cervical carcinoma, acute myeloid leukemia, osteosarcoma, basal cell carcinoma, glioma, renal cell carcinoma, multiple myeloma, melanoma, and Hodgkin's disease.

Compositions of the present invention are believed to be capable of stimulating natural killer cell activity. Accordingly, they may be used to treat any infection for which they are effective. Among the conditions that may find useful treatment by the present invention are *Cryptosporidium parvum* infection and multidrug-resistant pulmonary tuberculosis.

Compositions of the present invention are also believed to be useful as immunotherapeutic agents. Depending on whether an agonist or antagonist is used, the effect the compositions of the present invention may find use as immunosuppressive or immunoenhancing agents.

Because of their immunomodulatory function, compositions of the present invention may find use as a protective agents when administered prior to chemotherapy. They may also find use in treatment of hyperproliferation of lymphocytes, myeloid progenitors and bone marrow stem cells, as occurs, for example, in chronic myelogenous leukemia.

The compositions of the present invention may also find use in the prevention of graft vs. host rejection, or to curtail the progression of autoimmune diseases, such as arthritis, multiple sclerosis, systemic lupus or diabetes. The polynucleotides, polypeptides, or agonists or antagonists of the present invention are also useful in the treatment of allergies in mammals, e.g., by inhibiting the humoral response.

Compositions of the present invention may be used as an adjuvant or coadjuvant to enhance or stimulate the immune response in cases of prophylactic or therapeutic vaccination.

Further, there is provided a method of treating infection in a patient comprising administering an effective amount of a composition of the present invention to a patient in need of anti-infective therapy. In a preferred embodiment the infection is of viral, bacterial, or parasitic etiology. In a particularly preferred embodiment, the infection is a viral infection.

Further, there is provided a method of treating cancer in a patient comprising administering an effective amount of a composition of the present invention to a patient in need of anti-cancer therapy.

Further, there is provided a method of immunotherapy in a patient comprising administering an effective amount of a composition of the present invention to a patient in need of immunotherapy.

Compositions of the present invention, may be useful in treating diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, compositions of the present invention, can be used as a marker or detector of a particular immune system disease or disorder.

Compositions of the present invention may be useful in treating, preventing, and/or diagnosing diseases, disorders, and/or conditions of hematopoietic cells. Compositions of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxiatelangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, compositions of the present invention can also be used to modulate hemostatic (the stopping of bleeding) or thrombolytic activity (clot formation). For example, by increasing hemostatic or thrombolytic activity, Compositions of the present invention could be used to treat or prevent blood coagulation diseases, disorders, and/or conditions (e.g., a fibrinogenemia, factor deficiencies), blood platelet diseases, disorders, and/or conditions (e.g. thrombocytopenia), or wounds resulting from trauma, surgery, or other causes. Alternatively, Compositions of the present invention that can decrease hemostatic or thrombolytic activity could be used to inhibit or dissolve clotting. These molecules could be important in the treatment or prevention of heart attacks (infarction), strokes, or scarring.

Compositions of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of compositions of the present invention that can inhibit an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the compositions of the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated, prevented, and/or diagnosed by compositions of the present invention. Moreover, these molecules can be used to treat anaphylaxis, hypersensitivity to an antigenic molecule, or blood group incompatibility.

Compositions of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of compositions of the present invention that inhibits an immune response, particularly the proliferation, differentiation, or chemotaxis of T-cells, may be an effective therapy in preventing organ rejection or GVHD.

Similarly, compositions of the present invention may also be used to modulate inflammation. For example, compositions of the present invention may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

Compositions of the present invention can be used to treat, prevent, and/or diagnose hyperproliferative diseases, disorders, and/or conditions, including neoplasms. Compositions of the present invention may inhibit the proliferation of the disorder through direct or indirect interactions. Alternatively, compositions of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by using compositions of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by compositions of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative diseases, disorders, and/or conditions by inserting into an abnormally proliferating cell a polynucleotide of the present invention, wherein said polynucleotide represses said expression.

Another embodiment of the present invention provides a method of treating cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding a polynucleotide of the present invention is inserted into cells to be treated utilizing a retrovirus, or more preferrably an adenoviral vector (See G J. Nabel, et. al., PNAS 199996: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention concurrently to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art. As used herein, the term "concurrently" has the same meaning as its definition of U.S. Pat. No. 6,248,725, which is incorporated herein by reference in its entirety.

The present invention is further directed to antibody-based therapies which involve administering of anti-polypeptides and anti-polynucleotide antibodies to a mammalian, preferably human, patient for treating one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail herein. Those of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against a composition of the present invention, fragments or regions thereof, for both immunoassays and therapy of diseases, disorders, and/or conditions related to compositions of the present invention. Such antibodies, fragments, or regions, will preferably have an affinity for polynucleotides or polypeptides, including fragments thereof. Preferred binding affinities include those with a dissociation constant or Kd less than $5\times10^{-6}$ M, $10^{-6}$ M, $5\times10^{-7}$ M, $10^{-7}$M, $5\times10^{-8}$ M, $10^{-8}$M, $5\times10^{-9}$ M, $10^{-9}$ M, $5\times10^{-10}$ M, $10^{-10}$ M, $5\times10^{-11}$ M, $10^{-11}$ M, $5\times10^{-12}$M, $10^{-12}$ M, $5\times10^{-13}$ M, $10^{-13}$M, $5\times10^{-14}$ M, $10^{-14}$ M, $5\times10^{-15}$ M, and $10^{-15}$ M.

Moreover, polypeptides of the present invention may find one inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to compositions of the present invention may also result in inhibition of angiogenesis directly, or indirectly (See Witte L, et al., Cancer Metastasis Rev. 17(2):155-61 (1998), which is hereby incorporated by reference)).

Compositions of the present invention may be useful in inhibiting proliferative cells or tissues through the induction of apoptosis. Said compositions may act either directly, or indirectly to induce apoptosis of proliferative cells and tissues. Moreover, in another preferred embodiment of the present invention, said compositions, either alone or in combination with small molecule drugs or adjuvants, such as apoptonin, galectins, thioredoxins, antiinflammatory proteins may induce apoptosis through other mechanisms, such as in the activation of other proteins which will activate apoptosis, or through stimulating the expression of said proteins, (See for example, Mutat Res 400(1-2):447-55

(1998), Med Hypotheses. 50(5):423-33 (1998) Biol Interact. April 24; 111-112:23-34 (1998), J Mol Med. 76(6):402-12 (1998), Int J Tissue React; 20(1):3-15 (1998), which are all hereby incorporated by reference).

Compositions of the present invention are useful in inhibiting the metastasis of proliferative cells or tissues. Such therapeutic affects of the present invention may be achieved either alone, or in combination with small molecule drugs or adjuvants.

Compositions of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Nucleic acids of the present invention may be used to treat, prevent, and/or diagnose cardiovascular diseases, disorders, and/or conditions, including peripheral artery disease, such as limb ischemia. Other disorders listed in U.S. Pat. No. 6,472,512.

The present invention provides for treatment of diseases, disorders, and/or conditions associated with neovascularization by administration of a composition of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a composition of the invention. For example, polynucleotides, polypeptides, antagonists and/or agonists may be utilized in a variety of additional methods in order to therapeutically treat or prevent a cancer or tumor. Cancers which may be treated or diagnosed with compositions of the present invention are listed in U.S. Pat. No. 6,472,512, which is incorporated herein by reference in its entirety.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily.

The compositions of the present invention may also be administered along with other anti-angiogenic factors. Representative examples of other anti-angiogenic factors include: Anti-invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-I, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxyderivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267: 17321-17326, 1992); Chymostatin (Tomkinson et al., Biochem J. 286:475-480, 1992); Cyclodextrin Tetradecasulfate; Eponemycin; Campto thecin; Fumagillin (Ingber et al., Nature 348:555-557, 1990); Gold Sodium Thiomalate ("GST"; Matsubara and Ziff. J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynainiolmidazole; and metalloproteinase inhibitors such as BB94.

Diseases at the Cellular Level

Diseases associated with increased cell survival or the inhibition of apoptosis that could be treated, prevented, and/or diagnosed by compositions of the present invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as papilloma viruses, hepatitis virus, herpes viruses, pox viruses and adenoviruses), inflammation, graft v. host disease, acute graft rejection, and chronic graft rejection. In preferred embodiments, polynucleotides, polypeptides, agonists and/or antagonists of the present invention are used to inhibit growth, progression, and/or metasis of cancers, in particular those listed above.

Additional diseases or conditions associated with increased cell survival that could be treated, prevented, and/or diagnosed by a composition of the present invention include, but are not limited to, progression, and/or metastases of malignancies and related diseases, disorders, and/or conditions such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., fungoides mycosis, Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by a composition of the present invention include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing a composition of the present invention, for therapeutic purposes, for example, to stimulate epithelial cell proliferation and basal keratinocytes for the purpose of wound healing, and to stimulate hair follicle production and healing of dermal wounds. Compositions of the present invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Compositions of the present invention, could be used to promote dermal reestablishment subsequent to dermal loss.

Compositions of the present invention could be used to increase the adherence of skin grafts to a wound bed and to stimulate re-epithelialization from the wound bed. Other uses of the compositions of the present invention as they relate to wound healing and epithelial cell proliferation are listed in U.S. Pat. No. 6,472,512, which is incorporated herein by reference in its entirety.

Neurological Diseases

Nervous system diseases, disorders, and/or conditions, which can be treated with compositions of the present invention, include, but are not limited to, nervous system injuries, and diseases, disorders, and/or conditions which result in either a disconnection of axons, a diminution or degeneration of neurons, or demyelination. Nervous system lesions which may be treated in a patient (including human and non-human mammalian patients) Other uses of the compositions of the present invention as they relate to treatment of nervous system related conditions are listed in U.S. Pat. No. 6,472,512, which is incorporated herein by reference in its entirety.

In a specific embodiment, polynucleotides or polypeptides, as well as agonists or antagonists of the present invention of the invention are used to treat, prevent, detect, and/or diagnose multiple sclerosis.

The compositions of the invention which are useful for treating, preventing, and/or diagnosing a nervous system disorder may be selected by testing for biological activity in promoting the survival or differentiation of neurons. For example, and not byway of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

Infectious Disease

Compositions of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, compositions of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-11, Lentivirus), and Togaviridae (e.g., Rubivirus). Viruses falling within these families can cause a variety of diseases or symptoms, including, but not limited to: arthritis, bronchiollitis, respiratory syncytiai virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, condyloma acuminatum, laryngeal papillomatosis, hemorrhagic fever, Measles, Mumps, Parainfluenza, Rabies, the common cold, Polio, leukemia, Rubella, sexually transmitted diseases, skin diseases (e.g., Kaposi's, warts, fungoides mycosis), and viremia. Polynucleotides or polypeptides, or agonists or antagonists of the invention, can be used to treat, prevent, and/or diagnose any of these symptoms or diseases. In specific embodiments, compositions of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment compositions of the invention are used to treat, prevent, and/or diagnose AIDS.

In a specific embodiment, compositions of the present invention can be used to treat, detect, prevent and/or diagnose diseases associated with Hepatitis virus (e.g., chronic hepatitis C, chronic hepatitis B, chronic active hepatitis, and/or hepatitis D); diseases associated with Papilloma virus (e.g., condyloma acuminatum, warts, and/or laryngeal papillomatosis).

Similarly, bacterial or fungal agents that can cause disease or symptoms and that can be treated, prevented, and/or diagnosed by a polynucleotide or polypeptide and/or agonist or antagonist of the present invention include, but are not limited to, the following Gram-Negative and Gram-positive bacteria, bacterial families and fungi: *Actinomyces* (e.g., *Norcardia*), *Acinetobacter*, *Cryptococcus neoformans*, *Aspergillus*, *Bacillaceae* (e.g., *Bacillus anthrasis*), *Bacteroides* (e.g., *Bacteroides fragilis*), *Blastomycosis*, *Bordetella*, *Borrelia* (e.g., *Borrelia burgdorferi*), *Brucella*, *Candida*, *Campylobacter*, *Chlamydia*, *Clostridium* (e.g., *Clostridium botulinum*, *Clostridium dificile*, *Clostridium perfringens*, *Clostridium tetani*), *Coccidioides*, *Corynebacterium* (e.g., *Corynebacterium diptheriae*), *Cryptococcus*, *Dermatocycoses*, *E. coli* (e.g., Enterotoxigenic *E. coli* and Enterohemorrhagic *E. coli*), *Enterobacter* (e.g. Enterobacteraerogenes), *Enterobacteriaceae* (*Klebsiella*, *Salmonella* (e.g., *Salmonella typhi*, *Salmonella enteritidis*, *Salmonella paratyphi*), *Serratia*, *Yersinia*, *Shigella*), *Erysipelothrix*, *Haemophilus* (e.g., *Haemophilus* influenza type B), *Helicobacter*, *Iegionella* (e.g., *Legionella pneumophila*), *Leptospira*, *Listeria* (e.g., *Listeria monocytogenes*), *Mycoplasma*, *Mycobacterium* (e.g., *Mycobacterium leprae* and *Mycobacterium tuberculosis*), *Vibrio* (e.g., *Vibrio cholerae*), *Neisseriaceae* (e.g., *Neisseria gonorrhea*, *Neisseria meningitidis*), *Pasteurellacea*, *Proteus*, *Pseudomonas* (e.g., *Psuedomonas aeruginosa*), Rickettsiaceae, Spirochetes (e.g., *Treponema* spp., *Leptospira* spp., *Borrelia* spp.) *Shigella* spp., *Staphylococcus* (e.g., *Staphylococcus aureus*), *Meningiococcus*, *Pneumococcus* and *Streptococcus* (e.g., *Streptococcus pneumoniae* and Groups A, B, and C Streptococci), and *Ureaplasmas*. These bacterial, parasitic, and fungal families can cause diseases or symptoms, including, but not limited to: antibiotic-resistant infections, bacteremia, endocarditis, septicemia, eye infections (conjunctivitis) tuberculosis, uveitis, gingivitis, bacterial diarrhea, opportunistic infections (e.g., AIDS related infections), paronychia, prosthesis-related infections, dental caries, Reiter's Disease, respiratory tract infections (e.g., Whooping Cough or Empyema), sepsis, Lyme Disease, Cat-Scratch Disease, dysentery, paratyphoid fever, food poisoning, *Legionella* disease, chronic and acute inflammation, erythema, yeast infections, typhoid, pneumonia, gonorrhea, meningitis (e.g., meningitis types A and B), *chlamydia*, syphilis, diphtheria, leprosy, burcellosis, peptic ulcers, anthrax, spontaneous abortion, birth defects, lung infections, ear infections, deafness, blindness, lethargy, malaise, vomiting, chronic diarrhea, Crohn's disease, colitis, vaginosis, sterility, pelvic inflammatory disease, candidiasis, paratuberculosis, tuberculosis, lupus, botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections or noscomial infections. Compositions of the invention, can be used to treat or detect any of these symptoms or diseases. In specific embodiments.

Moreover, parasitic agents causing disease or symptoms that can be treated, prevented, and/or diagnosed by a composition of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, theileriasis, Toxoplasmosis, Trypanosomiasis, and *Trichomonas* and *Sporozoans* (e.g., *Plasmodium virax*, *Plasmodium falciparium*, *Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis.

Preferably, treatment or prevention using a composition of the present invention could either be by administering an effective amount of a polypeptide to the patient, or by removing cells from the patient, supplying the cells with a composition of the present invention, and returning the cells to the patient (ex vivo therapy).

Regeneration

Compositions of the present invention can be used to differentiate, proliferate, and attract cells, leading to the regeneration of tissues. (See, Science 276:59-87 (1997).) the regeneration of tissues could be used to repair, replace, or protect tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, compositions of the present invention may increase regeneration of tissues difficult to heal. For example, increased tendon/ligament regeneration would quicken recovery time after damage. Compositions of the present invention of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using Compositions of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using Compositions of the present invention.

Chemotaxis

Compositions of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Compositions of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotactic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that Compositions of the present invention may inhibit chemotactic activity. These molecules could also be used to treat, prevent, and/or diagnose diseases, disorders, and/or conditions. Thus, Compositions of the present invention could be used as an inhibitor of chemotaxis.

Formulations

The compositions of the present invention may be formulated and dosed in any effective manner consistent with good medical practice, taking into account the clinical condition of the individual patient (especially the side effects of treatment with the polypeptide alone), the site of delivery of the polypeptide composition, the method of administration, the scheduling of administration, and other factors known to practitioners. The "effective amount" of polypeptide to be administered may be determined by such considerations.

One embodiment of the present invention provides for pharmaceutical compositions comprising a polypeptide of the present invention. The invention also provides for pharmaceutical compositions comprising combinations of polypeptides of the present invention. In one embodiment, the invention provides for a pharmaceutical compositions comprising a combination of polypeptides of the present invention, wherein the ratio of IFN-$\lambda$1:IFN-$\lambda$2:IFN-$\lambda$3 is described by the formula m:n:o, wherein m may be any number between 0 and 1000, n may be any number between 0 and 1000 and o may be any number between 0 and 1000, and wherein at least one of m, n or o is different from 0. The invention also provides for pharmaceutical compositions comprising a combination of polypeptides of the present invention, wherein the ratio of IFN-$\lambda$1:IFN-$\lambda$2:IFN$\lambda$3 is described by the formula m:n:o, wherein m may be any number between 0 and 1000, n may be any number between 0 and 1000 and o may be any number between 0 and 1000, and wherein at least two of m, n or o are different from 0. The invention further provides for pharmaceutical compositions comprising a combination of polypeptides of the present invention, wherein the ratio of IFN-$\lambda$1:IFN-$\lambda$2:IFN-$\lambda$3 is described by the formula m:n:o, wherein m may be any number between 0 and 1000, n may be any number between 0 and 1000 and o may be any number between 0 and 1000, and wherein all three of m, n and o are different from 0. The combination may further comprise antibodies of the present invention. The combination may also further comprise an agonist and/or antagonist, or a combination of agonists and/or antagonists of the CRF2-12 receptor or the CRF2-12 receptor complex. In a preferred embodiment, the combination further comprises an antibody to the extracellular domain of CRF2-12 that acts as an agonist of the CRF2-12 receptor or the CRF2-12 receptor complex. The combination may further comprise other cytokines, interleukins and/or other pharmaceuticals, including anti-inflamatory agents.

The invention also provides for pharmaceutical compositions comprising an antibody of the present invention. The invention also provides for pharmaceutical compositions comprising combinations of antibodies of the present invention. In one embodiment, the invention provides a composition comprising a combination of anti-IFN-$\lambda$1 specific antibody, anti-IFN$\lambda$2 specific antibody and anti-IFN-$\lambda$3 specific antibody, wherein the ratio of anti-IFN-$\lambda$1 specific antibody:anti-IFN-$\lambda$2 specific antibody:anti-IFN-$\lambda$3 specific antibody is described by the formula x:y:z, wherein x may be any number between 0 and 1000, y may be any number between 0 and 1000 and z may be any number between 0 and 1000, and wherein at least one of x, y or z is different from 0. The invention also provides for pharmaceutical compositions comprising a combination of anti-IFN-λ1 specific antibody, anti-IFN-λ2 specific antibody and anti-IFN-λ3 specific antibody, wherein the ratio of anti-IFN-?J specific antibody:anti-IFN-λ2 specific antibody:anti-IFN-λ3 specific antibody is described by the formula x:y:z, wherein x may be any number between 0 and 1000, y may be any number between 0 and 1000 and z may be any number between 0 and 1000, and wherein at least two of x, y or z are different from 0. The invention also provides for pharmaceutical composition comprising a combination of anti-IFN-λ1 specific antibody, anti-IFN-λ2 specific antibody and anti-IFN-λ3 specific antibody, wherein the ratio of anti-IFN-λ1 specific antibody:anti-IFN-λ2 specific antibody:anti-IFN-λ3 specific antibody is described by the formula x:y:z, wherein x may be any number between 0 and 1000, y may be any number between 0 and 1000 and z may be any number between 0 and 1000, and wherein all three of x, y or z are different from 0. The combination may further comprise an IFN-λ or a combination of IFN-λs of the present invention. The combination may also further comprise an agonist and/or antagonist, or a combination of agonists and/or antagonists of the CRF2-12 receptor or the CRF2-12 receptor complex. In a preferred embodiment, the combination further comprises an antibody to the extracellular domain of CRF2-12 that acts as an agonist of the CRF2-12 receptor or the CRF2-12 receptor complex. The combination may further comprise other cytokines, interleukins and/or other pharmaceuticals, including anti-inflamatory agents.

Any effective amount of the polypeptides or polypeptide fragments of the present invention may be administered to an individual in need thereof. As a general proposition, the total pharmaceutically effective amount administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the composition is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the polypeptides or polypeptide fragments of the invention may be administered by any effective route, including, for example, orally, rectally, parenterally, intracisternally, intravaginally, intraperitoneally, topically (as by powders, ointments, drops or transdermal patch), bucally, or as an oral or nasal spray.

By "pharmaceutically acceptable carrier" is meant any effective pharmaceutically acceptable carriera, preferably a non-toxic solid, semisolid or liquid filler, diluent, encapsulating material or formulation auxiliary of any type.

The term "parenteral" as used herein refers to any effective parenteral mode of administration, including modes of administration such as intravenous, intramuscular, intraperitoneal, intrasternal, subcutaneous and intraarticular injection and infusion.

The compositions may also suitably be administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(-)-3-hydroxybutyric acid (EP 133,988).

In a preferred embodiment, compositions of the invention are formulated in a biodegradable, polymeric drug delivery system, for example as described in U.S. Pat. Nos. 4,938,763; 5,278,201; 5,278,202; 5,324,519; 5,340,849; and 5,487,897 and in International Publication Numbers WO01/35929, WO00/24374, and WO00/06117 which are hereby incorporated by reference in their entirety. In specific preferred embodiments the compositions of the invention are formulated using the ATRIGEL Biodegradable System of Atrix Laboratories, Inc. (Fort Collins, Colo.).

Examples of biodegradable polymers which can be used in the formulation of compositions of the present invention, include but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), polyvinylpyrrolidone, polyethylene glycol, polyhydroxycellulose, chitin, chitosan, and copolymers, terpolymers, or combinations or mixtures of the above materials. The preferred polymers are those that have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility. In specific preferred embodiments, the biodegradable polymers which can be used in the formulation of compositions are poly(lactide-co-glycosides).

Polymer properties such as molecular weight, hydrophobicity, and lactide/glycolide ratio may be modified to obtain the desired drug release profile (See, e.g., Ravivarapu et al., Journal of Pharmaceutical Sciences 89:732-741 (2000), which is hereby incorporated by reference in its entirety).

It is also preferred that the solvent for the biodegradable polymer be non-toxic, water miscible, and otherwise biocompatible. Examples of such solvents include, but are not limited to, N-methyl-2-pyrrolidone, 2-pyrrolidone, C2 to C6 alkanols, C1 to C15 alcohols, dils, triols, and tetraols such as ethanol, glycerine propylene glycol, butanol; C3 to C15 alkyl ketones such as acetone, diethyl ketone and methyl ethyl ketone; C3 to C15 esters such as methyl acetate, ethyl acetate, ethyl lactate; alkyl ketones such as methyl ethyl ketone, C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, 1-dodecylazacycloheptan-2-one, Other preferred solvents are benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of the solvating ability and their compatibility.

Additionally, formulations comprising compositions of the present invention and a biodegradable polymer may also include release-rate modification agents and/or pore-forming agents. Examples of release-rate modification agents include, but are not limited to, fatty acids, triglycerides, other like hydrophobic compounds, organic solvents, plasticizing compounds and hydrophilic compounds. Suitable release rate modification agents include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebeca'te, and the like; polyhydroxy alcohols, such as propylene glycol, polyethylene glycol, glycerin, sorbitol, and the like; fatty acids; triesters of glycerol, such as triglycerides, epoxidized soybean oil, and other epoxidized vegetable oils; sterols, such as cholesterol; alcohols, such as C6-C12 alkanols, 2-ethoxyethanol. The release rate modification agent may be used singly or in combination with other such agents. Suitable combinations of release rate modification agents include, but are not limited to, glycerin/propylene glycol, sorbitol/glycerine, ethylene oxide/propylene oxide, butylene glycol/adipic acid, and the like. Preferred release rate modification agents include, but are not limited to, dimethyl citrate, triethyl citrate, ethyl heptanoate, glycerin, and hexanediol. Suitable pore-forming agents that may be used in the polymer composition include, but are not limited to, sugars such as sucrose and dextrose, salts such as sodium chloride and sodium carbonate, polymers such as hydroxylpropylcellulose, carboxymethylcellulose, polyethylene glycol, and polyvinylpyrrolidone. Solid crystals that will provide a defined pore size, such as salt or sugar, are preferred.

In specific preferred embodiments the compositions of the invention are formulated using the BEMA BioErodible Mucoadhesive System, MCA MucoCutaneous Absorption System, SMP Solvent MicroParticle System, or BCP Bio-Compatible Polymer System of Atrix Laboratories, Inc. (Fort Collins, Colo.).

Sustained-release compositions also include liposomally entrapped polypeptides. Liposomes containing a polypeptide of the present invention are prepared by methods known, for example: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for effective polypeptide therapy.

A liposomally entrapped polypeptide of the present invention can be produced for clinically effective formulations. Modified interferons, such as PEGINTRON (Schering-Plough INTRON) are clinically effective and can be used in therapies with other agents, such as Ribavirin.

The polypeptide of the present invention may be administered in combination with other known anti-viral, immunomodulatory and anti-proliferative therapies, such as IL-2, alpha interferon, KDI, Ribavirin and temozolomide.

For parenteral administration, in one embodiment, the polypeptide of the invention is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers may result in the formation of polypeptide salts.

Polypeptide to be used for therapeutic administration must be sterile. Sterility may be achieved in any effective manner. For example, by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

Compositions of the present invention ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Having generally described the invention, the same will be more readily understood by reference to the following examples, which are provided by way of illustration and are not intended as limiting.

EXAMPLES

Example 1: Cloning of the CRF2-12 cDNA, Expression Pattern and Protein Characterization A search of the GenBank database was performed with the TBLASTN program using as a query a consensus amino acid motif shared by extracellular domains of class II cytokine receptor family members. A genomic fragment from human chromosome 1 encoding a novel amino acid (a.a.) sequence with homology to the consensus motif was identified. This genomic fragment mapped in the vicinity of a known member of the family, namely, the IL-22R1 (CRF2-9) gene (1p36+11 chromosomal region).

According to the present invention this fragment represented an exon of a novel receptor from this family of receptors.

The existence of a gene (Hs1_4548_30_10_1) in this region was predicted by GenomeScan (NCBI web site)(5). However, according to the present invention the last four exons were predicted incorrectly by the program, and the last exon encoding intracellular domain of the receptor of the present invention is different and distinct from that provided by GenomeScan.

Several ESTs were positioned in this genomic region representing the 3' untranslated region (3'-UTR) of a novel gene (the UniGene designation Hs.105866), which we predicted to be contingent with the Hs1_4548_30_10_1 gene.

In accordance with the present invention, several sets of primers were designed and used for RT-PCR with several human cDNA libraries as a template to obtain the receptor of the present invention. The primers and a human placental cDNA library (Clontech, catalog # HL4025AH) were used to obtain the genomic organization and exon-intron junctions of the CRF2-12 gene.

Primers
    (R12-10 forward primer, R12-10F; SEQ ID NO: 17)
5'-CCAGAACTTCAGCGTGTACCTGAC-3', (R12-11F; SEQ ID NO: 18)
5'-CCAGGATGTGACCTATTTTGTGGC-3', (R12-13 reverse primer, R12-13R; SEQ ID NO: 20)
5'-CCAGCAAGAAGCAGGTGGGCTTAG-3', (R12-14R; SEQ ID NO: 21)
5'-TTCGGGACACTGAACGTGTAGATG-3'.

Libraries containing cDNA isolated from HeLa cells (Clontech, catalog # HL4048AH) or from various human tissues, including placenta, fetal brain and liver, EBY-transformed lymphocytes, and leukocytes (Clontech, catalog # HL4025AH, HL4028AH, HL4029AH, HL4006AE and HL4050AH) were used for nested PCR to assess the presence of CRF2-12 cDNA in these libraries.

A first round was performed with R12-10F and R12-13R primers followed by the second round with R12-11F and R12-14R primers and the PCR product of the first round as a template.

The placental cDNA library was selected and further used for amplification of CRF2-12 cDNA by nested PCR. First round was performed with primers:

(R12-1F; SEQ ID NO: 13)
5'-GCCGCGGCAGGAAGGCCATGGCG-3'
and (R12-16R; SEQ ID NO: 22)
5'-CATCCTCCTCCTCITCGTCCTCTG-3'.

Then the PCR product of the first round was used as a template for the second round of PCR amplification with either primers.

(R12-2F; SEQ ID NO: 14)
5'-GCCGGTACCATGGCGGGGCCCGAGCGCTGG-3'
and (R12-9R; SEQ ID NO: 16)
5'-AGGGCTAGCCAGTTGGCTTCTGGGACCTCC-3'
or (R12-3F; SEQ ID NO: 15)
5'-GCCGGATCCCCGTCTGGCCCCTCCCCAGAA-3'
and (R12-9R; SEQ ID NO: 16)
5'-AGGGCTAGCCAGTTGGCl1CTGGGACCTCC-3' to clone the extracellular domain of the CRF2-12 protein into either plasmid pEF3-IL-10R1/γR1 (Kotenko, et al., (1997) EMBO J 16, 5894-5903) with the use of Kpnl and Nhel restriction endonucleases, resulting in plasmid pEF-CRF2-12/γR1, or plasmid pEF3-FLγR2/αR2c (Kotenko, et al., (1999.) Proc Natl Acad Sci USA96, 5007-5012) with the use of BamHI and Nhel restriction endonucleases, resulting in plasmid pEF-FL-CRF2-12/αR2c.

The intracellular domain of IFN-αR2c was replaced by the intracellular domain of IFN-γR1 by cloning of the fragment containing the intracellular domain of IFN-γRI from plasmid pEF-CRF2-12/γR1 into plasmid pEF-FL-CRF2-12/αR2c with the use of Nhel and BssHII restriction endonucleases, resulting in plasmid pEF-FL-CRF2-12/γR1.

Cloning of the CRF2-12 intracellular domain.

Primers
    (R12-12F; SEQ ID NO: 19)
5'-TCTAAGCCCACCTGCTTCTTGCTG-3', (R12-19F; SEQ ID NO: 23)
5'-CTGGCTAGCCCTGGTGCTGCCATCGC-3', (R12-8R; SEQ ID NO: 24)
5'-AGGCAGCAGCAGCATCAGATTCGG-3'
and (R12-7R; SEQ ID NO: 25)
5'-GGGTCTAGATCACCTGGCCATGTAATGCCCCA-3'.

Nested PCR of the same placental cDNA library with the above primers (R12-12F and R12-8R primers for the first round and R12-19F and R12-7R primers for the second round) to clone the CRF2-12 intracellular domain into the pCR2.1 vector (Invitrogen).

The CRF2-12 intracellular domain was then cloned into plasmids pEF-CRF2-12/γR1 and pEF-FL-CRF2-12/γRI with the use of Nhel and Notl restriction endonucleases, resulting in plasmids pEF-CRF2-12 and pEF-FLCRF2-12, respectively.

Plasmid pEF-CRF (pEF-CRF2-4 or pEF-IL-10R2) was previously described (Kotenko, et al., (1997) EMBO J 16, 5894-5903). Plasmid pEF-CRF2-11 (or pEF2-IL-20R2) was obtained by cloning PCR-derived CRF2-11 cDNA fragment into the pcDEF3 vector (Goldman 1996) with the use of Kpnl and EcoRI restriction endonucleases.

Accordingly, a human cDNA of the receptor of the present invention was obtained having SEQ. ID. NO. 1 and encoding a receptor having an amino acid sequence in SEQ. ID. NO. 2. The novel receptor of the present invention was designated CRF2-12 (12th member of the class II cytokine receptor family; FIG. 14A).

Example 2: CRF2-12 Characterization

In accordance with the present invention, CRF2-12 was found to possess a characteristic signal peptide of about 18 a.a. and a 23 a.a. transmembrane domain (227 to 249 a.a.), which divides the receptor into a 208 a.a. extracellular domain and a relatively long 271 a.a. intracellular domain (FIG. 14A).

Alignment of the extracellular domains of the class II cytokine receptors assigned CRF2-12 in a subgroup with several other receptors, CRF2-8, CRF2-9, CRF2-10, IL-10R1 and IFN-γR1 (FIG. 14B).

In accordance with the present invention, the entire CRF2-12 gene of the invention is composed of 7 exons (FIG. 14C). The structure of the gene of the present invention was found to correlate with the common conserved architecture of other genes encoding CRF members (Kotenko 2002).

The first exon of the CRF2-12 gene of the present invention contains the 5'-UTR and the signal peptide. Exons 2, 3, 4 and 5 and a part of exon 6 of the CRF2-12 gene of the present invention encode the extracellular domain. Exon 6 of the CRF2-12 gene of the present invention also encodes the transmembrane domain and the beginning of the intracellular domain. Exon 7 of the CRF2-12 gene of the present invention encodes the rest of the intracellular domain and the 3'-UTR.

Both genes, the CRF2-12 gene and the IL-22R1 gene, are transcribed in the same direction toward the telomere and positioned approximately 10 kb apart. All exon/intron and intron/exon splice sites within of the CRF2-12 gene of the present invention conform well to the consensus motifs (exon/GT-intron-AG/exon).

Example 3: CRF2-12 Expression

To determine what cell types express CRF2-12, a panel of RNA derived from various tumor cell lines was evaluated.
Expression of CRF2-12 mRNA.
Northern blotting was performed as described (Gallagher, et al., (2000) Genes Immun 1, 442-450 and Kotenko, et al., (2001) J Biol Chem 276, 2725-2732) with the use of a CRF2-12 probe corresponding to the coding region of the CRF2-12 cDNA.

Figure 15A:
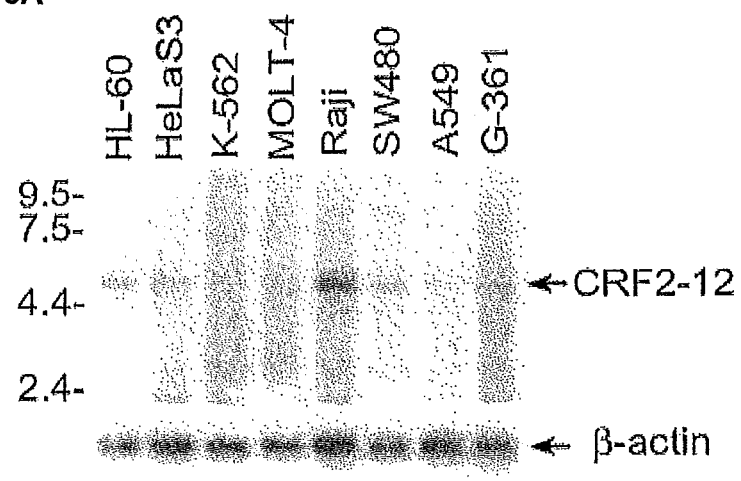
FIGS. 15A and B, as shown in these figures, CRF2-12 appears to be constitutively expressed in a variety of cell lines and tissues.
Figure 15B:
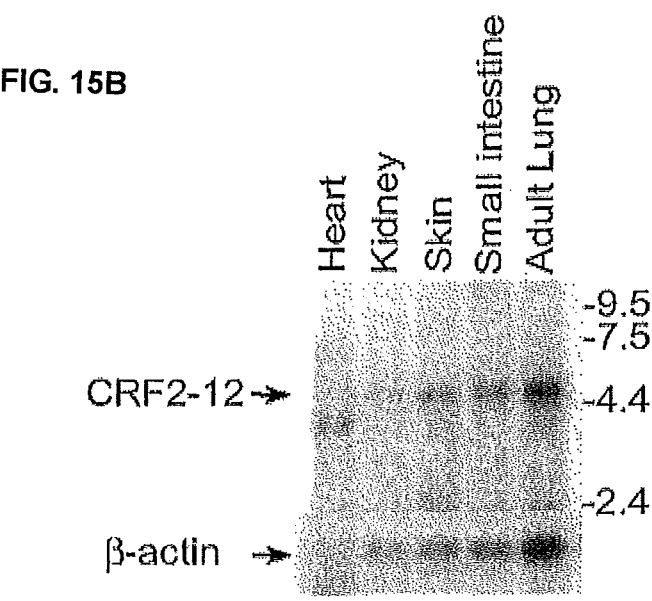
FIG. 15B is a northern blot, and shows that CRF2-12 was also expressed by various normal tissues, including heart, kidney, skin, small intestine, and lung. CRF2-12 mRNA was also present in skeletal muscle and liver.

Northern blotting was performed on two blots containing mRNA isolated from: human cancer cell lines (promyelocytic leukemia HL-60, epitheloid carcinoma HeLa S3, lymphoblastic leukemia MOLT-4, Burkitt's lymphoma Raji, colorectal adenocarcinoma, SW480, lung carcinoma A549 and melanoma G361) and normal human fetal tissues (heart, kidney, skin, small intestine) and adult lung (FIGS. 15A and 15B). Arrows point to the CRF2-12 and the b-actin transcripts. Equal RNA loading was assessed by evaluating the expression of the b-actin gene.

CRF2-12 mRNA was expressed at variable levels in all of the cell lines examined (FIG. 15A). These included both hematopoietic (HL-60, K-562, MOLT-4 and Raji) and non-hematopoietic (HeLa, SW480, A549, and G-361) cell lines. Of these cell lines, Raji cells displayed the highest levels of CRF2-12 gene expression. CRF2-12 was also expressed by various normal tissues, including heart, kidney, skin, small intestine, and lung (FIG. 15B). CRF2-12 mRNA was also present in skeletal muscle and liver. Therefore, CRF2-12 appears to be constitutively expressed in a variety of cell lines and tissues.

Example 4: Construction of Tandem Vectors Encoding Two Receptors and Construction of a Chimeric CRF2-12/IFN-γR1 Receptor To assay for the CRF2-12 receptor ligands, a chimeric CRF2-12/IFN-γR1 (CRF2-12/γR1) receptor (FIG. 20A) was created. The chimeric CRF2-12/IFN-γR1 receptor was expressed with different intact R2 chains in various combinations (CRF2-4 and CRF2-11) in 16-9 hamster cells.

To ensure that both receptors were expressed in a single transfected cell, tandem vectors, in which expression of CRF2-12/γR1 and either CRF2-4 or CRF2-11 is controlled by separate promoters and polyadenylation signal, were constructed. Tandem vectors encoding two receptors, CRF2-12/γR1 and either CRF2-4 or CRF2-11, in which the expression of each receptor is controlled by separate promoters and polyadenylation signals were created as follows. The fragment containing the EF-1a promoter, the CRF2-12 coding sequence, and the bovine growth hormone (BGH) polyadenylation signal was released from the pEF-CRF2-12/γR1 vector by digestion with BsaI and BssHII restriction endonucleases and ligated into the BsaI and MluI sites of either the pEF-CRF2-4 or pEF-CRF2-11 plasmid. The resulting plasmids were designated pEF-CRF2-12/γR1+CRF2-4 and pEF-CRF2-12/γR1+CRF2-11, respectively.

Example 5: Testing Known Cytokines for CRF2-12 Specificity

Plasmids pEF-CRF2-12/γR1+CRF2-A and pEF-CRF2-12/γR1+CRF2-11 were transfected into hamster cells and cellular pools of G418-resistant clones were collected. The ability of different cytokines to activate the chimeric receptor and the ability of resultant receptor complexes to transduce IFN-γ-like signaling in the transfected hamster cells was tested. In particular, the chimeric receptor was tested for responsiveness to different ligands utilizing EMSA to detect Stat1 activation and FACS to evaluate MHC class I antigen expression, the activities characteristic for IFN-γ signaling. Signaling by IL-19, IL-20, IL-22 and IL-24 in cells expressing CRF2-12/γR1 and either CRF2-4 or CRF2-11 chains was not observed.

Example 6: CRF2-12 Ligand Identification and Cloning

In accordance with the present invention, a group of highly conserved between themselves proteins named IFN-λ1, IFN-λ2 and IFN-λ3 which also demonstrated very limited primary homology to members of both type I IFN and IL-10 families, were identified. (FIGS. 16, 17, 18 and 19, SEQ. ID NO. 7, SEQ. ID NO. 8, SEQ. ID NO. 9, SEQ. ID NO. 10, SEQ. ID NO. 11, SEQ. ID NO. 12).

Genes for these three novel cytokines were cloned as follows.

Human genomic DNA and the following primers were used to amplify IFN-2 genes:

```
                                    (ifnl-1F; SEQ ID NO: 30)
5'-GCGGTACCATGGCTGCAGCTTGGACCGTGG-3',
```

-continued

```
                       (ifnl-2F; SEQ ID NO: 31)
5'-GCGGTACCATGACTGGGGACTGCACGCCAGTG-3', (ifnl-5F; SEQ ID NO: 32)
5'-GCGGATCCTGTCCCCACTTCCAAGCCCACC-3', (ifnl-6F; SEQ ID NO: 33)
5'-GCGGATCCTGTCGCCAGGCTCCGCGGGGCT-3', (ifnl-3R; SEQ ID NO: 34)
5'-CGGAATTCAGGTGGACTCAGGGTGGGTTGA-3'
and (ifnl-4R; SEQ ID NO: 35)
5'-CGGAATTCAGACACACAGGTCCCCACTGGCAACACA-3'.
```

First round was performed with either ifnl-1F and ifnl-3R primers or ifnl-2F and ifnl-4R primers followed by the second round with either ifnl-5F and ifnl-3R primers or ifnl-6F and ifnl-4R primers and corresponding PCR products of the first round as a template. Resulting PCR products were cloned into the pEF-SPFL vector with the use of BamHI and EcoRI restriction endonucleases, generating plasmid pEF-FL-IFN-λ1 gene, pEF-FL-IFN-λ2 gene and pEF-FL-IFN-λ3 gene.

The PCR-derived genomic fragments which encode mature IFN-λ1, IFN-λ2, IFN-λ3 proteins (Pro23 (FIG. 19A) was predicted to be the first a.a. of the mature proteins) were cloned into plasmid pEF-SPFL, resulting in plasmids pEF-FL-IFN-λ1 gene, pEF-FL-IFN-22 gene and pEF-FL-IFN-λ3 gene.

Plasmid pEF-SPFL encodes the signal peptide derived from the human IFN-γR2 chain followed by the FLAG epitope. The pEF-FL-IFN-λ1 gene, pEF-FL-IFN-λ2 gene and pEF-FL-IFN-λ3 gene constructs abutted each of IFN-λs reading frames to the frame of the FLAG epitope (FL-IFN-λs).

IFN-λs cDNAs were subsequently cloned by RT-PCR using as a template mRNAs from COS-1 cells independently transfected with plasmids pEF-FL-IFN-λ1 gene, pEF-FL-IFN-λ2 gene and pEF-FL-IFN-λ3 gene. cDNA fragments encoding mature IFN-λs proteins were cloned into the same plasmid pEF-SPFL resulting in plasmids pEF-FL-IFN-λ1, pEF-FL-IFN-λ2 and pEF-FL-IFN-λ3.

The same primers as for cloning genomic fragments and total RNA isolated from COS-1 cells transfected with plasmids pEF-FL-IFN-λ1 gene, pEF-FL-IFN-λ2 gene and pEF-FL-IFN-λ3 gene were used for RT-PCR to obtain IFN-λ1, IFN-λ2 and IFN-λ3 cDNA fragments, which were subsequently cloned into plasmid pEF-SPFL with the use of BamHI and EcoRI restriction endonucleases, resulting in plasmids pEF-FL-IFN-λ1, pEF-FL-IFN-λ2 and pEF-FL-IFN-λ3. These plasmids encode IFN-λ molecules tagged at their N-terminus with the FLAG epitope (FL-IFN-λ).

The PCR product obtained with primers:

```
ifnl-5F and
                       (ifnl-7R; SEQ ID NO: 36)
5'-GCGAATTCATGCGACGGATGCCCGCCGAATTGAGGTGGACTCAG
GGTGGG-3'
``` and plasmid pEF-FL-IFN-λ1 as a template was digested with BamHI and EcoRI restriction endonucleases and cloned into corresponding sites of the pEF-SPFL vector, resulting in plasmid pEF-FL-IFN-λ1-P. This plasmid encodes FL-IFN-λ tagged at its C-terminus with the Arg-Arg-Ala-Ser-Val-Ala sequence (FL-IFN-λ-P; SEQ ID NO:64), that contains the consensus amino acid sequence recognizable by the catalytic subunit of the cAMP-dependent protein kinase (Li, et al., (1989) Proc Natl Acad Sci USA 86, 558-562).

The PCR product obtained with primers 5'-GATAG-TACTTCCAAGCCCACCACA-3' (ifnl-5F; SEQ ID NO:38) and ifnl-3R and plasmid pEF-FL-IFN-λ1 as a template was digested with Seal and EcoRI restriction endonucleases and cloned into Xmnl and EcoRI sites of the pMAL-p2x vector (New England Biolabs), resulting in plasmid pMAL-IFN-λ1. This plasmid encodes MBP (maltose-binding protein)-IFN-λ fusion protein which is secreted to the periplasm of E. coli cells. The fusion protein was purified from the periplasm by the cold osmotic shock method according to the manufacturer's protocol.

In accordance with the present invention, IFN-λ1, IFN-λ2, IFN-λ3 were found to be encoded by genes including five exons, which resemble the structural organization of genes encoding IL-10-related cytokines.

Genes encoding three members of this family, designated IFN-λ1, IFN-λ2 and IFN-λ3, (FIGS. 16, 17, 18 and 19, SEQ. ID NO. 7, SEQ. ID NO. 8, SEQ. ID NO. 9, SEQ. ID NO. 10, SEQ. ID NO. 11, SEQ. ID NO. 12) were found to be clustered on human chromosome 19 (19q13+13 region).

Example 7: Expression of IFN-λs from pEF-FL-IFN-λ1 Gene, pEF-FL-IFN-λ2 Gene and pEF-FL-IFN-β3 Gene COS-1 cells were transiently transfected with pEF-FL-IFN-λ1 gene, pEF-FL-IFN-λ2 gene and pEF-FL-IFN-λ3 gene plasmids and three days after transfection conditioned media was collected and subjected to Western blotting and biological assays (FIGS. 20, 21, 22, 23 and 24). Western blotting revealed that FL-IFN-λs were secreted from COS cells and migrated on the SDS-PAGE gel as several bands in the region of about 35 kDa for IFN-λ1 and as a single band of about 25 kDa for IFN-λ2 and IFN-λ3 proteins (FIG. 20C). In accordance with the present invention, this observation suggests glycosylation of IFN-λ1. Further in accordance with the present invention, a potential site for N-linked glycosylation (Asn-X-Thr/Ser) is present in IFN-λ1 (FIG. 19A).

COS cells conditioned media containing IFN-λs were used to treat hamster cells expressing CRF2-12/γR1 and either CRF2-4 or CRF2-11 chains. All three proteins were able to induce Stat activation and up-regulate MHC class I antigen expression, but only iri cells expressing both CRF2-12/γR1 and CRF2-4 chains (FIGS. 21A, 23). Expression of neither CRF2-12/γR1 nor CRF2-4 alone rendered cells responsive to IFN-λ treatment.

Three days after transfection, conditioned media from COS-I cells transiently transfected with expression plasmids were collected. FLAG-tagged proteins in the conditioned media were identified by Western blotting with anti-FLAG epitope specific M2 monoclonal antibody (Sigma) as described (Kotenko, et al., (2000) Proc Natl Acad Sci USA 97, 1695-1700).

Conditioned media from COS-1 cells independently transiently transfected with plasmids pEF-FL-IFN-λ2 and pEF-FL-IFN-λ3 demonstrated indistinguishable biological activities and Western blotting pattern as conditioned media from COS-1 cells independently transfected with plasmids pEF-FL-IFN-λ1 gene, pEF-FL-IFN-22 gene and pEF-FL-IFN-λ3 gene (FIGS. 20C, 21A, 21B and 23).

In accordance with another embodiment of the present invention, the use of flow cytometry was used to detect binding of FLAG epitope-tagged IFN-λs to the cells expressing both CRF2-12/γR1 and CRF2-4 chains (FIG. 21A).

In accordance with another embodiment of the present invention, FL-IFN-λs were found to compete for receptor binding (FIG. 22). Cells expressing either chain alone did not bind FL-IFN-λs as measured by FACS.

In yet another embodiment of the present invention, the entire IFN-λ1 cDNA was cloned into the pcDEF3 vector Goldman, et al., (1996) Biotechniques 21, 1013-1015, resulting in the plasmid pEF-IFN-λ1. Conditioned medium of COS-1 cells transiently transfected with this expression vector competed for binding with FL-IFN-λs and was positive in MHC class I induction experiments and in the EMSA experiments (FIG. 21A), demonstrating that IFN-λs are secreted with their own signal peptides.

In another embodiment of the present invention, recombinant IFN-λ1 was produced in *E. coli*. The recombinant IFN-λ1 produced in *E. coli* was found to be active in all the experiments described above (FIG. 21).

Example 8

In another embodiment of the present invention, the interaction between IFN-λ and its receptor was characterized by crosslinking (FIG. 22). Crosslinking experiments were performed with radiolabeled IFN-2 (FIGS. 20B and C) and the IFN-λ receptor chains expressed in hamster cells (FIG. 22).

COS cell-expressed FL-IFN-λ1-P was purified to homogeneity and radiolabeled (FIGS. 20B and C). The FL-IFN-λ1-P protein was transiently expressed in COS cells and purified from conditioned media by immunoaffinity chromatography with the anti-FLAG M1 gel (Sigma) according to the manufacturer's suggested protocols. FL-IFN-λ1-P was labeled with [32P]ATP and used for crosslinking to cells as described (Li, et al., (1989) Proc Natl Acad Sci USA 86, 558-562; Kotenko, et al., (1995) J Biol Chem 270, 20915-20921; Pestka, et al., (1999) Protein Expr Purif 17, 203-214; Kotenko, et al., (2001) J Immunol 166, 7096-7103).

Parental hamster cells, cells expressing either the chimeric human CRF2-12/γR1 chain, the intact human CRF2-4 chain, or both, were incubated with radiolabeled FL-IFN-λ1-P. The cells were washed to remove unbound ligand, and bound ligand was crosslinked to the cells. After crosslinking, the cells were lysed and crosslinked complexes were resolved on 7.5% SDS-PAGE (FIG. 22).

The appearance of several labeled crosslinked complexes was observed only in cells expressing both IFN-λ1 receptor chains. Neither parental cells nor cells expressing either receptor chain alone were able to bind the ligand. (FIG. 22, lanes 3, 4 and 5.)

Specificity of binding was shown by a competition assay with an excess of unlabeled IFN-λ1 (FIG. 22, lane 7). The major radiolabeled band in the region of 35 kDa corresponds to free FL-IFN-λ1-P, and results from ligand bound to the cells but not crosslinked to receptors. A distinct crosslinked complex migrating in the region of 200 kDa which is not present in the ligand crosslinked to itself in solution, likely represents oligomers of IFN-λ1 and both receptor chains, formed as a result of the association of the IFN-λ1 receptor chains induced by ligand binding.

FL-IFN-λ1-P was also crosslinked to itself in solution to determine whether it can oligomerize. Patterns of radiolabeled bands for crosslinked or untreated ligand are identical (FIG. 22, lanes 1 and 2), strongly suggesting that IFN-λ1 is a monomer in solution. The crosslinking experiments demonstrated that IFN-λ1 requires the presence of the both IFN-λ receptor chains on the cell surface and is unable to interact with either chain expressed alone.

Thus, we identified a specific novel ligand-receptor complex, making a first step in assigning functions for these novel cytokines. The CRF2-12 protein can also be designated IFN-λR1 based on its function as the RI type subunit in the IFN-λ receptor complex.

Example 9: Signal Transduction and Biological Activity

Cytokines which utilize class II cytokine receptors for signaling primarily activate the Jak-Stat signal transduction pathway (Kotenko, S. V. (2002) Cytokine Growth Factor Rev. 13, 223-240 and Kotenko, S. V. & Pestka, S. (2000) Oncogene 19, 2557-2565). Activation of this pathway is generally considered essential for induction of cytokine-responsive genes.

To define which Stats are activated by the IFN-λs, we examined the activation of several Stats in wild-type HT-29 cells and an HT-29 clone, 1084, that overexpresses a chimeric receptor IL-10R1/IFN-λR1 (10R1/A.R1) composed of the extracellular domain of the IL-10R1 chain linked to the intracellular domain of IFN-λR1 (CRF2-12). This chimeric receptor is able to bind IL-10 and dimerize with CRF2-4 (IL-10R2), a common second chain for the IL-10, IL-22 and IFN-λ receptor complexes, to transduce a signal. The Stat proteins that are activated by signaling through this chimeric receptor upon IL-10 treatment represent those that are activated by signaling through the intact IFN-λ receptor complex. Stat activation was measured by immunoprecipitating specific Stat proteins from whole cell lysates, and then western blotting with phosphotyrosine-specific antibodies.

HT-29 cells do not normally express IL-10R1, therefore treatment with IL-10 did not induce activation of any Stats in these cells (FIGS. 23A and B). However, these cells do express IL-22R1 (CRF2-9), and treatment with IL-22 resulted in the activation of Stat1, Stat2 (weakly), Stat3 and Stat5. The parental HT-29 cell line was also fully responsive to IFN-α. because IFN-α treatment activated Stat1, Stat2 and Stat3 in these cells.

In 1084 cells, treatment with IL-10 induced activation (tyrosine phosphorylation) of Stat1, Stat2, Stat3 and Stat5.

Accordingly, since the chimeric receptor binds IL-10 and transduce an IFN-2 signal, in another embodiment of the present invention, modulation of the activity of the intracellular domain of CRF2-12, be it in a chimeric receptor by binding of the ligand specific for the extracellular domain, or in a CRF2-12 receptor by binding by an IFN-λ, or another agonist or antagonist of the receptor, results in modulation of Stat 1, Stat2, Stat3 and Stat5.

Activation of Stat2 is a unique feature of type I IFNs signaling. Thus, in another embodiment of the present invention, the pattern of Stat activation through the 10R1/λR1 chimeric receptor suggested that signaling through the IFN-λ receptor complex activates IFN-α-like responses.

Example 10

Type-I IFNs are unique insofar as they induce the activation of ISGF3. This transcription factor complex is composed of three subunits: Stat1, Stat2, and ISGF3γ (p48 or IRF-9, interferon regulatory factor 9). Activation of ISGF3 by type I IFNs induces expression of a distinct subset of IFN-responsive genes (Darnell, et al., (1994) Science 264, 1415-1421). To determine if IFN-λ activates ISGF3, we treated wild-type HT-29 and A549 cells with IFN-2 and then measured ISGF3 activity using an interferon-stimulated response element (ISRE) present in the proximal promoter region of the ISG-15 gene. Treatment with IFN-λs, like treatment with IFN-α, induces ISGF3 activity in HT-29 and A549 cells (FIGS. 23B and C). Accordingly, in accordance with another embodiment of the present invention, treatment with IFN-λs induces ISGF3 activity.

Example 11

IFN-λs also induce tyrosine phosphorylation of Stat1 and Stat2 in HT-29 cells as measured by western blotting with anti-pY-Stat antibodies. Accordingly, in yet another embodiment of the present invention, IFN-λs induce tyrosine phosphorylation of Stat1 and Stat2.

To determine whether IFN-λ and IFN-α possess overlapping biological activities, HT29 colorectal adenocarcinoma, HeLa cervix adenocarcinoma, A549 lung carcinoma, and HaCaT keratinocyte cells were treated with both ligands and MHC class I antigen expression was evaluated. Both IFN-λ and IFN-α were able to up-regulate expression of MHC class I antigens to comparable levels in all tested cell lines (FIG. 21A). Accordingly, in another embodiment of the present invention, IFN-λ, agonist and antagonist thereof modulate expression of MHC class I antigens.

Example 12: IFN-λ1 Induces Cellular Antiviral Protection

Antiviral protection in response to IFN-λ1 was evaluated on HT29 cells infected with vesicular stomatitis virus (FIG. 24A, row C). IFN-α was used as a positive control (FIG. 24A, row A). Equal amount of cells were plated in all wells and treated with two-fold serial dilutions of indicated ligands (FIG. 24A, rows A and C). Twenty-four hours later the virus was added in all wells except for the first seven wells in row F. As can be seen from FIG. 24A, IFN-λ1 was more effective than IFN-α in protecting cells from viral infection.

Accordingly, in another embodiment of the present invention, IFN-λs, alone or in combination, other agonists of CRF2-12, and modulators of the intracellular domain of CRF2-12, are effective in providing protection from viral infection. In another embodiment of the present invention, IFN-λ1, IFN-λ2 or IFN-λ3 or effective combinations thereof, induces overlapping signaling and biological activities with those of IFN-α in intact cells expressing an effective receptor.

Example 13: Expression of IFN-λs mRNA was Evaluated by RT-PCR in Virus-Infected Cells HeLa cells were left untreated (lane 3) or infected with either Dengue virus (DV, lanes 4-6) Sindbis virus (SV, lanes 7-9) or vesicular stomatitis virus (VSV, lanes 10-12). HT29 cells were left untreated (lane 13) or infected with VSV (lanes 14-16). HuH7 cells were left untreated (lane 17) or infected with DV (lanes 18-20) or SV (lanes 21-23). Cells were collected at post-infection times shown in the Figure, RNA was isolated and RT-PCR was performed as described in Materials and Methods. Water was used as a negative control for RT-PCR (lane 2). 1 kb ladder was run in lanes 1 and 24.

The expression of IFN-λ1, IFN-λ2 and IFN-λ3 mRNAs was detected in a number of cell lines infected with various viruses (FIG. 24B).

It was also found that dendritic cells, which are important producers of IFN-α (Siegal, et al., (1999) Science 284, 1835-1837) expressed IFN-λ1 mRNA in response to treatment with polyI:C.

Accordingly, in another embodiment of the present invention, the presence and/or quantity of IFN-λ1, IFN-λ2 and/or IFN-λ3 present, or mRNA expressed, is an indicator of infection, in particular viral infection. In another aspect of the present invention, IFN-λ expression is modulated in response to viral infections. In another embodiment of the present invention, the cytokines designated IFN-λs play a functional IFN-α independent role in an antiviral cellular defense.

Example 14: Signaling Through the CRF2-12 Intracellular Domain Induces Apoptosis We also evaluated whether biological activities induced by IFN-λs through the intact IFN-λ receptor complex composed of CRF2-12 and CRF2-4 chains, can be reproduced in cells expressing the FL-IL-10R1/CRF2-12 chimeric receptor upon IL-10 treatment. HT-29 cells expressing FL-IL-10R1/CRF2-12 were treated with various amounts of IL-10. Three days later the cells were collected to measure the level of MHC class I antigen expression. Surprisingly, cells treated with IL-10 at concentration of about 10 ng/ml and higher, appeared round-shaped, not attached to the plastic, and apparently did not proliferate, suggesting that the cells underwent apoptosis in response to IL-10. None of these changes were observed in untreated cells, in cells treated with IL-22 or IFN-γ, or in parental HT-29 cells treated with IL-10.

The induction of apoptosis in HT-29 cells expressing FL-IL-10R1/CRF2-12 chain by IL-10 was subsequent confirmed: i) by staining apoptotic cells with propidium iodide, and ii) by demonstrating phosphatidylserine externalization in apoptotic cells with the use of Anexin V-FITC and flow cytometry. The induction of apoptosis in these cells by IL-10 was dependent on the concentration of IL-10 and on the level of the FL-IL-10R1/CRF2-12 chain expression. Apoptotic effects were stronger at higher concentrations of IL-10 and in cell clones with higher level of FL-IL-10RI/CRF2-12 expression.

At lower concentration of IL-10 (about few ng/ml) cells demonstrated antiproliferative response and at concentration of IL-10 about 1 ng/ml demonstrated activities characteristic for IFN-λ (MHC class I antigen induction and antiviral activity).

Thus, with declining concentration of IL-10, various activities can be induced in cells starting from apoptosis, followed by antiproliferative effect and the induction of antiviral state. Accordingly, another embodiment of the present invention results that either apoptosis, antiproliferative effect or antiviral protection may be obtained by effectively modulating the activity of the intracellular domain of CRF2-12.

In all cells tested so far, the level of CRF2-12 expression appeared to be low. Thus, the fact that in all tested cell lines IFN-λ appeared to induce can be explained by the low level of CRF2-12 expression. Accordingly, in another embodiment of the present invention, when viruses or other natural or pharmaceutical agents modulate the level of CRF2-12 expression, IFN-λ, or other compositions that modulate effectively the activity of the intracellular domain of CRF2-

12, may be used to induce antiviral protection, apoptosis or to have an antiproliferative effect.

Example 15: Cloning of CRF2-11cDNA

CRF2-11 cDNA was obtained by PCR as follows.

```
First round primers:
                        (R11-2F; SEQ ID NO: 26)
5'-TTTGGAAAGAAACAATGTTCTAGGTC-3'
and
                        (R11-7R; SEQ ID NO: 27)
5'-CTTCACCTGGGCCCTTCCGC-3'
``` were used to amplify a libraries containing cDNA isolated from human leukocytes (Clontech, catalog # HL4050AH)

```
Second round primers:
                        (R11-3F; SEQ ID NO: 28)
5'-CTGAGGGTACCAAATGCAGACTTTCACAATG-3
and
                        (R11-6R: SEQ ID NO: 29)
5'-GGGAATTCATGAGATCCAGGCCCTGAGGAGTTC-3'
``` and the PCR product of the first round as a template.

Example 16

In another embodiment of the present invention IFN-λ1 induces cellular antiviral protection. As shown in FIG. 26A, IFN-λ1 induced antiviral protection in HT29, A549 and HaCaT cells infected with vesicular stomatitis virus (VSV, an RNA rhabdovirus) and in HT29 cells infected with encephalomyocarditis virus (EMCV, an RNA picornavirus). In antiviral assays IFN-λ1 demonstrated antiviral potency comparable with that of IFN-α, on the order of $10^7$-$10^8$ IFN-α-relevant units per mg. Moreover, when HT29 cells were pretreated with 500 pg/ml of IFN-λ1 prior to VSV infection, the titer of VSV in the conditioned media of infected cells (48 h after infection) dropped more then 3 orders of magnitude in comparison to the VSV titer produced by control untreated cells. In cells pretreated with 1250 pg/ml the viral titer dropped more then 6 orders of magnitude as determined by viral killing curve (data not shown). Accordingly, in another aspect of the present invention IFN-λs are used to induce antiviral protection.

In accordance with another embodiment of the present invention, IFN-λ1 is capable of inducing transcription of type I IFN-responsive ISRE-controlled genes encoding 2',5'-OAS and MxA protein (FIG. 26B). Thus, in intact cells, IFN-λ induces overlapping signaling and biological activities with those of IFN-λ. These signaling and biological activities, include, for example, upregulation of MHC class I antigen expression, induction of antiviral protection, and induction of IFN-regulated genes. Accordingly, in another aspect of the present invention IFN-λs are used to induce expression of a protein that mediates antiviral protection. These proteins may include, for example, 2',5'-oligoadenylate synthetase (2=, 5=–OAS) and Mx proteins.

In another embodiment of the present invention HT29 cells or A549 cells infected with EMCV secrete IFN-λ specific activity capable of stimulating STAT1 activation through the CRF2-12-λR1 and CRF2-4 heterodimer (FIG. 26C). Uninfected cells, in accordance with the present invention, do not produce IFN-λ activity. Accordingly, in another aspect of the present invention IFN-λs are used to detect the presence of infected cells. In yet another embodiment of the present invention, antagonists are used to modulate inflammation.

Other Materials and Methods

See, for example, Kotenko, et al., Nature Immunology 4:69-77 (2003), which is incorporated by reference herein in its entirety.

Cells, Transfection and Cytofluorographic Analysis.

The 16-9 hamster×human somatic cell hybrid line is the Chinese hamster ovary cell (CHO-K1) hybrid containing a translocation of the long arm of human Chromosome 6 encoding the human IFNGR1 (Hu-IFN-γR1) gene and a transfected human HLA-87 gene (Soh, J., Donnelly, R. J., Mariano, T. M., Cook, J. R., Schwartz, B. & Pestka, S. (1993) Proc. Natl. Acad. Sci. U.S.A 90, 8737-8741). The cells were maintained in F12 (Ham) medium (Sigma) containing 10% heat-inactivated fetal bovine serum (Sigma). COS-1 cells, an SV40 transformed fibroblast-like simian CV-1 cell line, were maintained in DMEM medium (GibcoBRL) with 10% heat-inactivated fetal bovine serum.

Colorectal adenocarcinoma HT29 cells were maintained in DMEM medium (GibcoBRL) with 10% heat-inactivated fetal bovine serum.

Cells were transfected as previously described (Kotenko, et al., (1997) EMBO J 16, 5894-5903 and Kotenko, et al., (2000) Proc Natl Acad Sci USA 97, 1695-1700). COS cell supernatants were collected at 72 hrs as a source of the expressed proteins.

To detect cytokine-induced MHC class I antigen (HLA-B7) expression, cells were treated with COS cell supernatants or purified recombinant proteins as indicated in the text for 72 hours and analyzed by flow cytometry.

Cell surface expression of the HLA-B7 antigen was detected by treatment with mouse anti-HLA (W6/32) (Barnstable, et al., (1978) Cell 14, 9-20) monoclonal antibody followed by fluorescein isothiocyanate-conjugated goat antimouse IgG (Santa Cruz Biotechnology Inc.). The cells then were analyzed by cytofluorography as previously described (Kotenko, et al., (1999) Proc Natl Acad Sci USA 96, 5007-5012).

Unless otherwise specified, whether a result is statistically significant, means that when appropriately measured in any effective manner, there is a probability of less than 50% that the result occurred by mere chance. Other preferred confidence levels include 70%, 75%, 80%, 85%, 90%, 95% and 99%.

Electrophoretic mobility shift assays (EMSAs) and Western and Northern blotting.

Cells were starved overnight in serum-free media and then treated with IL-10 or IL-22 as indicated in the text for 15 minutes at 37° C. and used for EMSA experiments to detect activation of Stat1, Stat3 and Stat5 as described (Kotenko, S. V., Krause, C. D., Izotova, L. S., Pollack, B. P., Wu, W. & Pestka, S. (1997) EMBO J 16, 5894-5903). EMSAs were performed with a 22-base pair sequence containing a Stat1a binding site corresponding to the GAS element in the promoter region of the human IRF-1 gene (5'-GATCGATTTCCCCGAAATCATG-3; SEQ ID NO:39) as described (Kotenko, et al. (1995) J Biol Chem 270, 20915-20921 and Kotenko, et al., (1996) J Biol Chem 271, 17174-17182).

SEQUENCE LISTING

<160> NUMBER OF SEQ ID NOS: 68

<210> SEQ ID NO 1
<211> LENGTH: 4539
<212> TYPE: DNA
<213> ORGANISM: Homo sapiens

<400> SEQUENCE: 1

| | | | | | | |
|---|---|---|---|---|---|---|
| gccatggcgg | ggcccgagcg | ctggggcccc | ctgctcctgt | gcctgctgca | ggccgctcca | 60 |
| gggaggcccc | gtctggcccc | tccccagaat | gtgacgctgc | tctcccagaa | cttcagcgtg | 120 |
| tacctgacat | ggctcccagg | gcttggcaac | ccccaggatg | tgacctattt | tgtggcctat | 180 |
| cagagctctc | ccacccgtag | acggtggcgc | gaagtggaag | agtgtgcggg | aaccaaggag | 240 |
| ctgctatgtt | ctatgatgtg | cctgaagaaa | caggacctgt | acaacaagtt | caagggacgc | 300 |
| gtgcggacgg | tttctcccag | ctccaagtcc | ccctgggtgg | agtccgaata | cctggattac | 360 |
| cttttgaag | tggagccggc | cccacctgtc | ctggtgctca | cccagacgga | ggagatcctg | 420 |
| agtgccaatg | ccacgtacca | gctgcccccc | tgcatgcccc | cactggatct | gaagtatgag | 480 |
| gtggcattct | ggaaggaggg | ggccggaaac | aagaccctat | tccagtcac | tccccatggc | 540 |
| cagccagtcc | agatcactct | ccagccagct | gccagcgaac | accactgcct | cagtgccaga | 600 |
| accatctaca | cgttcagtgt | cccgaaatac | agcaagttct | ctaagcccac | ctgcttcttg | 660 |
| ctggaggtcc | cagaagccaa | ctgggcttc | ctggtgctgc | catcgcttct | gatactgctg | 720 |
| ttagtaattg | ccgcaggggg | tgtgatctgg | aagaccctca | tggggaaccc | ctggtttcag | 780 |
| cgggcaaaga | tgccacgggc | cctggacttt | tctggacaca | cacccctgt | ggcaaccttt | 840 |
| cagcccagca | gaccagagtc | cgtgaatgac | ttgttcctct | gtccccaaaa | ggaactgacc | 900 |
| agagggtca | ggccgacgcc | tcgagtcagg | gccccagcca | cccaacagac | aagatggaag | 960 |
| aaggaccttg | cagaggacga | agaggaggag | gatgaggagg | acacagaaga | tggcgtcagc | 1020 |
| ttccagccct | acattgaacc | accttctttc | ctggggcaag | agcaccaggc | tccagggcac | 1080 |
| tcggaggctg | gtgggtgga | ctcagggagg | cccagggctc | ctctggtccc | aagcgaaggc | 1140 |
| tcctctgctt | gggattcttc | agacagaagc | tgggccagca | ctgtggactc | ctcctgggac | 1200 |
| agggctgggt | cctctggcta | tttggctgag | aaggggccag | gccaagggcc | gggtggggat | 1260 |
| gggcaccaag | aatctctccc | accacctgaa | ttctccaagg | actcgggttt | cctggaagag | 1320 |
| ctcccagaag | ataacctctc | ctcctgggcc | acctggggca | ccttaccacc | ggagccgaat | 1380 |
| ctggtccctg | ggggaccccc | agtttctctt | cagacactga | ccttctgctg | ggaaagcagc | 1440 |
| cctgaggagg | aagaggaggc | gagggaatca | gaaattgagg | acagcgatgc | gggcagctgg | 1500 |
| gggctgaga | gcacccagag | gaccgaggac | aggggccgga | cattgggca | ttacatggcc | 1560 |
| aggtgagctg | tcccccgaca | tcccaccgaa | tctgatgctg | ctgctgcctt | tgcaaggact | 1620 |
| actgggcttc | ccaagaaact | caagagcctc | cgtacctccc | ctgggcggcg | gagggcatt | 1680 |
| gcacttccgg | gaagtccacc | tagcggctgt | ttgcctgtcg | ggctgagcaa | caagatgccc | 1740 |
| ctccctcctg | tgacccgccc | tctttaggct | gagctataag | aggggtggac | acagggtggg | 1800 |
| ctgaggtcag | aggttggtgg | ggtgtcatca | ccccattgt | ccctagggtg | acaggccagg | 1860 |
| gggaaaaatt | atccccggac | aacatgaaac | aggtgaggtc | aggtcactgc | ggacatcaag | 1920 |
| ggcggacacc | accaaggggc | cctctggaac | ttgagaccac | tggaggcaca | cctgctatac | 1980 |
| ctcatgcctt | tcccagcagc | cactgaactc | ccccatccca | gggctcagcc | tcctgattca | 2040 |
| tgggtcccct | agttaggccc | agataaaaat | ccagttggct | gagggttttg | gatgggaagg | 2100 |

-continued

```
gaagggtggc tgtcctcaaa tcctggtctt tggagtcatg gcactgtacg gttttagtgt    2160
cagacagacc ggggttcaaa tcccagctct gctgttcact ggttgtatga tcttggggaa    2220
gacatcttcc ttctctgcct cggcttcctc atctgcagct acgcctgggt gtggtgaggg    2280
ttctagggga tctcagatgt gtgtagcacg gagcctgctg tgtcctgggt gctctctacg    2340
tggtggccgg tagaattctc catctatcca ggctccagga gacccctggg catctcccac    2400
ctgtggcccc taaacccaga gtgactgaga gcacttaaca ttcagcttgt ctcatcccca    2460
gtctacctcc ttccttctac cctcactgcc tcccagtcag gagagtgagc tctcagaagc    2520
cagagcccca cccaagggga ccctggtctc tccgccttca cctagcaatg ggaaccctgc    2580
ttcccagggg aggaaccaac tgctccacct tctagggacc cagtttgttg gagtaggaca    2640
gtaacatggc aggaatcgga cttctgggcc tgtaatccca gtttggatgg cacgttagac    2700
tcttggttga ccgttgtggt ccttagaagt cccattctcc cttccagtta tgagaaacca    2760
atgccttcta gattcaggtg actatcctta cctgggggtg ctgatgcatc ctcagttaac    2820
ctacacccac ctgaatatag atgagcgtag ctgagttttc acccgtagga ccgaagtgtt    2880
ttgtggtgga gtatctgaac aaccttggct ctgtggccat tcaacctgcc aggactaaca    2940
tttctggatt tgtgaagaag ggatcttcaa agccattgaa cccacagagc tgtgttgctt    3000
taaagccacc acaagggtac agcattaaat ggcagaactg gaaaagcttc ttagggcatc    3060
tcatccaggg attctcaaac catgtccccc agaggccttg ggctgcagtt gcaggggggcg   3120 ccatggggct ataggagcct cccactttca ccagagcagc ctcactgtgc cctgattcac    3180
acactgtggc tttccacgtg aggttttgtt tagagggatc cactactcaa gaaaaagtta    3240
gcaaaccact ccttttgttg caaaggagct gaggtcaagg gtggcaaagg cacttgtcca    3300
aggtcgccca gcagtgctgc tctgatgact tgtgcacatc cccaagggta agagcttcga    3360
tctctgcaca gccgggccaa cctctgaccc cttgtccatg tcagtaaaat atgaaggtca    3420
cagccaggat ttctaagggt caggaggcct tcaccgctgc tggggcacac acacacacat    3480
gcatacacac atacgacaca cacctgtgtc tccccagggg ttttccctgc agtgaggctt    3540
gtccagatga ttgagcccag gagaggaaga acaaacaaac tacggagctg ggagggctg    3600 tggcttgggg ccagctccca gggaaattcc cagacctgta ccgatgttct ctctggcacc    3660
agccgagctg cttcgtggag gtaacttcaa aaaagtaaaa gctatcatca gcatcatctt    3720
agacttgtat gaaataacca ctccgtttct attcttaaac cttaccatt ttgttttgtt    3780 ttgttttttt gagtcggagt tttgttcttt ttgcctaggc tggagtgcag tggtacaatc    3840
tcggctcact gcaacctcca cctcccgggt tcaagtgatt ctcctgcctc agcctcccaa    3900
gtagctggga ttacaggcac ccgccaccac acctggctaa ttttttttgta ttttttagtag  3960 agacggggtt tcaccatgtt ggccaggctg gtctcgaact cctgacctca ggtgatccgc    4020
ccgcctcggc ctcccaaagt gctgggatta caggcgtgag ccaccgcgcc cagccaaacc    4080
ttactatttt tttaaagaat ttttttccaga gtttaatttc tgacatagct taagttttcc    4140
agtaactcta aactccatct cctttatcgt cattaagtca ttcacaaaaa gccaggagaa    4200
gcatttggaa agggcatgat aatcagtata ataatttgcc ttgtgtggtc agcacttaac    4260
tgtttacaaa gcccttcac gtgcacagca ggtgggaact gcgcggtgtg ggctgggcct     4320
gcgctggaag catatcccgt gaaaagtgtt agtgccttag gtgaaagcaa catgtatccc    4380
tttagactac taacggtata tgttgttctt atgtatttgt atttatttct attttttcta    4440
```

```
tgtttatgtc atatttaaac gatatcctac tgcttgttgg tattacccta aactgtttaa    4500
ataaagagct ctattttta agaaaaaagg tacaattga                           4539
```

<210> SEQ ID NO 2
<211> LENGTH: 520
<212> TYPE: PRT
<213> ORGANISM: Homo sapiens

<400> SEQUENCE: 2

```
Met Ala Gly Pro Glu Arg Trp Gly Pro Leu Leu Leu Cys Leu Leu Gln
1               5                   10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala Phe Leu Val Leu Pro Ser Leu Leu Ile Leu Leu Leu
225                 230                 235                 240

Val Ile Ala Ala Gly Gly Val Ile Trp Lys Thr Leu Met Gly Asn Pro
                245                 250                 255

Trp Phe Gln Arg Ala Lys Met Pro Arg Ala Leu Asp Phe Ser Gly His
            260                 265                 270

Thr His Pro Val Ala Thr Phe Gln Pro Ser Arg Pro Glu Ser Val Asn
        275                 280                 285

Asp Leu Phe Leu Cys Pro Gln Lys Glu Leu Thr Arg Gly Val Arg Pro
    290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Asp Glu Asp Thr Glu Asp
                325                 330                 335

Gly Val Ser Phe Gln Pro Tyr Ile Glu Pro Pro Ser Phe Leu Gly Gln
            340                 345                 350

Glu His Gln Ala Pro Gly His Ser Glu Ala Gly Gly Val Asp Ser Gly
```

```
                        355                 360                 365
Arg Pro Arg Ala Pro Leu Val Pro Ser Glu Gly Ser Ser Ala Trp Asp
    370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                405                 410                 415

Gly Gly Asp Gly His Gln Glu Ser Leu Pro Pro Glu Phe Ser Lys
            420                 425                 430

Asp Ser Gly Phe Leu Glu Glu Leu Pro Glu Asp Asn Leu Ser Ser Trp
            435                 440                 445

Ala Thr Trp Gly Thr Leu Pro Pro Glu Pro Asn Leu Val Pro Gly Gly
            450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
            500                 505                 510

Thr Leu Gly His Tyr Met Ala Arg
            515                 520

<210> SEQ ID NO 3
<211> LENGTH: 1560
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
```

```
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
```

-continued

```
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
```

```
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
```

```
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
```

```
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
```

-continued

```
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
```

-continued

```
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
```

```
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
```

-continued

```
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
```

-continued

```
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
```

-continued

```
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1104)..(1104)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1116)..(1116)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1140)..(1140)
```

```
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1173)..(1173)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
```

-continued

```
<222> LOCATION: (1224)..(1224)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1305)..(1305)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t
<220> FEATURE:
```

-continued

```
<221> NAME/KEY: misc_feature
<222> LOCATION: (1335)..(1335)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1341)..(1341)
<223> OTHER INFORMATION: n is a, c, g, or t
<220> FEATURE:
<221> NAME/KEY: misc_feature
<222> LOCATION: (1347)..(1347)
<223> OTHER INFORMATION: n is a, c, g, or t
<220> FEATURE:
<221> NAME/KEY: misc_feature
<222> LOCATION: (1350)..(1350)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
<222> LOCATION: (1359)..(1359)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1365)..(1365)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1374)..(1374)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t
<220> FEATURE:
<221> NAME/KEY: misc_feature
<222> LOCATION: (1386)..(1386)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1392)..(1392)
<223> OTHER INFORMATION: n is a, c, g, or t
<220> FEATURE:
<221> NAME/KEY: misc_feature
<222> LOCATION: (1395)..(1395)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1401)..(1401)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
```

-continued

```
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1413)..(1413)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1434)..(1434)
<223> OTHER INFORMATION: n is a, c, g, or t
<220> FEATURE:
<221> NAME/KEY: misc_feature
<222> LOCATION: (1437)..(1437)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t
<220> FEATURE:
<221> NAME/KEY: misc_feature
<222> LOCATION: (1461)..(1461)
<223> OTHER INFORMATION: n is a, c, g, or t
<220> FEATURE:
<221> NAME/KEY: misc_feature
<222> LOCATION: (1467)..(1467)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t
<220> FEATURE:
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1494)..(1494)
<223> OTHER INFORMATION: n is a, c, g, or t
<220> FEATURE:
<221> NAME/KEY: misc_feature
<222> LOCATION: (1500)..(1500)
<223> OTHER INFORMATION: n is a, c, g, or t
<220> FEATURE:
<221> NAME/KEY: misc_feature
<222> LOCATION: (1503)..(1503)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1512)..(1512)
<223> OTHER INFORMATION: n is a, c, g, or t
<220> FEATURE:
<221> NAME/KEY: misc_feature
<222> LOCATION: (1518)..(1518)
<223> OTHER INFORMATION: n is a, c, g, or t
<220> FEATURE:
<221> NAME/KEY: misc_feature
<222> LOCATION: (1521)..(1521)
```

<223> OTHER INFORMATION: n is a, c, g, or t
<220> FEATURE:
<221> NAME/KEY: misc_feature
<222> LOCATION: (1530)..(1530)
<223> OTHER INFORMATION: n is a, c, g, or t
<220> FEATURE:
<221> NAME/KEY: misc_feature
<222> LOCATION: (1533)..(1533)
<223> OTHER INFORMATION: n is a, c, g, or t
<220> FEATURE:
<221> NAME/KEY: misc_feature
<222> LOCATION: (1536)..(1536)
<223> OTHER INFORMATION: n is a, c, g, or t
<220> FEATURE:
<221> NAME/KEY: misc_feature
<222> LOCATION: (1539)..(1539)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t
<220> FEATURE:
<221> NAME/KEY: misc_feature
<222> LOCATION: (1545)..(1545)
<223> OTHER INFORMATION: n is a, c, g, or t
<220> FEATURE:
<221> NAME/KEY: misc_feature
<222> LOCATION: (1557)..(1557)
<223> OTHER INFORMATION: n is a, c, g, or t
<220> FEATURE:
<221> NAME/KEY: misc_feature
<222> LOCATION: (1560)..(1560)
<223> OTHER INFORMATION: n is a, c, g, or t

<400> SEQUENCE: 3

```
atggcnggnc cngarmgntg gggnccnytn ytnytntgyy tnytncargc ngcnccnggn     60
mgnccnmgny tngcnccncc ncaraaygtn acnytnytnw sncaraaytt ywsngtntay    120
ytnacntggy tnccnggnyt nggnaayccn cargaygtna cntayttygt ngcntaycar    180
wsnwsnccna cnmgnmgnmg ntggmgngar gtngargart gygcnggnac naargarytn    240
ytntgywsna tgatgtgyyt naaraarcar gayytntaya ayaarttyaa rggnmgngtn    300
mgnacngtnw snccnwsnws naarwsnccn tgggtngarw sngartayyt ngaytayytm    360
ttygargtng arccngcncc nccngtnytn gtnytnacnc aracngarga rathytnwsn    420
gcnaaygcna cntaycaryt nccnccntgy atgccnccny tngayytnaa rtaygargtn    480
gcnttytgga argarggngc nggnaayaar acnytnttyc cngtnacncc ncayggncar    540
ccngtncara thacnytnca rccngcngcn wsngarcayc aytgyytnws ngcnmgnacn    600
athtayacnt tywsngtncc naartaywsn aarttywsna arccnacntg yttyytnytn    660
gargtnccng argcnaaytg ggcnttyytn gtnytnccnw snytnytnat hytnytnytn    720
gtnathgcng cnggnggngt nathtggaar acnytnatgg gnaayccntg gttycarmgn    780
gcnaaratgc cnmgngcnyt ngayttywsn ggncayacnc ayccngtngc nacnttycar    840
ccnwsnmgnc cngarwsngt naaygayytn ttyytntgyc cncaraarga rytnacnmgn    900
ggngtnmgnc cnacnccnmg ngtnmgngcn ccngcnacnc arcaracnmg ntggaaraar    960
gayytngcng argaygarga rgargargay gargargaya cngargaygg ngtnwsntty   1020
carccntaya thgarccncc nwsnttyytn ggncargarc aycargcncc nggncaywsn   1080
gargcnggng gngtngayws nggnmgnccn mgngcnccny tngtnccnws ngarggnwsn   1140
wsngcntggg aywsnwsnga ymgnwsntgg gcnwsnacng tngaywsnws ntgggaymgn   1200
gcnggnwsnw snggntayyt ngcngaraar ggnccnggnc arggnccngg nggngayggn   1260
caycargarw snytnccncc nccngartty wsnaargayw snggnttyyt ngargarytn   1320

```
ccngargaya ayytnwsnws ntgggcnacn tggggnacny tnccnccnga rccnaayytn   1380
gtnccnggng gnccnccngt nwsnytncar acnytnacnt tytgytggga rwsnwsnccn   1440
gargargarg argargcnmg ngarwsngar athgargayw sngaygcngg nwsntggggn   1500
gcngarwsna cncarmgnac ngargaymgn ggnmgnacny tnggncayta yatggcnmgn   1560

<210> SEQ ID NO 4
<211> LENGTH: 2973
<212> TYPE: DNA
<213> ORGANISM: Homo sapiens

<400> SEQUENCE: 4
gctgtccccc gacatcccac cgaatctgat gctgctgctg cctttgcaag gactactggg     60
cttcccaaga aactcaagag cctccgtacc tccctgggc ggcggagggg cattgcactt    120
ccgggaagtc cacctagcgg ctgtttgcct gtcgggctga gcaacaagat gcccctccct    180
cctgtgaccc gccctcttta ggctgagcta aagaggggt ggacacaggg tgggctgagg    240
tcagaggttg gtggggtgtc atcaccccca ttgtccctag ggtgacaggc caggggaaa    300 aattatcccc ggacaacatg aaacaggtga ggtcaggtca ctgcggacat caagggcgga    360
caccaccaag gggccctctg gaacttgaga ccactggagg cacacctgct atacctcatg    420
cctttcccag cagccactga actcccccat cccagggctc agcctcctga ttcatgggtc    480
ccctagttag gcccagataa aaatccagtt ggctgagggt tttggatggg aagggaaggg    540
tggctgtcct caaatcctgg tctttggagt catggcactg tacggttta gtgtcagaca    600 gaccggggtt caaatcccag ctctgctgtt cactggttgt atgatcttgg ggaagacatc    660
ttccttctct gcctcggctt cctcatctgc agctacgcct gggtgtggtg agggttctag    720
gggatctcag atgtgtgtag cacggagcct gctgtgtcct gggtgctctc tacgtggtgg    780
ccggtagaat tctccatcta tccaggctcc aggagacccc tgggcatctc ccacctgtgg    840
cccctaaacc cagagtgact gagagcactt aacattcagc ttgtctcatc cccagtctac    900
ctccttcctt ctaccctcac tgcctcccag tcaggagagt gagctctcag aagccagagc    960
cccacccaag gggaccctgg tctctccgcc ttcacctagc aatgggaacc ctgcttccca   1020
ggggaggaac caactgctcc accttctagg gacccagttt gttggagtag gacagtaaca   1080
tggcaggaat cggacttctg ggcctgtaat cccagtttgg atggcacgtt agactcttgg   1140
ttgaccgttc tggtccttag aagtcccatt ctcccttcca gttatgagaa accaatgcct   1200
tctagattca ggtgactatc cttacctggg ggtgctgatg catcctcagt taacctacac   1260
ccacctgaat atagatgagc gtagctgagt tttcacccgt aggaccgaag tgttttgtgg   1320
tggagtatct gaacaacctt ggctctgtgg ccattcaacc tgccaggact aacatttctg   1380
gatttgtgaa gaagggatct tcaaagccat gaacccaca gagctgtgtt gctttaaagc   1440
caccacaagg gtacagcatt aaatggcaga actggaaaag cttcttaggg catctcatcc   1500
agggattctc aaaccatgtc ccccagaggc cttgggctgc agttgcaggg ggcgccatgg   1560
ggctatagga gcctcccact ttcaccagag cagcctcact gtgccctgat tcacacactg   1620 tggcttttcca cgtgagggttt tgtttagagg gatccactac tcaagaaaaa gttagcaaac   1680 cactccttttt gttgcaaagg agctgaggtc aagggtggca aaggcacttg tccaaggtcg   1740
cccagcagtg ctgctctgat gacttgtgca catcccaag ggtaagagct tcgatctctg   1800
cacagccggg ccaacctctg accccttgtc catgtcagta aaatatgaag gtcacagcca   1860
```

-continued

| | |
|---|---|
| ggatttctaa gggtcaggag gccttcaccg ctgctgggc acacacacac acatgcatac | 1920 |
| acacatacga cacacacctg tgtctcccca ggggttttcc ctgcagtgag gcttgtccag | 1980 |
| atgattgagc ccaggagagg aagaacaaac aaactacgga gctggggagg gctgtggctt | 2040 |
| ggggccagct cccagggaaa ttcccagacc tgtaccgatg ttctctctgg caccagccga | 2100 |
| gctgcttcgt ggaggtaact tcaaaaaagt aaaagctatc atcagcatca tcttagactt | 2160 |
| gtatgaaata accactccgt ttctattctt aaaccttacc attttttgttt tgttttgttt | 2220 |
| ttttgagtcg gagttttgtt cttttttgcct aggctggagt gcagtggtac aatctcggct | 2280 |
| cactgcaacc tccacctccc gggttcaagt gattctcctg cctcagcctc ccaagtagct | 2340 |
| gggattacag gcacccgcca ccacacctgg ctaattttttt tgtatttttta gtagagacgg | 2400 |
| ggtttcacca tgttggccag gctggtctcg aactcctgac ctcaggtgat ccgcccgcct | 2460 |
| cggcctccca aagtgctggg attacaggcg tgagccaccg cgcccagcca aaccttacta | 2520 |
| tttttttaaa gaatttttttc cagagtttaa tttctgacat agcttaagtt ttccagtaac | 2580 |
| tctaaactcc atctccttta tcgtcattaa gtcattcaca aaaagccagg agaagcattt | 2640 |
| ggaaagggca tgataatcag tataataatt tgccttgtgt ggtcagcact taactgttta | 2700 |
| caaagcccctt tcacgtgcac agcaggtggg aactgcgcgg tgtgggctgg gcctgcgctg | 2760 |
| gaagcatatc ccgtgaaaag tgttagtgcc ttaggtgaaa gcaacatgta tccctttaga | 2820 |
| ctactaacgg tatatgttgt tcttatgtat ttgtatttat ttctattttt tctatgttta | 2880 |
| tgtcatatatt aaacgatatc ctactgcttg ttggtattac cctaaactgt ttaaataaag | 2940 |
| agctctattt ttaaagaaaaa aaggtacaat tga | 2973 |

<210> SEQ ID NO 5
<211> LENGTH: 2155
<212> TYPE: DNA
<213> ORGANISM: Mus musculus

<400> SEQUENCE: 5

| | |
|---|---|
| atgtggcggg ccgaccggtg ggcgcccta ctcctgttcc tgttgcagag cgccctagga | 60 |
| aggccccgtc tagccccacc cagaaacgtg acactcttct cccagaactt cactgtttac | 120 |
| ctgacatggc ttccggggct tgggagcccc ccaaatgtga cctatttcgt gacctaccaa | 180 |
| agctatatca aaaccggttg gcgaccagtg gagcattgtg caggtatcaa ggctctggtg | 240 |
| tgtcccctga tgtgcctgaa gaaactgaac ctgtactcca agttcaaagg acgagtacag | 300 |
| gcagcttccg cacacggcag gtccccacgg gtggagtccc ggtacctgga ataccttttt | 360 |
| gacgtggagc tagccccgcc caccctggtg ctcacccaga tggagaagat cctaagggtc | 420 |
| aacgctacct accagctgcc accttgcatg ccgtcgctgg aactgaagta ccaggtggaa | 480 |
| ttctggaagg agggtctggg aagcaagacc ctgtttcctg acactcccta tggccagcca | 540 |
| gtgcagattc ctctccagca aggtgctagc cgacgccact gcctcagcgc cagaaccgtc | 600 |
| tataccttaa ttgacattaa gtacagccag ttctctgagc ccagctgcat cttcctagag | 660 |
| gctccagggg acaaaagagc tgtcctggca atgccctcac tcttgcttct actgatagca | 720 |
| gccgttgcag caggtgtggc atggaagata atgaaggaa accccctggtt tcaggggtg | 780 |
| aagacgcccc gggcactgga cttttctgaa tacagatacc cagtggcaac ctttcagccc | 840 |
| agtggacctg agttctctga tgacttgatc ctttgtcccc agaaggaact gaccataagg | 900 |
| aacaggccca cccctcaggt cagaaaccca gccacgctac aggcaggacc agaaagagac | 960 |
| agtactgagg atgaagacga ggacacagac tacgatgacg acggtgacag cgtccagccc | 1020 |

```
tacctggaac ggcccctctt catcagcgag aagccccggg ttatggaaca ctcggagaca   1080
gacgagtctg gggtggattc aggggggcct tggacatccc cagttgggag tgacggctcc   1140
tctgcatggg actcttcaga caggagctgg tccagcacag gggactcctc atataaggat   1200
gaagttgggt cttccagctg tttgaccga aaggagccgg accaggcgcc ctgtggggat   1260
tggctccagg aggctctccc atgcctggaa ttttctgagg acttgggcac cgtggaagag   1320
cctctgaagg atggcctctc cgggtggagg atttctggtt ccttatcctc aaagagagat   1380
ctggctcctg tggagccccc agtttctctt cagacactga ctttctgctg ggtcaacaat   1440
cctgaggggg aggaggaaca ggaggacgag gaggaagagg aggaggagga ggaggaggaa   1500
gactgggaat cagaacctaa gggcagcaat gccggctgtt ggggcacttc aagcgtgcag   1560
aggacggagg tcaggggccg gatgctggga gattacttgg tcaggtgagc tggccctggt   1620
ggtccatcta cacattctct actgcacttc ccctggacca cagacacctc cgagagtcat   1680
gtccctttga gtggtagcca aggtcctggc cattcgtaat ggatctttat ggcactttgt   1740
cgttgggatt gagttgtaag atgtcaccat ttccaatgac ccaccagcta taggtgacct   1800
gtgagcggga cagagctgtg atcagagact agttgagttc caatctgccc attgtccctg   1860
ggatgacggg cctgatggaa aaatcatcct gtgataaaat gaaacaggtg aagccaggtg   1920
actgtggaca ccaagggtag atacgcccta gtccataagt cacacacagc attgcgcaaa   1980
acagacctcg gtccaaatca ctactctgct gtttctgata gtcactgagc aagcgactct   2040
taacctctca acctcagctt ccccttctgc agcagtcctg tgggtatggg gaggtaacag   2100
gtgacacagg gccaccaatg tcacatgtac tgactaggca ctagaaccct ccatc        2155
```

<210> SEQ ID NO 6
<211> LENGTH: 535
<212> TYPE: PRT
<213> ORGANISM: Mus musculus

<400> SEQUENCE: 6

```
Met Trp Arg Ala Asp Arg Trp Ala Pro Leu Leu Phe Leu Leu Gln
1               5                   10                  15

Ser Ala Leu Gly Arg Pro Arg Leu Ala Pro Pro Arg Asn Val Thr Leu
            20                  25                  30

Phe Ser Gln Asn Phe Thr Val Tyr Leu Thr Trp Leu Pro Gly Leu Gly
        35                  40                  45

Ser Pro Pro Asn Val Thr Tyr Phe Val Thr Tyr Gln Ser Tyr Ile Lys
    50                  55                  60

Thr Gly Trp Arg Pro Val Glu His Cys Ala Gly Ile Lys Ala Leu Val
65                  70                  75                  80

Cys Pro Leu Met Cys Leu Lys Lys Leu Asn Leu Tyr Ser Lys Phe Lys
                85                  90                  95

Gly Arg Val Gln Ala Ala Ser Ala His Gly Arg Ser Pro Arg Val Glu
            100                 105                 110

Ser Arg Tyr Leu Glu Tyr Leu Phe Asp Val Glu Leu Ala Pro Pro Thr
        115                 120                 125

Leu Val Leu Thr Gln Met Glu Lys Ile Leu Arg Val Asn Ala Thr Tyr
    130                 135                 140

Gln Leu Pro Pro Cys Met Pro Ser Leu Glu Leu Lys Tyr Gln Val Glu
145                 150                 155                 160

Phe Trp Lys Glu Gly Leu Gly Ser Lys Thr Leu Phe Pro Asp Thr Pro
                165                 170                 175
```

Tyr Gly Gln Pro Val Gln Ile Pro Leu Gln Gly Ala Ser Arg Arg
            180                 185                 190

His Cys Leu Ser Ala Arg Thr Val Tyr Thr Leu Ile Asp Ile Lys Tyr
            195                 200                 205

Ser Gln Pro Ser Glu Pro Ser Cys Ile Phe Leu Glu Ala Pro Gly Asp
        210                 215                 220

Lys Arg Ala Val Leu Ala Met Pro Ser Leu Leu Leu Leu Leu Ile Ala
225                 230                 235                 240

Ala Val Ala Ala Gly Val Ala Trp Lys Ile Met Lys Gly Asn Pro Trp
                245                 250                 255

Phe Gln Gly Val Lys Thr Pro Arg Ala Leu Asp Phe Ser Glu Tyr Arg
            260                 265                 270

Tyr Pro Val Ala Thr Phe Gln Pro Ser Gly Pro Glu Phe Ser Asp Asp
            275                 280                 285

Leu Ile Leu Cys Pro Gln Lys Glu Leu Thr Ile Arg Asn Arg Pro Ala
        290                 295                 300

Pro Gln Val Arg Asn Pro Ala Thr Leu Gln Ala Gly Pro Glu Arg Asp
305                 310                 315                 320

Ser Thr Glu Asp Glu Asp Thr Asp Tyr Asp Asp Gly Asp
                325                 330                 335

Ser Val Gln Pro Tyr Leu Glu Arg Pro Leu Phe Ile Ser Glu Lys Pro
            340                 345                 350

Arg Val Met Glu His Ser Glu Thr Asp Glu Ser Gly Val Asp Ser Gly
            355                 360                 365

Gly Pro Trp Thr Ser Pro Val Gly Ser Asp Gly Ser Ser Ala Trp Asp
        370                 375                 380

Ser Ser Asp Arg Ser Trp Ser Ser Thr Gly Asp Ser Tyr Lys Asp
385                 390                 395                 400

Glu Val Gly Ser Ser Cys Leu Asp Arg Lys Glu Pro Asp Gln Ala
            405                 410                 415

Pro Cys Gly Asp Trp Leu Gln Glu Ala Leu Pro Cys Leu Glu Phe Ser
            420                 425                 430

Glu Asp Leu Gly Thr Val Glu Gly Pro Leu Lys Asp Gly Leu Ser Gly
        435                 440                 445

Trp Arg Ile Ser Gly Ser Leu Ser Ser Lys Arg Asp Leu Ala Pro Val
450                 455                 460

Glu Pro Pro Val Ser Leu Gln Thr Leu Thr Phe Cys Trp Val Asn Asn
465                 470                 475                 480

Pro Glu Gly Glu Glu Glu Gln Asp Glu Glu Glu Glu Glu
            485                 490                 495

Glu Glu Glu Glu Asp Trp Glu Ser Glu Pro Lys Gly Ser Asn Ala Gly
                500                 505                 510

Cys Trp Gly Thr Ser Ser Val Gln Arg Thr Glu Val Arg Gly Arg Met
        515                 520                 525

Leu Gly Asp Tyr Leu Val Arg
        530                 535

<210> SEQ ID NO 7
<211> LENGTH: 603
<212> TYPE: DNA
<213> ORGANISM: Homo sapiens

<400> SEQUENCE: 7
atggctgcag cttggaccgt ggtgctggtg actttggtgc taggcttggc cgtggcaggc        60

```
cctgtcccca cttccaagcc caccacaact gggaagggct gccacattgg caggttcaaa    120
tctctgtcac cacaggagct agcgagcttc aagaaggcca gggacgcctt ggaagagtca    180
ctcaagctga aaaactggag ttgcagctct cctgtcttcc ccgggaattg ggacctgagg    240
cttctccagg tgagggagcg ccctgtggcc ttggaggctg agctggccct gacgctgaag    300
gtcctggagg ccgctgctgg cccagccctg gaggacgtcc tagaccagcc ccttcacacc    360
ctgcaccaca tcctctccca gctccaggcc tgtatccagc ctcagcccac agcagggccc    420
aggccccggg gccgcctcca ccactggctg caccggctcc aggaggcccc caaaaaggag    480
tccgctggct gcctggaggc atctgtcacc ttcaacctct ccgcctcct cacgcgagac     540 ctcaaatatg tggccgatgg gaacctgtgt ctgagaacgt caacccaccc tgagtccacc    600
tga                                                                  603
```

<210> SEQ ID NO 8
<211> LENGTH: 200
<212> TYPE: PRT
<213> ORGANISM: Homo sapiens

<400> SEQUENCE: 8

```
Met Ala Ala Ala Trp Thr Val Val Leu Val Thr Leu Val Leu Gly Leu
1               5                   10                  15

Ala Val Ala Gly Pro Val Pro Thr Ser Lys Pro Thr Pro Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200
```

<210> SEQ ID NO 9
<211> LENGTH: 591
<212> TYPE: DNA
<213> ORGANISM: Homo sapiens

<400> SEQUENCE: 9

```
atgactgggg actgcacgcc agtgctggtg ctgatggccg cagtgctgac cgtgactgga     60
gcagttcctg tcgccaggct ccacgggggct ctcccggatg caaggggctg ccacatagcc   120
```

```
cagttcaagt ccctgtctcc acaggagctg caggccttta agagggccaa agatgcctta      180
gaagagtcgc ttctgctgaa ggactgcagg tgccactccc gcctcttccc caggacctgg      240
gacctgaggc agctgcaggt gagggagcgc cccatggctt tggaggctga gctggccctg      300
acgctgaagg ttctggaggc caccgctgac actgacccag ccctggtgga cgtcttggac      360 cagcccttc acaccctgca ccatatcctc tcccagttcc gggcctgtat ccagcctcag       420
cccacggctg ggcccaggc ccggggccgc ctccaccatt ggctgtaccg gctccaggag       480
gccccaaaaa aggagtcccc tggctgcctc gaggcctctg tcaccttcaa cctcttccgc      540
ctcctcacgc gagacctgaa ttgtgttgcc agtggggacc tgtgtgtctg a               591
```

<210> SEQ ID NO 10
<211> LENGTH: 196
<212> TYPE: PRT
<213> ORGANISM: Homo sapiens

<400> SEQUENCE: 10

```
Met Thr Gly Asp Cys Thr Pro Val Leu Val Leu Met Ala Ala Val Leu
1               5                   10                  15

Thr Val Thr Gly Ala Val Pro Val Ala Arg Leu His Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Arg Cys His Ser Arg Leu Phe Pro Arg Thr Trp
65                  70                  75                  80

Asp Leu Arg Gln Leu Gln Val Arg Glu Arg Pro Met Ala Leu Glu Ala
                85                  90                  95

Glu Leu Ala Leu Thr Leu Lys Val Leu Glu Ala Thr Ala Asp Thr Asp
            100                 105                 110

Pro Ala Leu Val Asp Val Leu Asp Gln Pro Leu His Thr Leu His His
        115                 120                 125

Ile Leu Ser Gln Phe Arg Ala Cys Ile Gln Pro Gln Pro Thr Ala Gly
    130                 135                 140

Pro Arg Ala Arg Gly Arg Leu His His Trp Leu Tyr Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195
```

<210> SEQ ID NO 11
<211> LENGTH: 591
<212> TYPE: DNA
<213> ORGANISM: Homo sapiens

<400> SEQUENCE: 11

```
atgaccgggg actgcatgcc agtgctggtg ctgatggccg cagtgctgac cgtgactgga      60
gcagttcctg tcgccaggct ccgcggggct ctccggatg caaggggctg ccacatagcc      120
cagttcaagt ccctgtctcc acaggagctg caggccttta agagggccaa agatgcctta    180
gaagagtcgc ttctgctgaa ggactgcaag tgccgctccc gcctcttccc caggacctgg     240
```

```
gacctgaggc agctgcaggt gagggagcgc cccgtggctt tggaggctga gctggccctg    300
acgctgaagg ttctggaggc ctccgctgac actgacccag ccctggggga tgtcttggac    360
cagccccttc acaccctgca ccatatcctc tcccagctcc gggcctgtat ccagcctcag    420
cccacggcag ggcccaggac ccggggccgc ctccaccatt ggctgtaccg gctccaggag    480
gccccaaaaa aggagtcccc tggctgcctc gaggcctctg tcaccttcaa cctcttccgc    540
ctcctcacgc gagacctgaa ttgtgttgcc agcggggacc tgtgtgtctg a             591
```

<210> SEQ ID NO 12
<211> LENGTH: 196
<212> TYPE: PRT
<213> ORGANISM: Homo sapiens

<400> SEQUENCE: 12

```
Met Thr Gly Asp Cys Met Pro Val Leu Val Leu Met Ala Ala Val Leu
1               5                   10                  15

Thr Val Thr Gly Ala Val Pro Val Ala Arg Leu Arg Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Lys Cys Arg Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Ser Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu Tyr Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195
```

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13

```
gccgcggcag gaaggccatg gcg                                             23
```

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide -continued

```
<400> SEQUENCE: 14
gccggtacca tggcggggcc cgagcgctgg                                              30

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
gccggatccc cgtctggccc ctccccagaa                                              30

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
agggctagcc agttggcttc tgggacctcc                                              30

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
ccagaacttc agcgtgtacc tgac                                                    24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
ccaggatgtg acctattttg tggc                                                    24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
tctaagccca cctgcttctt gctg                                                    24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
ccagcaagaa gcaggtgggc ttag                                                    24

<210> SEQ ID NO 21
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ttcgggacac tgaacgtgta gatg                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
catcctcctc ctcttcgtcc tctg                                              24

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 23
ctggctagcc ctggtgctgc catcgc                                            26

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
aggcagcagc agcatcagat tcgg                                              24

<210> SEQ ID NO 25
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 25
gggtctagat cacctggcca tgtaatgccc ca                                     32

<210> SEQ ID NO 26
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 26
tttggaaaga aacaatgttc taggtc                                            26

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
```

```
cttcacctgg gcccttccgc                                              20

<210> SEQ ID NO 28
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 28
ctgagggtac caaatgcaga ctttcacaat g                                 31

<210> SEQ ID NO 29
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 29
gggaattcat gagatccagg ccctgaggag ttc                               33

<210> SEQ ID NO 30
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 30
gcggtaccat ggctgcagct tggaccgtgg                                   30

<210> SEQ ID NO 31
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 31
gcggtaccat gactggggac tgcacgccag tg                                32

<210> SEQ ID NO 32
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 32
gcggatcctg tccccacttc caagcccacc                                   30

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 33
gcggatcctg tcgccaggct ccgcggggct                                   30

<210> SEQ ID NO 34
<211> LENGTH: 30
<212> TYPE: DNA
```

<213> ORGANISM: Artificial Sequence
<220> FEATURE:
<223> OTHER INFORMATION: Synthetic oligonucleotide

<400> SEQUENCE: 34
cggaattcag gtggactcag ggtgggttga                              30

<210> SEQ ID NO 35
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 35
cggaattcag acacacaggt ccccactggc aacaca                       36

<210> SEQ ID NO 36
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 36
gcgaattcat gcgacggatg cccgccgaat tgaggtggac tcagggtggg        50

<210> SEQ ID NO 37
<211> LENGTH: 18
<212> TYPE: PRT
<213> ORGANISM: Homo sapiens

<400> SEQUENCE: 37

Ala Arg Gly Ala Arg Gly Ala Leu Ala Ser Glu Arg Val Ala Leu Ala
1               5                   10                  15

Leu Ala

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
gatagtactt ccaagcccac caca                                    24

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
gatcgatttc cccgaaatca tg                                      22

<210> SEQ ID NO 40
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 40
tgtgatggtg ggaatgggtc agtttgatgt cacgcacgat ttcc 44

<210> SEQ ID NO 41
<211> LENGTH: 18
<212> TYPE: PRT
<213> ORGANISM: Homo sapiens

<400> SEQUENCE: 41

Ala Arg Gly Ala Arg Gly Ala Leu Ala Ser Glu Arg Val Ala Leu
1               5                   10                  15

Leu Ala

<210> SEQ ID NO 42
<211> LENGTH: 164
<212> TYPE: PRT
<213> ORGANISM: Homo sapiens

<400> SEQUENCE: 42

Pro Leu Leu Cys Leu Leu Gln Ala Ala Pro Gly Arg Pro Arg Leu
1               5                   10                  15

Ala Pro Pro Gln Asn Val Thr Leu Leu Ser Gln Asn Phe Ser Val Tyr
                20                  25                  30

Leu Thr Trp Leu Pro Gly Leu Gly Asn Pro Gln Asp Val Thr Tyr Phe
            35                  40                  45

Val Ala Tyr Gln Ser Ser Pro Thr Arg Arg Arg Trp Arg Glu Val Glu
50                  55                  60

Glu Cys Ala Gly Thr Lys Glu Leu Leu Cys Ser Met Met Cys Leu Lys
65                  70                  75                  80

Lys Gln Asp Leu Tyr Asn Lys Phe Lys Gly Arg Val Arg Thr Val Ser
                85                  90                  95

Pro Ser Ser Lys Ser Pro Trp Val Glu Ser Glu Tyr Leu Asp Tyr Leu
            100                 105                 110

Phe Glu Val Glu Pro Ala Pro Pro Val Leu Val Leu Thr Gln Thr Glu
        115                 120                 125

Glu Ile Leu Ser Ala Asn Ala Thr Tyr Gln Leu Pro Pro Cys Met Pro
130                 135                 140

Pro Leu Asp Leu Lys Tyr Glu Val Ala Phe Trp Lys Glu Gly Ala Gly
145                 150                 155                 160

Asn Lys Thr Leu

<210> SEQ ID NO 43
<211> LENGTH: 188
<212> TYPE: PRT
<213> ORGANISM: Homo sapiens

<400> SEQUENCE: 43

Pro Leu Leu Leu Leu Leu Ala Ala Pro Trp Gly Arg Ala Val Pro
1               5                   10                  15

Cys Val Ser Gly Gly Leu Pro Lys Pro Ala Asn Ile Thr Phe Leu Ser
                20                  25                  30

Ile Asn Met Lys Asn Val Leu Gln Trp Thr Pro Pro Glu Gly Leu Gln
            35                  40                  45

Gly Val Lys Val Thr Tyr Thr Val Gln Tyr Phe Ile Tyr Gly Gln Lys
        50                  55                  60

Lys Trp Leu Asn Lys Ser Glu Cys Arg Asn Ile Asn Arg Thr Tyr Cys
65                  70                  75                  80

Asp Leu Ser Ala Glu Thr Ser Asp Tyr Glu His Gln Tyr Tyr Ala Lys

```
                85                  90                  95
Val Lys Ala Ile Trp Gly Thr Lys Cys Ser Lys Trp Ala Glu Ser Gly
            100                 105                 110

Arg Phe Tyr Pro Phe Leu Glu Thr Gln Ile Gly Pro Glu Val Ala
        115                 120                 125

Leu Thr Thr Asp Glu Lys Ser Ile Ser Val Val Leu Thr Ala Pro Glu
130                 135                 140

Lys Trp Lys Arg Asn Pro Glu Asp Leu Pro Val Ser Met Gln Gln Ile
145                 150                 155                 160

Tyr Ser Asn Leu Lys Tyr Asn Val Ser Val Leu Asn Thr Lys Ser Asn
                165                 170                 175

Arg Thr Trp Ser Gln Cys Val Thr Asn His Thr Leu
            180                 185
```

<210> SEQ ID NO 44
<211> LENGTH: 232
<212> TYPE: PRT
<213> ORGANISM: Homo sapiens

<400> SEQUENCE: 44

```
Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Phe Ser Pro
225                 230
```

<210> SEQ ID NO 45
<211> LENGTH: 272
<212> TYPE: PRT
<213> ORGANISM: Homo sapiens -continued

<400> SEQUENCE: 45

Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

<210> SEQ ID NO 46
<211> LENGTH: 299
<212> TYPE: PRT
<213> ORGANISM: Homo sapiens

<400> SEQUENCE: 46

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

Asn Met Lys Asn Val Leu Gln Trp Thr Pro Pro Glu Gly Leu Gln Gly
    50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
            210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Val Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg
            290                 295

<210> SEQ ID NO 47
<211> LENGTH: 239
<212> TYPE: PRT
<213> ORGANISM: Homo sapiens

<400> SEQUENCE: 47

Met Lys His Leu Leu Met Trp Ser Pro Val Ile Ala Pro Gly Glu Thr
1               5                   10                  15

Val Tyr Tyr Ser Val Glu Tyr Gln Gly Glu Tyr Glu Ser Leu Tyr Thr
            20                  25                  30

Ser His Ile Trp Ile Pro Ser Ser Trp Cys Ser Leu Thr Glu Gly Pro
            35                  40                  45

Glu Cys Asp Val Thr Asp Asp Ile Thr Ala Thr Val Pro Tyr Asn Leu
        50                  55                  60

Arg Val Arg Ala Thr Leu Gly Ser Gln Thr Ser Ala Trp Ser Ile Leu
65                  70                  75                  80

Lys His Pro Phe Asn Arg Asn Ser Thr Ile Leu Thr Arg Pro Gly Met
                85                  90                  95

Glu Ile Thr Lys Asp Gly Phe His Leu Val Ile Glu Leu Glu Asp Leu
            100                 105                 110

Gly Pro Gln Phe Glu Phe Leu Val Ala Tyr Trp Arg Arg Glu Pro Gly
            115                 120                 125

Ala Glu Glu His Val Lys Met Val Arg Ser Gly Gly Ile Pro Val His
            130                 135                 140

Leu Glu Thr Met Glu Pro Gly Ala Ala Tyr Cys Val Lys Ala Gln Thr
145                 150                 155                 160

Phe Val Lys Ala Ile Gly Arg Tyr Ser Ala Phe Ser Gln Thr Glu Cys
                165                 170                 175

```
Val Glu Val Gln Gly Glu Ala Ile Pro Leu Val Leu Ala Leu Phe Ala
                180                 185                 190

Phe Val Gly Phe Met Leu Ile Leu Val Val Pro Leu Phe Val Trp
            195                 200                 205

Lys Met Gly Arg Leu Leu Gln Tyr Ser Cys Cys Pro Val Val Val Leu
    210                 215                 220

Pro Asp Thr Leu Lys Ile Thr Asn Ser Pro Gln Lys Leu Ile Ser
225                 230                 235

<210> SEQ ID NO 48
<211> LENGTH: 281
<212> TYPE: PRT
<213> ORGANISM: Homo sapiens

<400> SEQUENCE: 48

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His
        275                 280

<210> SEQ ID NO 49
<211> LENGTH: 231
<212> TYPE: PRT
```

<213> ORGANISM: Homo sapiens

<400> SEQUENCE: 49

Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 50
<211> LENGTH: 243
<212> TYPE: PRT
<213> ORGANISM: Homo sapiens

<400> SEQUENCE: 50

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu

```
            115                 120                 125
Ala Ile Asp Met Ser Phe Glu Pro Pro Glu Phe Glu Ile Val Gly Phe
        130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
            195                 200                 205

Ser Val Tyr Leu Glu His Ser Asp Glu Gln Ala Val Ile Lys Ser Pro
        210                 215                 220

Leu Lys Cys Thr Leu Leu Pro Pro Gly Gln Glu Ser Glu Ser Ala Glu
225                 230                 235                 240

Ser Ala Lys

<210> SEQ ID NO 51
<211> LENGTH: 251
<212> TYPE: PRT
<213> ORGANISM: Homo sapiens

<400> SEQUENCE: 51

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
                35                  40                  45

Thr Asn Phe Lys Thr Ile Leu Glu Trp Glu Pro Lys Pro Val Asn Gln
50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
        130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
        210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu
```

<210> SEQ ID NO 52
<211> LENGTH: 250
<212> TYPE: PRT
<213> ORGANISM: Homo sapiens

<400> SEQUENCE: 52

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
        130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
                180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys
                245                 250

<210> SEQ ID NO 53
<211> LENGTH: 231
<212> TYPE: PRT
<213> ORGANISM: Homo sapiens

<400> SEQUENCE: 53

Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
                20                  25                  30

Arg Val Gln Phe Gln Ser Arg Asn Phe His Asn Ile Leu Gln Trp Gln
            35                  40                  45

Pro Gly Arg Ala Leu Thr Gly Asn Ser Ser Val Tyr Phe Val Gln Tyr
        50                  55                  60

Lys Ile Tyr Gly Gln Arg Gln Trp Lys Asn Lys Glu Asp Cys Trp Gly

```
            65                  70                  75                  80
Thr Gln Glu Leu Ser Cys Asp Leu Thr Ser Glu Thr Ser Asp Ile Gln
                     85                  90                  95
Glu Pro Tyr Tyr Gly Arg Val Arg Ala Ala Ser Ala Gly Ser Tyr Ser
                    100                 105                 110
Glu Trp Ser Met Thr Pro Arg Phe Thr Pro Trp Trp Glu Thr Lys Ile
                    115                 120                 125
Asp Pro Pro Val Met Asn Ile Thr Gln Val Asn Gly Ser Leu Leu Val
            130                 135                 140
Ile Leu His Ala Pro Asn Leu Pro Tyr Arg Tyr Gln Lys Glu Lys Asn
145                 150                 155                 160
Val Ser Ile Glu Asp Tyr Tyr Glu Leu Leu Tyr Arg Val Phe Ile Ile
                    165                 170                 175
Asn Asn Ser Leu Glu Lys Glu Gln Lys Val Tyr Glu Gly Ala His Arg
                    180                 185                 190
Ala Val Glu Ile Glu Ala Leu Thr Pro His Ser Ser Tyr Cys Val Val
                    195                 200                 205
Ala Glu Ile Tyr Gln Pro Met Leu Asp Arg Arg Ser Gln Arg Ser Glu
            210                 215                 220
Glu Arg Cys Val Glu Ile Pro
225                 230

<210> SEQ ID NO 54
<211> LENGTH: 228
<212> TYPE: PRT
<213> ORGANISM: Homo sapiens

<400> SEQUENCE: 54

Met Arg Thr Leu Leu Thr Ile Leu Thr Val Gly Ser Leu Ala Ala His
1                   5                   10                  15
Ala Pro Glu Asp Pro Ser Asp Leu Leu Gln His Val Lys Phe Gln Ser
                    20                  25                  30
Ser Asn Phe Glu Asn Ile Leu Thr Trp Asp Ser Gly Pro Glu Gly Thr
            35                  40                  45
Pro Asp Thr Val Tyr Ser Ile Glu Tyr Lys Thr Tyr Gly Glu Arg Asp
        50                  55                  60
Trp Val Ala Lys Lys Gly Cys Gln Arg Ile Thr Arg Lys Ser Cys Asn
65                  70                  75                  80
Leu Thr Val Glu Thr Gly Asn Leu Thr Glu Leu Tyr Tyr Ala Arg Val
                    85                  90                  95
Thr Ala Val Ser Ala Gly Gly Arg Ser Ala Thr Lys Met Thr Asp Arg
                    100                 105                 110
Phe Ser Ser Leu Gln His Thr Thr Leu Lys Pro Pro Asp Val Thr Cys
            115                 120                 125
Ile Ser Lys Val Arg Ser Ile Gln Met Ile Val His Pro Thr Pro Thr
        130                 135                 140
Pro Ile Arg Ala Gly Asp Gly His Arg Leu Thr Leu Glu Asp Ile Phe
145                 150                 155                 160
His Asp Leu Phe Tyr His Leu Glu Leu Gln Val Asn Arg Thr Tyr Gln
                    165                 170                 175
Met His Leu Gly Gly Lys Gln Arg Glu Tyr Glu Phe Phe Gly Leu Thr
                    180                 185                 190
Pro Asp Thr Glu Phe Leu Gly Thr Ile Met Ile Cys Val Pro Thr Trp
            195                 200                 205
```

```
Ala Lys Glu Ser Ala Pro Tyr Met Cys Arg Val Lys Thr Leu Pro Asp
    210                 215                 220

Arg Thr Trp Thr
225

<210> SEQ ID NO 55
<211> LENGTH: 235
<212> TYPE: PRT
<213> ORGANISM: Homo sapiens

<400> SEQUENCE: 55

Met Leu Pro Cys Leu Val Val Leu Ala Leu Leu Ser Leu Arg
1               5                   10                  15

Leu Gly Ser Asp Ala His Gly Thr Glu Leu Pro Ser Pro Pro Ser Val
                20                  25                  30

Trp Phe Glu Ala Glu Phe Phe His His Ile Leu His Trp Thr Pro Ile
                35                  40                  45

Pro Asn Gln Ser Glu Ser Thr Cys Tyr Glu Val Ala Leu Leu Arg Tyr
            50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
                115                 120                 125

Ser Val Asn Leu Glu Ile His Asn Gly Phe Ile Leu Gly Lys Ile Gln
130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
                195                 200                 205

Val Ala Ser Arg Ser Asn Lys Gly Met Trp Ser Lys Glu Glu Cys Ile
                210                 215                 220

Ser Leu Thr Arg Gln Tyr Phe Thr Val Thr Asn
225                 230                 235

<210> SEQ ID NO 56
<211> LENGTH: 224
<212> TYPE: PRT
<213> ORGANISM: Homo sapiens

<400> SEQUENCE: 56

Met Met Val Val Leu Leu Gly Ala Thr Thr Leu Val Leu Val Ala Val
1               5                   10                  15

Gly Pro Trp Val Leu Ser Ala Ala Ala Gly Gly Lys Asn Leu Lys Ser
                20                  25                  30

Pro Gln Lys Val Glu Val Asp Ile Ile Asp Asp Asn Phe Ile Leu Arg
                35                  40                  45

Trp Asn Arg Ser Asp Glu Ser Val Gly Asn Val Thr Phe Ser Phe Asp
            50                  55                  60
```

```
Tyr Gln Lys Thr Gly Met Asp Asn Trp Ile Lys Leu Ser Gly Cys Gln
 65                  70                  75                  80

Asn Ile Thr Ser Thr Lys Cys Asn Phe Ser Ser Leu Lys Leu Asn Val
                 85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile
    130                 135                 140

His Ile Ser Pro Gly Thr Lys Asp Ser Val Met Trp Ala Leu Asp Gly
145                 150                 155                 160

Leu Ser Phe Thr Tyr Ser Leu Leu Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
210                 215                 220

<210> SEQ ID NO 57
<211> LENGTH: 220
<212> TYPE: PRT
<213> ORGANISM: Homo sapiens

<400> SEQUENCE: 57

Met Ala Trp Ser Leu Gly Ser Trp Leu Gly Gly Cys Leu Leu Val Ser
  1               5                  10                  15

Ala Leu Gly Met Val Arg Pro Pro Glu Asn Val Arg Met Asn Ser Val
                 20                  25                  30

Asn Phe Lys Asn Ile Leu Gln Trp Glu Ser Pro Ala Phe Ala Lys Gly
             35                  40                  45

Asn Leu Thr Phe Thr Ala Gln Tyr Leu Ser Tyr Arg Ile Phe Gln Asp
 50                  55                  60

Lys Cys Met Asn Thr Thr Leu Thr Glu Cys Asp Phe Ser Ser Leu Ser
 65                  70                  75                  80

Lys Tyr Gly Asp His Thr Leu Arg Val Arg Ala Glu Phe Ala Asp Glu
                 85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Pro Asn Lys Ala Gly Glu Trp Ser Glu Pro Val
        195                 200                 205

Cys Glu Gln Thr Thr His Asp Glu Thr Val Pro Ser
210                 215                 220
```

<210> SEQ ID NO 58
<211> LENGTH: 212
<212> TYPE: PRT
<213> ORGANISM: Homo sapiens

<400> SEQUENCE: 58

Val Glu Asn Glu Leu Pro Pro Glu Asn Ile Glu Val Ser Val Gln
1               5                   10                  15

Asn Gln Asn Tyr Val Leu Lys Trp Asp Tyr Thr Tyr Ala Asn Met Thr
                20                  25                  30

Phe Gln Val Gln Trp Leu His Ala Phe Leu Lys Arg Asn Pro Gly Asn
            35                  40                  45

His Leu Tyr Lys Trp Lys Gln Ile Pro Asp Cys Glu Asn Val Lys Thr
    50                  55                  60

Thr Gln Cys Val Phe Pro Gln Asn Val Phe Gln Lys Gly Ile Tyr Leu
65                  70                  75                  80

Leu Arg Val Gln Ala Ser Asp Gly Asn Asn Thr Ser Phe Trp Ser Glu
                85                  90                  95

Glu Ile Lys Phe Asp Thr Glu Ile Gln Ala Phe Leu Leu Pro Pro Val
            100                 105                 110

Phe Asn Ile Arg Ser Leu Ser Asp Ser Phe His Ile Tyr Ile Gly Ala
        115                 120                 125

Pro Lys Gln Ser Gly Asn Thr Pro Val Ile Gln Asp Tyr Pro Leu Ile
    130                 135                 140

Tyr Glu Ile Ile Phe Trp Glu Asn Thr Ser Asn Ala Glu Arg Lys Ile
145                 150                 155                 160

Ile Glu Lys Lys Thr Asp Val Thr Val Pro Asn Leu Lys Pro Leu Thr
                165                 170                 175

Val Tyr Cys Val Lys Ala Arg Ala His Thr Met Asp Glu Lys Leu Asn
            180                 185                 190

Lys Ser Ser Val Phe Ser Asp Ala Val Cys Glu Lys Thr Lys Pro Gly
        195                 200                 205

Asn Thr Ser Lys
    210

<210> SEQ ID NO 59
<211> LENGTH: 247
<212> TYPE: PRT
<213> ORGANISM: Homo sapiens

<400> SEQUENCE: 59

Met Arg Pro Thr Leu Trp Ser Leu Leu Leu Leu Gly Val Phe
1               5                   10                  15

Ala Ala Ala Ala Ala Pro Pro Asp Pro Leu Ser Gln Leu Pro Ala
                20                  25                  30

Pro Gln His Pro Lys Ile Arg Leu Tyr Asn Ala Glu Gln Val Leu Ser
            35                  40                  45

Trp Glu Pro Val Ala Leu Ser Asn Ser Thr Arg Pro Val Val Tyr Gln
        50                  55                  60

Val Gln Phe Lys Tyr Thr Asp Ser Lys Trp Phe Thr Ala Asp Ile Met
65                  70                  75                  80

Ser Ile Gly Val Asn Cys Thr Gln Ile Thr Ala Thr Glu Cys Asp Phe
                85                  90                  95

Thr Ala Ala Ser Pro Ser Ala Gly Phe Pro Met Asp Phe Asn Val Thr
            100                 105                 110

```
Leu Arg Leu Arg Ala Glu Leu Gly Ala Leu His Ser Ala Trp Val Thr
        115                 120                 125

Met Pro Trp Phe Gln His Tyr Arg Asn Val Thr Val Gly Pro Pro Glu
    130                 135                 140

Asn Ile Glu Val Thr Pro Gly Glu Gly Ser Leu Ile Ile Arg Phe Ser
145                 150                 155                 160

Ser Pro Phe Asp Ile Ala Asp Thr Ser Thr Ala Phe Phe Cys Tyr Tyr
                165                 170                 175

Val His Tyr Trp Glu Lys Gly Gly Ile Gln Gln Val Lys Gly Pro Phe
                180                 185                 190

Arg Ser Asn Ser Ile Ser Leu Asp Asn Leu Lys Pro Ser Arg Val Tyr
                195                 200                 205

Cys Leu Gln Val Gln Ala Gln Leu Leu Trp Asn Lys Ser Asn Ile Phe
        210                 215                 220

Arg Val Gly His Leu Ser Asn Ile Ser Cys Tyr Glu Thr Met Ala Asp
225                 230                 235                 240

Ala Ser Thr Glu Leu Gln Gln
                245

<210> SEQ ID NO 60
<211> LENGTH: 229
<212> TYPE: PRT
<213> ORGANISM: Homo sapiens

<400> SEQUENCE: 60

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Thr Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
                100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
                180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu
```

<210> SEQ ID NO 61
<211> LENGTH: 246
<212> TYPE: PRT
<213> ORGANISM: Homo sapiens

<400> SEQUENCE: 61

Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160

Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser
                245

<210> SEQ ID NO 62
<211> LENGTH: 1563
<212> TYPE: DNA
<213> ORGANISM: Homo sapiens

<400> SEQUENCE: 62
atggcggggc cgagcgctg gggcccctg ctcctgtgcc tgctgcaggc cgctccaggg       60
aggccccgtc tggcccctcc ccagaatgtg acgctgctct cccagaactt cagcgtgtac      120
ctgacatggc tcccagggct tggcaaccccc aggatgtga cctatttgt ggcctatcag      180 agctctccca cccgtagacg gtggcgcgaa gtggaagagt gtgcgggaac caaggagctg      240
ctatgttcta tgatgtgcct gaagaaacag gacctgtaca acaagttcaa gggacgcgtg      300
cggacggttt ctcccagctc caagtccccc tgggtggagt ccgaataccc tggattacctt      360 tttgaagtgg agccggcccc acctgtcctg gtgctcaccc agacggagga gatcctgagt      420

```
gccaatgcca cgtaccagct gccccctgc atgccccac tggatctgaa gtatgaggtg      480
gcattctgga aggaggggc cggaaacaag accctatttc cagtcactcc ccatggccag      540
ccagtccaga tcactctcca gccagctgcc agcgaacacc actgcctcag tgccagaacc      600
atctacacgt tcagtgtccc gaaatacagc aagttctcta agcccacctg cttcttgctg      660
gaggtcccag aagccaactg ggctttcctg gtgctgccat cgcttctgat actgctgtta      720
gtaattgccg caggggtgt gatctggaag accctcatgg ggaaccctg gtttcagcgg       780
gcaaagatgc cacgggccct ggactttct ggacacacac accctgtggc aacctttcag      840
cccagcagac cagagtccgt gaatgacttg ttcctctgtc cccaaaagga actgaccaga      900
ggggtcaggc cgacgcctcg agtcagggcc ccagccaccc aacagacaag atggaagaag      960
gaccttgcag aggacgaaga ggaggaggat gaggaggaca cagaagatgg cgtcagcttc     1020
cagccctaca ttgaaccacc ttctttcctg gggcaagagc accaggctcc agggcactcg     1080
gaggctggtg gggtggactc agggaggccc agggctcctc tggtcccaag cgaaggctcc     1140
tctgcttggg attcttcaga cagaagctgg gccagcactg tggactcctc ctgggacagg     1200
gctgggtcct ctggctattt ggctgagaag gggccaggcc aagggccggg tggggatggg     1260
caccaagaat ctctcccacc acctgaattc tccaaggact cgggtttcct ggaagagctc     1320
ccagaagata acctctcctc ctgggccacc tggggcacct taccaccgga gccgaatctg     1380
gtccctgggg accccagt ttctcttcag acactgacct tctgctggga aagcagccct      1440
gaggaggaag aggaggcgag ggaatcagaa attgaggaca gcgatgcggg cagctggggg     1500
gctgagagca cccagaggac cgaggacagg ggccggacat tggggcatta catggccagg     1560
tga                                                                  1563
```

<210> SEQ ID NO 63
<211> LENGTH: 196
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (116)..(116)
<223> OTHER INFORMATION: Xaa can be any naturally occurring amino acid

<400> SEQUENCE: 63

```
Met Thr Gly Asp Cys Thr Pro Val Leu Val Leu Met Ala Ala Val Leu
1               5                   10                  15

Thr Val Thr Gly Ala Val Pro Val Ala Arg Leu His Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Ile Leu Lys Asp Cys Arg Cys His Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Xaa Asp Val Leu Asp Gln Pro Leu His Thr Leu His His
        115                 120                 125
```

```
Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195

<210> SEQ ID NO 64
<211> LENGTH: 6
<212> TYPE: PRT
<213> ORGANISM: Artificial sequence
<220> FEATURE:
<223> OTHER INFORMATION: Synthetic peptide

<400> SEQUENCE: 64

Arg Arg Ala Ser Val Ala
1               5

<210> SEQ ID NO 65
<211> LENGTH: 200
<212> TYPE: PRT
<213> ORGANISM: Homo sapiens

<400> SEQUENCE: 65

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Pro Thr Gly Lys
                20                  25                  30

Gly Cys His Ile Gly Arg Phe Lys Ser Leu Ser Pro Gln Glu Leu Ala
            35                  40                  45

Ser Phe Lys Lys Ala Arg Asp Ala Leu Glu Glu Ser Leu Lys Leu Lys
    50                  55                  60

Asn Thr Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asp Leu Cys Leu Arg
            180                 185                 190

Thr Ser Thr His Pro Glu Ser Thr
        195                 200

<210> SEQ ID NO 66
<211> LENGTH: 4
<212> TYPE: PRT
```

```
<213> ORGANISM: Artificial sequence
<220> FEATURE:
<223> OTHER INFORMATION: Synthetic peptide

<400> SEQUENCE: 66

Tyr Met Ala Arg
1

<210> SEQ ID NO 67
<211> LENGTH: 4
<212> TYPE: PRT
<213> ORGANISM: Artificial sequence
<220> FEATURE:
<223> OTHER INFORMATION: Synthetic peptide

<400> SEQUENCE: 67

Tyr Ile Met Arg
1

<210> SEQ ID NO 68
<211> LENGTH: 4
<212> TYPE: PRT
<213> ORGANISM: Artificial sequence
<220> FEATURE:
<223> OTHER INFORMATION: Synthetic peptide

<400> SEQUENCE: 68

Tyr Leu Val Arg
1
```

The invention claimed is:

1. A method for upregulating MHC class I antigen expression, said method comprising administering to an individual a composition comprising an effective amount of an interferon lambda 3 (IFN-λ3) polypeptide.

2. The method of claim 1 wherein the IFN-λ3 polypeptide is selected from the group consisting of:
a polypeptide having the complete amino acid sequence of SEQ ID NO: 12; amino acids 2-196 of SEQ ID NO: 12;
amino acids 23-196 of SEQ ID NO: 12;
amino acids 6-196 of SEQ ID NO: 12; amino acids 12-196 of SEQ ID NO: 12;
amino acids 7-196 of SEQ ID NO: 12;
amino acids 13-196 of SEQ ID NO: 12; and
amino acids 31-196 of SEQ ID NO: 12.

3. The method of claim 1 wherein the IFN-λ3 polypeptide is modified by translational or post-translational processing or by a chemical modification technique.

4. The method of claim 3 wherein the IFN-λ3 polypeptide is modified by acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, or transfer-RNA mediated addition of amino acids to proteins.

5. The method of claim 3 wherein the IFN-23 polypeptide is modified by pegylation.

* * * * *